US010767188B2

(12) United States Patent
Mackenzie et al.

(10) Patent No.: US 10,767,188 B2
(45) Date of Patent: Sep. 8, 2020

(54) METHODS AND COMPOSITIONS FOR OBTAINING USEFUL PLANT TRAITS

(71) Applicant: NUtech Ventures, Lincoln, NE (US)

(72) Inventors: Sally Mackenzie, Lincoln, NE (US);
Michael Fromm, Lincoln, NE (US);
Kamaldeep Virdi, Lincoln, NE (US);
Yashitola Wamboldt, Lincoln, NE (US)

(73) Assignee: NUTECH VENTURES, Lincoln, NE (US)

( * ) Notice: Subject to any disclaimer, the term of this patent is extended or adjusted under 35 U.S.C. 154(b) by 938 days.

(21) Appl. No.: 14/495,498

(22) Filed: Sep. 24, 2014

(65) Prior Publication Data
US 2015/0113679 A1 Apr. 23, 2015

Related U.S. Application Data

(60) Provisional application No. 61/882,140, filed on Sep. 25, 2013.

(51) Int. Cl.
C12N 15/82 (2006.01)

(52) U.S. Cl.
CPC ....... C12N 15/8273 (2013.01); C12N 15/827 (2013.01); C12N 15/8218 (2013.01); C12N 15/8261 (2013.01); C12N 15/8269 (2013.01); C12N 15/8271 (2013.01)

(58) Field of Classification Search
None
See application file for complete search history.

(56) References Cited

U.S. PATENT DOCUMENTS

| | | |
|---|---|---|
| 9,476,040 B2 | 10/2016 | Mackenzie et al. |
| 9,708,672 B2 | 7/2017 | Mackenzie et al. |
| 10,058,044 B2 | 8/2018 | Mackenzie et al. |
| 10,344,340 B2 | 7/2019 | Mackenzie et al. |
| 2002/0010953 A1 | 1/2002 | Vliet |
| 2004/0210962 A1 | 10/2004 | Mackenzie et al. |
| 2006/0248613 A1 | 11/2006 | Mackenzie et al. |
| 2006/0248614 A1 | 11/2006 | Mackenzie et al. |
| 2012/0284814 A1 | 11/2012 | Mackenzie et al. |
| 2014/0157452 A1 | 6/2014 | Mackenzie et al. |
| 2015/0052630 A1 | 2/2015 | Mackenzie et al. |
| 2015/0113679 A1 | 4/2015 | Mackenzie et al. |
| 2015/0189842 A1 | 7/2015 | Mackenzie et al. |
| 2017/0009308 A1 | 1/2017 | Mackenzie et al. |
| 2018/0343816 A1 | 12/2018 | Mackenzie et al. |
| 2019/0284644 A1 | 9/2019 | Mackenzie et al. |

FOREIGN PATENT DOCUMENTS

| | | |
|---|---|---|
| WO | 2005/118805 A1 | 12/2005 |
| WO | 2007/033436 A1 | 3/2007 |
| WO | 2012/151254 A1 | 11/2012 |

OTHER PUBLICATIONS

Machczynska et al. Plant Cell, Tissue and Organ Culture (PCTOC) 119.2 (2014): 289-299. (Year: 2014).*
Xu et al. Plant physiology 159.2 (2012): 710-720. (Year: 2012).*
Palauqui et al. The EMBO journal 16.15 (1997): 4738-4745. (Year: 1997).*
Raju et al. (Plant Direct 2.8 (2018): e00079). (Year: 2018).*
Abdelnoor et al., "Mitochondrial Genome Dynamics in Plants and Animals: Convergent Gene Fusions of a MutS Homologue" J Mol. Evol, Mar. 1, 2006, pp. 165-173, vol. 63.
Accession No. NP_565131 dated Jan. 22, 2014.
Arrieta-Montiel et al., "Diversity of the Arabidopsis Mitochondrial Genome Occurs via Nuclear-Controlled Recombination Activitiy", Genetics, 2009, pp. 1261-1268, vol. 183.
Becker et al., "Spontaneous epigenetic variation in the Arabidopsis thaliana methylome" Nature, 2011, vol. 480, pp. 245-249.
Boyko et al., "Transgenerational Adaptation of *Arabidopsis* to Stress Requires DNA Methylation and the Function of Dicer-Like Proteins", Public Library in Science One, Mar. 2010, pp. 1-12, vol. 5, Issue 3, e9514.
Dahlgren et al., "Analysis of siRNA Specificity on Targets with Double-Nucleotide Mismatches", Nucleic Acids Research, 2008, pp. 1-7, vol. 36 No. 9.
Davila et al., "Double-Strand Break Repair Processes Drive Evolution of the Mitochondrial Genome in *Arabidopsis*", BMC Biology: Journal of Biology, 2011, pp. 1-14, vol. 9, No. 64.
Du et al., "A Systematic Analysis of the Silencing Effects of an Active siRNA at all Single-Nucleotide Mismatched Target Sites", Nucleic Acids Research, 2005, pp. 1671-1677, vol. 33, No. 5.
European Search Report and Written Opinion dated Feb. 11, 2015 issued in EP Patent Application No. EP 14 18 6459.
Gao et al., "Analysis of the Leaf Methylomes of Parents and Their Hybrids Provides New Insight Into Hybrid Vigor in Populus Deltoides", BMC Genetics, 2014, 17 pages, vol. 15, Suppl. 1, No. S8.
Giannelos et al., "Tobacco Seed Oil as an Alternative Diesel Fuel: Physical and Chemical Properties", Industrial Crops and Products, Jul. 2002, pp. 1-9, vol. 16 Issue 1.
Greaves et al., "Inheritance of Trans Chromosomal Methylation Patterns from *Arabidopsis* F1 Hybrids", Proceedings of the National Academy of Sciences, Feb. 4, 2014, pp. 2017-2022, vol. 111, No. 5.
Groszmann et al. "Epigenetics in plants-vernalisation and hybrid vigour", Biochimica et Biophysica Acta, 2011, 1809, pp. 427-437.
Groszmann et al., "Intraspecific *Arabidopsis* Hybrids Show Different Patterns of Heterosis Despite the Close Relatedness of the Parental Genomes", Plant Physiology, Sep. 2014, pp. 265-280, vol. 166.
Groszmann et al., "The Role of Epigenetics in Hybrid Vigour", Trends in Genetics, Dec. 2013, pp. 684-690, vol. 29 No. 12.

(Continued)

Primary Examiner — Charles Logsdon
(74) Attorney, Agent, or Firm — Thompson Coburn LLP; Charles P. Romano

(57) ABSTRACT

The present invention provides methods for obtaining plants that exhibit useful traits by perturbation of plastid function in plant rootstocks and grafting the rootstocks to scions. Methods for identifying genetic loci that provide for useful traits in plants and plants produced with those loci are also provided. In addition, plants that exhibit the useful traits, parts of the plants including seeds, and products of the plants are provided as well as methods of using the plants. Recombinant DNA vectors and transgenic plants comprising those vectors that provide for plastid perturbation are also provided.

14 Claims, 82 Drawing Sheets

Specification includes a Sequence Listing.

(56) References Cited

OTHER PUBLICATIONS

Grouneva et al., "Phylogenetic viewpoints on regulation of light harvesting and electron transport in eukaryotic photosynthetic organisms", Planta, 2013, vol. 237, pp. 399-412.
Hauben et al. "Energy use efficiency is characterized by an epigenetic component that can be directed through artificial selection to increase yield", PNAS, 2009, vol. 106, No. 47, pp. 20109-20114.
Ifuku et al., "Molecular Functions of Oxygen-Evolving Complex Family Proteins in Photosynthetic Electron Flow", Journal of Integrative Plant Biology, Aug. 2010, pp. 723-734, vol. 52 No. 8.
Johannes et al., "Assessing the Impact of Transgenerational Epigenetic Variation on Complex Traits", Plos Genetics, 2009, vol. 5, Issue 6, e1000530.
Molinier et al., "Transgeneration Memory of Stress in Plants", Nature, Aug. 31, 2006, pp. 1046-1049, vol. 442, Nature Publishing Group, 2006.
Nisar et al., "Inflorescence Stem Grafting Made Easy in *Arabidopsis*", Plant Methods, Dec. 19, 2012, pp. 50, vol. 8 No. 1.
Reinders et al., "Compromised Stability of DNA methylation and transposon immobilization in mosaic *Arabidopsis* apigenomes", Genes & Development, 2009, vol. 23, pp. 939-950.
Roux et al., "Genome-Wide Epigenetic Perturbation Jump-Starts Patterns of Heritable Variation Found in Nature", Genetics, 2011, vol. 188, pp. 1015-1017.
Sandhu et al., "Trangenic Induction of Mitochondrial Rearrangements for Cytoplasmic Male Sterility in Crop Plants", Proceedings of the National Academy of Sciences, 2007, pp. 1766-1770, vol. 104, No. 6.
Santamaria et al., "MSH1-Induced Non-Genetic Variation Provides a Source of Phenotypic Diversity in Sorghum Bicolor", PLOS One, Oct. 2014, 8 pages, vol. 9, Issue 10, e108407.
Schmitz et al., "Transgenerational Epigenetic Instability is a Source of Novel Methylation Variants" Science, 2011, 334(6054): 369-373, 10 pages.
Shao et al., "Ws-2 Introgression in a Proportion of *Arabidopsis thaliana* Col-0 Stock Seed Produces Specific Phenotypes and Highlights the Importance of Routine Genetic Verification", Department of Agronomy and Horticulture, University of Nebraska, pp. 1-47, manuscript received for publication in the Plant Cell Jan. 26, 2016.
Shedge et al., "Extensive Rearrangement of the *Arabidopsis* Mitochondrial Genome Elicits Cellular Conditions for Thermotolerance", Plant Physiology, Apr. 2010, pp. 1960-1970, vol. 152, No. 4.
Shen et al., "Genome-Wide Analysis of DNA Methylation and Gene Expression Changes in Two *Arabidopsis* Ecotypes and Their Reciprocal Hybrids", the Plant Cell, Mar. 2012, pp. 875-892, vol. 24.
Stroud et al., "Plants regenerated from tissue culture contain stable epigenome changes in rice", eLife, 2013, No. 2: e00354, 14 pages.
Virdi et al., "*Arabidopsis* MSH1 Mutation Alters the Epigenome and Produces Heritable Changes in Plant Growth", Nature Communications, Feb. 27, 2015, 9 pages.
Virdi et al., "*Arabidopsis* MSH1 Mutation Alters the Epigenome and Produces Heritable Changes in Plant Growth", Nature Communications, Feb. 27, 2015, 23 pages including Supplemental Figures_2015b.
Virdi et al., "MSH1 is a Plant Organellar DNA Binding and Thylakoid Protein under Precise Spatial Regulation to Alter Development", Molecular Plant, 2015, pp. 1-16.
Wesley et al., "Construct Design for Efficient, Effective and High-Throughput Gene Silencing in Plants", the Plant Journal, Sep. 2001, pp. 581-590, vol. 27 Issue 6.
Xu et al., "MutS Homolog1 is a Nucleoid Protein that Alters Mitochondrial and Plastid Properties and Plant Response to High Light", the Plant Cell, 2011, pp. 3428-3441, vol. 23.

Xu et al., "The Chloroplast Triggers Developmental Reprogramming When MutS Homolog1 is Supressed in Plants", Plant Physiology, 2012, pp. 710-720, vol. 159.
Yang et al., "MSH1-Derived Epigenetic Breeding Potential in Tomato", Plant Physiology Preview, Mar. 3, 2015, 34 pages.
Galloway et al., "Transgenerational Plasticity is Adaptive in the Wild", Science, Nov. 16, 2007, pp. 1134-1136, vol. 318, No. 5853.
Kimura et al., "Identification of *Arabidopsis* Genes Regulated by High Light-Stress Using cDNA Microarray", Photochemistry and Photobiology, Feb. 2003, pp. 226-233, vol. 77, No. 2.
Shag et al., "Stress-Responsive Pathways and Small RNA Changes Distinguish Variable Developmental Phenotypes Caused by MSH1 Loss", BMC Plant Biology, 2017, 14 pages, vol. 17.
Abdelnoor et al., "Substoichiometric Shifting in the Plant Mitochondrial Genome is Influenced by a Gene Homologous to MutS", Proc. Natl. Acad. Sci. USA, May 13, 2003, pp. 5968-5973 vol. 100, No. 10, Epub May 1, 2003.
Dai et al., "Methylation Linear Discriminant Analysis (MLDA) for Identifying Differentially Methylated CpG Islands", NMC Bioinformatics, Aug. 8, 2008, 12 pages.
Davila et al., "Double-Strand Break Repair Processes Drive Evolution of the Mitochondrial Genome in *Arabidopsis*", BMC Biol, Sep. 27, 2011, 9:64, doi: 10.1186/1741-7007-9-64.
Melnyk et al., "Mobile 24 nt Small RNAs Direct Transcriptional Gene Silencing in the Root Meristems of *Arabidopsis thaliana*", Current Biology, Oct. 11, 2011, 1678-1683, vol. 21, Issue 19.
Molnar et al., "Small Silencing RNAs in Plants are Mobile and Direct Epigenetic Modification in Receipient Cells", Science, May 14, 2010, pp. 872-875, vol. 328.
Morrison et al., "Combinatorial Alanine-Scanning", Current Opinion in Chemical Biology, Jun. 2001, pp. 302-307, vol. 5, No. 3.
Raju et al., "An Epigenetic Breeding System in Soybean for Increased Yield and Stability," Plant Biotechnology Journal, Mar. 2018, 37 pages.
Shao et al., "Stress-Responsive Pathways and Small RNA Changes Distinguish Variable Developmental Phenotypes Caused by MSH1 Loss," BMC Plant Biology, 2017, 14 pages, vol. 17, Issue 47.
Shao et al., "Ws-2 Introgression in a Proportion of *Arabidopsis thaliana* Col-0 Stock Seed Produces Specific Phenotypes and Highlights the Importance of Routine Genetic Verification", the Plant Cell, Mar. 2016, pp. 603-605, vol. 28.
Shedge et al., "Plant Mitochondrial Recombination Surveillance Requires Unusual RecA and MutS Homologs", Plant Cell., Apr. 2007, pp. 1251-1264, vol. 19, No. 4, Epub Apr. 27, 2007.
Sun et al., "Utility of in Vitro Culture to the Study of Plant Mitochondrial Genome Configuration and its Dynamic Features", Theor. Appl. Genet., Aug. 2012, pp. 449-454, vol. 25, No. 3, doi: 10.1007/s00122-012-1844-4, Epub Mar. 18, 2012.
Beltran, J. et al., "Specialized Plastids Trigger Tissue-Specific Signaling for Systemic Stress Response in Plants", Plant Physiol, Oct. 2018, 178(2):672-683. doi: 10.1104/pp. 18.00804. Epub Aug. 22, 2018.
Extended European Search Report for EP Application 19167998.4 dated Aug. 30, 2019.
Nanda et al., "The Role of Plant Hormones During Grafting", Journal of Plant Research, 2018, pp. 49-58, vol. 131.
Pagliarani et al., "Small RNA Mobility: Spread of RNA Silencing Effectors and its Effect on Developmental Processes and Stress Adaptation in Plants", International Journal of Molecular Sciences, 2019, pp. 1-19, vol. 20.
Peng et al., "Plant Genomic DNA Methylation in Response to Stresses: Potential Applications and Challenges in Plant Breeding", Progress in Natural Science, Sep. 10, 2009, pp. 1037-1045, vol. 19, Issue No. 9.
Wu et al., "Inter-Species Grafting Caused Extensive and Heritable Alterations Of Dna Methlation in Solanaceae Plants", Plant Grafting and Epigenetics, Apr. 2013, pp. 1-11, vol. 8, No. 4.

* cited by examiner

Col-0    Col-0/msh1    Col-0/Col-0    msh1/Col-0

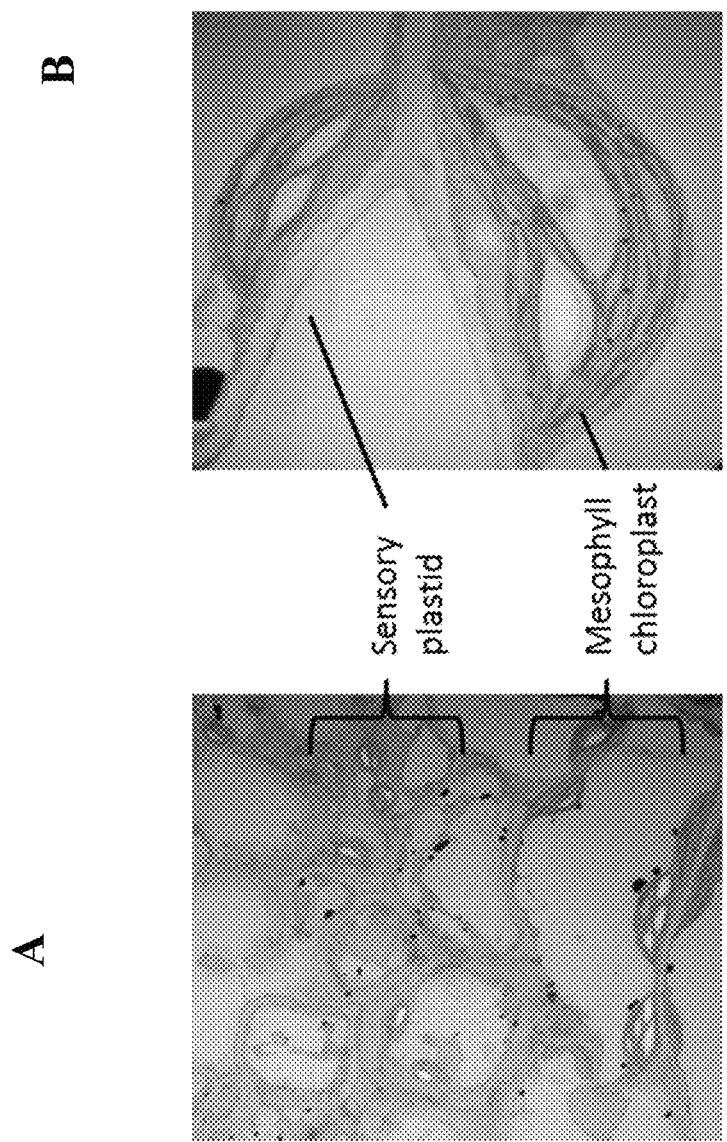
Figure 9A, B

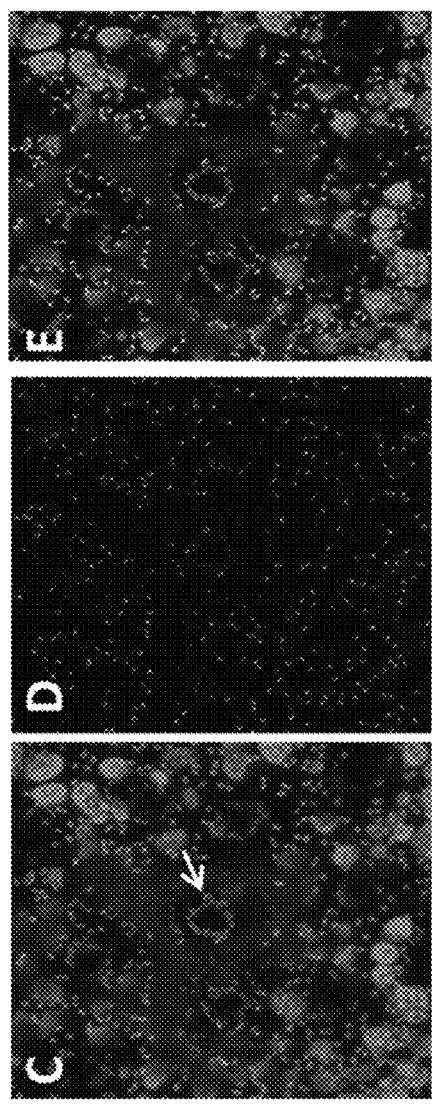
Figure 9C, D, E

Total Soluble Membrane
 α GFP
 α MSH1
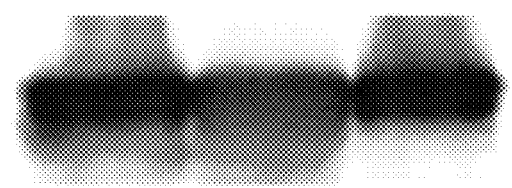 α PsbO
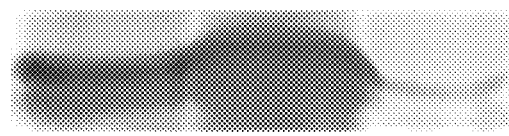 α PsbP
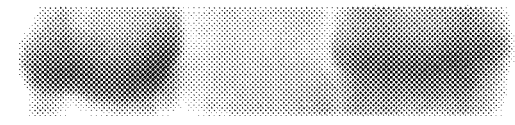 α D1
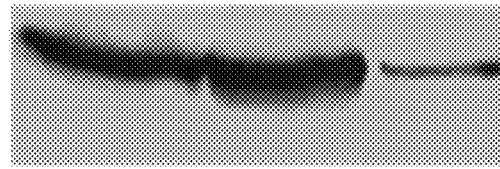 α rubisco
Figure 11B

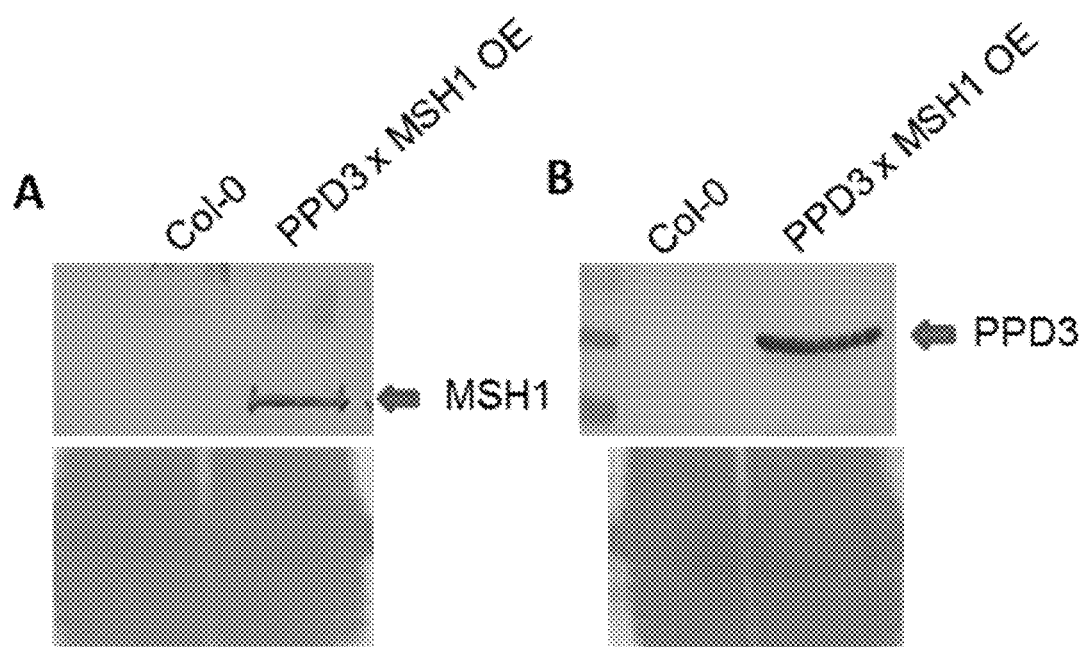
Figure 12 A,B

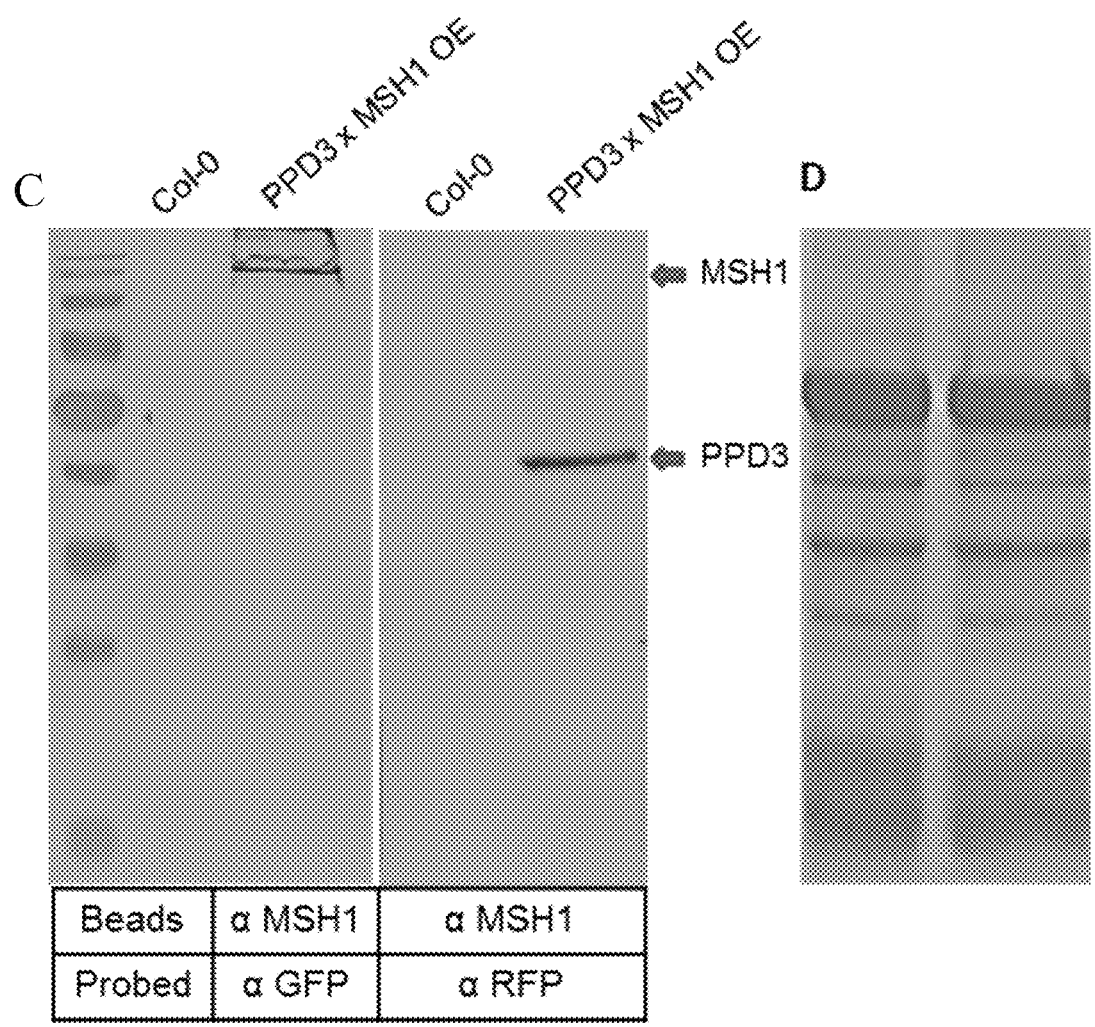
Figure 12C,D

B

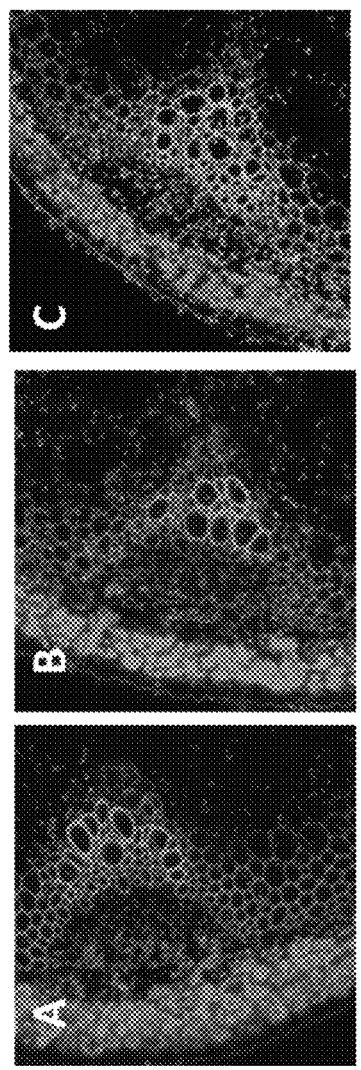
Figure 14A,B,C

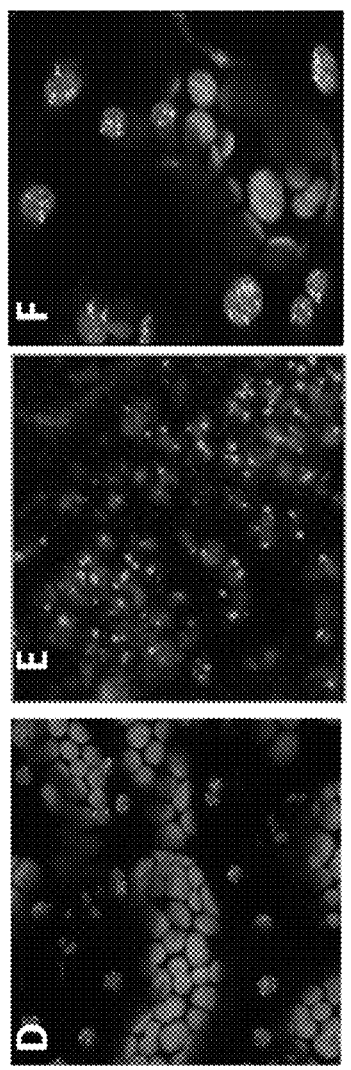
Figure 14D,E,F

A

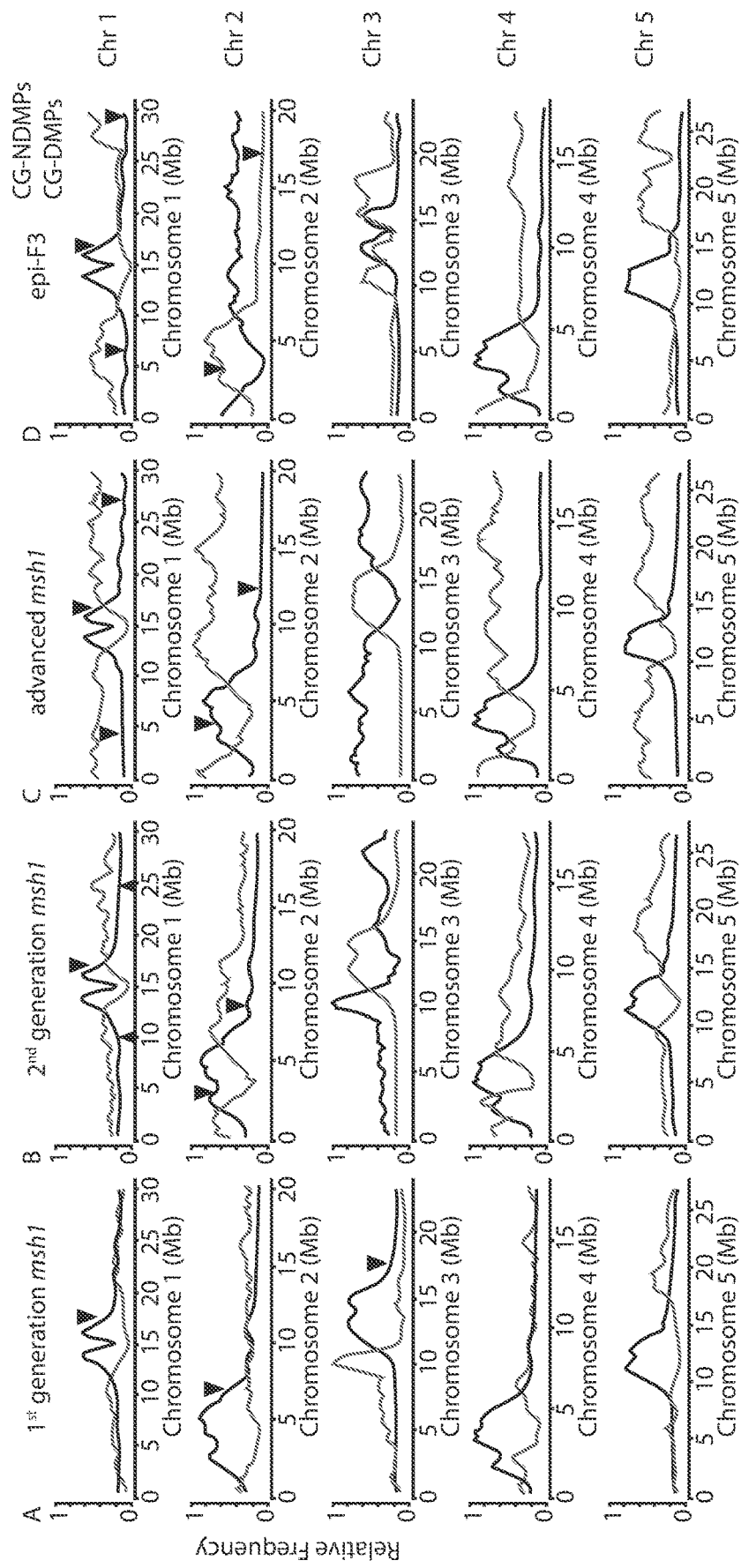
Figure 21A, B, C, D

A    Col-0    plastid hemi-complement

B   F1

SEQUENCE LISTING

```
<160> NUMBER OF SEQ ID NOS: 56

<210> SEQ ID NO 1
<211> LENGTH: 3730
<212> TYPE: DNA
<213> ORGANISM: Arabidopsis thaliana

<400> SEQUENCE: 1
agaggactgt gagattgtga attgcatagt cgtcgtcttc tggcgggaaa agaagcccta      60
gaaaaagggt gaaaggtgaa aactctactt cttcttcttc ttcttcttca gagtgtgaga     120
gagatgcatt ggattgctac cagaaacgcc gtcgtttcat tcccaaaatg gcggttcttc     180
ttccgctcct catatcgcac ttactcttcc ctcaaaccct cctcccaat  tctacttaat     240 agaaggtact ctgaggggat atcttgtctc agagatggaa agtctttgaa aagaatcaca     300
acggcttcta agaaagtgaa gacgtcaagt gatgttctca ctgacaaaga tctctctcat     360
ttggtttggt ggaaggagag attgcagaca tgtaagaaac catctactct tcagcttatt     420
gaaaggctta tgtacaccaa tttacttggt ttggaccta  gcttgaggaa tggaagttta     480
aaagatggaa acctcaactg ggagatgttg cagtttaagt caaggtttcc acgcgaagtt     540
ttgctctgca gagtaggaga attttatgag gctattggaa tagatgcttg tatacttgtt     600
gaatatgctg gtctcaatcc ttttggtggt cttcgatcag atagtattcc aaaggctggc     660
tgcccaatta tgaatcttcg acagactttg gatgacctga cacgcaatgg ttattcagtg     720
tgtattgtgg aggaagttca ggggccaaca ccagcacgct cccgtaaagg tcgatttatt     780
tcagggcatg cacatccagg aagtccttat gtatatgggc ttgtcggtgt tgaccatgat     840
cttgactttc ctgatcctat gcctgttgtt gggatatctc gttcagcaag ggggtattgt     900
atgatatcta ttttcgagac tatgaaagca tattcgctag atgatggtct aacagaagaa     960
gccttagtta ccaagctccg cactcgtcgc tgtcatcatc ttttcttaca tgcatcgttg    1020
```

```
aggcacaatg catcagggac gtgccgctgg ggagagtttg gggaaggggg tctactctgg      1080
ggagaatgca gtagcaggaa ttttgaatgg tttgaaggag atactctttc cgagctctta      1140
tcaagggtca aagatgttta tggtcttgat gatgaagttt cctttagaaa tgtcaatgta      1200
ccttcaaaaa atcggccacg tccgttgcat cttggaacgg ctacacaaat tggtgcctta      1260
cctactgaag gaataccttg tttgttgaag gtgttacttc catctacgtg cagtggtctg      1320 ccttcttttgt atgttaggga tcttcttctg aaccctcctg cttacgatat tgctctgaaa      1380
attcaagaaa cgtgcaagct catgagcaca gtaacatgtt caattccaga gtttacctgc      1440
gtctcttctg ctaagcttgt gaagcttctt gagcaacggg aagccaacta cattgagttc      1500
tgtcgaataa aaaatgtgct tgatgatgta ttacatatgc atagacatgc tgagcttgtg      1560
gaaatcctga aattattgat ggatcctacc tgggtggcta ctggtttgaa aattgacttt      1620
gacacttttg tcaacgaatg tcattgggcg tctgatacaa ttggtgaaat gatctcttta      1680
gatgagaatg aaagtcatca gaatgtaagt aaatgtgaca atgtcccgaa cgaattcttt      1740
tatgatatgg agtcttcatg gcgaggtcgc gttaaggaa ttcatataga ggaagaaatc       1800
actcaagtag aaaaatcagc tgaggcttta tctttagcag tagctgagga ttttcaccct      1860
attatatcaa gaattaaggc caccactgct tcacttggtg gcccgaaagg cgaaatcgca      1920
tatgcaagag agcatgagtc tgtttggttc aaggggaaac ggtttacgcc atctatctgg      1980
gctggtactg caggggaaga ccaaataaaa cagctgaaac ctgccttaga ctcgaaagga      2040
aaaaaggttg gagaagaatg gtttacgacc ccaaggtgg aaattgcttt agtcagatac       2100
catgaagcta gtgagaatgc aaaagctcgg gtgttggaac tgttgcgcga gttatccgtt      2160
aaattgcaaa caaaaataaa tgttcttgtc tttgcatcta tgcttctggt catttcaaaa      2220
gcattatttt cccatgcttg tgaagggaga aggcgaaagt gggttttttcc aacgcttgtc     2280 ggattcagtt tagatgaggg cgcaaaacca ttagatggtg ccagtcgaat gaagctgaca      2340
ggcctgtcac cttattggtt tgatgtatct tctggaaccg ctgttcacaa taccgttgac      2400
atgcaatcac tgtttcttct aactggacct aacggtggtg gtaaatcgag tttgctcaga      2460
tcaatatgcg cagctgctct acttggaatt ccggtttaa tggttccagc tgaatcagct       2520
tgtattcctc actttgattc catcatgctt cacatgaaat catatgacag ccctgtagac      2580
ggaaaaagtt ctttccaggt agaaatgtcg gaaatacgat ctattgtaag ccaggctact      2640
tcgagaagcc tagtgcttat agatgagata tgccgaggga cagagacagc aaaaggcacc      2700
tgtatcgctg gtagtgtggt agagagtctt gacacaagtg gttgtttggg tattgtatct      2760
actcatctcc atggaatctt cagtttacct cttacagcga aaacatcac atataaagca       2820 atgggagccg aaaatgtcga agggcaaacc aagccaactt ggaaattgac agatggagtc      2880
tgcagagaga gtcttgcgtt tgaaacagct aagagggaag gtgttcccga gtcagttatc      2940
caaagagctg aagctctttta cctctcggtc tatgcaaaag acgcatcagc tgaagttgtc     3000
aaacccgacc aaatcataac ttcatccaac aatgaccagc agatccaaaa accagtcagc      3060
tctgagagaa gtttggagaa ggacttagca aaagctatcg tcaaaatctg tgggaaaaag      3120
atgattgagc ctgaagcaat agaatgtctt tcaattggtg ctcgtgagct tccacctcca      3180
tctacagttg gttcttcatg cgtgtatgtg atgcggagac ccgataagag attgtacatt      3240
ggacagaccg atgatcttga aggacgaata cgtgcgcatc gagcaaagga aggactgcaa      3300
gggtcaagtt ttctatacct tatggttcaa ggtaagagca tggcttgtca gttagagact      3360
ctattgatta atcaactcca tgaacaaggc tactctctgg ctaacctagc cgatggaaag      3420
```

```
caccgtaatt tcggaacgtc ctcaagcttg agtacatcag acgtagtcag catcttatag    3480
tttgaaacat tagctgtgtt tgtagttgat catctctatg tgcaattgaa caagtcagtt    3540
tgctagaact agagtagatt actaagaaac catgccgttt ttcattttga gattttgcaa    3600
aacggcatgc agttcgggta agtcggatgc cgcaattacc aatttttgggt cagtctgtgt    3660 aattgtcgtt tcataaatcc gattaacgtg tactttgaac aaaactcagc agtaaacttc    3720
tttattcatc                                                            3730
```

<210> SEQ ID NO 2
<211> LENGTH: 1118
<212> TYPE: PRT
<213> ORGANISM: Arabidopsis thaliana

<400> SEQUENCE: 2

```
Met His Trp Ile Ala Thr Arg Asn Ala Val Ser Phe Pro Lys Trp
1               5                   10                  15

Arg Phe Phe Arg Ser Ser Tyr Arg Thr Tyr Ser Ser Leu Lys Pro
            20                  25                  30

Ser Ser Pro Ile Leu Leu Asn Arg Arg Tyr Ser Glu Gly Ile Ser Cys
        35                  40                      45

Leu Arg Asp Gly Lys Ser Leu Lys Arg Ile Thr Thr Ala Ser Lys Lys
    50                  55                  60

Val Lys Thr Ser Ser Asp Val Leu Thr Asp Lys Asp Leu Ser His Leu
65              70                  75                      80

Val Trp Trp Lys Glu Arg Leu Gln Thr Cys Lys Lys Pro Ser Thr Leu
                85                  90                  95

Gln Leu Ile Glu Arg Leu Met Tyr Thr Asn Leu Leu Gly Leu Asp Pro
            100                 105                 110

Ser Leu Arg Asn Gly Ser Leu Lys Asp Gly Asn Leu Asn Trp Glu Met
        115                 120                 125

Leu Gln Phe Lys Ser Arg Phe Pro Arg Glu Val Leu Leu Cys Arg Val
    130                 135                 140

Gly Glu Phe Tyr Glu Ala Ile Gly Ile Asp Ala Cys Ile Leu Val Glu
145                 150                 155                 160

Tyr Ala Gly Leu Asn Pro Phe Gly Gly Leu Arg Ser Asp Ser Ile Pro
                165                 170                 175

Lys Ala Gly Cys Pro Ile Met Asn Leu Arg Gln Thr Leu Asp Asp Leu
            180                 185                 190

Thr Arg Asn Gly Tyr Ser Val Cys Ile Val Glu Glu Val Gln Gly Pro
        195                 200                 205

Thr Pro Ala Arg Ser Arg Lys Gly Arg Phe Ile Ser Gly His Ala His
    210                 215                 220

Pro Gly Ser Pro Tyr Val Tyr Gly Leu Val Gly Val Asp His Asp Leu
225                 230                 235                 240

Asp Phe Pro Asp Pro Met Pro Val Val Gly Ile Ser Arg Ser Ala Arg
                245                 250                 255

Gly Tyr Cys Met Ile Ser Ile Phe Glu Thr Met Lys Ala Tyr Ser Leu
            260                 265                 270

Asp Asp Gly Leu Thr Glu Glu Ala Leu Val Thr Lys Leu Arg Thr Arg
        275                 280                 285

Arg Cys His His Leu Phe Leu His Ala Ser Leu Arg His Asn Ala Ser
    290                 295                 300

Gly Thr Cys Arg Trp Gly Glu Phe Gly Glu Gly Gly Leu Leu Trp Gly
```

-continued

```
            305                 310                 315                 320
Glu Cys Ser Ser Arg Asn Phe Glu Trp Phe Glu Gly Asp Thr Leu Ser
                325                 330                 335
Glu Leu Leu Ser Arg Val Lys Asp Val Tyr Gly Leu Asp Asp Glu Val
                340                 345                 350
Ser Phe Arg Asn Val Asn Val Pro Ser Lys Asn Arg Pro Arg Pro Leu
                355                 360                 365
His Leu Gly Thr Ala Thr Gln Ile Gly Ala Leu Pro Thr Glu Gly Ile
                370                 375                 380
Pro Cys Leu Leu Lys Val Leu Leu Pro Ser Thr Cys Ser Gly Leu Pro
385                 390                 395                 400
Ser Leu Tyr Val Arg Asp Leu Leu Asn Pro Pro Ala Tyr Asp Ile
                405                 410                 415
Ala Leu Lys Ile Gln Glu Thr Cys Lys Leu Met Ser Thr Val Thr Cys
                420                 425                 430
Ser Ile Pro Glu Phe Thr Cys Val Ser Ser Ala Lys Leu Val Lys Leu
                435                 440                 445
Leu Glu Gln Arg Glu Ala Asn Tyr Ile Glu Phe Cys Arg Ile Lys Asn
                450                 455                 460
Val Leu Asp Asp Val Leu His Met His Arg His Ala Glu Leu Val Glu
465                 470                 475                 480
Ile Leu Lys Leu Leu Met Asp Pro Thr Trp Val Ala Thr Gly Leu Lys
                485                 490                 495
Ile Asp Phe Asp Thr Phe Val Asn Glu Cys His Trp Ala Ser Asp Thr
                500                 505                 510
Ile Gly Glu Met Ile Ser Leu Asp Glu Asn Glu Ser His Gln Asn Val
                515                 520                 525
Ser Lys Cys Asp Asn Val Pro Asn Glu Phe Phe Tyr Asp Met Glu Ser
                530                 535                 540
Ser Trp Arg Gly Arg Val Lys Gly Ile His Ile Glu Glu Ile Thr
545                 550                 555                 560
Gln Val Glu Lys Ser Ala Glu Ala Leu Ser Leu Ala Val Ala Glu Asp
                565                 570                 575
Phe His Pro Ile Ile Ser Arg Ile Lys Ala Thr Thr Ala Ser Leu Gly
                580                 585                 590
Gly Pro Lys Gly Glu Ile Ala Tyr Ala Arg Glu His Glu Ser Val Trp
                595                 600                 605
Phe Lys Gly Lys Arg Phe Thr Pro Ser Ile Trp Ala Gly Thr Ala Gly
                610                 615                 620
Glu Asp Gln Ile Lys Gln Leu Lys Pro Ala Leu Asp Ser Lys Gly Lys
625                 630                 635                 640
Lys Val Gly Glu Glu Trp Phe Thr Thr Pro Lys Val Glu Ile Ala Leu
                645                 650                 655
Val Arg Tyr His Glu Ala Ser Glu Asn Ala Lys Ala Arg Val Leu Glu
                660                 665                 670
Leu Leu Arg Glu Leu Ser Val Lys Leu Gln Thr Lys Ile Asn Val Leu
                675                 680                 685
Val Phe Ala Ser Met Leu Leu Val Ile Ser Lys Ala Leu Phe Ser His
                690                 695                 700
Ala Cys Glu Gly Arg Arg Arg Lys Trp Val Phe Pro Thr Leu Val Gly
705                 710                 715                 720
Phe Ser Leu Asp Glu Gly Ala Lys Pro Leu Asp Gly Ala Ser Arg Met
                725                 730                 735
```

Lys Leu Thr Gly Leu Ser Pro Tyr Trp Phe Asp Val Ser Gly Thr
            740                 745                 750

Ala Val His Asn Thr Val Asp Met Gln Ser Leu Phe Leu Leu Thr Gly
            755                 760                 765

Pro Asn Gly Gly Lys Ser Ser Leu Leu Arg Ser Ile Cys Ala Ala
        770                 775                 780

Ala Leu Leu Gly Ile Ser Gly Leu Met Val Pro Ala Glu Ser Ala Cys
785                 790                 795                 800

Ile Pro His Phe Asp Ser Ile Met Leu His Met Lys Ser Tyr Asp Ser
                805                 810                 815

Pro Val Asp Gly Lys Ser Ser Phe Gln Val Glu Met Ser Glu Ile Arg
            820                 825                 830

Ser Ile Val Ser Gln Ala Thr Ser Arg Ser Leu Val Leu Ile Asp Glu
            835                 840                 845

Ile Cys Arg Gly Thr Glu Thr Ala Lys Gly Thr Cys Ile Ala Gly Ser
            850                 855                 860

Val Val Glu Ser Leu Asp Thr Ser Gly Cys Leu Gly Ile Val Ser Thr
865                 870                 875                 880

His Leu His Gly Ile Phe Ser Leu Pro Leu Thr Ala Lys Asn Ile Thr
                885                 890                 895

Tyr Lys Ala Met Gly Ala Glu Asn Val Glu Gly Gln Thr Lys Pro Thr
            900                 905                 910

Trp Lys Leu Thr Asp Gly Val Cys Arg Glu Ser Leu Ala Phe Glu Thr
            915                 920                 925

Ala Lys Arg Glu Gly Val Pro Glu Ser Val Ile Gln Arg Ala Glu Ala
            930                 935                 940

Leu Tyr Leu Ser Val Tyr Ala Lys Asp Ala Ser Ala Glu Val Val Lys
945                 950                 955                 960

Pro Asp Gln Ile Ile Thr Ser Ser Asn Asn Asp Gln Ile Gln Lys
                965                 970                 975

Pro Val Ser Ser Glu Arg Ser Leu Glu Lys Asp Leu Ala Lys Ala Ile
            980                 985                 990

Val Lys Ile Cys Gly Lys Lys Met Ile Glu Pro Glu Ala Ile Glu Cys
        995                 1000                1005

Leu Ser Ile Gly Ala Arg Glu Leu Pro Pro Ser Thr Val Gly
        1010                1015                1020

Ser Ser Cys Val Tyr Val Met Arg Arg Pro Asp Lys Arg Leu Tyr
        1025                1030                1035

Ile Gly Gln Thr Asp Asp Leu Glu Gly Arg Ile Arg Ala His Arg
        1040                1045                1050

Ala Lys Glu Gly Leu Gln Gly Ser Ser Phe Leu Tyr Leu Met Val
        1055                1060                1065

Gln Gly Lys Ser Met Ala Cys Gln Leu Glu Thr Leu Leu Ile Asn
        1070                1075                1080

Gln Leu His Glu Gln Gly Tyr Ser Leu Ala Asn Leu Ala Asp Gly
        1085                1090                1095

Lys His Arg Asn Phe Gly Thr Ser Ser Ser Leu Ser Thr Ser Asp
        1100                1105                1110

Val Val Ser Ile Leu
        1115

<210> SEQ ID NO 3
<211> LENGTH: 3765

<212> TYPE: DNA
<213> ORGANISM: Glycine max

<400> SEQUENCE: 3

| | | | | | |
|---|---|---|---|---|---|
| gtcagataca | gagtccttcc | ctcctcgtgt | gtggactgtg | gcgggaactc | attttgctag | 60 |
| tttgcttcct | ctctctctct | cgttcccatt | caacgcaatg | tacagggtag | ccacaagaaa | 120 |
| cgtcgccgtt | ttcttccctc | gttgctgttc | cctcgcgcac | tacactcctt | ctctatttcc | 180 |
| cattttcact | tcattcgctc | cctctcgttt | ccttagaata | aatggatgtg | taaagaatgt | 240 |
| gtcgagttat | acggataaga | aggtttcaag | ggggagtagt | agggccacca | agaagcccaa | 300 |
| aataccaaat | aacgttttag | atgataaaga | ccttcctcac | atactgtggt | ggaaggagag | 360 |
| gttgcaaatg | tgcagaaagt | tttcaactgt | ccagttaatt | gaaagacttg | aattttctaa | 420 |
| tttgcttggc | ctgaattcca | acttgaaaaa | tggaagtctg | aaggaaggaa | cactcaactg | 480 |
| ggaaatgttg | caattcaagt | caaaatttcc | acgtcaagta | ttgctttgca | gagttggga | 540 |
| attctatgaa | gctggggaa | tagatgcttg | tattcttgtt | gaatatgtgg | gtttaaatcc | 600 |
| cattggtggt | ctgcgatcag | atagtatccc | aagagctagt | tgtcctgtcg | tgaatcttcg | 660 |
| gcagacttta | tgatgatctga | caacaaatgg | ttattcagtg | tgcattgtgg | aggaggctca | 720 |
| gggcccaagt | caagctcgat | ccaggaaacg | tcgctttata | tctgggcatg | ctcatcctgg | 780 |
| aaatccctat | gtatatggac | ttgctacagt | tgatcatgat | cttaactttc | cagaaccaat | 840 |
| gcctgtagta | ggaatatctc | attctgcgag | gggttattgc | attaatatgg | tactagagac | 900 |
| catgaagaca | tattcttctg | aagattgctt | gacagaagaa | gcagttgtta | cgaagcttcg | 960 |
| tacttgccaa | tatcattact | tattttgca | tacatccttg | aggcggaatt | cttgtggaac | 1020 |
| ctgcaactgg | ggagaatttg | gtgagggagg | gctattatgg | ggagaatgta | gttctagaca | 1080 |
| ttttgattgg | tttgatggca | accctgtctc | cgatcttttg | gccaaggtaa | aggaacttta | 1140 |
| tagtattgat | gatgaggtta | cctttcggaa | cacaactgtg | tcttcaggac | atagggctcg | 1200 |
| accattaact | cttggaacat | ctactcaaat | tggtgccatt | ccaacagaag | gaataccttc | 1260 |
| tttgttgaag | gttttacttc | catcaaattg | caatggatta | ccagtattgt | acataaggga | 1320 |
| acttcttttg | aatcctcctt | catatgagat | tgcatccaaa | attcaagcaa | catgcaaact | 1380 |
| tatgagcagt | gtaacgtgtt | caattccaga | atttacatgt | gtttcgtcag | caaagcttgt | 1440 |
| aaagctactt | gaatggaggg | aggtcaatca | tatggaattt | tgtagaataa | agaatgtact | 1500 |
| ggatgaaatt | ttgcagatgt | atagtacctc | tgagctcaat | gaaatattga | acatttaat | 1560 |
| cgagcccaca | tgggtggcaa | ctgggttaga | aattgacttt | gaaaccttgg | ttgcaggatg | 1620 |
| tgagatcgca | tctagtaaga | ttggtgaaat | agtatctctg | gatgatgaga | atgatcagaa | 1680 |
| aatcaactcg | ttctcttta | ttcctcacga | atttttgag | gatatggagt | ctaaatggaa | 1740 |
| aggtcgaata | aaaagaatcc | acatagatga | tgtattcact | gcagtggaaa | aagcagctga | 1800 |
| ggccttacat | atagcagtca | ctgaagattt | tgttcctgtt | gtttctagaa | taaaggctat | 1860 |
| tgtagcccct | ctcggaggtc | ctaagggaga | aatatcttat | gctcgggagc | aagaagcagt | 1920 |
| ttggttcaaa | ggcaaacgct | ttacaccgaa | tttgtgggct | ggtagccctg | gagaggaaca | 1980 |
| aattaaacag | cttaggcatg | ctttagattc | taaaggtaga | aaggtagggg | aggaatggtt | 2040 |
| taccacacca | aaggtcgagg | ctgcattaac | aaggtaccat | gaagcaaatg | ccaaggcaaa | 2100 |
| agaaagagtt | ttgaaatttt | taaggggact | cgctgctgag | ttgcaataca | gtataaacat | 2160 |
| tcttgtcttt | tcttccatgt | tgcttgttat | tgccaaagct | ttatttgctc | atgcaagtga | 2220 |

```
agggagaaga aggagatggg tctttcccac gcttgtagaa tcccatgggt ttgaggatgt      2280
gaagtcattg acaaaaccc atgggatgaa gataagtggt ttattgccat attggttcca      2340
catagcagaa ggtgttgtgc gtaatgatgt tgatatgcaa tcattatttc tgttgacagg      2400
accgaatggt ggtgggaaat caagttttct taggtcaatt tgtgctgctg cactacttgg      2460
gatatgtgga ctcatggttc ctgcagaatc agccctaatt ccttattttg actccatcac      2520
gcttcatatg aagtcatatg atagtccagc tgataaaaag agttcctttc aggttgaaat      2580
gtcagaactt cgatccatca ttggcggaac aaccaacagg agccttgtac ttgttgatga      2640
aatatgccga ggaacagaaa ctgcaaaagg gacttgcatt gctggtagca tcattgaaac      2700
ccttgatgga attgggtgtc tgggtattgt atccactcac ttgcatggaa tatttacttt      2760
gcccctaaac aaaaaaaaca ctgtgcacaa agcaatgggc acaacatcca ttgatggaca      2820
aataatgcct acatggaagt tgacagatgg agtttgtaaa gaaagtcttg cttttgaaac      2880
ggctaagagg gaaggaattc ctgagcatat tgttagaaga gctgaatatc tttatcagtt      2940
ggtttatgct aaggaaatgc ttttgcaga aaatttccca aatgaagaaa agttttctac      3000
ctgcatcaat gttaataatt tgaatggaac acatcttcat tcaaaaaggt tcctatcagg      3060
agctaatcaa atggaagttt tacgcgagga agttgagaga gctgtcactg tgatttgcca      3120
ggatcatata aaggacctaa aatgcaaaaa gattgcattg gagcttactg agataaaatg      3180
tctcataatt ggtacaaggg agctaccacc tccatcggtt gtaggttctt caagcgtcta      3240
tgtgatgttc agaccagata agaaaactcta tgtaggagag actgatgatc tcgagggacg      3300
ggtccgaaga catcgattaa aggaaggaat gcatgatgca tcattccttt attttcttgt      3360
cccaggtaaa agcttggcat gccaatttga atctctgctc atcaaccaac tttctggtca      3420
aggcttccaa ctgagcaata tagctgatgg taaacatagg aattttggca cttccaacct      3480
gtatacataa ctagtctata gacattgata ttatctacct caatcgcgta tttttgcctc      3540
ttttaaatgg ctcaaagact tcaatcatcg atgttaagtt taggaaacaa tgtctgcagc      3600 attttttgtta gaattagttg ctgcagctgc atttatgtcc acatcttcaa gtgtggaaat      3660
tcttgttcat tagcttgtaa gtacaaaagt gtttgtgtac gtttggagtc ccgagagaat      3720
atacaagtac aaatgaacaa atatattagt aatgaatgca ctaga                     3765

<210> SEQ ID NO 4
<211> LENGTH: 3642
<212> TYPE: DNA
<213> ORGANISM: Zea mays

<400> SEQUENCE: 4
gcgcactacc ccgagaaacg tgcgacggga acctccgcgg ttccccaagt tcgcctcctt       60
cactactctc gcgccccggc acgcctgaaa accccaccc ctcctgccgc tccgcctctc      120
ccatcacttc ccacgcccct cgccgcctcc cattccagcg tggacacgac gccactcgcc      180
agcacggaga cgcgcgcctc gaagcactac tgcactagcc agccgtcgtt cttccgcgcc      240
ggcgccatgc accgggtgct cgtgagctcg cttgtggccg ccacgccgcg atggctgccc      300
ctcgccgact ccatcctccg gcgccgccgg ccgcgctgct cccctcttcc cgtgctgatg      360
ttcgatcgga gggcttggtc caagccaagg aaggtctcac gaggcatttc agtggcgtcc      420
aggaaagcta acaaacaggg agaatactgt gatgaaagta tgctgtcgca tatcatgtgg      480
tggaaagaga aaatggagag gtgcagaaaa ccatcatcca tacaattgac tcagaggctt      540
gtgtattcaa atatattagg gttggatccg aatttaagaa acggaagctt gaaagatgga      600
```

```
accctgaaca tggagatttt ggtatttaaa tcaaaatttc ctcgtgaggt tctactttgc    660
agagtaggag atttctatga agctatcggt tttgatgcct gtattctcgt agagcatgca    720
ggcttaaatc cttttggagg tttgcgttcc gacagtattc ctaaagctgg gtgtccagtc    780
gtgaatttac ggcagacatt ggatgatttg actcgatgtg gttattccgt gtgcatagtc    840
gaggaaattc aaggcccaac tcaagcccgt gctcggaaaa gtcgatttat ttctgggcat    900
gcccatcctg gtagtcctta tgtatttggt cttgctgaag tagaccatga tgtagagttc    960
cctgatccga tgcctgttgt tgggatttca cattctgcaa aaggttattg cttgatatct   1020
gtgctagaga caatgaaaac ttattcagct gaggagggct taacagagga ggctattgtt   1080
actaagctcc gcatatgtcg ttatcaccat ctataccttc acaattcttt gaagaataat   1140
tcttcaggga catcacgctg gggtgaattc ggtgaaggtg ggctcttgtg gggagagtgc   1200
agtgggaagt cctttgagtg gtttgacggt tcacctattc aagaacttt atgcaaggta    1260 cgggaaatat atggccttga tgagaaaacg gttttcgcg atgtcaccgt ctcattggaa    1320
ggcaggcccc aacctcttca tcttgggact gctactcaaa ttggagtcat accaactgag   1380
ggaataccga gtttgttaag aatggtgctt ccttcaaatt gtggcgggct tccatcaatg   1440
tatattagag atcttcttct taatcctcca tcatttgagg ttgcagcagc gatccaagag   1500
gcttgcaggc ttatgggcaa cataacctgc tccattcctg aatttacatg catatcagca   1560
gcaaagcttg tgaaactact tgagtcgaaa ggggtcaatc acattgaatt ttgtagaata   1620
aaaaatgtcc ttgatgagat tatgctcatg aacagggatg ctgagctttc tgcaatcctg   1680
catgaattac tggtacctgc ttctgtggct actggtttca aagttgaagc tgatatgcta   1740
atgaacggat gtagcattat ttcacaacga atagctgaag tgatttcttt aggtgttgaa   1800
agtgatcagg caataacttc attggaatat attccaaagg agttcttcaa tgatatggag   1860
tcatcttgga aggggcgcgt gaaaaggatc catgctgaag aagagtttgc aaatgttgat   1920
agggctgctg aggcattatc aattgcggtc attgaagatt ttatgccaat tatttcgagg   1980
gtgaaatctg tagtgtcctc gaatggaggt ttgaaaggag aaatcggtta tgcaaaagaa   2040
catgaagctg tttggtttaa aggaaagaga ttcataccaa atgtatgggc taacacacct   2100
ggtgagcagc aaataaaaca actgaagcct gcaattgatt caaaaggcag aaaggttggg   2160
gaggaatggt ttacaacaag caaagttgag aatgctttag ccaggtacca tgaagcttgt   2220
gataatgcaa gaaataaagt tcttgagctg ttgagaggcc tttctagtga attgcaggac   2280
aaaattaaca tacttgtctt ttgctcaaca ctgctcatca ttgcaaaagc acttttggt    2340 catgttagtg aggctcgaag aagaggttgg atgcttccta ctatatctcc cttatcaaag   2400
gactgtgttg tggaggaaag ttcaagtgca atggatttag taggactatt tccttactgg   2460
cttgatgtta atcaaggaaa tgcaatattg aatgatgtcc acatgcactc tttatttgtt   2520
cttactggcc caaatggtgg tggtaaatct agcatgttgc gatcagtctg tgcagctgtg   2580
cttcttggaa tatgtggcct gatggtacct tcaacttcag ctgtaatccc acattttgat   2640
tccattatgc tgcatatgaa agcctatgat agcccagcag atgggaaaag ttcatttcag   2700
attgaaatgt cggagatacg tgctttagtc agccgagcta ctgctaggag tcttgttctg   2760
attgatgaaa tatgtagagg cacagaaact gcaaaaggaa catgtatagc tggtagcatc   2820
attgaaagac ttgataatgt tggctgccta ggcatcatat caactcacct gcatgggatt   2880
ttcgacctgc ctctctcact tagcaacact gatttcaaag ctatgggaac tgaagtggtc   2940
```

```
gatggatgca ttcatccaac atggaaactg attgatggca tatgtagaga aagccttgct   3000
tttcaaacag caaggaggga aggcatgcct gacttgataa tcaccagggc tgaggagcta   3060
tatttgagta tgagtacaaa taacaagcag ggagcatcag tggcgcacaa tgagcctcct   3120
aatggcagcc ccagtgtaaa tggcttggtt gaggagcctg aatctctgaa gaacagacta   3180
gaaatgctgc ctggtacctt tgagccgctg cggaaggaag ttgagagtgc tgttactacg   3240
atgtgtaaga aaatactgtc ggacctttac aacaaaagta gcatcccaga actggtcgag   3300
gtggtctgcg ttgctgtagg tgctagagag caaccaccgc cttccactgt tggcagatct   3360
agcatctacg tgattatcag aagcgacaac aggctctatg ttggacagac ggacgatctt   3420
ctggggcgct gaacgcccca cagatcgaag gaaggcatgc gggacgctac ggtattatac   3480
gtcttggtcc ctggcaagag cgttgcctgc cagctggaaa cccttctcat aaaccagctc   3540
ccttcgaggg gcttcaagct catcaacaag gcagacggga agcacaggaa cttcggtata   3600
tctcgaatct ctggcgaggc agttgctact ggacggaact ag                     3642
```

<210> SEQ ID NO 5
<211> LENGTH: 3373
<212> TYPE: DNA
<213> ORGANISM: Lycopersicon esculentum

<400> SEQUENCE: 5

```
atgtattggg ttacggcaaa aaacgtcgtc gtttcagttc cccgttggcg ttcactgtcc     60
cttttcctcc gtccaccact tcgccggcgt ttcttatctt tctctccaca tactctgtgc    120
cgagagcaga tacgttgcgt gaaggagcgg aagttttttg ccacaacggc aaaaaaactc    180
aaacaaccaa aaagtattcc agaggaaaaa gactatgtta atattatgtg gtggaaagag    240
agaatggaat tcttgagaaa gccttcttcc gctcttctgg ctaagaggct tacatattgt    300
aacttgctgg gtgtggatcc gagtttgaga atggaagtc ttaaagaggg aacacttaac     360
tcggagatgt tgcagttcaa gtcaaaattt ccacgtgaag ttttgctctg tagagtaggt    420
gatttttatg aagctattgg attcgatgct tgtattcttg tggaatatgc tggtttaaat    480
ccatttggtg gcctgcactc agatagtata ccaaaagctg gttgtccagt tgtgaatcta    540
agacagacgc ttgatgatct cacacgtaat ggtttctctg tgtgcgtcgt ggaggaagtt    600
cagggtccaa ctcaagctcg tgctcgtaag agtcgattta tatcagggca tgcacatcca    660
ggcagtccct atgttttttgg ccttgttgga gatgatcaag atcttgattt tccagaacca    720
atgcctgttg ttggaatatc ccgttcagcg aagggggtatt gcattatctc tgtttacgag    780
actatgaaga cttactctgt ggaagatggc ctaactgaag aagccgtagt caccaaactt    840
cgtacttgtc gatgccatca ttttttttttg cataattcat tgaagaacaa ttcctcagga    900
acatcgcgtt ggggagagtt tggtgaaggt ggactttgt ggggagaatg taatgctaga     960
cagcaggaat ggttggatgg caatcctatc gatgagcttt tgttcaaggt aaaagagctt   1020
tatggtctca atgatgacat tccattcaga aatgtcactg ttgtttcaga aataggccc    1080 cgtcctttac accttggaac tgccacacaa attggtgcta ttccaaccga agggattcca   1140
tgtttgttaa aggtgttgct tcctcctcat tgcagtggtc taccagtcct gtatattagg   1200
gatcttcttt taaatccacc agcctatgag atttcttcag acattcaaga ggcatgcaga   1260
cttatgatga gtgtcacatg ttcaattcct gattttacct gtatttcatc tgcaaagctg   1320
gtcaagctgc ttgagttgag ggaggcaaat cacgttgagt tctgcaaaat aaagagcatg   1380
gtcgaagaga tactgcagtt gtatagaaat tcagagcttc gtgctattgt agagttactg   1440
```

```
atggatccta cttgggtggc aactgggttg aaagttgatt ttgatacact agtaaatgaa   1500
tgtggaaaga tttcttgtag aatcagtgaa ataatatccg tacatggtga aaatgatcaa   1560
aagattagtt cctatcctat catcccaaat gatttctttg aagatatgga gttgttgtgg   1620
aaaggccgtg tcaagaggat ccatttggag gaagcatatg cagaagtaga aaaggctgcg   1680
gatgctttat ctttagccat aacagaagat ttcctaccta ttatttcaag aataagggcc   1740
acgatggccc cacttggagg aactaaaggg gagattttgt atgcccgtga gcatggagct   1800
gtatggttta agggaaagag atttgtacca actgtttggg ctggaaccgc tggagaagaa   1860
caaattaagc aactcagacc tgctctagat tcaaagggga agaaggttgg agaagaatgg   1920
ttcactacaa tgagggtgga agatgcaata gctaggtatc acgaggcaag tgctaaggca   1980
aagtcaaggg tcttggaatt gctaagggga ctttcttctg aattactatc taagatcaat   2040
atccttatct ttgcatctgt cttgaatgtg atagcaaaat cattattttc tcatgtgagt   2100
gaaggaagaa gaagaaattg gattttccca acaatcacac aatttaacaa atgtcaggac   2160
acagaggcac ttaatggaac tgatggaatg aagataattg gtctatctcc ttattggttt   2220
gatgcagcac gagggactgg tgtacagaat acagtagata tgcagtccat gtttctttta   2280
acaggtccaa atggtggggg caaatcaagc ttgctgcgtt cgttgtgtgc agctgcattg   2340
ctaggaatgt gtgggttcat ggttccagct gaatcagctg tcattcctca ttttgactca   2400
attatgctgc atatgaaatc atatgatagt cctgttgatg gaaaaagttc atttcagatt   2460
gaaatgtctg aaattcggtc tctgattact ggtgccactt caagaagtct tgtacttata   2520
gatgaaatat gtcgaggaac agaaacagca aagggacat gtattgctgg aagtgtcata   2580
gaaaccctgg acgaaattgg ctgtttggga attgtatcaa cccacttgca tggaatattt   2640
gatttacccc tgaaaatcaa gaagaccgtg tataaagcaa tgggagctga atatgttgac   2700
ggtcaaccaa taccaacttg gaaactcatt gatgggatct gtaaagagag tctagcattt   2760
gaaacagctc agagagaagg aattccagaa atattaatcc aaagagcaga agaattgtat   2820
aattcagctt acgggaatca gataccaagg aagatagacc aaataagacc tctttgttca   2880
gatattgacc tcaatagcac agataacagt tctgaccaat taaatggtac aagacaaata   2940
gctttggatt ctagcacaaa gttaatgcat cgaatgggaa tttcaagcaa gaaacttgaa   3000
gatgctatct gtcttatctg tgagaagaag ttaattgagc tgtataaaat gaaaaatccg   3060
tcagaaatgc caatggtgaa ttgcgttctt attgctgcca gggaacagcc ggctccatca   3120
acaattggtg cttcaagtgt ctatataatg ctaagacctg acaaaaagtt gtatgttgga   3180
cagactgatg atcttgaggg cagagtacgt gctcatcgct tgaaggaggg aatggaaaac   3240
gcgtcattcc tatatttctt agtctctggc aagagcatcg cctgccaatt ggaaactctt   3300
ctaataaatc aacttcctaa tcatggtttt cagctaacaa acgttgctga tggtaagcat   3360
cgtaattttg gca                                                     3373

<210> SEQ ID NO 6
<211> LENGTH: 3180
<212> TYPE: DNA
<213> ORGANISM: Sorghum bicolor

<400> SEQUENCE: 6
atgcaccggg tgctcgtgag ctcgctcgtg gccgccacgc cgcggtggct ccccctcgcc   60
gactccatcc tccggcgccg ccgcccgcgc tgctctcctc ttcccatgct gctattcgac   120
```

```
cggagggctt ggtccaagcc aaggaaggtc tcacgaggca tctcagtggc gtctaggaaa    180
gctaacaaac agggagaata ttgtgatgaa agcatgctat cgcatatcat gtggtggaaa    240
gagaaaatgg agaagtgcag aaaaccatca tccgtacaat tgactcagag gcttgtgtat    300
tcaaatatat tagggttgga tccaaatcta agaaatggaa gcttgaaaga tggaaccctg    360
aacatggaga ttttgctatt taaatcaaaa tttcctcgtg aggttctact ttgcagagta    420
ggagacttct atgaagctat tggttttgat gcctgtattc tcgtagagca tgcaggctta    480
aatccttttg gaggtttgcg ttctgacagt atccctaaag ctgggtgtcc agtcgtgaat    540
ttacggcaga cattggatga tttgactcga tgtggttatt ctgtgtgcat agttgaggaa    600
attcaaggcc aacacaagc ccgttcccgg aaaagtcgat ttatttctgg gcatgcccat    660
cctggtagtc cttatgtatt tggtcttgct gaagtagacc atgatgtaga gttccctgat    720
ccgatgcctg ttgttgggat ttcacattct gcaaaaggtt attgcttgat atctgtgcta    780
gagacaatga aaacttattc agctgaggag ggcttaacag aagaggctat tgttactaag    840
ctccgcatat gtcgttatca tcatctatac cttcacaatt ctttgaagaa taattcttca    900 gggcatcac gctggggtga attcggtgaa ggagggctct tgtggggaga gtgcagtggg    960
aagtcctttg agtggtttga tggtttacct attgaagaac ttttatgcaa ggtacggaa    1020 atatatggcc ttgatgagaa aactgttttt cgcaatgtca ccgtctcatt ggaaggcagg    1080
ccccaacctc tttatcttgg aactgctact caaattggag tcataccaac tgagggaata    1140
ccgagtttgc taaaaatggc actcccttca agttgtggcg gcttccatc aatgtatatt    1200 agagatcttc ttcttaatcc tccatcattt gatgttgcgg cagcggtcca agaggcttgc    1260
aggcttatgg ggagcataac ttgttctgtt cctgaattta cttgcatatc acttgtgaag    1320
ctacttgagt ctaaagaggt caatcacatt gaatttgta gaataaaaaa tgtccttgat    1380
gagattatgc tcatgaacag gaatgctgag cttttctgcaa tcctgaacaa attgctggta    1440
cctggttctg tggctactgg tttgaaagtt gaagctgata tgctagtcat tgaagatttt    1500
atgccaatta tttcaagggt gaaatctgta gtgtcctcaa atggaggttc gaaaggagaa    1560
atctgttatg caaaagaaca tgaagctgtt tggtttaaag gaaagcgatt cacaccaact    1620
gtatgggcta acacacctgg tgagcagcaa ataaaacaac tgaagcctgc aattgattcg    1680
aaaggcagaa aggttgggga ggaatggttt acaacaagca aagttgagaa tgctttagcc    1740
aggtaccatg aagcttgtga taatgcaaga aataaagttg ttgagctgtt gagagggctt    1800
tcaagtgaat tgcaggacaa aattaacata cttgtctttt gctcaacact gctcatcatt    1860
gcaaaagcac ttttttggtca tgttagtgag gctcggagaa gaggctggat gcttcctact    1920
atatttccct tgtcaaagga ctgtgttgca gaggaaagtt caaatgcaat ggatttagta    1980
ggactctttc cttactggct tgatgttaat caaggaaatg caatattgaa tgatgtccac    2040
atgcactctt tatttgttct tactggtcca aatggtggtg gtaaatctag tatgttgcga    2100
tcagtctgtg cagctgcgct gcttggaata tgtggcctga tggtaccttc aacttcagct    2160
gtaatcccgc attttgattc cattatgctg catatgaaag cctacgatag cccagccgat    2220
gggaaaagtt catttcagat tgaaatgtcg gagatacgtg ctttagtcag ccgagctact    2280
gctaggagtc ttgtcctgat tgatgaaata tgtaggggca cagaaactgc aaaaggaacc    2340
tgtattgctg gtagcatcat cgaaaggctg ataatgttg ctgcctagg catcatatca    2400 actcacctgc atgggatttt tgacttgcct ctctcactca gcactactga tttcaaagct    2460
atgggaactg aagtggtcga cgggtgcatt catccaacat ggaaactgat ggatggcatc    2520
```

| | |
|---|---|
| tgtagagaaa gccttgcttt tcaaacagcc aggagggaag gcatgcctga gttcataatc | 2580 |
| agaagggctg aggagctata tttgactatg agtacaaata acaagcagac cgcatcaatg | 2640 |
| gtccacaatg agcctcgtaa tgacagcccc agtgtaaatg gcttggttga gaagcctgaa | 2700 |
| tatctgaaat acagactaga aattctgcct ggtacctttg agccgttgcg gagggaagtt | 2760 |
| gagagtgctg ttactatgat atgcaagaaa aaactgttgg atctttacaa taaaagtagc | 2820 |
| atcccagaac tggttgaggt ggtctgtgtt gctgtaggtg ctagagagca accaccacct | 2880 |
| tccactgttg gcaggtctag catctatgtg attatcagaa gcgacaacaa gctttatgtt | 2940 |
| ggacagacgg atgatcttct ggggcgcctt cacgcccaca gatcgaagga aggcatgcag | 3000 |
| gatgctacga tattatacat cttggttcct ggcaagagcg ttgcctgcca gctggaaacc | 3060 |
| cttctcataa atcagcttcc ttcgaggggc ttcaagctca tcaacaaggc agacggaaag | 3120 |
| cataggaact tcggtatatc tcgaatctct ggagaggcaa tcgccaccca gctaaactaa | 3180 |

<210> SEQ ID NO 7
<211> LENGTH: 3399
<212> TYPE: DNA
<213> ORGANISM: Oryza sativa

<400> SEQUENCE: 7

| | |
|---|---|
| atggccattc agcggctgct cgcgagctcg ctcgtggccg ccacgccgcg gtggcttccc | 60 |
| gtcgccgccg actcgtttct ccggcgccgc caccgccctc gctgctcccc gctccccgcg | 120 |
| ctgctatttta acaggaggtc ctggtctaaa ccaaggaaag tctcacgaag catttccatt | 180 |
| gtgtctagga agatgaacaa acaaggagat ctctgtaatg aaggcatgct gccacatatt | 240 |
| ctgtggtgga agagaaaat ggagaggtgc aggaaaccat catcaatgca attgactcag | 300 |
| agacttgtgt attcaaatat tttaggattg gatccaactt taagaaatgg aagcttgaag | 360 |
| gatggaagcc tgaacacgga aatgttgcaa ttcaaatcga agtttcctcg tgaagttcta | 420 |
| cttttgcagag tgggagattt ctacgaggct gttgggtttg atgcatgtat ccttgtggag | 480 |
| catgcaggct aaatcctttt ggaggcttg cgttctgata gtattccaaa gctggatgt | 540 |
| ccagtcatga atttgcggca gacattggat gatttgactc gatgtggtta ctctgtgtgc | 600 |
| atagttgaag aaattcaagg cccaacccaa gctcgtgcta ggaaaggccg atttatttct | 660 |
| ggccatgcac atcctggtag tccttatgta tttggtcttg ctgaagtaga ccatgatgtt | 720 |
| gagttccctg atccaatgcc tgtagttggg atttcacgat ctgcaaaagg ctattgcctg | 780 |
| atttctgtgc tagagacaat gaaaacatat tcagctgagg agggcttaac agaggaagca | 840 |
| gttgttacta agcttcgcat atgccgttat catcatctat accttcatag ttctttgagg | 900 |
| aacaattctt caggcacatc acgctgggga gaatttggcg aagtgggct attgtgggga | 960 |
| gagtgcagtg gaaaatcttt tgagtggttt gatggtaatc ctattgaaga actgttatgc | 1020 |
| aaggtaaggg aaatatatgg gcttgaagag aagactgttt ccgtaatgt cagtgtctca | 1080 |
| ttggaaggga ggcctcaacc cttgtatctt ggaacagcta ctcaaattgg ggtgataccca | 1140 |
| actgagggaa tacccagttt gctaaaaatt gttctccctc caaactttgg tggccttcca | 1200 |
| tcattgtata ttagagatct tcttcttaac cctccatctt ttgatgttgc atcatcagtt | 1260 |
| caagaggctt gcaggcttat gggtagcata acttgctcga ttcctgaatt tacatgcata | 1320 |
| ccggcagcaa agcttgtgaa attactcgag tcaaaagagg ttaatcacat cgaattttgt | 1380 |
| agaataaaga atgtcctcga tgaggtgttg ttcatgggta gcaatgctga gctttctgct | 1440 |

```
atcctgaata aattgcttga tcctgccgcc atagttactg ggttcaaagt tgaagccgat    1500
atactagtga atgaatgtag ctttatttca caacgtatag ctgaagtaat ctctttaggt    1560
ggtgaaagtg accaggcaat aacttcatct gaatatattc cgaaagagtt cttcaatgat    1620
atggagtcat cttggaaggg acgtgtaaaa agggtgcatg ctgaagagga gttctcaaat    1680
gttgatatag ctgctgaggc actgtcaaca gcggtcattg aagattttct gccaattatt    1740
tcaagagtaa aatctgtgat gtcctcaaat ggaagttcga agggagaaat cagttatgca    1800
aaagagcatg aatctgtttg gtttaaaggg aggcgattca caccaaatgt gtgggccaac    1860
actcctggtg aactacagat aaagcaattg aagcctgcaa ttgactcaaa aggtagaaag    1920
gtcggagaag aatggttcac cactatcaaa gttgagaatg ctttaaccag gtaccatgaa    1980
gcttgtgata atgcaaaacg taaagttctt gagttgttga gaggactttc aagtgaattg    2040
caggacaaga ttaatgtcct tgtcttttgc tcaacgatgc tcatcataac aaaagcactt    2100
tttggtcatg ttagtgaagg acgaagaagg ggttgggtgc ttcctactat atctcccttg    2160
tgtaaggata atgttacaga ggaaatctca agtgaaatgg aattgtcagg aacttttcct    2220
tactggcttg atactaacca agggaatgca atactgaatg atgtccatat gcactctttg    2280
tttattctta ctggtccaaa cggtggtggt aaatccagta tgctgagatc agtctgtgct    2340
gctgcattac ttggaatatg tggcctgatg gtgccagctg cttcagctgt catcccacat    2400
ttcgattcca tcatgctgca tatgaaagca tatgatagcc cagctgatgg taaaagttcg    2460
tttcagattg aaatgtcaga gatacgatct ttagtctgcc gagctacagc taggagtctt    2520
gttctaattg atgaaatatg taggggcaca gaaacagcaa aaggaacatg tatagctggt    2580
agcatcattg aaagactcga taatgttggc tgcataggca tcatatcaac tcatttgcat    2640
ggcattttg accttccact gtcactccac aatactgatt tcaaagctat gggaaccgaa    2700
atcatcgata ggtgcattca gccaacatgg aaattaatgg atggcatctg tagagagagt    2760
cttgcttttc aaacagccag gaaagaaggt atgcctgact tgataattag aagagctgag    2820
gaactatatt tggctatgag cacaaacagc aagcagacat catcagctgt ccaccatgaa    2880
atatccatag ccaactctac tgtaaatagc ttggttgaga agcctaatta cctgagaaat    2940
ggactagagc ttcaatctgg ttccttcgga ttactaagaa aagaaattga gagtgttgtt    3000
accacaatat gcaagaagaa actgttggat ctctacaaca aaaggagcat ctcagaactg    3060
attgaggtgg tctgtgttgc tgtgggtgct agggagcaac ccccaccttc aactgttggc    3120
aggtccagca tttatgtaat tatcagacgt gacagcaagc tctatattgg acagacggat    3180
gatcttgtgg gtcgacttag tgctcacaga tcgaaggaag gtatgcagga tgccacgata    3240
ttatatattt tggtacctgg gaagagcatt gcatgccaac tggaaactct tctcataaat    3300
cagctacctt tgaaaggttt caagctcatc aacaaggcag atggcaagca tcgaaatttc    3360
ggtatatctc ttgtcccagg agaggcaatt gccgcatag              3399
```

<210> SEQ ID NO 8
<211> LENGTH: 3381
<212> TYPE: DNA
<213> ORGANISM: Brachypodium distachyon

<400> SEQUENCE: 8

```
atgcagcggc ttctggcgag cacgatcgtg gccgccacgc gcgttggct cccctcgcc      60
gactctatcg tccggcgccg ccgccgcgc cgttccccgc tccccgtcct gctattccac    120
agatcattgt acaaaccaag gaaggtttca cgaggcatta caatggtgtc taataaggtg    180
```

```
aacaaacagg gagatctctg caatgaaggc atgctgtcac atattatgtg gtggaaagag    240
aaaatggaga gctgcaggaa accatcatct gtgcagttga ctcagagact tgtgtactct    300
aatatattag ggttggatcc aactttaagg aatggaagct taaaagatgg aaccctgaac    360
atggagatgt tacaatttaa atcaaagttt ccacgtgagg tcctactttg cagagtagga    420
gatttctatg aagccattgg gtttgatgcc tgcattcttg tagagcatgc aggcctaaat    480
cctttggggg gcttgcgttc tgacagtatt ccaaaagctg gatgtccaat catgaatttg    540
cggcaaacat tggatgattt gactcggtct ggttattctg tgtgcatagt tgaggaaatt    600
caaggcccaa ctcaagcccg tgctcggaaa ggtcgattta tctctggcca tgcgcatcct    660
ggcagtcctt atgtatttgg tcttgctgaa gtagatcatg atcttgagtt tcctgaccca    720
atgcctgtag ttgggatttc acgctctgca aaaggctatt gcttgatttc tgtgctagag    780
acgatgaaaa cttattcagc tgaggagggc ctaacagaag aagctgtagt gactaagctg    840
cgcatatgcc gttatcatca tctataccct cacagttctt tgaggaataa ttcttcaggg    900
acatcacgct gggggaatt cggagaggga ggactcttgt ggggagagtg cagtggaaag    960
tgttttgaat ggtttgatgg ttctcctatt gaggaacttt tatgcaaggt aagggagata   1020
tatgggctgg atgagaaaac taatttccgc aatgtcactg tctcattgga agggaggcct   1080
caacctttat atcttggaac tgctactcaa attggagtga tacaaacgga gggaattccc   1140
agtttactaa aaatgctact ccctccaaac tatggcgggc ttccatcaat gtatatcaga   1200
gatcttcttc ttaatcctcc atcttttgat gtcgcgtctg caattcagga ggcttgcagg   1260
cttatgggca gcataacttg ttcgattcct gaatttactt gcataccatc agcgaagctt   1320
gtgaaattac tcgagtcaaa agaggttaat cacattgaat tttgtagaat aaagaatgtc   1380
cttgatgaca ttatattaat gaatggaaac actgagcttt ctgctatcat ggacaaattg   1440
ctcgaacctg cttcggtggt tactggtttg aaagttgatg ctgatatact aattagagaa   1500
tgtagcctta tctcacaacg tataggtgaa gtcatctctt taggtgggga aagcgatcag   1560
gcaataactt catcggaata tattcccaag gagttctta atgatatgga gtcatcttgg   1620 aagggcgtg tgaaagggt tcatgctgaa gaagagttca caaatgtcga tgtagctgct   1680
gaagcattat caaccgcggt aactgaagat tttctgccaa ttattgtaag agttaaatct   1740
gtgatatctt cacatggagg ttctaaaggg gaaatctctt atgcaaaaga acacgaagct   1800
gtttggttta agggaagcg attcacacca aatgtctggg cgaacacacc tggtgaacaa   1860
cagataaaac aactaaagcc tgcgattgat tcaaaaggta gaaaagttgg ggaggaatgg   1920
tttacaacaa tcaaagttga gaatgcttta gccaggtatc atgaagcttg tgatagtgca   1980
aaaggcaaag ttcttgagct gttgagaggt ctttcaagtg aattgcagga caagattaat   2040
atacttgtct tctgctcgac gctgctcatc atagcaaaag cacttttttgg tcatgttagc   2100 gagggtctta aaggggttg ggtgcttcct gccatatctc ccctatctaa ggactatagt   2160
actgaagaag gctcaagtga aatggattta ttgagactct ttccttactg gcttgacagt   2220
aatcaaggga atgcaatact gaatgatgtc aatatgcact cttttgtttat tctgactggc   2280 ccaaatggtg gaggtaaatc cagtatgttg cgatcagtct gtgcagctgc attgcttgga   2340
atatgtggtc tgatggtgcc agctgcttca gctgtcatcc cacactttga ttccatcatg   2400
ctgcatatga aggcctatga tagcccagct gatgggaaaa gttcgtttca gattgaaatg   2460
tcagagatcc gatctttagt cagccgtgct actggtagga gtcttgttct cattgatgaa   2520
```

| | |
|---|---:|
| atatgtaggg gcacagaaac tgcaaaagga acttgtatag ctggtagcat catcgaaagg | 2580 |
| ctcgacgatg ttggctgcct aggcatcata tcaacccatt tgcatggcat ttttgacttg | 2640 |
| cctctgtcac tcggcaatac tgatttcaaa gctatgggaa cagaagttgt caatgggtgc | 2700 |
| attcagccaa catggagatt aatggatggt atctgtagag aaagccttgc ttttcaaaca | 2760 |
| gcaaggaagg aaggtatgcc tgacttgata attaaaagag cagaggagct atacagtact | 2820 |
| atgggcagaa gcaagacgtc atcaacagtc caccatggtc catccgttgc taagtctaaa | 2880 |
| gcaagtggat tggttgatat gcctgatggt ctgggaaatg gattagaact tccatctggt | 2940 |
| gcttttgcac tgctgcgaaa ggatgtcgaa ataattgtga ccgcaatatg caaggataaa | 3000 |
| ttgttggatc tctacaacaa aagaagcatc tcagagctgg ttgaggtggt ttgtgttact | 3060 |
| gtaggtgcta gggagcaacc gccaccttca actgttggca ggtccagcat ctacatagtt | 3120 |
| atcaggcgtg acaacaagct ctatgttgga cagacggatg atcttgttgg ccgtcttgct | 3180 |
| gttcatagat ccaaggaagg tatgcagggt gccacaatat tatatatcgt ggttcctggc | 3240 |
| aagagcgttg cgtgccagct ggagacactt ctcataaacc agcttccctc gaaaggtttt | 3300 |
| aagctcacga acaaggcaga tgcaagcat cggaacttcg gcatgtctgt tatctctgga | 3360 |
| gaagccattg ctgcacactg a | 3381 |

<210> SEQ ID NO 9
<211> LENGTH: 3520
<212> TYPE: DNA
<213> ORGANISM: Vitis vinifera

<400> SEQUENCE: 9

| | |
|---|---:|
| atgtactggc tgtcaaccaa aaacgtcgtc gtttcattcc ctcgattcta ctctctcgct | 60 |
| cttcttctcc gttcccctgc ctgcaaatac acttcatttc gttcttctac acttctactc | 120 |
| caacagtttg agaagagccg atgtctcaac gaaaggaggg ttttgaaagg agctggaaga | 180 |
| atgacaaaaa atgttatagg attgcaaaat gagctagatg aaaaggatct ttctcacata | 240 |
| atgtggtgga aggagaggat gcaaatgtgt aaaaagccgt ccactgtcca ccttgttaaa | 300 |
| aggcttatat attccaattt gctaggagtg datcctaact tgaaaaatgg gaatctaaaa | 360 |
| gaaggaacgc tgaactggga gatgttgcag ttcaagtcaa agtttcctcg tgaagtttta | 420 |
| ctctgcagag tagggatttt ttatgaagcc atcggaattg atgcttgtat tcttgttgaa | 480 |
| tatgctggtt tgaatccttt tggtggtttg cgctcagaca gtataccaag agctggctgc | 540 |
| ccagtcatga atctacgaca aactttggat gacctgacac gtagcgggta ttcagtttgc | 600 |
| atagtggagg aagttcaggg tccaactcaa gctcgttctc gtaaaggtcg ttttatctct | 660 |
| gggcatgcgc atccgggtag tccttatgta tttggacttg ttggggttga tcatgatctt | 720 |
| gattttccag aaccaatgcc tgtagttgga atttctcgtt ctgcgaaggg ttattctata | 780 |
| attttagtcc ttgagactat gaagacgttt tcagtagagg atggtctgac agaagaggct | 840 |
| ttagttacca agcttcgcac ttgtcactac catcatttat tgctgcatac atctctgaga | 900 |
| cgcaactcct caggtacttg tcgttgggga gaatttggtg agggaggact attatgggga | 960 |
| gaatgtagtg ctagacactt tgaatggttt gaagggatc ctgtatctca acttttgttt | 1020 |
| aaggtgaagg agctctatgg ttttgatgat caagttacat ttagaaatgt cactgtgtct | 1080 |
| tcagagaaaa gaccccgttc tttacacctt ggcacagcta cacaaattgg tgccatacca | 1140 |
| acagagggca taccgtgttt gttaaaggtg ttgcttccat caaattgcac tggtctacct | 1200 |
| cttttgtatg ttagagatct tcttctcaac cctcctgctt atgagattgc atccataatt | 1260 |

```
caagcaacat gcagactcat gaacaatgta acgtgctcga ttcctgagtt tacttgtgtt    1320 tccoctgcaa agcttgtgaa gctacttgag cttagggagg ctaatcatat tgagttctgc    1380
agaataaaaa gtgtacttga tgaaatattg cagatgcata gaaactctga tcttaacaaa    1440
atccttaaat tattgatgga tcctacctgg gtggcaactg gattgaagat tgactttgac    1500
acattggtga acgaatgtga atggatttca gctagaattg gtaaaatgat ctttcttgat    1560
ggtgaaaatg atcaaaagat aagttaccat cctatcattc caaatgactt ttttgaggac    1620
atggaatctc cttggaaggg tcgtgtgaag aggatccatg tagaagaagc atttgctgaa    1680
gtggaaagag cagctgaggc attatcttta gctatctccg aagatttttct acctattatt   1740 tcaagaataa aagctaccac agccccactt ggaggtccaa aaggagaagt tgtatatgct    1800
cgagagcatg aagctgtttg gttcaaggga aaacgttttg caccagttgc atgggcaggt    1860
actccagggg aagaacaaat taagcagctt agacctgcta tagattcaaa aggtagaaag    1920
gttggattgg aatggtttac cacagtgaag gtggaggatg cactaacaag gtaccatgag    1980
gctggggaca aggcaaaagc aagggtcttg gaattgttga ggggactttc tgcggagtta    2040
caaactaaaa ttaacatcct tatctttgct tccatgttgc ttgtcattgc aaaggcatta    2100
tttgctcatg tgagtgaagg gagaagaagg aaatggggttt tcccctctct tgtagagttg    2160
cataggtcta aggacatgga acctctggat ggagctaatt ggatgaagat aactggttta    2220
tcaccatatt ggttggacgt ggcacaaggc agtgctgtgc ataatacagt tgatatgaaa    2280
tcattgtttc ttttgacagg acctaatggg ggtggtaaat caagtttgct tcgatcaatt    2340
tgtgcagccg cattacttgg aatatgtgga tttatggtgc ctgcagaatc ggccttgatt    2400
cctcattttg attctattat gcttcacatg aaatcttatg atagcccagc tgatggaaaa    2460
agttcatttc agattgaaat gtcagagatg cgatccataa tcactggagc cacttcaaga    2520
agcctggtgc tgatagatga aatctgccga ggaacagaaa cagcaaaggg gacatgtatt    2580
gctggtagca tagttgaaac tcttgataag attggttgtc tgggtattgt atccactcac    2640
ttgcatggta tatttacctt gggactgaat actaagaatg ctatttgtaa agcaatggga    2700
actgaatatg ttgatggcaa aacaaaaccg acctggaagt tgatagatgg aatctgtaga    2760
gaaagccttg cctttgaaac agctcagaag gagggaattc ctgaaacaat tatccgaaga    2820
gcagaagagc tgtatctttc aatccattca aaagacttaa ttacaggggg aactatttgt    2880
cctaaaattg agtcaacaaa tgaaatggaa gtcttacata agaaagttga gagtgcagtc    2940
accattgttt gccaaaagaa gctgaaggag ctctataagc agaaaacac gtcaaaactt    3000 ccagagataa actgtgtggc cattttgcca ggggaacagc cgccgccatc aacaattggt    3060
gcttcaagtg tgtatgtgtt gtttagcact gataagaaac tttatgttgg agagacagat    3120
gatcttgaag gcagagtccg tgcgcatcga tcaaggaag gaatgcagaa ggcctcattc    3180
ctttattttg tggtcccagg gaagagcttg gcatgccaac tcgaaacgct tctcatcaac    3240
cagctccctg tccaggggtt ccaactggtc aatagagctg atggtaaaca tcgaaatttt    3300
ggcacattgg atcactccgt ggaagttgtg accttgcatc aatgagcctg cgctccttgc    3360
cacccatttt gtagaatggt tccatctttg aaatatgtac ttgaatgaca aaaaccgat    3420 gaaagtggct gcagcaattt tggtttttttg atgtacgttg ctccacttgc attagtatta    3480
tctacctgat gaaatatgca ttgatattgc ttgctctaca                         3520
```

<210> SEQ ID NO 10

<211> LENGTH: 3615
<212> TYPE: DNA
<213> ORGANISM: Cucumis sativus

<400> SEQUENCE: 10

| | | | | | |
|---|---|---|---|---|---|
| atggaaatat | ccatctatgt | cgatgtggca | ttgtggcggg | aagtatcgga | aaccaagggt | 60 |
| tttctgttcc | ggcgacgacg | agttacaaac | accctcctca | tttcaaacca | aaacgcttta | 120 |
| aaacttccaa | tcacaacaag | attgaagctc | acaaaccatc | cattttttatc | caccgccatg | 180 |
| tactgggcgg | caacacgaac | cgttgtttct | gcttcccggt | ggcgttttct | ggctcttttg | 240 |
| attcgcttcc | ctccgcgtaa | cttcacctca | gttactcatt | cgccggcatt | tatagaaagg | 300 |
| caacagcttg | aaaagttgca | ctgttggaaa | agcagaaaag | gttcaagagg | aagcatcaaa | 360 |
| gctgctaaga | agtttaagga | taataatatt | ctccaagaca | ataagttttct | ttctcacatt | 420 |
| ttatggtgga | aagagacggt | ggaatcatgc | aagaagccgt | catctgtcca | gctggttaag | 480 |
| aggcttgact | tttccaactt | gctaggttta | gatacaaacc | tgaaaaatgg | gagtcttaaa | 540 |
| gaaggaactc | ttaactgtga | gattctacag | ttcaaggcaa | agtttcctcg | agaagttttg | 600 |
| ctctgtagag | ttggagattt | ttatgaagca | attggaatag | atgcttgcat | acttgtggaa | 660 |
| tatgctggtt | taaatccttt | tggaggtcag | cgtatggata | gtattccaaa | agctggttgc | 720 |
| cccgttgtga | atcttcgtca | aactttggat | gatctgacac | gcaatgggtt | ctcagtgtgc | 780 |
| atagtggaag | aagttcaggg | cccaattcaa | gctcgttctc | gcaaaggacg | ttttatatct | 840 |
| gggcatgcac | acccaggcag | tccctatgtt | tttgggcttg | tcggggttga | tcacgatctt | 900 |
| gactttccag | aaccgatgcc | tgtgattgga | atatctcgat | ccgcaagggg | ctattgcatg | 960 |
| agccttgtca | tagagaccat | gaagacatat | tcatcagagg | atggtttgac | agaagaggcc | 1020 |
| ttagttacta | aactgcgcac | ttgtcaatac | catcatttat | ttcttcacac | gtcattaagg | 1080 |
| aacaactcct | caggcacttg | ccgctggggt | gaatttggtg | agggtggccg | gctatggggg | 1140 |
| gaatgtaatc | ccagacattt | tgagtggttc | gatggaaagc | ctcttgataa | tcttatttct | 1200 |
| aaggttaaag | agctttatgg | tcttgatgat | gaagttacat | ttagaaatgt | tacaatatcg | 1260 |
| tcagaaaata | ggccacatcc | gttaactcta | ggaactgcaa | cacagattgg | tgccatacca | 1320 |
| acagagggaa | taccttgttt | gctgaaggtt | ttgcttccat | ccaattgtgc | tggccttcct | 1380 |
| gcattgtata | tgagggatct | tcttctcaat | cctcctgctt | atgagactgc | atcgactatt | 1440 |
| caagctatat | gcaggcttat | gagcaatgtc | acatgtgcaa | ttccagactt | cacttgcttt | 1500 |
| cccccagcca | agcttgtgaa | gttattggaa | acgagggagg | cgaatcatat | tgaattctgt | 1560 |
| agaatgaaga | atgtacttga | cgaaatatta | caaatgcaca | aaaattgcaa | gctaaacaat | 1620 |
| atcctgaaat | tgctgatgga | tcctgcatct | gtggcaactg | ggttgaaaat | tgactatgat | 1680 |
| acatttgtca | acgaatgtga | atgggcttcc | agtagagttg | atgaaatgat | ttttcttggt | 1740 |
| agtgaaagtg | aaagtgatca | gaaaatcagt | tcttatccta | ttattcctaa | tggttttttc | 1800 |
| gaggacatgg | aattttcttg | gaaaggtcgt | gtgaagagga | ttcacattga | agaatcttgt | 1860 |
| acagaagttg | aacgggcagc | tgaagcactc | tcccttgcag | ttactgaaga | ttttgtccca | 1920 |
| atcatttcta | gaatcagggc | tactaatgca | ccactaggag | gtccaaaggg | agaaatatta | 1980 |
| tatgctcggg | accatcaatc | tgtctggttc | aaaggaaaac | ggtttgcacc | atctgtatgg | 2040 |
| gctggaagcc | ctggagaagc | agaaattaaa | caactgaaac | ctgctcttga | ttcaaaggga | 2100 |
| aaaaagttg | gggaggagtg | gtttaccacg | aagaaggtgg | aggattcttt | aacaaggtac | 2160 |
| caagaggcca | ataccaaagc | aaaagcaaaa | gtagtagatc | tgctgaggga | actttcttct | 2220 |

```
gaattgttag ctaaaattaa cgtcctaata tttgcttcca tgctactcat aattgccaag    2280
gcgttatttg ctcatgtgag tgaagggagg aggaggaaat gggttttttcc cacccttgct   2340 gcacccagtg ataggtccaa ggggaaagtt gcgatgaagc tggttggtct atctccctat   2400
tggtttgatg ttgtcgaagg caatgctgtg cagaatacta ttgagatgga atcattattt   2460
cttttgactg gtccaaatgg gggtggaaaa tctagtttgc ttcgatcgat ttgtgctgct   2520
actttgcttg ggatatgtgg atttatggta ccggcagagt ccgccctgat tccccacttc   2580
gactcaatta tgcttcatat gaaatctttt gatagtcctg ctgatggaaa aagttctttt   2640
caggtggaaa tgtcagagat gagatccatt gtcaatagag taacggagag aagtcttgta   2700
cttatcgatg aaatctgtcg tggaacagaa acagcaaaag gaacttgtat tgccgggagc   2760
attattgaag ctcttgataa agcaggttgt cttggcattg tctccactca cttgcatgga   2820
atatttgatt tgcctttaga tacccaaaac attgtgtaca aagcaatggg aactgtttct   2880
gcggaaggac gcacggttcc cacttggaag ttgattagtg aatatgtcg agagagcctt   2940 gcctttgaaa cagcaaagaa tgaaggaatc tctgaagcta taattcaaag ggctgaagat   3000
ttgtatctct caaattatgc taagaagggg atttcaggaa aagagacgac agatctgaac   3060
ttttttgttt cttctcatcc aagccttaat ggtaatggca ctggaaaatc caatctcaag   3120
tcaaacggtg tgattgtaaa ggctgatcag ccaaaaacag agacaactag caaaacaggt   3180
gtcttgtgga agaaacttga gagggctatc acaaagatat gccaaaagaa gttgatagag   3240
tttcatagag ataaaaacac attgacacct gctgaaattc aatgtgttct aattgatgca   3300
agagagaagc cacctccatc aacaataggt gcttcgagcg tatatgtgat tcttagaccg   3360
gatggcaaat tctatgttgg acagactgat gatctggatg gtagggtcca atcacatcgt   3420
ttaaaggaag gaatgcggga tgctgcattc cttttatctta tggtgcctgg gaagagctta   3480
gcttgccaac ttgaaactct tctcatcaat cgacttcctg atcacgggtt ccagctaact   3540
aacgttgctg atgaaaagca tcggaatttt ggcacagcca atctcttatc cgacaatgtg   3600
actgtttgct catga                                                    3615
```

<210> SEQ ID NO 11
<211> LENGTH: 660
<212> TYPE: DNA
<213> ORGANISM: Gossypium hirsutum

<400> SEQUENCE: 11

```
ggcacgaggt tgctattgct gcaagggaac agccacctcc atcaactatc ggtgcttctt     60
gcgtatatgt catgttcaga cctgataaga aactatacat tggagagacg gatgatcttg    120
atggtcgaat tcgttcgcat cgttcaaagg acgggatgga aaatgcttct ttcctatatt    180
tcacagttcc agggaagagt attgctcgcc aactcgaaac tcttctaatc aaccaactct    240
taagtcaagg cttcccgatc gccaacttgg ctgacggtaa gcatcagaat tttggcacat    300
ccagtctctc atttgacggc ataaccgtag cctaacgagt taaaatgtat atcaatacgt    360
aatttatatc gaaattgaca tagaagtggc ggcagcaatt ttgcctttga tctcggttgc    420
tccacttgct ttgtacatgc atcacccttt taaccaaggg taaagttttc tagtcataat    480
ttaatagcat gtatctatta agtccatttt gaggtttata tgaatcaggt tttcatcatt    540
aattggttaa attctgttat tagctcctct actttactaa agttgtagat ttagttctta    600
tactttaatt agattatttt tactctatac ttttcgaatg ataaaatttt agtcttcatt    660
```

<210> SEQ ID NO 12
<211> LENGTH: 2225
<212> TYPE: DNA
<213> ORGANISM: Oryza sativa

<400> SEQUENCE: 12

```
agaaaagcta aaatggatga aaaaaacaga gaaaagaaa tcctaccctc catagcgagc      60
agtggtggtc tgcactctgc aggcaggcag gcacccaggc ctgcagctcg atggcgccgc    120
cgccgccgtc gccgccgcga tctctcacct ccgtctccct ccggactcct ctgagccctc    180
tcctcttcct acggccagct tcttgcaatc catcggcggt ctccggctcc tgcagcagcg    240
gagcatgccg cggcgtgcgc tgctcggcgg cgaacaagcc ttctccttcc accgctccgg    300
gcaccgaggt aaggtagccg gctagccgcc ccccatattc ttgtttctgt gttgatcgga    360
gctcgatggc tggggtgctc tgggctcgtc gtcgtcggtc gatcgtcatg gcttgcttcg    420
tttcttgcag ctcgacctcc atggcaaaga taaggagtga ggtgctgtcc ccgttccgct    480
ccgtgcggat gttcttctac ctcgcgttca tggccagcgc cgggctcggg gccctcatcg    540
cgctcacgca gctcatcccg gcgctgtcca gcccggcgag ggcggccgcc gcggggggaga   600
cgctcaaggg cctgggcatc gacgtcgcgg cggtctccgt cttcgcgttc ctctactggc    660
gcgagagcaa ggccaaggac gcgcaggtgg cgaagctcac gcgggaggag aacctgtcca    720
ggctcaggat ccgcgccggc gagggccgcc cgcccgtccc gctcggcgag ctgaggggca    780
ccgcgcggct cgtcatcgtc gccggccccg ggcgttcgt caccgagtcg ttccgccgga     840
gcaagccgtt cttgaaggac ctcatggagc gcggcgtgct tgtcgtgccc ttctcgacgg    900
acggcaacgc gccggacctg cagttcgacg aggccgacga ggaggaggag gaggcggcgg    960
cggcggctgg gaagatgaag cggaggctct ggcagctcac tccggtttac acttctgaat   1020
gggccaagta cgcgcaaagc cgggatccca tgaatttagc tgcttaaatt tcttcttcat   1080
gtcaatcgaa attcaaatgc aaattagtat ctcattttca aatcgattgc tgcttcttgc   1140
agatggctag atgagcagaa gaagctagcc aacgtgtcac ctgattcccc cgtgtgagta   1200
tcaaaaacta ctctgaattt gtctgaaaat ataactgaag tttctgcagc tgctgaactg   1260
aaaccgcatc actcttgcag gtatctctcg ctccggctgg acggccgcgt ccgtggcagc   1320
ggcgtcgggt acccgccgtg gcaagcgttc gtggcgcagc tgccgccggt gaaggggatg   1380
tggtccggcc tccttgatgg gatggacggg agggtgcttt gaatatttga ctgatacaga   1440
ccgtgaaaac attagttgat tggagaaaaa aaaggacggc cgggttcgat ctatagctta   1500
tactagaaca agaacaggaa gagtttgatg attgctttaa cttctgtggg gttgattttg   1560
cttcctgcat cccagcgaca tcgcccaagt gaatgtgata tgccatgtgc ccatgtacat   1620
gttgttttgc agcctacgtg acttgattat taacgagaat cctgtgtcaa agatcgcttt   1680
ttccgtggta ggcttctcca ttttatttta tttttgaata tatatacgaa ccgtgacaaa   1740
tctgatggaa cactggacca tgggggtaat gatactgtag tcgcctggtc ttttatcag    1800
gcgctaaatg caaacaatca gacagcttaa acaacctgag gttgttcagc cagcccagaa   1860
tacaaaaagc ccatgaccg tgagcccgtg aaaccatggc ccacccatca gtcacgtcac    1920
gtcgggacgt gtgcgcacta ccccgagaag cgcgcggccg taagccacaa ccacaacccc   1980
acaccgcctc ttggctgctc gcgccctgac acttcccaaa accccaaacc gcccatatct   2040
ctctcctctt ctccgctcct cgcttccccc aaaaccctcg cggtggcggt gggccgccgg   2100
tctcattccg ccggcgtcca cggaggcggc cggagccagg cgctccgcgg gccggggagc   2160
```

```
caccggaagg ctggaaccct agcggcggcg ggtctcctcc ccctccccgc gcgccgggcg    2220
gcgcc                                                                2225

<210> SEQ ID NO 13
<211> LENGTH: 2000
<212> TYPE: DNA
<213> ORGANISM: Solanum lycopersicum

<400> SEQUENCE: 13
cacgcatcaa catgtactag ctaactttgt ccaccaagga atatctatta ccttcaacca      60
gcaacaagta tcagctaact ttgtccattt aggttaaaac cttgactaaa tccattgaaa     120
acctattacc tcccaccagc aacttatgcc aactaacatt gtctaccaag ggatatccgt     180
tgcctcaaca ttgtccatcg agggatatcc attgcctccc agcagcaaca agtaccagct     240
aacattgtcc aatcgaggga catccatacc aaataatttt tgagaaagta attatttagg     300
gtgatgttta tttgtgcttg gaaacaaat agccattgaa ttagtaaaat ttgcaattaa      360
atcacattac aaaaatgtct aaggtaattt atcctaaata caatagtgat atcaataata     420
atatatttga gtgtaatgtc ataatcaaga atttataaaa ataatatgtc agtaggttta     480
attactgata tattaaaatt gtttcgataa attcttgatt taaagagtac aatcaacaaa     540
taaaagaaca aatagtaaaa tataagatac gtatattttt aaatagtagt gtacagtagg     600
actagatgac aaaataaaat tgtaagaaga agaggatagt ctttaccatt ctcacacaaa     660
atcatatctc gtcacaaatg aatttacagt tactcataaa tatatttaat aaaatgatag     720
tattagcaaa acataattga tgtgttagtt catcagttat tatgcactta agttatttta     780
taaaaaaaaa aggtcaaatg ccccccctaa tctgttgtcc gatttctaag tacgtacgta     840
aactttagag gggtcatatc accctgaac tgtttaaaat tgaattttt gtactcctaa       900 aaagccataa ccatatttat gttgatgagt gaaactcacg cgttttgaca catgaaaaat     960
ccattagaaa aagtttttct tcaattttt cattattctt tattcttttc ttctatttt      1020 tcaccatctc tccaacacaa aaatattttc actattttct ccattatcat aaacaccaaa   1080
ggttcactaa tcactacaat cttcaaaacg aaaaggtcgg cagtgatttt gattcttatt   1140
tgtcatttcg cccactactt agttggtgct aagatcattt tcatgaatac atgtgtcaaa   1200
tttctcaaat tagagtaaat gaataacaat ggaggaaagt cgaatgtggg tttattaaa    1260 aatttaaaat tcttcgtttg tttgaattaa aattacaaat ttggagcttt gaagaaccaa   1320
aaaaagaatt tgccgaccta attgaccta atttgtcgtt tgaccatgta caaggatgat    1380
taacaactcc aataatatcg ataaagagtt gattttcaaa aactcttaat tccatacaca   1440
aattaaaatc aagaaaaatg cgaaaatttt atgaacaaat ctaataacaa agaacgaaaa   1500
aatttctacg aagaacaaag aaaagaataa ggaagaagat aaaatatttg ttttggtgct   1560
cactctatca gggagtgaaa tacattcact atggagatga taattttcaat tttaaacagt   1620 tcaggaaggt gatatgcgta aagtttaagt taatagataa tcaaagatat ctgttgacgt   1680
attgattcaa tgttaaatat acagttgagt tacttataac ttataaatac aataagtaat   1740
ttttttcctt ctaccatttg aaaaaaaata acgcgtacgt cattgtcttc aatcatcaac   1800 gattattat tttcaatgtg attatattat taagtaatta attcgtccca aataccaata    1860
tctactaaca ttctttgcct aatgtttaat tgtaattcct acagatttta tttttttgaa   1920
aataatataa agtacaccat ttctctgccg ggaagaacaa atacacagag agagagtgta   1980
```

```
ttgtgcactg atatcgagca                                               2000

<210> SEQ ID NO 14
<211> LENGTH: 2000
<212> TYPE: DNA
<213> ORGANISM: Sorghum bicolor

<400> SEQUENCE: 14
tggcacataa gtaaaattgc tgacttggta gggtcatttta atgaaggaat ttcatgagat     60
gagagagaag tttcatcccc atgaaactca tatggctcgg ttacttggta actgtgtcat    120
caaactatgc attgagactg gcctgcatgt tcatgagag tgtcatgcac attaaataag     180
atatcacata agcaaaattg ctgacttagc tgggtcatta aatgaaggag tttcatcaga    240
tgagagagga gtttcatctt cataaaactc ttgtggctcg gttacctagt ttttagtctc    300
ggtaactgtg tcatgaaact ataatacatg ttttatggaa gtgtcacgca tattataggg    360
tgccacataa gtaaaattgt taacttgaca gagtcattaa atgaagaagt ttcatcagat    420
gagagaggag tttcatcccc ataaaattca tgtggctcag ttacctagtt tatagtcttg    480
gtaactgtgc catgaaacta tgcattgaga ctagcctaac aaggtgataa ggccagtctc    540
aatgcatgtt tcataagagt gtcatgcaca ttaaataaga tgccacataa gcaaaattgc    600
tgacttgaca gggtcattaa atgaaggagt tcgttagat gagagaggag tttcatcccc    660
atgaaactct tatggctcga ttacctagtt tatagtcttg ataactgtgt catgaaacta    720
tgtattaaga ctggagactc aaatacaaat tgtatatagc ctatggctct atttgtttcc    780
gcgaccggcc aaccgtgac cacgattaag caaacacgac tcgagatcgt gtatgtataa    840
atttggatct tcggtggttt aattttagtt tttttagcta agagaattta tatacatttt    900
ccattattaa accatgtttc aaggtttcta attccatgct ctaaataat atattatttt     960
atggaaaata gatatttttg aaattaaatg tatgtataaa ttttcaagac tatataaaat   1020
aataaaagct ctaatctatt gatgtagttc aattttatc tccctagagc tgatgtggca    1080
ccacatacgg tgccacctag gttaaaacta acctcaaaac ccggctaggt ttgtgatttg   1140
cctcgtattt gatagtttag ggtgtactcc gtataagatt atctgtatat tcagagatta   1200
gaaaatcaaa cacatctact aaattttaga acaagcatca ccctgtttgg cggctagtcg   1260
taaaagtaac tgatgttaat ttattgtgag agtaaaatac tgttgtttga taataaaact   1320
tttacttata atttcaagct aatagagccc ataaagacaa acctgtctca caagttagaa   1380
ttcttacaac ttttcgtcta atcacatcga atatttgaac acatgtatat agtattaaat   1440
ataataaaaa tatttaattg tacagtttac ctatatttac aagacgaata ttttaaatat   1500
aattagttta ttattaaaca ctaattacta taattataaa tatactacaa tataaaaaaa   1560
aaactttcgt ttttgcgagc taaacaccgg acacaaaac gctcctgtct cctgggcggc    1620
ttgggcctgc cagagcccgg gaaccgtgag cccgtgaccc cagcgggccc aaccagtcag   1680
acgagagtcg aaaggcgtgc gcactacccc gagaaacgtg cgacaggaac ctccccttc    1740
ccggcctggg agcggcctgg cgagtggcga ctggcgtctt ccgcggttcc cccagttcg    1800
cctccttcac tgccgcccgc gcgccccgac acgcctgaaa acccaccct ctcccctccg    1860
ctccgcctct ctcgccctcc acttcccacg ccccacgccg cctgccattc cagttccagc   1920
gtggactcga cgccagcgcg gagacgcgcg tctcgaagca ctagcccccc gttgttctgc   1980
cgcgccggcg cgccggcgcc                                              2000
```

<210> SEQ ID NO 15
<211> LENGTH: 2049
<212> TYPE: DNA
<213> ORGANISM: Arabidopsis thaliana

<400> SEQUENCE: 15

| | | | | | |
|---|---|---|---|---|---|
| catatgaaac | atttcctgta | gcagtgagat | ggttacaaga | ggatccatac | ccgagtgctg | 60 |
| tgcaatcaga | caaactacaa | gcatagtcga | tattatcagg | caagtcatcg | aggttatatg | 120 |
| cattagggtc | aagaatacac | caagttttgg | gcagatactt | cacatcttcc | acaggaacca | 180 |
| aaggcttgtc | atttccttta | cctgacaagt | caagctcata | tttcggtctc | ccatcaaact | 240 |
| caaagatccc | ccagtgcctc | tcaaaagtcc | ccggtgctat | actcttggcg | tcctcatcaa | 300 |
| caaggctgaa | aaggtaaaca | tccataatca | ctcctttcct | cgcaggcgtt | ccatttccag | 360 |
| acatagcatg | ctttaccatt | ccctgattga | atctctttgc | actctttaca | ttagcgttct | 420 |
| tgtctccatc | cgtaggccac | ccgacctctc | ctacaatgat | cttcatcccc | aagaagctat | 480 |
| atctctccat | agcacaaatc | aaagtgtcga | gattcgcatc | aaacacattg | gtgtagacca | 540 |
| aatttccatc | tctcaaagac | ttgttagtcc | catcaaagaa | ggcaaaatcc | aaggaaagt | 600 |
| aagcatttcc | atagagacta | agaaaagggt | atatgttaac | cgtgaaaggc | gaatcatgtg | 660 |
| aatacaagaa | attgattatc | tcaatcgttg | catcccttag | ctcaggtcta | aagtctccag | 720 |
| ctgatggaac | agggttcgct | tcaggggaaa | aatagatgtc | tgcgttgaaa | ggaacagtga | 780 |
| cttttcacatt | tttcagatca | gcttcctcta | gtgctcgttg | gatgttgata | agagctggta | 840 |
| atgtgaactc | aacgtaagtt | ccattatatg | tctgaaggaa | aggctcgttt | ccaacagcta | 900 |
| tgtacttgat | gttgactcca | ccgttgtaag | aataagcagt | aacgttttct | tcaacccatg | 960 |
| aagctgctac | agatgtatct | tgagccattt | ctttaagaaa | ccggtttggt | attcctatca | 1020 |
| tgacttcaat | gtctgagcca | attagagcgt | ctaagatgtt | ttggtcggct | tcaaatagtt | 1080 |
| tcagcttagt | gaaactattg | tccattagca | tcttcacaac | cttttctggt | ggaagctggt | 1140 |
| gactcgccat | tattccccag | ttaactccta | cattactcgt | gttgcttgag | gcaatggaaa | 1200 |
| cttgtgagat | gataagaaag | taacaagaa | taatctgatg | attataaaag | tggtttgttg | 1260 |
| ttaactttga | tctctctcct | gccatttttt | tctctgttta | tgagtctttt | cttctcttt | 1320 |
| ctttatggag | tctttgttaa | gggagaagat | gaaatgtgat | tggatatttg | tgatttgtac | 1380 |
| ttagttcagt | taaagaagca | gacacaacat | gcaaaatagc | cattggtgaa | acactttgtg | 1440 |
| catgcctatc | tgataaatcc | attgactcac | cacaaattct | tatgtaattc | tagatgtttc | 1500 |
| gtatttgttg | tgccaaacaa | acacacacac | tcacacactg | cactgagtct | agacatttag | 1560 |
| tggttttgtt | ttcttattat | taatactcat | tagagtatta | agtttgtata | gaattcagaa | 1620 |
| acaactgata | gtcattttaa | gatttctaat | tacaaaactt | tgatcctct | ttgaaaagca | 1680 |
| gagaaattac | aatctttaca | aacaaaactg | agagattaga | gatgtgttca | tagagatggg | 1740 |
| ttctttgtta | gacattccaa | aaagatacaa | aactagccga | tgattaattt | tggtaaatta | 1800 |
| atgaacaaga | atgtaatttg | aaacattata | gggagcaaat | gagaaattac | tcttttttaaa | 1860 |
| aggctaaaat | cctaattacc | tttaaactaa | gaagacaaga | agagaagaga | aaacatgttt | 1920 |
| tccattagag | gactgtgaga | ttgtgaattg | catagtcgtc | gtcttctggc | gggaaaagaa | 1980 |
| gccctagaaa | aagggtgaaa | ggtgaaaact | ctacttcttc | ttcttcttct | tcttcagagt | 2040 |
| gtgagagag | | | | | 2049 |

<210> SEQ ID NO 16

<211> LENGTH: 946
<212> TYPE: DNA
<213> ORGANISM: Arabidopsis thaliana

<400> SEQUENCE: 16

```
aaaagttgaa acagcaaagt agcgatagat ttcgtgaaaa cagagaagcg gacatatctt    60
gaaacacatg gcagcgattt ctccatggtt atcttctcct cagagctttt cgaatccccg   120
cgttaccatt acagattcca gaagatgttc atcaatttct gcggcaatct ctgttcttga   180
cagctccaac gaggaacaac atcgaatttc gtctagagat catgttggga tgaagagaag   240
agacgtcatg ttacagatag cttcctctgt tttcttcctt ccattggcca tttcacctgc   300
atttgcagag acaaatgcat cagaagcttt ccgtgtgtac acagatgaaa cgaacaaatt   360
cgagatatca atcccacaag attggcaagt cgggcaagca gaacctaatg gattcaagtc   420
aatcacagct ttttacccac aagaaacttc aacttccaat gtgagtatag cgatcactgg   480
actaggtcca gacttcacca ggatggaatc attcggaaag gtcgaagctt cgccgaaac    540
attggtcagt ggattggata aagctggca aaaaccagta ggagtgactg caaagctaat   600
cgatagcaga gcttctaagg gattctatta catcgagtac accttacaaa accctggaga   660
agctcgcaag catttgtact ctgcaattgg aatggcaaca aacggatggt acaaccgttt   720
atacactgtc acaggacagt ttacagatga agaatctgct gaacaaagct ctaagatcca   780
gaagacagtc aagtctttca gattcatctg agaatgtcat tcatatctat cagcggaact   840
aaattataga attgatcaaa caatttgttt actgaacaat tacttttttg caatgaaatt   900
ctgagaaaag agcctactcc atactttgaa gtaagcttca gtaaac                  946
```

<210> SEQ ID NO 17
<211> LENGTH: 807
<212> TYPE: DNA
<213> ORGANISM: Arabidopsis lyrata

<400> SEQUENCE: 17

```
tccagaagat gttcatcaat tcctgtagca atctcagctc tagacagctc caacgaggaa    60
caacatcgaa tttcgtctag agatcatgtg gggattaaaa gaagagaagc catgttacag   120
atagcttcct ctgttttctt ccttccattg gccgtttcac ctgcatttgc agagacaaat   180
gcatcagaag ctttccgtgt gtacacagat gaagcgaaca aattcgagat atcaatccca   240
caagaagatt ggcaagtcgg gcaagcagaa cctaatggat tcaagtcaat cacagccttt   300
taccctcagg aaacttcaac ttccaacgtg agcatagcga tcactggact aggtccggac   360
ttcaccagga tggaatcttt tggaaaggtc gaagctttcg ctgaaacact ggtcagtgga   420
ttggatagaa gttggcaaaa accagcagga gtgactgcaa agctaatcga tagcagatct   480
tccaagggat tctattacat cgagtacacc ttacaaaacc ctggagaagc tcgcaagcat   540
ctgtactctg caattggaat ggcaacaaac ggttggtaca accgcttata cactgtcaca   600
ggacagttta cagatgaaga atctgctgaa caaagctcca gatccaaaa gacagtcaag   660
tctttcagat tcatctgaga atgttattca tatctatcag cggaactata ttattgaatt   720
gatcaagcaa tttgtttact gaacaatcac ttttttcaat gaaattctga gaaaagagcc   780
aactccatac tttgaagtaa gcttcag                                       807
```

<210> SEQ ID NO 18
<211> LENGTH: 1054
<212> TYPE: DNA
<213> ORGANISM: Cucumis sativus

<400> SEQUENCE: 18

```
ggagcgcatt gtacaaagaa aatccatctc taatctttga gtggactaca agcatggcga      60
tggcgtccct tctttcaccc agcgctgtaa tcctacgccc tcactcattc cgcttctcac     120
aatcatcact ctccaatgga ttctccatta ttcctatccg ctcaacactt cgtgttttct     180
gctctgccaa tggcaacagc atccacactt ctaacaaaaa cccagttatt ggcgagcgg      240
ggtcaacaga cgagaaatta tgctagggat tggattcact gcattttcat ttcaagaagt     300
tgtttctaat gccctagctg agagtgttgt ggttgctgaa gattatcgga cgtatacaga     360
cgaagcgaat aagttcagct tggtgattcc tcaagattgg caagtgggta atggtgaacc     420
gaatggattc aagtcggtta cggcatttt tcctcaagaa acttcaactt ccaatgtcag     480
tgttgtaatc tcggggcttg gtcctgatta acgaggatg gaatcctttg caaggttga      540
ggaatttgct gatacattgg tgagtggact ggacagaagc tggaaaaggc accaggtgt     600
ggcggcgaaa cttatcgact gtagatcatc taaagggata tattacatag agtcacact     660
gcagaatcca ggtgaaagcc gcaaacattt atactcagca attgggatgt catccaatgg     720
ctggtacaat agactttaca ccataacagg acagtatgca gatgaagaat cggagagcta     780
tagctccaaa atcgagaagg ttgtcaattc cttcgctttc atttgatgat gccacagaa     840
ttggcctcca ccacactatc ataatggtta aatgttttcc acatctctct ctaattatag     900
ttctcttttg ttattattat tattattatt ttttgtaatg agttctaaac ataatattga     960
attgtctttg atgcatctat attttacat tttcacgagg aatgaattca catttctatt    1020
aattcataaa agaatccaca aaacagaaaa aaaa                                1054
```

<210> SEQ ID NO 19
<211> LENGTH: 795
<212> TYPE: DNA
<213> ORGANISM: Ricinus communis

<400> SEQUENCE: 19

```
atggcttcaa tttctttact ctgttgcaat tgctacttca catctttctc caacaagaca      60
cctctccatc ttttgaaacc taacttaaac ttcctctctg cttcaccttc ttttcgattt     120
aacagttgca gaaagcaaca tcttccatgt tgcaccaact ctttcccaga cgaagaccaa     180
caccaaccat tattctgtcg ttttaggctt caagaaccat atggaagaag agaagctttg     240
ttcagcgtgg catttaccac tgggtttact tttccagggc ttatttctaa tgcatttgca     300
gagattgatg acttccgcct ttatactgat gatgccaaca agttccaaat atcgattccc     360
caagactgga gagtaggtgc tggagaacct aatgggttca aatcagtgac cgctttctac     420
ccagaagaag cttcaggctc tagtgtcagt gtagtgatca caggactcgg tccggatttt     480
actagaatgg agtcttttgg caaagtggaa gccttcgccg aaactctggt tagtggattg     540
gacagaagct ggcaaaggcc cccaggcgtt gcagcaaaac ttatcgactg taaagcgact     600
aaagggattt actacattga gtacacatta caaaacccag gcgaaggtcg caaacatctg     660
ttttctgctc ttgggatggc tttcaatggt tggtataaca gactgtatac agtgacaggg     720
cagtttgtgg aagaggagtc agagaattat ggatcaaagg ttcagaaggt tgtttcatca     780
ttcaagttca tctga                                                      795
```

<210> SEQ ID NO 20
<211> LENGTH: 1028
<212> TYPE: DNA

<213> ORGANISM: Vitis vinifera

<400> SEQUENCE: 20

```
caatcaaaaa aagcatggct ctgtattttc acttcctct ccgttctggg tcctgcgact      60
tctcagctta ttcgagtaaa aaaggttatg ggtcaagaac cgggaaatgt ggaaaaaagc    120
aacgtgttgt cttctgcaag aatgagaaca aggaagaaga aaaacaagt tttgggatta    180
aagaacaaca tggaggtgga agaagggagg ttgtgctaca gatggtgttc agtacaattt    240
cccttcaggc aattgttcct aacgcactgg ccgatactga ggtgccagag gatttcaagg    300
tttactcaga tgaggtcaac aagttcaaaa tacagattcc caagattgg caggtgggtt    360
caggagaacc aagtggattt aaatcagtga cagcattcta cccagaagaa gcttctggtt    420
caaatgtcag cgtagttatc actgggcttg gcgcggattt taccagactc gagtcttttg    480
gcaaagttga tgcttttgca gagaatctgg taaatggatt ggatagaagc tggcaaaggc    540
cccctggtat tgctgcaaaa ctcattgact gcagagctgc taatgggttt tattacattg    600
agtattggct tcagaatcct ggggaaagtc gtagacattt attttcagct gttgggatgg    660
caaacaacgg ttggtacaac aggctttata ctgtgaccgg acagtatttg gaagaagaat    720
cagaaaaatt cagttctaaa attgagaagg ttgttgcatc cttcaggttt atttgaagaa    780
aaatttgcat gttcaggata taaactgagg ctgaagatta ctggttcagc aactctgtgg    840
atttcacaat gcacacgaat tggcattgtg caaaaagatg agatgattta tatactcaga    900
ttgcatcagg tgtcttttgt tgtaaaattg taaggaaggg gaagggaaat tatctctatg    960
ctaccattga aaattttttc cacaccttttg cagttgcttc acattcattt gcagaattga  1020
tggatgag                                                             1028
```

<210> SEQ ID NO 21
<211> LENGTH: 726
<212> TYPE: DNA
<213> ORGANISM: Medicago truncatula

<400> SEQUENCE: 21

```
atggcatcca tttcatggtt cagctgtcta cacatccgac caacagccac tgccggcgac     60
aaaggtttat catctcccat aaccgtggaa catcataaaa caagaccaca aaatttactc    120
tcatcctcgg aagaaggact tgcgattaat agaagacaac taattctta cacatccact    180
gcagcaattg cagcttcatc tactgactca aatgcattgg cactcaatga tgtatctgag    240
gattttagta tctacactga tgatgagaac aagttcaaga tagatattcc acaagagtgg    300
caaattggaa caggagagtc tgcagggttc aaatcattaa ctgctttcta cccaaaagag    360
caatctaatt ccaatgtgag cgttgtgatc acaggagtgg gtccagattt cactaagatg    420
gaatcattcg gcaaagttga agaatttgct gacactctgg ttagtgggtt ggatagaagc    480
tggaaaaaac cacctggtgt ggctgctaaa ctcatagatt gtaaatcatc taaggatttt    540
tatttcattg agtatacgct gcaaagtcct ggtgagggtc gcaaacatct atattcagct    600
attgggatgt taacaaatgg ctggtataac agactgtata cagtgacagg acagtatggg    660
gaagaggaaa cagacaagta tgcttccaaa attcagaagg cagttcgatc gtttaagttc    720
atataa                                                                726
```

<210> SEQ ID NO 22
<211> LENGTH: 579
<212> TYPE: DNA
<213> ORGANISM: Populus trichocarpa

<400> SEQUENCE: 22

```
ggaactaaaa gaagagaagc tttattcaat atggtattta ctgcttttac tttccctgca    60
attgcctcta ctgcattggc agccacaggc gtggcagagg attcacgtgt ttataccgat   120
gatgcgaaca agtttaagat atctattccc caaggctggc aagtaggtgc aggagaacca   180
agtggataca aatccgtcac tgctttctat ccagaagaag cttctaattc aagtgtcagc   240
gttgtgatca ccgggcttgg tccagatttt actagattgg aatcatttgg caaagttgat   300
gcctttgctg agactctggt gggtggattg acaggagct ggcagaggcc cccgggcgtg   360
gcagcaaaac ttatagactc taaagctgct aatgggcttt actacatcga gtatacgctg   420
caaaatccag gcgaaagtcg cagacatttg ctttcagcac ttggagttac attcaatggt   480
tggtacaaca gactatatac ggtgacaggg cagtttgtcg atgaagaatc agagaaattc   540
ggcaccgaga tcaggaaggt atatcagaac tcttcattt               579
```

<210> SEQ ID NO 23
<211> LENGTH: 951
<212> TYPE: DNA
<213> ORGANISM: Lotus japonicus

<400> SEQUENCE: 23

```
ggaatggcgt ccatttcctg gtcttgttgt ctgcgttggc gaccaacaat atccgaccgc    60
acagcctctg cggccgacaa aggtttctca cctcccataa cattggagca tcataaaaaa   120
acaccatgtt tactatcagc acgcaattcc tccattgaag aaggacatgc ggttaacaga   180
agacaacttg ttttctacac gtcactagct gcatttgcag ctgccccatc tactgtcctg   240
aaggcattgg cactcaatga tgtggttgag gatgttcgta tctacattga tgatgagaac   300
aagttcaaga tagagattcc ccaagattgg gaagtaggaa caggagactc tagtgggttc   360
aaatcattaa ctgcattcta ccccaaagag gcatctagtt ccaatgtgag tgttgctatc   420
acagggttgg ggccggattt cactaagatg gagtcgtttg gcaaggttga tgagtttgct   480
gagactctgg ttagtgggct ggacagaagc tggagaaaac cgcctggtgt agctgctaaa   540
ctcataaata gtaaaccatc taaaggaatt tattatatcg agtactcgtt gcaaaatcct   600
ggtgagagtc gcagacatct atattcagct atagggatgg caacaaatgg ttggtataac   660
agactgtata ctgtgacagg acagtatgtg aagaggaaa cagacaagta tgcttccgaa   720
attcagaagg cggtcacatc atttaagttc atataaagaa atgctcatga tgaaggagaa   780
atttccccac agccatcttt cctatataaa tacagatttg tgccttccta cagtgtagga   840
ttcttatgag caagagagga ttcttatatt tgtctttatg agcaaaatgg aatacttcat   900
tatttcattc ctctcttatg tctcttgctc ctcagattat gtatattgta t            951
```

<210> SEQ ID NO 24
<211> LENGTH: 866
<212> TYPE: DNA
<213> ORGANISM: Fragaria vesca

<400> SEQUENCE: 24

```
atggcttctg ttgcgtcttg gcatcctctg ttccttcgac ctcgcacatc ccatttcacc    60
acgacctcct acaacacagg caccgccata tgtagaaaga gctatctgca atgttgcaac   120
aacaaagaac aagaaccaca accagaacaa gaagaaaaat cggttttgg gatgcaatgc   180
caagccaaga gaagacaagt tttgcttggg actactttg ctgcattttc ttttccggaa   240
```

| | |
|---|---|
| atttattcca acattgcatt ggccgagaat gacgattttc gtgttttcac cgatgatgtc | 300 |
| aacaagttcc agatatcaat tcccctagac tggcaagtag gcgcagggga accaagtggg | 360 |
| ttcaagtcag ttactgcttt ttacccggaa gagggatcta gctcaattag tgtcgtaatc | 420 |
| acggggcttg gtccggattt tacgaagatg gaatcctttg gcaaagttga cgaattcgct | 480 |
| gagactctgg tcagtggact agataggagc tggcaaagga cagcaggagt tgcagcaaaa | 540 |
| ctcatagatt gcaaatcatc taagggatt tactacattg agtattcgct acagaaacct | 600 |
| ggtgaaagta tcaagcacct ctattcagct cttgggatgg caaacaacgg ctggtacaac | 660 |
| agactatata ccgtcactgg ccagtttgga gaggaggaag cggataaata cagatccaaa | 720 |
| attgagaagg ctgtaaaatc cttcaagttc atatgataaa caacctccag aggggcagag | 780 |
| tttgaattgt gaactacggt ttaccaattt tgattgggtc agttgtacac aaatttttca | 840 |
| tcgtaatcta atgtaataca tttgaa | 866 |

<210> SEQ ID NO 25
<211> LENGTH: 1015
<212> TYPE: DNA
<213> ORGANISM: Glycine max

<400> SEQUENCE: 25

| | |
|---|---|
| gtgaataata atcagaacaa aaccaaccat ttaaaaaaaa aaaaaaaaga aatggtggca | 60 |
| gagaagctga tctgaaagga atggcgttca tttggcggtt ctgtggtgtg tctctatgca | 120 |
| acttcacagc ctctaatgcc cagaaaggtc cttctccttc tctgcccata accttggact | 180 |
| tggagcatca tataacaacc ccatctttac tttcttccat cgaagaagaa gaaggacgcg | 240 |
| cggttaatag gagacaactt attcttcaca cgccagtagc tgcagcagct gcatttgcag | 300 |
| tcccaaatgc attggcactc aatgatgtgt ctgaggatgt tcgtgtctac actgacgatg | 360 |
| agaacaagtt caagattgag attcccgaag agtggcaagt gggaacagga gacggagaat | 420 |
| ctagtggggtt taaatccata actgcttct acccaacaca ggcatccaat tccaatgtga | 480 |
| gcgttgtgat cacagggctg gaccggatt tcaccaggat ggaatccttt ggcaaagttg | 540 |
| acgagtttgc tcagactcta gttagtgggc ttgacagaag ctggcgaaaa ccccgggtg | 600 |
| tggctgctaa actcatagat tgtaaatcat ctaatgggat ttattacatc gagtatttgc | 660 |
| tgcaaaatcc tggtgagagt cgcaggtatt tgtattcagc tattgggatg gcatcaaatg | 720 |
| gttggtataa cagactgtat accgtgacag gacagtatgt ggaagaggac acagacaagt | 780 |
| atgcttcaaa agttcagaag gtagttgcat catttaggtt catatgaaga aaatggtcat | 840 |
| gacgaggaag aattttttatc acagcacttc atctattcta tttcattatg gattttcctg | 900 |
| gcattgttct ttaagctaga tatggcattc tagatcggac tggtatgata aaaccatga | 960 |
| catttccttc gagattgttg aatgaaagta atatacttag tggccataat tgaca | 1015 |

<210> SEQ ID NO 26
<211> LENGTH: 1159
<212> TYPE: DNA
<213> ORGANISM: Solanum lycopersicum

<400> SEQUENCE: 26

| | |
|---|---|
| ggctgtgaat tggatacacc aatatctctg cttcttcaaa gaaaacaaaa aaaataaaaa | 60 |
| cagaaatggc gactctttca tcttcatctt catcttcatc ttcatcttca tctccatgtt | 120 |
| tgaaccagta ccagtatcaa gctattcttc gcttgccacg tgtcccttta atttcctctc | 180 |
| atcttcttaa agttcccaag aaaaatcgaa actcacttat tttctgctgc aacaacactg | 240 |

| | |
|---|---|
| tgcctgattc aagaacaggt gagcaagtta aaggagaatg cttaaccaag agaagagagc | 300 |
| tcctgctaca ggcaggctct gttgcatttt ctctgtccgc ctttacatcg attgcattgg | 360 |
| cagagaagga tgtcccggag gagtttcgtg tttattcaga tgatgtcaac aagtttaaga | 420 |
| tcatgatacc tagtgattgg caaataggcg cgggagaagg tgatggagta aggtcactct | 480 |
| tagctttcta tcctccagaa gcttctaact caaatgtcag catagtaatc acaagccttg | 540 |
| gtgctgattt caccaagttg gaatctttcg ggaaagttga tgcttttgct gagaatctgg | 600 |
| tcagcggatt tgatagaagc tggcaaaggc ctccgggagt gaaagcaaaa ctcatagata | 660 |
| gcaaagcttc taaagggttg tattacatcg agtacactct ccaaaatccc ggtgaaagtc | 720 |
| tcagacatct attttcagtg cttgggatag caaacaatgg gatttacaac agactgtata | 780 |
| ctctcactgg acagtttgta gacgaggagg cagagaaata tggtgccaaa atacagaagg | 840 |
| ctgtttcttc tttcagatta atatgatgac atgaacagag agcgcgatat cgcaaatttt | 900 |
| ggcttgagct tctggttttt ctcgtttggt gaatggtaaa cataattgag agcgcgatat | 960 |
| cacagattca agttctggtt aaggtatatt atgacgactc gagaaaaaac tggagttgta | 1020 |
| agtatgaact agcaacttga tcaatgttag agttagtatt tgcatatatc gttatatacc | 1080 |
| aaaactgtat cgattttttg ataaaaatat gaccttagtg caaataattt gatgctcaag | 1140 |
| ttttgattat atatttgta | 1159 |

<210> SEQ ID NO 27
<211> LENGTH: 1680
<212> TYPE: DNA
<213> ORGANISM: Cicer arietinum

<400> SEQUENCE: 27

| | |
|---|---|
| tctcgtaaaa gaatgagatt cagttgaagt tatcgaagaa gaagaatgca gcagaggaaa | 60 |
| aggcaaagta tggatgggcc tagcatctat gcgtggttgt tttgtgtcat tggaatgaca | 120 |
| tcacttttcg gtgctgcttt cctaccacca gatataggga ttgtgttttt tctcagacaa | 180 |
| atatgtctgt ttgtgtttcg atctatgtgg atgacaaggt tggtgttttt tctagctgca | 240 |
| gctgcacatg tcattgaggc tatctatgct tggtgcttgg ctagaagact ggatccttcc | 300 |
| aattcaaggg cttggttttg gcaaacattg gctctaggct tttttcatt gcgttttcta | 360 |
| ttgaaattga aaagatcaaa ggaataactt tgaaataatc acttcttgta ccattgttat | 420 |
| tttcagaaat caattatctt tcccatcaat tgtatgcctt tttttatgt aaaattaata | 480 |
| tttttacaag ttgttattag ttatcactgt cgaataaatt taccatgaca gtacatatct | 540 |
| tttaattttg aaaattgtcc attttgttt cttatctata atggttttct tctctattta | 600 |
| attttggatt taattaaatt agaaatagtg tcttctctgt ggaggataaa agtgtaatta | 660 |
| aatagataat aataataaag gaaatgaagg gtgagaaaga gaagctgatc taaaaaggaa | 720 |
| tggcatcaat tcatggttc agctgtttac acattccacc aacatcctct gctgccgata | 780 |
| aaggtttatc atcatctccc ataaccgtgg aacatcataa acaacaaca cgtttaatct | 840 |
| cttcctttga aggacaacaa catgttgtta atagaagaca actgattctt tatacatcca | 900 |
| cagcagcaat tgcagcacta tctactgtcc caaatgcatt ggcactaaat gatgtgtctg | 960 |
| aggatgttag tatctacact gatgatgaga acaagttcaa gatagaaatt cctcaagagt | 1020 |
| ggcagatagg aacaggagag tctgcagggt ttaaatcctt aactgctttc tacccaaaag | 1080 |
| atgaatctaa ttccaacgtg agcgttgtga tcacaggggt cggaccggat ttcactaaga | 1140 |

| | |
|---|---:|
| tggaatcatt cggcaaagtt gaagaatttg ctgacactct ggtaagtggg cttgacagaa | 1200 |
| gctggaaaag accccctggt gtggctgcta aactcataaa ttgtaaatca tctaaaggat | 1260 |
| tttattacat tgagtatacg ctgcaaaatc ccggcgagag tcgcaagcat ctatattcag | 1320 |
| ttattgggat gtcaacagtt ggctggtata acagactgta tactgtgaca ggacagtttg | 1380 |
| tggaagagga acagaaaag tatgcttcca aaattttgaa ggcggttgca tcgtttaagt | 1440 |
| tcatataaag aaatgcttgt gacgggagag aaatgttctc attggttttct ttcatgggct | 1500 |
| gccgtttaat gttttcatga cattttttgt aagctagaaa tggcgtctaa atgttataaa | 1560 |
| tatgatattt gctatggtac ttccttcaaa aactgataaa ccagagtagg ctaaatgaat | 1620 |
| ggcacaaatt gatgtaatgg ataagatatt ttgcagtgaa tatcagcacc ttcagttaaa | 1680 |

<210> SEQ ID NO 28
<211> LENGTH: 1068
<212> TYPE: DNA
<213> ORGANISM: Triticum aestivum

<400> SEQUENCE: 28

| | |
|---|---:|
| gaagcacagc agcgtcgtcg accaccatcg agccgtactc catggctgcc gtgaccaccg | 60 |
| cctctctctg tcccggcctc ggcaagcccc gccgagacca cgcgaagcca ccgagaacca | 120 |
| cggtctgcca ttgcctccct gctcggagga cggaggaggg ggtgaagcgg cgggacgccc | 180 |
| tgctcggcgt cctcctctcc gctaccgccg cgtcgtcggc gccgctgctc gtccccgccg | 240 |
| aggctttcgc cgaggtcgcc gatgcgcagg aggggttcac cgcgtacgag gacgaggcca | 300 |
| acaagttcac cctcgtgatt ccacaaggct ggcaggtcgg cgcaggtgaa cgcagcggct | 360 |
| tcaagaacgt gacagcgttc ttccccgagc aaaaccccaa ctccagcgtc agcgtcgtga | 420 |
| tcaccgggat cgggccggac ttcaccagcc tcaagtcctt cggtaacgtc gacgagttcg | 480 |
| ccgaaaacct ggtgaccggc ctggacagga gctggcagag gccggcgggg ctcgcagcga | 540 |
| agctcatcga ctccaaggca tcaaacggct tgtactacat cgagtacacg ctgcagaacc | 600 |
| ccggcgagaa gcgccgccac atcgtctccg ccatcgggat ggcattcaac ggctggtaca | 660 |
| atcggctgta cacggtgaca gggcagtaca tcgacgacga cgaggagtca gccatataca | 720 |
| aacctgagat agagaagtct gtcaagtcgt tcaagttcac atgaaatgcc cccaaaaagg | 780 |
| aagttcaggt gagaacaagt atagagtgac agagaagaga gagtatacaa agctagtagc | 840 |
| tcctgatgtc aagttcaatt agtgagtatg catatgtttg tcgaatttac cggaaagaaa | 900 |
| agatgaacac cagatgttcg aagacttcga tggcgtagct tggctgagaa cagcattggc | 960 |
| agcatgagtg tgagatagag catgagtgtc gttggttcta agaaaattgc tagaactctg | 1020 |
| ttacaaggaa actaaaattg ctctgatgta aaaaaaaaa aaaaacga | 1068 |

<210> SEQ ID NO 29
<211> LENGTH: 1037
<212> TYPE: DNA
<213> ORGANISM: Oryza sativa

<400> SEQUENCE: 29

| | |
|---|---:|
| gcaaggcagg cagcagcgac cagacgaagc agagagagcg cccgcgccgc gccggccatg | 60 |
| gctgccgccg tgaccaccac caccaccgcc acaaccaccc atctctgccg tggcctctcc | 120 |
| tcctcctccg ccgccgccgc caagccgcgc cgagcgacga cgctcagatg cggcgccgct | 180 |
| gctcgggtgg aagggctggg gcggagggag gcgttgctcg gcgtgctcct ctccacggcg | 240 |
| acggcggcgt ccgcgcccgt cgccgccgtg gccgcgaccg ccgagttgca ggaggggttc | 300 |

```
cgcacgtacg aggatgaggc caacaagttc agcatcgcca ttccacaaga ctggctgatc    360
ggcgccggcg aggtcagcgg cttcaagtcc gtcacggcgt tctaccctga ccaagtcgcc    420
gactccaatg tcagcgtagc catcaccgga atcgccccg atttcaccag cctcaagtcg     480
ttcggcgacg tcgacgcctt cgcagagacc ctggtgaacg gcctggacag gagctggaaa    540
cggccgccgg ggtcgccgc gaagctcatc aactccaggg cagccaacgg gttttactac     600
atcgagtaca cgctgcagaa ccccggcgag cagcgccggc acattgtctc ggccatcggg    660
atggcgttca acggctggta caaccggctc tacacggtga caggccagta catcgatgag    720
gacggggatg tagacaagta cagggctcag atagagaagt gtgttcagtc attcaggttc    780
acatgaaaga ggagcatcct acacaacatc aacaaggcg aggacgaaaa acattttgta     840
aaccaacgta tttcgttata attgtaaatc aatcagtata ttcatgtcat cagttcaacc    900
aactaaatgt acaccaattg ttccgagatt ttgacgatgc ggccttgccg aggccaacat    960
gagctaatta tgttgtggca agtcataagc attgttttct atgcattttt aagggagaaa   1020
aaacaggtgt atttgtt                                                  1037

<210> SEQ ID NO 30
<211> LENGTH: 1269
<212> TYPE: DNA
<213> ORGANISM: Brachypodium distachyon

<400> SEQUENCE: 30
atggcccggc tcggcccggc ccacgtgttt tacagccgtt gggctgggcc gtactgccaa     60
aacgtgtcca atggcccac gtcgaagacg aactctcacg ggccgacgtc cttggcgcgc    120
ggccatggcc catgggtaag taagatacga ggggccgaa gcaatgtgcg gcggaagttc     180
ccggacgacg acacgacggc cggccaccgt acaaagcttc tcagcaaaat atcctccccc    240
tcgaaagcca ccagcgcagc agcagcgcag agccattcgc tcgccatggc tgccgtgacc    300
accgcctcct ccgccatctg ccccggcttc agcagcaacc cccgccgagg ccacgcgaag    360
ccgcggagat ccacggcctg gcctgccat tgccgccgct cccctgccct gcgcgagcaa     420
caacctacgg cggccgttgc cgggacggcg gaggagggggc tcaggcggag ggatgccctg    480
ctcggcgtcg tcttctcggc cggcacggcg acgctgctcg ctagtcccgc cggtgctctc    540
gccgaggccg ctgccgaggt gcaggagggg ttcagcgagt accaggacga ggccaacaag    600
ttcagcatcg tggttccgca aggatggcag atgggcgctg gtgagggcag cggcttcaag    660
aacgtcacgg cgttcttccc ggacaaggcc gccgactcga gcgttagcgt ggtcatcacc    720
gggatcgggc cggacttcac cagcctcaag tccttcggcg acgtcgacgc cttcgccgag    780
aacctggtga ccgggctgga caggagctgg cagcggcctg cggggtcac cgcgaagctc    840 atcgactcca gggcgtccaa cggcatgtac tacatcgagt acacactgca gaaccccggc    900
gataagcgcc ggcacatcgt ctccgccatc ggcatggcgt tcaacggctg gtacaaccgg    960
ctctacacgg tgacagggca gtacatcgaa gatgacgagg agtccgtcaa gttcaagcct   1020
cagattgaga agtctgtcaa atcattcaag ttcacatgaa atgccttcaa acaaaggtc    1080 acatgaaaat aagtactgct actactttg aatgaagtac tatatctaag cagagaagag   1140
aaggtatata aaggcagctt ccggtaatgt gtgcagaacg aaatgaacta aaccctttgtg  1200 aatgtaaggg ttgtgagctt tgagaatata tatgtttgtc aattttactg aatacatagc   1260
tctagactt                                                           1269
```

<210> SEQ ID NO 31
<211> LENGTH: 1024
<212> TYPE: DNA
<213> ORGANISM: Phyllostachys edulis

<400> SEQUENCE: 31

```
atagtgccat acgccatggc cgccgtaact accgcctccc tctttcctgg cctctcctcc      60
tgcagcccca agcccagaag ccacaggaag ctgcagagaa cgacggtctg ccaatgccgc     120
cctgctcgga tggaggggat gaaacggagg gaggccttgc ttagcatcct cctctccact     180
gccgcttcgg cgccgccgct tgctcctgcc gaagctttgg ccgagaccac cgagttgcag     240
gagggcttcc gtacgtacga ggacgaggct aacaagttta gcattgcggt tccacaagac     300
tggatggtcg gcgcaggcga gggcagcggc ttcaagtccg tcacggcgtt ctaccctgaa     360
ggcgccgact cgagcgtcag cgtcgtgatc accggaatcg gaccggattt caccagcctc     420
aagtccttcg gcgacgtcga cgccttcgcc gagagcctgg tgaacggcct ggacaggagc     480
tggcagaggc cgccggggct cgccgcgaag ctcatcgact ccagggcagc gaacggtctg     540
tactacgtcg agtacacgct gcagaacccc ggcgaaaagc ggcggcatat cgtctcggcc     600
gtcgggatgg cgttcaacgg ctggtacaac aggctctaca cggtgacagg cagtacatc     660
gatgacgacg acgagccagg caagtacaag cctcagatag agaagtctgt cctatcgttc     720
aggttcacat gaaagaacta aactacagtc tacccagagt gcaacaatat gcagagaaga     780
taaagtagat aaaagcccct ccgcagataa gttcagaacg aagatacgt tgtgattttt      840
gtcaatcagt gagcatatgt ttgtcgattt gaccaaataa aatatgtact ccacatgttc     900
gacgacttgc tgtgcccagc atgagttaat tgtaagagaa gttaccatgc gccggacctg     960
tcattctgaa actgtgatga gtgacattct gaaactgtaa catagtaaac gtatgttcag    1020
tttt                                                                  1024
```

<210> SEQ ID NO 32
<211> LENGTH: 1053
<212> TYPE: DNA
<213> ORGANISM: Hordeum vulgare

<400> SEQUENCE: 32

```
agagccgtac tccatggccg ccgtgaccac cgcctccctc tgcccgggcc tcggcaagac      60
ccaacgaggc cacgcgaagc cgccgagaac aacggtctgc cattgcctcc ctgctcggag     120
gacggaggag ggggtgaagc ggcgggacgc cctgctcggc gtcctcctct ccgctaccgc     180
cgcgtcgtcg gcgccactgc tcgtccccgc cgaggctttc gccgaggccg ccgaggcgca     240
ggagggggttc accgcgtacg aggatgaggc caacaagttc accctcgcga ttccacaagg     300
ctggcaggtc ggcgcaggtg aacgcagcgg cttcaagaac gtgacggcgt tcttccccga     360
gcaaaacccc aactcgagtg tcagcgtcgt gatcaccgga atcgggccag acttcaccag     420
cctcaagtcc ttcggtaatg tcgacgagtt cgccgagaac ctggtgacag gcctggacag     480
gagctggcag cggccggcgg ggctcaccgc gaagctcatc gactccaagg cagcaaacgg     540
tctctactac atcgagtaca cgctgcagaa ccccggcgag aagcgccgcc acatcgtgtc     600
cgccatcggg atggcgttca acggctggta caaccggctc tacacggtga caggacagta     660
catcgatgac gacgaggatt cagccatata caagcctgag atagagaagt ctgtcaagtc     720
tttcaagttc acatgaaatg cctccaaaaa ggaagttcag gtgagaacaa gtatagagga     780
acagagaaga gaaagtatac aaaaactggta gctcttcatg ttaagttcaa ttagtgagtg     840
```

```
tgtatatgtt tgtcgaattt accggaagaa aatatgaaca ccaaatgttc aaagacttcg    900
atggcgttgc ttggctgagg acagcaatgg cagcatgagg gtatgagata gagcatgaga    960
atgtcgtttg ttctgagaac attgctagaa ctccttataa gaaactaaaa ttgctccgat   1020
gtaaacttct tcctagcatc tattttttggg ctc                               1053
```

<210> SEQ ID NO 33  
<211> LENGTH: 1138  
<212> TYPE: DNA  
<213> ORGANISM: Zea mays

<400> SEQUENCE: 33

```
cccgttgcca cacatacgga tccaacaaaa tctcccgcaa agacaacggc gagccaacca     60
ccaccagcgt cccgcgctag ctgcggcacc gcatggctgc cgtgaccagc accgcctcca    120
tctgcccggc cgcagccggc gccctctctt cgctgccgtc cttcatcacg cgcaagccca    180
ccagcggcag caggaggttg cagcaggcag cagcgacgac agtctgccac tgccgctctg    240
ctcgggtaga ggaggggctg ctgggccgga gggacgcctt attgctcggc atcgtcttct    300
ccgccgcgac gccgccgctg ctcgcccctg ccggcgctct ggcggacgag gccaccgccg    360
agtcgcagga gggcttcact acgtacgagg atgaggccaa caagttcagc attcaagttc    420
cgcaaggctg gctggtcggc gccggcgagg ccagcggcat caagtctgtc acggcgttct    480
accccgagca ggccgccacc gactccaatg tcagcgtcgc catcaccggg atcgggccgg    540
acttcaccag cctcaagtcc ttcggcgacg tcgatgcctt cgccgagggt ctggtgaacg    600
gcctggacag gagctggcag aggccgccgg ggctcgccgc caagctcatc gactccaggg    660
cggcaaacgg cctgtactac ctggagtaca cgctgcagaa ccccggcgag cgacggcgcc    720
acatcgtctc ggccatcggg atggccttca acggctggta caaccgcctc tacactgtga    780
cgggccagta catcgacgac gatgactcgg agaagtacag gcctcagata gagaaggctg    840
ttggatcgtt caggctgaca tgaaagatgc gatgtcatcc agcaccagca gcagcagccg    900
cccacggtac ataaaccctaa aatatgtatg cggagaggtc cagcaacatg ttgtgcccga    960
aaattgacac cttgccattt cgatgagaca agacaaggca tgtgcctatt gcccctatcc   1020
aattcttgag cactgtaaca ctgccaatat gcagagtata tgttttctgc ctgttgaggt   1080
ggatacaaat gcatgctttt tttttttatta ataactcatg tgtaacactg ctgcctttt    1138
```

<210> SEQ ID NO 34  
<211> LENGTH: 1162  
<212> TYPE: DNA  
<213> ORGANISM: Sorghum bicolor

<400> SEQUENCE: 34

```
agcgcgagcc tgccagccaa ccaccgccac cggctttcat cccgcgcgtg cgtcctgcgc     60
tagctgcgcc catggctgcc gtgaccagca ccgcctccct ctgccgcc gcagccggcg     120 gcctctctgc ctcgtcgtcg tcgccgttca cgcgcaagcc cagcagcagc aggaggctgc    180
aggcagcgtc cacggcctgc cactgccgcc ctgctcgggt agtagagggg ctggaccgga    240
gggacgcctt gctcggcatc gtcctctccg ccgcggtggc ccgctgctc gccctgccg     300 gtgctctagc ggacgagccc accaccgagt cgcaggaggg cttcactacg tacgaagatg    360
aggccaacaa gttcagcatt caagttccac agggctggct ggtcggcgcc ggcgaggcca    420
gcggcatcaa gtcggtcacg gcgttctacc cggagcaggc agccgccgat tccaacgtca    480
```

| | |
|---|---|
| gcgtcgccat caccgggatc gggccggact tcaccagcct caagtccttc ggcgacgtcg | 540 |
| actccttcgc cgagggcctt gtgaacggcc tggacaggag ctggcagagg ccgccggggc | 600 |
| tcgccgccaa gctcatcgac tccagggcgg caaacggttt gtactacctg gagtacacgc | 660 |
| tgcagaaccc cggcgagcgg cggcggcaca tcgtctcggc catcgggatg gcgttcaacg | 720 |
| gctggtacaa ccgcctctac acggtgacag gccagtacat cgacgacgat gacgattccg | 780 |
| aaaagtacag gcctcagata gagaaggctg ttcgatcgtt caggctgaca tgaaagatgc | 840 |
| catgtcattc agcagaggtc ttgtgcctga aaattgacac cttgccattt ccatgagatg | 900 |
| agacaagaca agacatgtat gccaattctt gagcactgta acactgcaag tatgcgaata | 960 |
| tattttctcc tttttgaggt ggatataaat atgttttttg taactcttgt gtaacgttgc | 1020 |
| tgcggtgttt tttgttgt gtatatgtaa tgtttagagg gtcgggctga aggagcaact | 1080 |
| atgtgacctt tattctcttt ttaaggcaaa gttcgtgtca cttcttttca aaacaagcaa | 1140 |
| atggttttgt ttcttgagct gg | 1162 |

<210> SEQ ID NO 35
<211> LENGTH: 1062
<212> TYPE: DNA
<213> ORGANISM: Setaria italica

<400> SEQUENCE: 35

| | |
|---|---|
| cggtgcctac caaaacacac ggctggaaca aaatatcccc cacgaaaaca aacggcgagc | 60 |
| caaccgcaac caccactcgg caccggctgg cctgcggcgc gcgccatggc tgccgtgacc | 120 |
| agcaccgcct tcctctgccc ggccgccggc ggcctctccc cctcgccgcc cttcaggcgc | 180 |
| aatcccggca gcagcagcag ccgcaggagg ctgcagctgc aggtctgcca ctgccgccct | 240 |
| gctcgggtag aggggctgga ccggagggag gccttgctcg gcgtcgccct ctccgccgcc | 300 |
| gcgccggcgc tcttcgcccc cgcggctgct ctggcggccg aggccaccgg tactttgcag | 360 |
| gagggcttca ccacgtacga ggatgaggcc aacaagttca gcattgtggt tccacaaggc | 420 |
| tggctgatcg gcgccggcga gtccagcggc atcaagtccg tcacggcgtt ctaccccgag | 480 |
| caggccgccg actccaacgt cagcgtcgcg atcaccggca tcgggccgga cttcaccagc | 540 |
| ctcaagtcct tcggcgatgt cgacgccttc gccgagggcc tggtgaacgg cctggacagg | 600 |
| agctggcaga ggccgccggg gctcgccgcg aagctcatcg attccaaggc ggcaaacggt | 660 |
| ctgtactacg tggagtacac gctgcagaac cccggcgagc ggcggcggca catcctctct | 720 |
| gcaatcggga tggcgttcaa cggctggtac aaccgcctct acacggtgac aggccagtac | 780 |
| atcgacgacg aggagtcgga aagttcagg cctcagattg agaaggcggt tcgatcgttc | 840 |
| aggctgacat gagagtgctt cgcactgtgt agcattcaga gatgcacggt atgcaggtgg | 900 |
| acgcctgtaa attgaccaac tcgtcttcca cattattaag tttttttta agcaagtctc | 960 |
| acggtatgtt ggaaagtaca ttgctacacc tcaacaatcc catagatcgt ctcatgtaat | 1020 |
| gccacatata atttttgctg gtgtggagga aggagggtga tg | 1062 |

<210> SEQ ID NO 36
<211> LENGTH: 1091
<212> TYPE: DNA
<213> ORGANISM: Picea glauca

<400> SEQUENCE: 36

| | |
|---|---|
| acttcaaaat cccaaaccca tcagaggagg gagttccaac agatgactat cgtggtgaag | 60 |
| atgggcatgc ttggcctggt gtcatcacca tcaattccca ctactcacaa tctatgctct | 120 |

```
ccagtccaac cattcagaag gaatttcaag aatttcaagc aggggaaaaa gcaagtcaca      180
ggctgtttcg aaatccagaa caatctgtcc tcccatgaat tgtcaagaaa tggaagaagg      240
caggccatat gtcagattgc tgctttgttc tcagcgattc cttgtactgt ttcagcggca      300
agggcagcag aaactgagct tcaagaagat tacgagttgt ataaggacga gacagacaaa      360 tttttcactac tagttcctcg agactggata aagggtgaag gaaaacaga tggacagaga       420 gcagtgactg ccttctaccc tgaaagcggc atagtttcta atgtgaatgt aataataaca      480
ggactttctg ctgactatac aaaaatggaa tcatttggca ctgttgatgc atttgctgag      540
accctggtta attctctaga tagaagctgg aaaagaccgc agggcaagc agcaaagctg       600 cttaatgcaa atccaaaaa cggcttgtat tatatagagt attcattgca aaagcctggg      660
gagagtaaga tccatcttct ctctgcgatc ggaatggcaa tgaatggttg gtacaacagg      720
ctttacactg taacggggca gtatctagaa gacgatgctg gcaaatatgg ctcaaagatt      780
gaaaagtcca tttcatcttt cagattagtt tgaaagatta attaccttcc atgtgaggca      840
tcaagtatgt tgggaaaaga cttataatat acaagagcat aaaggtgata aatattaaat      900
aattaaaaat ccccccatttt attcatcttc aattatgtct ggaataaact tgatttacct      960
tgtaatatat aatgtatgac ctaatatctt atttggaact aagtgtgaaa ccactcatag     1020
ttattccaac taaatttttag tttagacaag ggaataaaat acattcaatg tccttattgt     1080
ttactaaaaa a                                                          1091

<210> SEQ ID NO 37
<211> LENGTH: 355
<212> TYPE: DNA
<213> ORGANISM: Arachis diogoi

<400> SEQUENCE: 37
ggggtgggtc cggattttac taagatggaa tcgtttggta aagtggaaga atttgccgag       60
actctgattg gtggattgga cagaagctgg caaagaccac cgggtgtggc tgccaaactc      120
atagattgta aatcatccaa gggggtttat tacatagagt attcactgca aaatccgggt      180
gagagtcgca gaaccttata ttctgctatt ggaatggcat caaatggttg gtataacaga      240
ctctacacgg tgacaggaca gtttgtagaa gaggaaactg acaagtatgc ttccaaagtg      300
aaaaaggctg ttgcatcatt taggttcata tgaacaaaga gttcatgagg gagat          355

<210> SEQ ID NO 38
<211> LENGTH: 1089
<212> TYPE: DNA
<213> ORGANISM: Physcomitrella patens

<400> SEQUENCE: 38
gcaggagcaa tggacgctgt cgttggtcgc acctcatgcc ccttgtctct gtcttcctcg       60
tatcaatgga ttgctgggtc gccatctgct tctcgtgcta cagtcgttgt tagaggtaca      120
agccggcgtg acggtaaaca caaagcagtg cgttgcgagc aggttccaga atgcagcacc      180
agcaattgtc aaacaatgca gagacgagag gttatcggtc aagctctatt agccatgtcc      240
atgagctttg ctcctccagc tcgttcggcc acagacacag atgctgctac tgaatttacg      300
acttacgagg atgcagccga taaattcaca ttgctcgtgc cacaagcctg aacagaggc       360 gaagggaaaa cgtccgggca aggaaagtc acggctttct atcctgcgga tggcggtctt      420
accaatgtaa atatagtcat aacaggactc ggagcagatt tcacgagttt aggatccttt      480
```

| | |
|---|---|
| ggcacggccg acaatttcgc ggagaatttg gtgaacagtt tggacaggag ttggcagaaa | 540 |
| cccccgggcc agaaagcaag gcttgtggat tgtaaatcaa gagcagataa atactatgta | 600 |
| gaatacacta tacagagact cggagagcag cagcggcact tagtctcagt tgttgggatt | 660 |
| ggaaacaatg gatgggtcaa cagattatac accgtcacgg ccagtacttt tgaggaagac | 720 |
| tcagccaaat ataaacaaga cattaacaag atcatctcct ctttcaaaat actgtagttc | 780 |
| atagatcgaa gactcggggc acagactgca gaccatggag tttatgactg accagcattg | 840 |
| tggtaaaacc tgggattttc gttcctcatg cttcgtgtca cagagaagct cattgagttg | 900 |
| ggagaactga gtggttgtg taaacacgct ggggttgttt tgcatgtggt gagagcagat | 960 |
| gtccttcgag cagccattca taaatctcaa gatgagttta ttctgttctg cagaaactgc | 1020 |
| cgaacctgga ttcttgtaat agaaccattc ataatttcc aaggtcacca ttgggcctga | 1080 |
| gatatcatc | 1089 |

<210> SEQ ID NO 39
<211> LENGTH: 2425
<212> TYPE: DNA
<213> ORGANISM: Selaginella moellendorffii

<400> SEQUENCE: 39

| | |
|---|---|
| atgggggagg agaagcgcga gaatctcatg gagtcgctct tcggggagga gtcggatgac | 60 |
| gacgccgatg ccgctgcctc ctactctgag gaggagggcg aaggcgaagg cgaggcagag | 120 |
| ggcggtggtg ccgagagcgg tggcgacagg gaagagagcg agggcgagcg ggaagccagt | 180 |
| gagggcgaca ggaggagag cgagcatgag agagtgtcca ggaggagcag tgatgacgga | 240 |
| ggtggtgaag aagggagcgc cgccagcggc tctgagaacg atggacaagt ccaggaaagg | 300 |
| gaagcaactc gcagcgagga ggtggaggag cagcgtggtg ctagaattcg tgcagcattg | 360 |
| ggtgattctg atgacgacga tcaggaggaa ggaggagttg acggccctcg caagccatcg | 420 |
| agtccagagg gggagggctc ggacttggag ggaagctacc acaaagatag taagcggggt | 480 |
| gcagaggatg acgaggagca gtattactct gatgaagagc gcgcagaaat caagaaaccc | 540 |
| aagggtgaac tcttacagt agaagttcca ctcaggcaac ctccaactca ggctcacaac | 600 |
| gcaagtagtt tggcacttgt ttctttttca ttatctcgtg agcttacggg cctttgctt | 660 |
| cagatgaatc tcgtcaggat ctccaacatt atggatatag agcaaaggcc ttttgatcca | 720 |
| aagacatacg tcgaagagga tggatttgtt gatgaaactg gccgacgccg tatacgtata | 780 |
| gaggagaacg tggtgcgctg gagatacgtc aggaatcggg atggctcgcg ctcggccgag | 840 |
| agcaacgccc ggtttgtgaa gtggtccgat ggtagcatgc aacttcttct cggcaatgaa | 900 |
| gttctggatc ttgctgttca agatgggcaa caagacgaat cacacttgtt tatccgtcag | 960 |
| cccaagggat tattacaagc ccaagggagg ctggcacgta gatgagatt catgccttcg | 1020 |
| tcgttgagat cgaagtcgca ccgtctctta actgctctcg tggattctac gcacaagaag | 1080 |
| gtgttcaaag tgaagaatgt gatcacggac ttcgatcccg agaaggacaa gaacaaaaa | 1140 |
| gagaaggcag cagaacagag gattaaaagc aaagaagatc tccaaaaaaa gcaggagaag | 1200 |
| acgatgcgta ataccccccc tacacggag agagaacctc agctttctcc tggataccttt | 1260 |
| gaaggggcgc ttgaagagga ggatgaagat tatgacgacg aggggcgtag caaccgacgg | 1320 |
| taccaagacc agcttgatgc cgaaagcagg gcggagagac gaatcaacca ggttaagcgg | 1380 |
| caaccaccaa aggcaatgga gcgacgccct tcttcgcgga gcaggaggga tattttggaa | 1440 |
| gacgaggatt cagacgagag cgaccgcaat agaggtgcgc gaggtgatga aggtgaggaa | 1500 |

```
gagcaggaag atgacgaggg ggaggaagaa gaggaggaag tggaggcaag ggatagccgc    1560
cgcaagagga aagacaggga cagggaacag ctgcagcagc agcaaaattc gcctcccaga    1620
aagcagcaaa cgcacaggcg gagagcagta gtttggtttc tcgccacagg ttgcaagagt    1680
agaatagata ggggcagcca gggaagtgtg gcgtcatggc aagtgtgcat acaaactgct    1740
atgttcgtcc agcagttcca gccagttcaa gtcgaccgcc attcaatgct cctgctactg    1800
ctgcctgtcc accgctgagc aagagaaatc tcttattgct ggtgcctctg ttggcgatgc    1860
cggcgacgcc tgtgtttgct gctggtattg tacttgtcaa tcgttcgtta aactttgatg    1920
caagacagga gcctcagatg aatatcaagt atacgaggaa caagacaagt tctccctcac    1980
tgtacccaaa gactggataa aaggcgaggg gaaagtcgga tccagaagag tggtggcatt    2040
ccatccatcc aaggctactt tcccaaacgt gaacgtgatc atcacgaacc tgggtgccga    2100
tttcaccggg atcggctcac tgggatccgt ggactcgttc gccgcgagcg tggttggcag    2160
catggataga agctacaagc ggccgcctgg aacagcggct cggctggtga atgctgtgtc    2220
gagaaacggc atgtattatc tcgactacac cgtccagacg cccggggaag cccagcgcca    2280
tttcttctcg gtggccggtg ttggcgagac acagttttac aagcagctct acacggcaac    2340
cggccagtac tgggaggctg atggagacag ggacaggaaa gcattgcaag aggcgataga    2400
gtcattccgg attgttcaca agtga                                         2425

<210> SEQ ID NO 40
<211> LENGTH: 832
<212> TYPE: DNA
<213> ORGANISM: Camellia sinensis
<220> FEATURE:
<221> NAME/KEY: misc_feature
<222> LOCATION: (90)..(90)
<223> OTHER INFORMATION: n is a, c, g, or t

<400> SEQUENCE: 40
atacccaaag ttgccaagtg gggccggggg aaataaagga gatcaagtca gtaacggagt      60
tgtacccgat gggacctctg atgaaagtcn cgtggtaatc gcggcctggt gcgggtttta     120
ccagaataga aatcttttgg taaagatgat gcttttgcag agaatctgct acgggctggg     180
acaagaagct ggcaaaggcc accgggggt aagagcaaaa ctcatagact ctaaaactgc     240
taatggtttg tattacattg aatatacact gcaaaatcct ggccaaagtt gcagacattt     300
atttcagtgc ttgggatccg aacaatggtt ggtatccaga ctatataccg tcactggaca     360
gtttgttgat gaggattcag aaaaatatgg ctccaaaatt gagaaggctg tttcatcgtt     420
cagattaaac tgagattttg aggatccttt ccatttttgc tttcaacatc ggctctcatc     480
gctgcaacat gtccaattga agtcaagttt actaaaggaa gcaaagcatt gaatgatgtt     540
tgcatcctgg ccgaggattt ccatgcacct ggagccagct gtttggaaga caccaagagg     600
cggctagatt gtggcatatt tactctctgt tttacttttg ttattcctag cctttcttgc     660
aacttttctt gaagtatgct ggaaccttta ttatttattt gactaggaaa tttattctta     720
ataccaccag aaagagatag acaaaaacta ccttggtgat tgcattgaat taacataaag     780
tgcccaaaaa tattttgcta agaaaaaaaa aaaaaaaaaa aaaaaaaaaa aa             832

<210> SEQ ID NO 41
<211> LENGTH: 2246
<212> TYPE: DNA
<213> ORGANISM: Zea mays
```

<400> SEQUENCE: 41

```
tttggtgttt ctcgcagtgc gcagagggct tcagtcatta tcgtctcgtg ctctctattg      60
atggtagttt tttgcttggg aagtataggg gcacattgtt ggttgccatt tcatgtgacg     120
tggacaacgc attggttctt ttggcatttg ctttggtggt gagggagaac agagatagtt     180
cgttttggtt cttgcgactt gttcggatcc atgtcgtggg ccctggtcgg gagattggtg     240
tcatatatga cagaaaccag ggtattctta atgtagtgca agagcagatt cctggctaca     300
cacccatgca ccacagatgg agcactcgac acctagtaga aaatcttttt cgaaagggtt     360
gtaccaagaa taattccccc cttttgagg aggtctgtcg acagttggag gtttcgttat      420
tcgaggataa gttgaaggaa ttaaaagata caacaaatga tgaaggtgaa aaatggattg     480
ctagatttcc taactgtatt tcctcgtctc ctacacaaaa aacagtaagt acgaatgcaa     540
cattacgact gatgctatca aaaagcaata tcaacctcat cgtaatctac cacatgtcca     600
aaaataaccc acaccaagat cagaaggaac taatccatac ttagcttcat taaaaccgcc     660
actcattttt tctttttctt tgcctctggc tcaggccaat gggacctagg accatacaac     720
cactctatga aactacactt acgcccaccg tatggccgta ggggaataaa ttagtaaatt     780
tgtgaaaaaa taacaaaatt ttggacatttt gttatgcact cacataatta ctgttgggac     840
acacgaagta cttcacagtg tccttacata agacaacacg atctccgcaa tcacaccgag     900
gcggagactt cagtcgtctt tctgcgacta agttcttctt ctcatccgtc attggtgtcg     960
tgtcggggga ggaggcaccc aacgcttaaa acactgtata ttccttctgg acaaccaatt    1020
agcgaaaagg agatatcgat ggtcaaattt atgaggaccg tcgatccatt ggaaaacaca    1080
tcaagtgatc ctacagaaat ggaatgaagc attagtacac atgtagtaaa catcaataac    1140
acacaagtca taagctacat atgttaaaaa cgccacaagt gtagaagcag cgagcagccg    1200
tgtctagata tttgaattga catacccaag gcggtctgcc acagtcacaa ttaggtacag    1260
gaagatcagg aggaacatga gcatccttac tagatacatc cagatacaac tcccgaggac    1320
gatctctctt ctgccacaac gactcctaat acatgtcttt tcatctaaca aacgattata    1380
tattaacaca actatataga aataacagaa atgattttaa cttataaata catgtatttc    1440
ataaattatc taacaaactg tagtcattat atgaaccata tatcatagga ttcataacta    1500
atagcaatat gagcaacaat caaaactaat taatcgaaaa catacaacgc aatatacgta    1560
acaaatgaat cagtgagaca ctataccttg gtcttcaaag ttttccaact cgaatacgaa    1620
gattggagca cctctgggtg gtatggaaga agatacaaat ggttgggtgc agctctcggc    1680
taggaaacaa ccgatttata ggccttccta gctcggcgcc acagatccat ggcgccgagc    1740
tagtgccatg tcggtgctgc atcagccctc gacgctagcg gccttgtgtt accttggtgc    1800
tacaacttat gatattgagc aacgagtcca aatgcagaaa taagttatct aggggtctaa    1860
acattaaaca cgatttttttt cttaaaaagg accaacataa aaaaaactcg ggctggcggc    1920
ctgccagcgc ccggggaccg tgagcccgtg accccagcgg gcccaaccag tcaaaaccgc    1980
aagagagagt cgtgaggcgt gcgcactacc ccgagaaacg tgcgacggga acctccgcgg    2040
ttccccaagt tcgcctcctt cactactctc gcgcccggc acgcctgaaa accccaccc     2100
ctcctgccgc tccgcctctc ccatcacttc ccacgcccct cgccgcctcc cattccagcg    2160
tggacacgac gccactcgcc agcacggaga cgcgcgcctc gaagcactac tgcactagcc    2220
agccgtcgtt cttccgcgcc ggcgcc                                         2246
```

<210> SEQ ID NO 42
<211> LENGTH: 27
<212> TYPE: DNA
<213> ORGANISM: Artificial
<220> FEATURE:
<223> OTHER INFORMATION: synthetic

<400> SEQUENCE: 42 ttttaggaa ttattgagta ttattga                                27

<210> SEQ ID NO 43
<211> LENGTH: 24
<212> TYPE: DNA
<213> ORGANISM: Artificial
<220> FEATURE:
<223> OTHER INFORMATION: synthetic

<400> SEQUENCE: 43
aaataaaaat catacccaca tccc                                  24

<210> SEQ ID NO 44
<211> LENGTH: 26
<212> TYPE: DNA
<213> ORGANISM: Artificial
<220> FEATURE:
<223> OTHER INFORMATION: synthetic

<400> SEQUENCE: 44
tgttgaatta ttaagatatt taagat                                26

<210> SEQ ID NO 45
<211> LENGTH: 25
<212> TYPE: DNA
<213> ORGANISM: Artificial
<220> FEATURE:
<223> OTHER INFORMATION: synthetic

<400> SEQUENCE: 45
tcaaccaata aaaattacca tctac                                 25

<210> SEQ ID NO 46
<211> LENGTH: 30
<212> TYPE: DNA
<213> ORGANISM: Artificial
<220> FEATURE:
<223> OTHER INFORMATION: synthetic

<400> SEQUENCE: 46
taagtttttt ttaagagttt gtatttgtat                            30

<210> SEQ ID NO 47
<211> LENGTH: 25
<212> TYPE: DNA
<213> ORGANISM: Artificial
<220> FEATURE:
<223> OTHER INFORMATION: synthetic

<400> SEQUENCE: 47
taaaaataat caaaacctaa cttac                                 25

<210> SEQ ID NO 48
<211> LENGTH: 25
<212> TYPE: DNA
<213> ORGANISM: Artificial
<220> FEATURE:
<223> OTHER INFORMATION: synthetic

<400> SEQUENCE: 48
attgtttatt aaatgtttttt tagtt                                          25

<210> SEQ ID NO 49
<211> LENGTH: 24
<212> TYPE: DNA
<213> ORGANISM: Artificial
<220> FEATURE:
<223> OTHER INFORMATION: synthetic

<400> SEQUENCE: 49
ctaacaattc ccaaaaccct tatc                                            24

<210> SEQ ID NO 50
<211> LENGTH: 24
<212> TYPE: DNA
<213> ORGANISM: Artificial
<220> FEATURE:
<223> OTHER INFORMATION: synthetic

<400> SEQUENCE: 50
gtgtactcat ctggatctgt attg                                            24

<210> SEQ ID NO 51
<211> LENGTH: 25
<212> TYPE: DNA
<213> ORGANISM: Artificial
<220> FEATURE:
<223> OTHER INFORMATION: synthetic

<400> SEQUENCE: 51
ggttgaggag cctgaatctc tgaac                                           25

<210> SEQ ID NO 52
<211> LENGTH: 1000
<212> TYPE: DNA
<213> ORGANISM: Arabidopsis thaliana

<400> SEQUENCE: 52
acagaaaaaa aaaaactaat ttcgattcca caatgccgaa acccagaaaa attctcaaaa      60
cgaagtcact caagaagata atcaacaaag cgaaaacgga gaagggtttg ggtttaaggt     120
accgtaacga actccggtaa gttccgatga tggtgttgac agcgaagctt cgtggaacag     180
cgtgaccgtc gttactcact ggatttgccg gtgaatttga tgagtcaaaa atataactag     240
cagctggtca aagtaaccac tctgaataag acacgtgtca gaaactttgt tgaccattct     300
gactaaagaa accttgtaac caaaaacatc cacatttta catgctctgt catatttcaa      360
ctgtatacta aagttgaaat atgactatgg taacttatgt ttttttagtt gaaaactaag     420
gtaaactatt ctatgccagc aggtaaaaga tgtggatgac caactactgc tggcataatt     480
tattctatga ctaaggtaaa actaaaagtt aatatcactc gaaatattta caaaagtatt     540
agataaagta ctaaaaattt taagttagaa atgatgaaat taaagatat atgtggctta     600 tttaggaaaa tagatacttt taatatgatg gttgggtagt tttattattg tttgggattg     660
aaaaaaacta tgaaagtgtc tccaagtaca gtaatattta acaactaact aggaaggtgt     720
acattgttca gtattcatca ttctaattaa tacaaataat tttaaaaatt tggggtcgtc     780
aattgctcaa agatattcat tattttataa ttttctacat tttatcaaaa acagaattgt     840
gtaaatgttg tgtcattatg tgtcgacttg gatgtatgca ttacataatt ttattttata     900
tatgttttta attgttagag catttattcg aaaattataa atattgaatt ttaatcctca     960

```
gtcacttaat aaaaacatta ttttaggact aaaaaataat                          1000
```

<210> SEQ ID NO 53
<211> LENGTH: 1000
<212> TYPE: DNA
<213> ORGANISM: Oryza sativa

<400> SEQUENCE: 53

```
caacgacggc ttgcaggaat ttttaaaaaa ctataaaaaa aatcatatca ataatacgga      60
tcttaccggt gtagtgagat gacaaagaag agaagcaatg ggcaggtgag cgtgcgcaaa     120
caaatgagat aggaggcagt tgccacagga gggcatgccg agggtggtaa agtaaataaa     180
aaaataatta taagagttca agtagaatta caatttataa atgaaagaaa tatcacaata     240
agaaatattt attttgaaa aaaatagtcc atacagacca caacatgaca aattataata     300
aaaaacaag agaatagacc cataaaaaat tagagtggtg taggtagatg ggacatctaa     360
aaactataaa caaaacctta aatagaatat caatgataat taagaggagg acaacgagc     420
cggtcgttaa gcagcacgat ctcgacgatt ggagggattt ctagaaagta aaaaaaaact     480
ctcaattata atcatgttcg attttcaaat ctcaacgata ataaaaatgg gaagcaatgg     540
acgggccaaa gaggagtata gtggcggcgt ttagcgagac ttataaaaat tataaaaatg     600
aaacccaaca atacaatgaa ctctaaaacc acaaggtcaa atttgtagag gttccaggaa     660
ggatgaatga aagcattggt agatcgagca agtaaataaa gcgatgataa agaaataatg     720
cgtagtgatt agcatgacta ttaaaagcac cgggatgata aagtcggttt ctaacatata     780
gttatttaac aaattttaag taaaatcata tgtaaaaaat agataatttt gtatgggtgc     840
tagcccgcgc aattgcgcgg gccacctagc tagttttttt aaaaatgtaa atataaaaaa     900
ttcgaccacc acgcatcgcc tgctctgccg cggcgacgcg agccacaaag ccgtcgacca     960
ccgcaacaac aaaatatcct cctcccgacg caaaccggtt                          1000
```

<210> SEQ ID NO 54
<211> LENGTH: 1000
<212> TYPE: DNA
<213> ORGANISM: Solanum lycopersicum

<400> SEQUENCE: 54

```
atgtttaatt tatgggtaat gtagaagtgt atttaaaaaa aaaaaattga taaatatgtt      60
tatattatat gtgtaatgtg tgttaatatt ttcggtgatg gaataatata tgataaatca     120
tttagactca tgaagctctt cttaaatata atgaaaagac ttccaatgta aaaaattata     180
atcggaagcg gagccaatat atatttaggg gttcatttga attctcttta gcgaaaaata     240
tagtactatt tatatatgat cagttatttt tttttatgca tatgtagtag atattaaatc     300
tccttcgatt atttcgtgtg tttacttctt gagattttaa attccctatt caaaaatcct     360
agcctcgcca ttgtccgtaa caagagata ctaaatcgta tcttgtactc cctgtgtccc     420
aatttatgcg acttacgttg cttttagtc agtccaaaaa taatgacaca attctatatt     480
aagtaacaat ttaactataa aacgtcgatt ttatccttaa tgaaacgatt taccaccaca     540
caaatttctc attttagact gcaagttttt taaaaatttt catttctttc ttaaaactct     600
gtgccgaata aaactacttt acgtaaaata gaaaggagga aatatttatt tacacatcat     660
aaaaagtctc gaggaaaatc aaaaaaacgt cacaacaaac ataatatttt cattgaaaaa     720
atcgtttcat acctatttct tttgttgtct cttttttcatc cagtgttcag tactcactat     780
```

```
                                             -continued aaacactgac caatataaaa ctattcgcgc tccaaaatac cacattaaat aaaagcaact      840
tcatacataa aactcgaact cataatctcc cgttataaaa ggataccaca acttttagt       900 gctcttttc aataataact ttttttttat aaaaaaaaac taactgccag agtggaattt       960
ccaactgtat ctatttgatg aaaatagcag aaaactggtt                          1000

<210> SEQ ID NO 55
<211> LENGTH: 26
<212> TYPE: DNA
<213> ORGANISM: Artificial
<220> FEATURE:
<223> OTHER INFORMATION: synthetic

<400> SEQUENCE: 55
cgcaggtatc acgaggcaag tgctaa                                           26

<210> SEQ ID NO 56
<211> LENGTH: 26
<212> TYPE: DNA
<213> ORGANISM: Artificial
<220> FEATURE:
<223> OTHER INFORMATION: synthetic

<400> SEQUENCE: 56
gtgtactcat gtgcatctga cttgac                                           26
```

METHODS AND COMPOSITIONS FOR OBTAINING USEFUL PLANT TRAITS

CROSS-REFERENCE TO RELATED APPLICATIONS

This application claims the benefit of U.S. Provisional Patent Application No. 61/882,140, filed Sep. 25, 2013, which is incorporated herein by reference in its entirety.

STATEMENT REGARDING FEDERALLY SPONSORED RESEARCH OR DEVELOPMENT

This invention was made with Government Support under a grant from the Department of Energy (DE-FG02-10ER16189 and 25-1215-0051-001), United States Department of Agriculture-National Institute for Food and Agriculture (USDA/NIFA 2012-31100-06031) and the National Science Foundation (IOS 1126935). The government has certain rights to this invention.

INCORPORATION OF SEQUENCE LISTING

The sequence listing contained in the file named "46589_136655_SEQ_LST.txt", which is 110,612 bytes in size (measured in operating system MS-Windows), contains 56 sequences, and which was created on Sep. 18, 2014, is contemporaneously filed with this specification by electronic submission (using the United States Patent Office EFS-Web filing system) and is incorporated herein by reference in its entirety.

BACKGROUND OF INVENTION

Evidence exists in support of a link between environmental sensing and epigenetic changes in both plants and animals (Bonasio et al., Science 330, 612, 2010). Trans-generational heritability of these changes remains a subject of active investigation (Youngson et al. *Annu. Rev. Genom. Human Genet.* 9, 233, 2008). Previous studies have shown that altered methylation patterns are highly heritable over multiple generations and can be incorporated into a quantitative analysis of variation (Vaughn et al. 2007; Zhang et al. 2008; Johannes et al. 2009). Earlier studies of methylation changes in *Arabidopsis* suggest amenability of the epigenome to recurrent selection and also suggest that it is feasible to establish new and stable epigenetic states (F. Johannes et al. *PLoS Genet.* 5, e1000530 (2009); F. Roux et al. *Genetics* 188, 1015 (2011). Manipulation of the *Arabidopsis* met1 and ddmt mutants has allowed the creation of epi-RIL populations that show both heritability of novel methylation patterning and epiallelic segregation, underscoring the likely influence of epigenomic variation in plant adaptation (F. Roux et al. *Genetics* 188, 1015 (2011)). In natural populations, a large proportion of the epiallelic variation detected in *Arabidopsis* is found as CpG methylation within gene-rich regions of the genome (C. Becker et al. *Nature* 480, 245 (2011), R. J. Schmitz et al. *Science* 334, 369 (2011).

Induction of traits that exhibit cytoplasmic inheritance (Redei Mutat. Res. 18, 149-162, 1973; Sandhu et al. Proc Natl Acad Sci USA. 104:1766-70, 2007) or that exhibit nuclear inheritance by suppression of the MSH1 gene has also been reported (WO 2012/151254; Xu et al. Plant Physiol. Vol. 159:711-720, 2012).

SUMMARY

Plants comprising a scion grafted to rootstock that had been subjected to perturbation of plastid function are provided herewith. Such grafted plants can be used in methods for producing a plant exhibiting useful traits, methods for identifying one or more altered chromosomal loci in a plant that can confer a useful trait, and in methods for obtaining plants comprising modified chromosomal loci that can confer a useful trait. Such grafted plants that exhibit useful traits, progeny of the grafted plants exhibiting the useful traits, parts of the grafted or progeny plants including cells, leafs, stems, flowers and seeds, methods of using the grafted or progeny plants and plant parts, and products of those plants and plant parts, including processed products such as a feed or a meal are also provided herein.

Plants comprising a scion to which a rootstock had been grafted, where the rootstock is obtained from a plant or a parent plant thereof that had been subjected to perturbation of plastid function are provided herein. In certain embodiments, the rootstock confers to the grafted plant or to the progeny thereof an improvement in a useful trait in comparison to a control plant which lacks a graft to the rootstock or in comparison to progeny of the control plant. In certain embodiments, the rootstock that is grafted to the scion in step (a) is obtained from a plant that was selected for the useful trait and that was derived from a parent plant that had been subjected to plastid perturbation. In certain embodiments, the plant comprising rootstock obtained from a plant that was selected for the useful trait and that was derived from a parent plant that had been subjected to plastid perturbation exhibits the useful trait. In certain embodiments, the plastid function that is perturbed is selected from the group consisting of a sensor, photosystem I, photosystem II, NAD(P)H dehydrogenase (NDH) complex, cytochrome b6f complex, and plastocyanin function. In certain embodiments, the perturbation comprises suppression of a sensor gene selected from the group consisting of MSH1 and PPD3. In certain embodiments, the photosystem II function is perturbed by suppressing expression of a gene selected from the group consisting of an PsbO-1, a PsbO-2, PsbY, PsbW, PsbX, PsbR, PsbTn, PsbP1, PsbP2, PsbS, PsbQ-1, PsbQ-2, PPL1, PSAE-1, LPA2, PQL1, PQL2, and a PQL3 gene. In certain embodiments, the control plant comprises either: (i) a scion grafted to rootstock that had not been subjected to plastid perturbation; or (ii) a whole plant that lacks any root graft and that had not been subjected to plastid perturbation. In certain embodiments, any of the aforementioned plants, parental plants or progeny thereof exhibit a useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. In certain embodiments, plastid function has been recovered in the plant from which the rootstock was obtained. In certain embodiments, the scion contains one or more epigenetic changes in one or more nuclear chromosomes, wherein the epigenetic changes are absent from the nuclear chromosomes of a control plant or are absent from nuclear chromosomes of a plant from which the scion was obtained. In certain embodiments, the epigenetic change(s) are also present in the rootstock that had been subjected to perturbation of plastid function. In certain embodiments, the epigenetic changes are associated with the improvement in the useful trait. In certain embodiments, the rootstock contain(s) one or more epigenetic changes in one or more nuclear chromosomes that are absent from nuclear chromosomes of rootstock obtained from a plant or are absent from nuclear chromosomals of a parent plant thereof had not been subjected to perturbation of plastid function. In certain embodiments, the scion and/or the rootstock exhibit CG hypermethylation of a region encompassing a MSH1 locus in comparison to a control plant that had not been subjected to the plastid perturbation. In certain embodiments of any of the aforementioned plants, the scion and/or the rootstock exhibit pericentromeric CHG hyper-methylation in comparison to a control plant that had not been subjected to the plastid perturbation. In certain embodiments of any of the aforementioned plants, the scion and/or the rootstock exhibit CG hypermethylation and/or CHG hypermethylation at one or more nuclear chromosomal loci in comparison to corresponding nuclear chromosomal loci of a control plant that had not been subjected to the plastid perturbation. In certain embodiments, the plant is selected from the group consisting of a crop plant, a tree, a bush, turf grass, pasture grass, and a vine. In certain embodiments, the crop plant is selected from the group consisting of corn, soybean, cotton, canola, wheat, rice, tomato, tobacco, millet, potato, sugarbeet, cassava, alfalfa, barley, oats, sugarcane, sunflower, strawberry, and sorghum. In certain embodiments, the tree is selected from the group consisting of an apple, apricot, grapefruit, orange, peach, pear, plum, lemon, coconut, poplar, eucalyptus, date palm, palm oil, pine, and an olive tree. In certain embodiments, the bush is selected from the group consisting of a blueberry, raspberry, and blackberry bush. Also provided are progeny plants, populations of progeny plants, and clonal propagates obtained from any of the aforementioned grafted plants. Such progeny plants, populations of progeny plants, and clonal propagates can exhibit an improvement in a useful trait in comparison to control progeny plants, control populations of progeny plants, and control clonal propagates obtained from a control plant. Plant parts obtained from any of these progeny plants, populations of progeny plants, and clonal propagates are also provided. Such plant parts can include, but are not limited to, a part is selected from the group consisting of a seed, leaf, stem, fruit, and a root.

Also provided are methods for producing a plant exhibiting a useful trait comprising the steps of (a) obtaining a population of progeny plants from a grafted plant comprising a scion to which a rootstock had been grafted, wherein the rootstock is obtained from a plant or a parent plant thereof had been subjected to perturbation of plastid function; and, (b) selecting one or more progeny plants from the population, wherein the selected progeny plant exhibit an improvement in the useful trait in comparison to a control plant, thereby producing a plant that exhibits a useful trait. In certain embodiments, the population of progeny plants are obtained from seed of the grafted plant of step (a). In certain embodiments, the population of progeny plants are obtained from clonal propagates of the grafted plant of step (a). In certain embodiments, plastid function has been recovered in the rootstock that is grafted to the scion in step (a). In certain embodiments, the rootstock that is grafted to the scion in step (a) is obtained from a plant that was selected for the useful trait and that was derived from a parent plant that had been subjected to plastid perturbation. In certain embodiments, the grafted plant comprising rootstock obtained from a plant that was selected for the useful trait and that was derived from a parent plant that had been subjected to plastid perturbation exhibits the useful trait. In certain embodiments, the plant comprising rootstock obtained from a plant that was selected for the useful trait and that was derived from a parent plant that had been subjected to plastid perturbation exhibits the useful trait the plastid function is selected from the group consisting of a sensor, photosystem I, photosystem II, NAD(P)H dehydrogenase (NDH) complex, cytochrome b6f complex, and plastocyanin function. In certain embodiments, the perturbation comprises suppression of a sensor gene selected from the group consisting of MSH1 and PPD3. In certain embodiments, the photosystem II function was perturbed by suppressing expression of a gene selected from the group consisting of an PsbO-1, a PsbO-2, PsbY, PsbW, PsbX, PsbR, PsbTn, PsbP1, PsbP2, PsbS, PsbQ-1, PsbQ-2, PPL1, PSAE-1, LPA2, PQL1, PQL2, and a PQL3 gene. In certain embodiments, the control plant comprises either: (i) a scion grafted to rootstock that had not been subjected to plastid perturbation; or (ii) a whole plant that lacks any root graft and that had not been subjected to plastid perturbation. In certain embodiments of any of the aforementioned methods, the useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. In certain embodiments, the scion contain(s) one or more epigenetic changes in one or more nuclear chromosomes, wherein the epigenetic changes are absent from nuclear chromosomes of the control plant or are absent from nuclear chromosomes of a plant from which the scion was obtained. In certain embodiments, the epigenetic change(s) are also present in the rootstock that had been subjected to perturbation of plastid function. In certain embodiments, the epigenetic changes are associated with the improvement in the useful trait. In certain embodiments, the rootstock contain(s) one or more epigenetic changes in one or more nuclear chromosomes that are absent from nuclear chromosomes of rootstock obtained from a plant or are absent from nuclear chromosomes of a parent plant thereof had not been subjected to perturbation of plastid function. In certain embodiments, the scion and/or the rootstock exhibit CG hypermethylation of a region encompassing a MSH1 locus in comparison to a control plant that had not been subjected to the plastid perturbation. In certain embodiments, the scion and/or the rootstock exhibit pericentromeric CHG hyper-methylation in comparison to a control plant that had not been subjected to the plastid perturbation. In certain embodiments, the scion and/or the rootstock exhibit CG hypermethylation and/or CHG hypermethylation at one or more nuclear chromosomal loci in comparison to corresponding nuclear chromosomal loci of a control plant that had not been subjected to the plastid perturbation. In certain embodiments, the plant is selected from the group consisting of a crop plant, a tree, a bush, and a vine. In certain embodiments, the crop plant is selected from the group consisting of corn, soybean, cotton, canola, wheat, rice, tomato, tobacco, millet, potato, sugarbeet, cassava, alfalfa, barley, oats, sugarcane, sunflower, strawberry, and sorghum. In certain embodiments, the tree is selected from the group consisting of an apple, apricot, grapefruit, orange, peach, pear, plum, lemon, coconut, poplar, eucalyptus, date palm, palm oil, pine, and an olive tree. In certain embodiments, the bush is selected from the group consisting of a blueberry, raspberry, and blackberry bush. Also provided are plants or progeny thereof obtained by any of the aforementioned methods. Also provided are plant parts obtained from the plant or progeny thereof that were made by any of the aforementioned methods. In certain embodiments, the plant part is selected from the group consisting of a seed, leaf, stem, fruit, and a root. Also provided are clonal propagates obtained from the plant or progeny thereof that were made by any of the aforementioned methods.

Also provided are methods for producing a plant exhibiting a useful trait comprising the steps of: (a) crossing a first plant to a second plant, wherein the first plant is any of the aforementioned plants comprising a scion to which a rootstock had been grafted; and, (b) selecting one or more progeny plants obtained from the cross for an improvement in the useful trait in comparison to a control plant, thereby producing a plant exhibiting a useful trait. In certain embodiments, the control plant is selected from the group consisting of progeny of a cross between a plant which lacks a graft to the rootstock and a plant that is isogenic to the second plant, progeny of a self of a plant that lacks a graft to the rootstock, and progeny of a self of the second plant. In certain embodiments, at least the scion of the first plant is from a different heterotic group than the second plant. In certain embodiments, the scion and the rootstock of the first plant are from a different heterotic group than the second plant. In certain embodiments, the scion and the rootstock of the first plant are both from the same heterotic group but are from a different heterotic group than the second plant. In certain embodiments, at least the scion of the first plant is from the same heterotic group as the second plant. In certain embodiments, the scion and the rootstock of the first plant are from the same heterotic group as the second plant. In certain embodiments the second plant and at least the scion of the first plant are isogenic. In certain embodiments, the second plant and the scion and the rootstock of the first plant are isogenic. In certain embodiments of any of the aforementioned methods, the second plant or a parent thereof had also been subjected to perturbation of plastid function. In certain embodiments of any of the aforementioned methods, the useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. Also provided are plants obtained by any of the aforementioned methods. Also provided are plant parts obtained from plants made by any of the aforementioned methods. In certain embodiments, the plant part is selected from the group consisting of a seed, leaf, stem, fruit, and a root. Also provided are processed plant products obtained from plants made by any of the aforementioned methods or plant parts obtained from those plants.

Also provided are methods for producing a plant exhibiting a useful trait comprising the steps of: (a) selfing a plant, wherein the plant is any of the aforementioned plants comprising a scion to which a rootstock had been grafted or wherein the plant is a plant made by any of the aforementioned methods; and, (b) selecting one or more progeny plants obtained from the self for an improvement in the useful trait in comparison to a control plant, thereby producing a plant exhibiting a useful trait. In certain embodiments, the control plant is a progeny plant of a self of a plant which lacks a graft to the rootstock. In certain embodiments of any of the aforementioned methods, the useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. Also provided are plants obtained by any of the aforementioned methods. Also provided are plant parts obtained from plants made by any of the aforementioned methods. In certain embodiments, the plant part is selected from the group consisting of a seed, leaf, stem, fruit, and a root. Also provided are processed plant products obtained from plants made by any of the aforementioned methods or plant parts obtained from those plants.

Also provided are methods for producing a seed lot comprising: (i) growing a population of plants, wherein said population comprises two or more of any of the aforementioned plants comprising a scion to which a rootstock had been grafted and/or plants made by any of the aforementioned methods; (ii) selecting a first sub-population of plants exhibiting a useful trait; and, (ii) obtaining a seed lot from the first selected sub-population of step (i) or, optionally, repeating steps (i) and (ii) on a second population of plants grown from the seed obtained from the first selected sub-population of plants. Also provided are seed lots produced by the aforementioned methods, as well as plants, plant parts, and processed plant products obtained from the seed lots.

Also provided are methods for producing a seed lot comprising: (i) growing a population of plants, wherein said population comprises two or more of any of the aforementioned plants comprising a scion to which a rootstock had been grafted and/or plants made by any of the aforementioned methods; and (ii) obtaining a seed lot from the population. Also provided are seed lots produced by the aforementioned method as well as plants, plant parts, and processed plant products obtained from the seed lots.

Also provided are methods for identifying plants harboring a useful trait comprising the steps of: (a) crossing a candidate plant to a second plant, wherein the candidate plant is progeny of: (i) any of the aforementioned grafted plants comprising a scion to which a rootstock had been grafted, wherein the rootstock is obtained from a plant or a parent plant thereof had been subjected to perturbation of plastid function and/or plants made by any of the aforementioned methods; or (ii) a plant that had been subjected to perturbation of plastid function or progeny thereof; and, (b) identifying one or more progeny plants from the cross in step (a) that exhibit a useful trait to a greater extent than the candidate plant, the second plant, or a control plant, thereby identifying the candidate plant as a plant that harbors a useful trait. In certain embodiments of the methods, the control plant is progeny of a cross between a plant that is not progeny of a plant or a grafted plant that had been subjected to plastid perturbation and a plant that is isogenic to the second plant. Also provided are plants or progeny thereof that harbor a useful trait, wherein said plant or progeny thereof is identified or identifiable by any of the aforementioned methods.

Also provided are methods of identifying a plant harboring a useful trait comprising the steps of: (a) selfing a candidate plant, wherein the candidate plant is progeny of: (i) any of the aforementioned grafted plants comprising a scion to which a rootstock had been grafted, wherein the rootstock is obtained from a plant or a parent plant thereof that had been subjected to perturbation of plastid function; or (ii) a plant that had been subjected to perturbation of plastid function or progeny thereof; and, (b) identifying one or more progeny plants from the self in step (a) that exhibit a useful trait to a greater extent than the candidate plant or a control plant, thereby identifying the candidate plant as a plant that harbors a useful trait. In certain embodiments of the methods, the control plant is progeny of a self of plant that is not progeny of a plant or a grafted plant that had been subjected to plastid perturbation but is otherwise isogenic to the candidate plant. Plants or progeny thereof that harbor a useful trait, wherein the plant or progeny thereof is identified or identifiable by the aforementioned methods are also provided.

BRIEF DESCRIPTION OF THE DRAWINGS

The accompanying drawings, which are incorporated in and form a part of the specification, illustrate certain embodiments of the present invention. In the drawings:

FIG. 9A-E shows that MSH1 is located in a specialized plastid type. (A) Sensory plastids in vascular parenchyma adjacent to mesophyll cell chloroplasts in *Arabidopsis*. (B) Enlargement of a sensory plastid and adjacent mesophyll chloroplast. Note difference in size and grana organization. (C) Tobacco leaf epidermal and mesophyll chloroplasts, red channel (arrow indicates stomate) (D) green channel image, showing MSH1-GFP localization. (E) Merged image showing association of MSH1-GFP with smaller epidermal plastids. Note the punctate appearance of GFP signal Within the smaller organelles.

FIG. 11A-C shows that MSH1 co-purifies with the thylakoid membrane fraction. (A) Total Col-0 plastid preparations were separated to stromal and thylakoid fractions for protein gel blot analysis, with antibodies specific for MSH1, Rubisco and PsbO proteins. The lower panel is a Coomassie-stained gel sample of the preparations. (B) Total plastid preparations from a MSH1-GFP stable transformant were fractionated for immunoblot analysis that included milder detergent washes. (C) Influence of increased concentration salt washes on membrane association of MSH1, PsbO and PsbP. In each case, experimental results shown are spliced from single experiments.

FIG. 12A, B, C, D shows that MSH1 and PPD3 show evidence of protein interaction by co-immunoprecipitation. Stable double transformants for MSH1-GFP and PPD3-RFP fusion genes (PPD3×MSH1 OE) were used for coIP analysis. In each experiment, the left lane is a marker. (A) Immunoblot with anti-MSH1 antibodies on blotted total protein. (B) Immunoblot with anti-RFP antibodies on total protein. (C) CoIP from incubation of total protein with anti-MSH1 beads, probed with anti-GFP and anti-RFP antibodies. (D) Coomassie stained gel of the coIP precipitate from panel C.

FIG. 14A-F shows that MSH1 and PPD3 appear to be co-expressed in the vascular parenchyma and epidermal cell plastids. (A) Floral stem cross-section showing xylem (blue) and chloroplast autofluorescence (red). (B) Floral stem cross-section showing MSH1-GFP expression localized to the parenchyma of phloem and xylem, epidermal cells and in the pith. (C) Floral stem cross-section showing PPD3-GFP expression localized to plastids in a similar pattern to MSH1. (D) Confocal micrograph of leaf epidermal cells showing PPD3-GFP localization to plastids. (E) Enlargement showing GFP signal for MSH1 in the vascular tissue. Note that the signal is localized within small plastids. (F) MSH1 (GFP, green) and the nucleoid protein MFP1 (RFP, red) localization in epidermal plastids. Larger sized chloroplasts of the underlying mesophyll cells are shown in blue. Note that MSH1 and MFP1 do not completely co-localize (co-localization signal is yellow).

FIG. 21A-D shows Genome-wide 5-methyl-cytosine CG patterns in *Arabidopsis*. Distribution of CG-DMPs and CG-N-DMPs along each chromosome in a comparison of first and second-generation msh1/msh1 versus a wildtype sib MSH1/MSH1, advanced-generation msh1 versus Col-0, and epiF3 versus Col-0, with data normalized across all chromosomes. The arrow indicates the position of MSH1 on Chromosome 3. Solid arrowheads indicate the CG-N-DMP distribution.

DESCRIPTION

Figure 1:
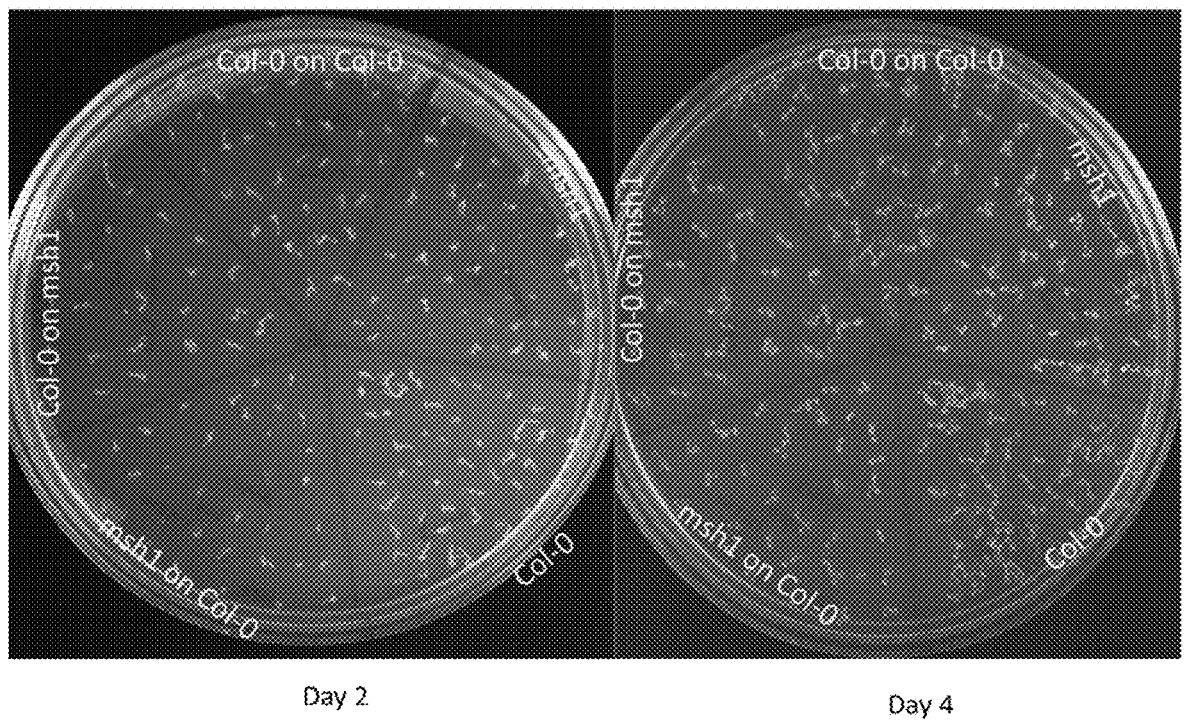
FIG. 1 illustrates the growth of seedlings at 2 days and 4 days post-germination as follows (clockwise from left): (a) progeny of a wild-type Columbia-0 ecotype scion grafted to msh1 rootstock (Col-0 on msh1); (b) progeny of a wild-type Columbia-0 ecotype scion grafted to wild-type Columbia-0 ecotype rootstock (Col-0 on Col-0); (c) progeny of an ungrafted msh1 plant (msh1); (d) progeny of an ungrafted wild-type Columbia-0 ecotype plant (Col-0); and (e) progeny of a msh1 scion grafted to wild-type Columbia-0 ecotype rootstock (msh1 on Col-0).
Figure 2:
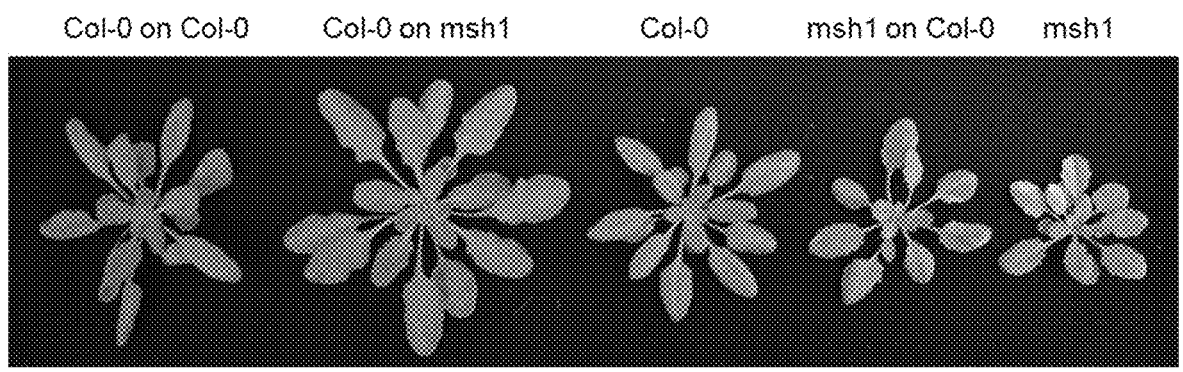
FIG. 2 illustrates, from left to right, progeny plants obtained from: (a) a wild-type Columbia-0 ecotype scion grafted to wild-type Columbia-0 ecotype rootstock (Col-0 on Col-0); (b) a wild-type Columbia-0 ecotype scion grafted to msh1 rootstock (Col-0 on msh1); (c) an ungrafted wild-type Columbia-0 ecotype plant (Col-0); (d) a msh1 scion grafted to wild-type Columbia-0 ecotype rootstock (msh1 on Col-0); and (d) an ungrafted msh1 plant (msh1).

As used herein, the phrase "chromosomal modification" refers to any of: a) an "altered chromosomal loci" and an "altered chromosomal locus"; b) "mutated chromosomal loci", a "mutated chromosomal locus", "chromosomal mutations" and a "chromosomal mutation"; or c) a transgene.

As used herein, the phrases "altered chromosomal loci" (plural) or "altered chromosomal locus" (singular) refer to portions of a chromosome that have undergone a heritable and reversible epigenetic change relative to the corresponding parental chromosomal loci. Heritable and reversible genetic changes in altered chromosomal loci include, but are not limited to, methylation of chromosomal DNA, and in particular, methylation of cytosine residues to 5-methylcytosine residues, and/or post-translational modification of histone proteins, and in particular, histone modifications that include, but are not limited to, acetylation, methylation, ubiquitinylation, phosphorylation, and sumoylation (covalent attachment of small ubiquitin-like modifier proteins). As used herein, "chromosomal loci" refer to loci in chromosomes located in the nucleus of a cell.

As used herein, the phrase "clonal propagate" refers to a plant or progeny thereof obtained from a plant cell. Clonal propagates can be obtained by methods including but not limited to regenerating whole plants from plant cells, plant embryos, cuttings, and the like. Various techniques used for such clonal propagation include, but are not limited to, meristem culture, somatic embryogenesis, thin cell layer cultures, adventitious shoot culture, and callus culture.

As used herein, the term "comprising" means "including but not limited to".

As used herein, the phrase "crop plant" includes, but is not limited to, cereal, seed, grain, fruit, and vegetable crop plants.

As used herein, the phrases "mutated chromosomal loci" (plural), "mutated chromosomal locus" (singular), "chromosomal mutations" and "chromosomal mutation" refer to portions of a chromosome that have undergone a heritable genetic change in a nucleotide sequence relative to the nucleotide sequence in the corresponding parental chromosomal loci. Mutated chromosomal loci comprise mutations that include, but are not limited to, nucleotide sequence inversions, insertions, deletions, substitutions, or combinations thereof. In certain embodiments, the mutated chromosomal loci can comprise mutations that are reversible. In this context, reversible mutations in the chromosome can include, but are not limited to, insertions of transposable elements, defective transposable elements, and certain inversions. In certain embodiments, the chromosomal loci comprise mutations are irreversible. In this context, irreversible mutations in the chromosome can include, but are not limited to, deletions.

As used herein, the term "discrete variation" or "$V_D$" refers to distinct, heritable phenotypic variation, that includes traits of male sterility, dwarfing, variegation, and/or delayed flowering time that can be observed either in any combination or in isolation.

As used herein, the phrase "heterologous sequence", when used in the context of an operably linked promoter, refers to any sequence or any arrangement of a sequence that is distinct from the sequence or arrangement of the sequence with the promoter as it is found in nature. As such, an MSH1 promoter can be operably linked to a heterologous sequence that includes, but is not limited to, MSH1 sense, MSH1 antisense, combinations of MSH1 antisense and MSH1 sense, and other MSH1 sequences that are distinct from, or arranged differently than, the operably linked sequences of the MSH1 transcription unit as they are found in nature.

As used herein, the term "MSH-dr" refers to leaf variegation, cytoplasmic male sterility (CMS), a reduced growth-rate phenotype, delayed or non-flowering phenotype, increased plant tillering, decreased height, decreased internode elongation, plant tillering, and/or stomatal density changes that are observed in plants subjected to suppression of plastid perturbation target genes. Plastid perturbation target genes that can be suppressed to produce an MSH-dr phenotype include, but are not limited to, MSH1 and PPD3.

As used herein, the term "heterotic group" refers to genetically related germplasm that produce superior hybrids when crossed to genetically distinct germplasm of another heterotic group.

As used herein, the term "progeny" refers to any one of a first, second, third, or subsequent generation obtained from a parent plant or plant cell.

As used herein, the phrase "quantitative variation" or "$V_Q$" refers to phenotypic variation that is observed in individual progeny lines derived from outcrosses of plants where MSH1 expression was suppressed and that exhibit discrete variation to other plants.

As used herein the terms "microRNA" or "miRNA" refers to both a miRNA that is substantially similar to a native miRNA that occurs in a plant as well as to an artificial miRNA. In certain embodiments, a transgene can be used to produce either a miRNA that is substantially similar to a native miRNA that occurs in a plant or an artificial miRNA.

As used herein, the phrase "obtaining a nucleic acid associated with the altered chromosomal locus" refers to any method that provides for the physical separation or enrichment of the nucleic acid associated with the altered chromosomal locus from covalently linked nucleic that has not been altered. In this context, the nucleic acid does not necessarily comprise the alteration (i.e. such as methylation) but at least comprises one or more of the nucleotide base or bases that are altered. Nucleic acids associated with an altered chromosomal locus can thus be obtained by methods including, but not limited to, molecular cloning, PCR, or direct synthesis based on sequence data.

The phrase "operably linked" as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter is linked such that the resulting translation product is in frame with the translational open reading frame that encodes the protein desired. Nucleic acid sequences that can be operably linked include, but are not limited to, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration functions (i.e., site specific recombinase recognition sites, integrase recognition sites), sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences, homologous recombination sequences), and sequences that provide replication functions (i.e., bacterial origins of replication, autonomous replication sequences, centromeric sequences).

As used herein, the phrase "suppressing expression of MSH1 gene(s)" refers to any genetic or environmental manipulation that provides for decreased levels of functional MSH1 activity in a plant or plant cell relative to the levels of functional MSH1 activity that occur in an otherwise isogenic plant or plant cell that had not been subjected to this genetic or environmental manipulation.

As used herein, the term "transgene", in the context of a chromosomal modification, refers to any DNA from a heterologous source that has been integrated into a chromosome that is stably maintained in a host cell. In this context, heterologous sources for the DNA include, but are not limited to, DNAs from an organism distinct from the host cell organism, species distinct from the host cell species, varieties of the same species that are either distinct varieties or identical varieties, DNA that has been subjected to any in vitro modification, recombinant DNA, and any combination thereof.

As used herein, the term "non-regenerable" refers to a plant part or plant cell that can not give rise to a whole plant.

Methods for introducing heritable and epigenetic and/or genetic variation that result in plants that exhibit useful traits are provided herewith along with plants, plant seeds, plant parts, plant cells, and processed plant products obtainable by these methods. In certain embodiments, methods provided herewith can be used to introduce epigenetic and/or genetic variation into varietal or non-hybrid plants that result in useful traits as well as useful plants, plant parts including, but not limited to, seeds, plant cells, and processed plant products that exhibit, carry, or otherwise reflect benefits conferred by the useful traits. In other embodiments, methods provided herewith can be used to introduce epigenetic and/or genetic variation into plants that are also amenable to hybridization.

In certain embodiments, the methods for introducing heritable epigenetic or genetic variation in a plant or progeny thereof can comprise the step of grafting rootstock obtained from a plant or a parent plant thereof had been subjected to perturbation of plastid function to a scion. In certain embodiments, perturbation of plastid function is by suppression of a gene selected from the group consisting of MSH1 and PPD3. In certain embodiments of any of the aforementioned methods, the heritable epigenetic variation provides a useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. In certain embodiments, the plant, progeny of the plant, or scion contain(s) one or more epigenetic changes in one or more nuclear chromosomes, wherein the epigenetic changes are absent from nuclear chromosomes of the control plant or are absent from nuclear chromosomes of a plant from which the scion was obtained. In certain embodiments, the epigenetic change(s) are also present in the rootstock that had been subjected to perturbation of plastid function. In certain embodiments, the epigenetic changes in the plant, progeny of the plant, scion, or rootstock are associated with the improvement in the useful trait. In certain embodiments, the epigenetic changes in the plant, progeny of the plant, scion, or rootstock induced by suppression of a gene selected from the group consisting of MSH1 and PPD3 are associated with the improvement in the useful trait. In certain embodiments, the plant, progeny of the plant, scion, or rootstock contain(s) one or more epigenetic changes in one or more nuclear chromosomes that are absent from nuclear chromosomes of rootstock obtained from a plant or are absent from nuclear chromosomes of a parent plant thereof had not been subjected to perturbation of plastid function. In certain embodiments, the plant, progeny of the plant, scion and/or the rootstock exhibit CG hypermethylation of a region encompassing a MSH1 locus in comparison to a control plant that had not been subjected to the plastid perturbation. In certain embodiments, the plant, progeny of the plant, scion and/or the rootstock exhibit pericentromeric CHG hyper-methylation in comparison to a control plant that had not been subjected to the plastid perturbation. In certain embodiments, the plant, progeny of the plant, scion and/or the rootstock exhibit CG hypermethylation and/or CHG hypermethylation at one or more nuclear chromosomal loci in comparison to corresponding nuclear chromosomal loci of a control plant that had not been subjected to the plastid perturbation. In certain embodiments, the plant is selected from the group consisting of a crop plant, a tree, a bush, and a vine. In certain embodiments, the crop plant is selected from the group consisting of corn, soybean, cotton, canola, wheat, rice, tomato, tobacco, millet, potato, sugarbeet, cassava, alfalfa, barley, oats, sugarcane, sunflower, strawberry, and sorghum. In certain embodiments, the tree is selected from the group consisting of an apple, apricot, grapefruit, orange, peach, pear, plum, lemon, coconut, poplar, eucalyptus, date palm, palm oil, pine, and an olive tree. In certain embodiments, the bush is selected from the group consisting of a blueberry, raspberry, and blackberry bush. In certain embodiments, the vine is a grape vine. Also provided are plants or progeny thereof obtained by any of the aforementioned methods. Also provided are plant parts obtained from the plant or progeny thereof that were made by any of the aforementioned methods.

Also provided herein are grafted plants comprising a scion to which a rootstock had been grafted, wherein the rootstock is obtained from a plant or a parent plant thereof that had been subjected to perturbation of plastid function, as well as progeny plants and clonal propagates obtained from the grafted plant. Such rootstocks can be also used to introduce epigenetic and/or genetic variation into varietal or non-hybrid plants that result in useful traits as well as useful plants, plant parts including, but not limited to, seeds, plant cells, and processed plant products that exhibit, carry, or otherwise reflect benefits conferred by the useful traits. In other embodiments, such rootstocks can also be used to introduce epigenetic and/or genetic variation into plants that are also amenable to hybridization.

Rootstocks useful for introducing epigenetic and/or genetic variation into plants can be obtained from a variety of rootstock source plants that had been subjected to plastid perturbation. In certain embodiments, the rootstock source plant is a plant that had itself been subjected to plastid perturbation. In other embodiments, the rootstock source plant is the progeny of a parental plant that had itself been subjected to plastid perturbation. Various methods of making rootstock source plants by plastid perturbation are provided herein. Plants that can serve as rootstock source plants and methods of making such plants are also disclosed in US Patent Application Publication No. 20120284814, which is specifically incorporated herein by reference in its entirety. The use of plants with useful traits and methods of making such plants disclosed in para. [0072], [0085], and [0089] in US Patent Application Publication No. 20120284814 as rootstock sources is specifically provided, and each of those paragraphs is specifically herein incorporated by reference in their entireties.

In certain embodiments where the rootstock source plant, or a parental plant thereof, had been subjected to plastid perturbation, a population of progeny plants obtained from the grafted plant are screened and individual progeny plants are selected for one or more useful traits. Such populations of progeny plants can be obtained by methods including, but not limited to, selfing or outcrossing the grafted plant comprising the rootstock to obtain seed that give rise to the population. Such populations of progeny plants can also be obtained by methods including, but not limited to, growing a population of plants that are derived from independent clonal propagates obtained from the grafted plant comprising the rootstock. Such selected individual progeny plants that exhibit the useful trait can then be sexually or asexually propagated to yield populations of plants that exhibit the useful trait or seed lots that exhibit or harbor the useful trait. Such sexual propagation can be accomplished by selfing or outcrossing the selected individual progeny plants that exhibit the useful trait.

In certain embodiments where the rootstock source plant is the progeny of a parental plant that had been subjected to plastid perturbation, the rootstock source plant itself can be a plant that was selected for one or more useful traits. Grafting rootstock from a plant that had been selected for a useful trait to a scion that does not exhibit the trait can impart the trait to the resultant grafted plant or to progeny thereof. Resultant grafted plants or progeny thereof that exhibit the useful trait can then be sexually or asexually propagated to yield populations of plants that exhibit the useful trait or seed lots that exhibit or harbor the useful trait.

In grafted plants or progeny thereof, perturbation of plastid function in the rootstock can be continuous and ongoing or can be transient. Non-limiting and exemplary methods for effecting continuous and ongoing perturbation of plastid function in the rootstock include suppressing expression of a plastid perturbation target gene with mutations in the endogenous gene or with a transgene that yields a product that suppresses expression of the endogenous gene. Alternatively, the perturbation of plastid function in the rootstock can be transient or have occurred in a parental plant from which the rootstock was obtained but not in the rootstock that was used in the graft. Non-limiting and exemplary methods for effecting transient suppressing of plastid function in the rootstock include suppressing expression of a plastid perturbation target gene with a transgene that provides for inducible or repressible expression of a product that suppresses expression of the endogenous gene, with a transgene that can be excised, or with a heterozygous transgene insert that is removed from the rootstock by segregation. Any of the methods described herein for restoring plastid function after perturbation can be used to generate rootstock used in certain embodiments.

Grafting can be effected by any method that provides for establishment of a vascular connection between the rootstock and the scion. Methods of grafting that can be used to effect the connection between the scion and the rootstock include, but are not limited to, apical graftage, side graftage, bark graftage, and root graftage. Such methods for effecting grafts of scions to rootstock are disclosed in "Plant Propagation: Principles and Practices; Chapter 12: Techniques of Grafting" Ed. Hartman, Kester, Davies, and Geneve, 7th Edition. Methods for effecting grafts of monocot plant scions to rootstocks that can be used with the scions and rootstocks provided herein are disclosed in Muzik and La Rue, The Grafting of Large Monocotyledonous Plants, Science 116, No. 3022: 589-591, 1952.

Rootstocks subjected to plastid perturbation or obtained from a parental plant that had been subjected to plastid perturbation can exhibit modifications of one or more nuclear chromosomes. In certain embodiments, such rootstocks can exhibit characteristic DNA methylation and/or gene transcription patterns that occur in plants subjected to suppression of an MSH1 target gene. Such characteristic DNA methylation and/or gene transcription patterns that occur in plants or seeds subjected to suppression of an MSH1 target gene can include, but are not limited to, those patterns disclosed in Example 5. In certain embodiments, rootstock of first generation progeny of a plant subjected to suppression of a plastid perturbation target gene will exhibit CG differentially methylated regions (DMR) of various discrete chromosomal regions that include, but are not limited to, regions that encompass the MSH1 locus. In certain embodiments, a CG hypermethylated region that encompasses the MSH1 locus will be about 5 to about 8 MBp (mega base pairs) in length. In certain embodiments, rootstock of first generation progeny of a plant subjected to suppression of a plastid perturbation target gene will also exhibit changes in plant defense and stress response gene expression. In certain embodiments, a rootstock, a scion grafted thereto, and/or a plant cell, a seed, a progeny plant, plant populations, seed populations, and/or processed products obtained therefrom that has been subject to suppression of a plastid perturbation target gene will exhibit pericentromeric CHG hypermethylation and CG hypermethlation of various discrete or localized chromosomal regions. Such discrete or localized hypermethylation is distinct from generalized hypermethylation across chromosomes that have been previously observed (U.S. Pat. No. 6,444,469). Such CHG hypermethylation is understood to be methylation at the sequence "CHG" where H=A, T, or C. Such CG and CHG hypermethylation can be assessed by comparing the methylation status of a sample from rootstocks, scions of plants grafted to root stocks, plants or seed that had been subjected to suppression of a plastid perturbation target gene, or a sample from progeny plants or seed derived therefrom, to a sample from control plants or seed that had not been subjected to suppression of a plastid perturbation target gene. In this and certain other contexts, such control plants include, but are not limited to, plants, grafted plants, scions thereof and rootstocks thereof that had not been subjected to plastid perturbation. In certain embodiments, such aforementioned changes in the methylation patterns exhibited by scions that are grafted to the rootstocks, or exhibited by a plant cell, a seed, a progeny plant, plant populations, seed populations, and/or processed products obtained from the grafted plant, be used to monitor the effectiveness of the graft in transmitting desirable epigenetic changes or to identify a plant cell, a seed, a progeny plant, plant populations, seed populations, and/or processed products obtained from the grafted plant.

Also provided herein are various methods for producing a plant exhibiting a useful trait that comprise crossing grafted plants comprising a scion grafted to rootstock that had been subjected to perturbation of plastid function with another plant, or crossing progeny plants obtained from the grafted plant with another plant, and selecting one or more progeny plants obtained from the cross for an improvement in the useful trait in comparison to a control plant. In certain embodiments, the second plant can also be a grafted plant comprising a scion grafted to rootstock that had been subjected to perturbation of plastid function, a progeny plants obtained from a grafted plant comprising a scion grafted to rootstock that had been subjected to perturbation of plastid function, any other ungrafted plant that had been subjected to perturbation of plastid function, or any other ungrafted plant obtained from one or more parental plants that had been subjected to perturbation of plastid function. Such second plants can be plants that were selected for a useful trait and that were progeny of any plant or grafted plant that had subjected to perturbation of plastid function. Control plants used as comparators to identify progeny of the cross that exhibit an improvement in the useful trait include, but are not limited to: progeny of a cross between a plant which lacks a graft to the rootstock and a plant that is isogenic to the second plant, progeny of a self of a plant that lacks a graft to the rootstock, progeny of a self of the second plant; progeny of a cross between a plant that is isogenic to the plant source of the scion of the grafted plant and a plant that is isogenic to the second plant; and, progeny of a cross between a plant that is isogenic to the plant source of the scion of the grafted plant and that is isogenic to the plant source of a scion of the second plant when the second plant is a grafted plant. Also provided are methods where at least the scion of the first plant is from a different heterotic group than the second plant or where at least the scion of the first plant is from the same heterotic group as the second plant.

Also provided herein are various methods for producing a plant exhibiting a useful trait that comprise selfing grafted plants comprising a scion grafted to rootstock that had been subjected to perturbation of plastid function with another plant, or selfing progeny plants obtained from the grafted plant, and selecting one or more progeny plants obtained from the self for an improvement in the useful trait in comparison to a control plant to produce a plant exhibiting a useful trait. In certain embodiments, the selfed plant is a grafted plant where the rootstock source plant is the progeny of a parental plant that had been subjected to plastid perturbation and the rootstock source plant itself was selected for and exhibits one or more useful traits. Control plants used as comparators to identify progeny of the self that exhibit an improvement in the useful trait include, but are not limited to: progeny of a self of a plant which lacks a graft to the rootstock, progeny of a self of a plant that has a graft to rootstock that had not been subjected to plastid perturbation, and progeny of a self of a plant that is isogenic to the plant source of the scion of the grafted plant.

In certain embodiments, useful traits provided herein can be exhibited to a greater extent in subsequent generations of plants that are obtained from any of the grafted plants, parental plants, or parental plant cells that had been subjected to plastid perturbation that are provided herein. As such, a given initial plant obtained from a parent plant that was subjected to plastid perturbation can be selfed to obtain first, second, third, or later generations of progeny that exhibit a given useful trait to a greater extent in comparison to either the initial plant or in comparison to a control plant. An initial grafted plant comprising a scion grafted to rootstock subjected to plastid perturbation or to rootstock obtained from a parent plant that had been subjected to plastid perturbation can be selfed to obtain first, second, third, or later generations of progeny that exhibit a given useful trait to a greater extent in comparison to either the grafted initial plant or in comparison to a control plant. In other embodiments, a given initial plant obtained from a parent plant that was subjected to plastid perturbation can be outcrossed to obtain F1, F2, F3, or later generations of progeny that exhibit a given useful trait to a greater extent in comparison to either the initial plant or in comparison to a control plant. In certain embodiments, a useful trait harbored by an initial plant or an initial grafted plant is not exhibited, or is exhibited to a lesser degree extent, in the initial plant or an initial grafted plant. However, the useful trait harbored by such an initial plant or an initial grafted plant is exhibited or is exhibited to a greater extent in progeny obtained by outcrossing the initial plant or the initial grafted plant to another plant. A useful trait harbored by such an initial plant or an initial grafted plant can also be exhibited or is exhibited to a greater extent in progeny obtained by selfing the initial plant or the initial grafted plant. In certain embodiments, plants or grafted plants that are selfed or outcrossed can be inbred lines. In certain embodiments, a useful trait harbored by an inbred line is not exhibited, or is exhibited to a lesser degree extent, in the inbred line. However, the useful trait harbored by such inbred lines is exhibited or is exhibited to a greater extent in progeny obtained by outcrossing the inbred line to another plant. An initial grafted plant comprising a scion grafted to rootstock subjected to plastid perturbation or to rootstock obtained from a parent plant that had been subjected to plastid perturbation can be outcrossed to obtain F1, F2, F3, or later generations of progeny that exhibit a given useful trait to a greater extent in comparison to either the initial grafted plant or in comparison to a control plant. Outcrosses of such initial plants or grafted plants can be to isogenic plants or to genetically distinct plants. In the methods provided herein, initial or subsequent generations of progeny obtained from such selfs or crosses can thus be selected for useful traits. The methods provided herein also permit the identification of plants that harbor, but do not necessarily exhibit to a full extent, various useful traits.

Clonal propagates can be obtained by methods including, but not limited to, regenerating whole plants from plant cells, plant embryos, cuttings, and the like that are obtained from scions of the grafted plants provided herein or progeny thereof. Various techniques used for such clonal propagation include, but are not limited to, meristem culture, somatic embryogenesis, thin cell layer cultures, adventitious shoot culture, and callus culture. In certain embodiments, clonal propagation is effected by placing sterile plant cells, plant embryos, cuttings, and the like in sterile plant culture media containing suitable salts, sugars, and plant growth regulators to support regeneration of a plant or plant part. Such techniques suitable for clonal propagation are often referred to as "micropropagation." Typically, cytokinins are used to stimulate shoot formation while auxins are used to stimulate root formation in the cultured material. Techniques that can be used for clonal propagation of potato plants provided herein include, but are not limited to, methods where sterile cuttings from tubers are multiplied in a modified Murashige-Skoog media to produce micropropagated plants that can be explanted to soil to produce micro-tubers that can then serve as seed potato tubers (Ahloowalia, Euphytica 75:163, 1994).

Other methods that can be used for clonal propagation of potato plants provided herein include, but are not limited to, methods where nodal, meristem, or shoot tip tissues are cultured and multiplied (Rosell, G. et al. Potato Research 30:111, 1987, and references cited therein). Still other methods that can be used for clonal propagation of potato plants provided herein include, but are not limited to, methods where nodal segments are cultured in a bioreactor to mass produce microtubers that can then serve as seed potato tubers (Piao et al., Current Science 84 (8): 1129, 2003). Techniques that can be used for clonal propagation of sugar beet plants provided herein include, but are not limited, to petiole explant propagation (Grieve, et al. Plant Growth Regulation 21:15, 1997), or propagation of leaf blades, apical meristems, stalk, embryo, or hypocotyls (Mezei, S. et al. Biotechnology & Biotechnological Equipment, 20:1, 9-14, 2006).

In certain embodiments, methods provided herewith involve suppressing expression of plant plastid perturbation target genes, restoring expression of a functional plant plastid perturbation target gene, and selecting progeny plants that exhibit one or more useful traits. In certain embodiments, these useful traits are associated with either one or more altered chromosomal loci that have undergone a heritable and reversible epigenetic changes.

In certain embodiments, methods for selectively suppressing expression of plant plastid perturbation target genes in sub-populations of cells found in plants that contain plastids referred to herein as "sensory plastids" are provided. Sensory plastids are plastids that occur in cells that exhibit preferential expression of at least the MSH1 promoter. In certain embodiments, MSH1 and other promoters active in sensory plastids can thus be operably linked to a heterologous sequence that perturbs plastid function to effect selective suppression of genes in cells containing the sensory plastids. In addition to the distinguishing characteristic of expressing MSH1, such cells containing sensory plastids can also be readily identified as their plastids are only about 30-40% of the size of the chloroplasts contained within mesophyll cells. Other promoters believed to be active in sensory plastids include, but are not limited to, PPD3 gene promoters. Selective suppression of plastid perturbation target genes in cells containing sensory plastids can trigger epigenetic changes that provide useful plant traits. Suppression of plant plastid perturbation target genes including but not limited to, photosynthetic components, in specific subsets of plant cells that contain the sensory plastids is preferred as suppression of those genes in most other plant cell types is detrimental or lethal to the plant due to impairment of its photosynthetic or other capabilities.

Plastid perturbation target genes that can be suppressed by various methods provided herein to trigger epigenetic or other changes that provide useful traits include, but are not limited to, genes that encode components of plant plastid thylakoid membranes and the thylakoid membrane lumen. In certain embodiments, the plastid perturbation target genes are selected from the group consisting of sensor, photosystem I, photosystem II, the NAD(P)H dehydrogenase (NDH) complex of the thylakoid membrane, the Cytochrome b6f complex, and plastocyanin genes. A non-limiting and exemplary list of plastid pertubation targets is provided in Table 1.

TABLE 1

Exemplary Plastid Perturbation Target Genes

| Category | Gene name(s) and/or Activity | Exemplary Genes Database Accession Numbers and/or SEQ ID NO |
|---|---|---|
| Sensor | MSH1 | SEQ ID NO: 1, 3-11. |
| Sensor | PPD3 | AT1G76450; SEQ ID NO: 16-40 |
| Photosystem I | PHOTOSYSTEM I SUBUNIT G, PSAG | PSAG AT1G55670.1 |
| Photosystem I | PHOTOSYSTEM I SUBUNIT D-2, PSAD-2 | PSAD-2 AT1G03130.1 |
| Photosystem I | PHOTOSYSTEM I SUBUNIT O, PSAO | PSAO AT1G08380 |
| Photosystem I | PHOTOSYSTEM I SUBUNIT K, PSAK | PSAK AT1G30380.1 |
| Photosystem I | PHOTOSYSTEM I SUBUNIT F, PSAF | PSAF AT1G31330.1 |
| Photosystem I | Photosystem I PsaN, reaction centre subunit N | PsaN AT1G49975.1 |
| Photosystem I | PHOTOSYSTEM I SUBUNIT H-2, PHOTOSYSTEM I SUBUNIT H2, PSAH-2, PSAH2, PSI-H | PSAH-2, PSAH2, PSI-H AT1G52230.1 |
| Photosystem I | PHOTOSYSTEM I SUBUNIT E-2, PSAE-2 | PSAE-2 AT2G20260.1 |
| Photosystem I | PHOTOSYSTEM I P SUBUNIT, PLASTID TRANSCRIPTIONALLY ACTIVE 8, PSAP, PSI-P, PTAC8, THYLAKOID MEMBRANE PHOSPHOPROTEIN OF 14 KDA, TMP14 | PSAP AT2G46820.1 |
| Photosystem I | PHOTOSYSTEM I SUBUNIT H-1, PSAH-1 | PSAH-1 AT3G16140.1 |
| Photosystem I | PHOTOSYSTEM I SUBUNIT D-1, PSAD-1 | PSAD-1 AT4G02770 |
| Photosystem I | PHOTOSYSTEM I SUBUNIT L, PSAL | PSAL AT4G12800 |
| Photosystem I | PSAN | PSAN AT5G64040 |
| | LHCA5, PHOTOSYSTEM I LIGHT HARVESTING COMPLEX GENE 5 | LHCA5 AT1G45474 |
| Photosystem II | PsbY | PsbY AT1G67740 |
| Photosystem II | PsbW | PsbW AT2G30570 |
| Photosystem II | PsbW-like | PsbW-like AT4G28660 |
| Photosystem II | PsbX | PsbX AT2G06520 |
| Photosystem II | PsbR | PsbR AT1G79040 |
| Photosystem II | PsbTn | PsbTn AT3G21055 |
| Photosystem II | PsbO-1 | PsbO-1 AT5G66570 |
| Photosystem II | PsbO-2 | PsbO-2 AT3G50820 |
| Photosystem II | PsbP1 | PsbP1 AT1G06680 |
| Photosystem II | PsbP2 | PsbP2 At2g30790 |
| Photosystem II | PsbS | PsbS AT1G44575 |
| Photosystem II | PsbQ-1 | PsbQ-1, AT4G21280 |
| Photosystem II | PsbQ-2, | PsbQ-2, AT4G05180 |
| Photosystem II | PPL1 | PPL1 At3g55330 |
| Photosystem II | PSAE-1 | PSAE-1 AT4G28750 |
| Photosystem II | LPA2 | LPA2 AT5G51545 |
| Photosystem II | PsbQ-like PQL1 | PQL1 AT1G14150 |
| Photosystem II | PsbQ-like PQL2 | PQL2 AT3G01440, |
| Photosystem II | PsbQ-like PQL3 | PQL3 AT2G01918 |
| NAD(P)H dehydrogenase (NDH) Complex | PHOTOSYNTHETIC NDH SUBCOMPLEX L 1, PNSL1, PPL2, PSBP-LIKE PROTEIN 2 | PPL2 At2g39470 |
| NAD(P)H dehydrogenase (NDH) Complex | NAD(P)H DEHYDROGENASE SUBUNIT 48, NDF1, NDH-DEPENDENT CYCLIC ELECTRON FLOW 1, NDH48, PHOTOSYNTHETIC NDH SUBCOMPLEX B 1, PNSB1 | NDH48 AT1G15980 |
| NAD(P)H dehydrogenase (NDH) Complex | NDF6, NDH DEPENDENT FLOW 6, PHOTOSYNTHETIC NDH SUBCOMPLEX B 4, PNSB4 | NDF6 AT1G18730 |

TABLE 1-continued

Exemplary Plastid Perturbation Target Genes

| Category | Gene name(s) and/or Activity | Exemplary Genes Database Accession Numbers and/or SEQ ID NO |
|---|---|---|
| NAD(P)H dehydrogenase (NDH) Complex | NAD(P)H DEHYDROGENASE SUBUNIT 45, NDF2, NDH-DEPENDENT CYCLIC ELECTRON FLOW 1, NDH45, PHOTOSYNTHETIC NDH SUBCOMPLEX B 2, PNSB2 | NDH45 AT1G64770 |
| NAD(P)H dehydrogenase (NDH) Complex | NDF5, NDH-DEPENDENT CYCLIC ELECTRON FLOW 5 | NDF5 AT1G55370 |
| NAD(P)H dehydrogenase (NDH) Complex | CHLORORESPIRATORY REDUCTION 23, CRR23, NADH DEHYDROGENASE-LIKE COMPLEX L, NDHL | NDHL AT1G70760 |
| NAD(P)H dehydrogenase (NDH) Complex | NAD(P)H:PLASTOQUINONE DEHYDROGENASE COMPLEX SUBUNIT O, NADH DEHYDROGENASE-LIKE COMPLEX), NDH-O, NDHO | NDHO AT1G74880 |
| NAD(P)H dehydrogenase (NDH) Complex | PIFI, POST-ILLUMINATION CHLOROPHYLL FLUORESCENCE INCREASE | PIFI AT3G15840 |
| NAD(P)H dehydrogenase (NDH) Complex | NDF4, NDH-DEPENDENT CYCLIC ELECTRON FLOW 1, PHOTOSYNTHETIC NDH SUBCOMPLEX B 3, PNSB3 | NDF4AT3G16250 |
| NAD(P)H dehydrogenase (NDH) Complex | NADH DEHYDROGENASE-LIKE COMPLEX M, NDH-M, NDHM, SUBUNIT NDH-M OF NAD(P)H:PLASTOQUINONE DEHYDROGENASE COMPLEX | NDHM AT4G37925 |
| NAD(P)H dehydrogenase (NDH) Complex | FK506-BINDING PROTEIN 16-2, FKBP16-2, PHOTOSYNTHETIC NDH SUBCOMPLEX L 4, PNSL4 | AT4G39710 |
| NAD(P)H dehydrogenase (NDH) Complex | CYCLOPHILIN 20-2, , CYCLOPHILIN 20-2, CYP20-2, PHOTOSYNTHETIC NDH SUBCOMPLEX L 5, PNSL5 | PNSL5 AT5G13120 |
| NAD(P)H dehydrogenase (NDH) Complex | CHLORORESPIRATORY REDUCTION L, CRRL, NADH DEHYDROGENASE-LIKE COMPLEX U, NDHU | NDHU AT5G21430 |
| NAD(P)H dehydrogenase (NDH) Complex | CHLORORESPIRATORY REDUCTION 7, CRR7 | CRR7 AT5G39210 |
| NAD(P)H dehydrogenase (NDH) Complex | NAD(P)H DEHYDROGENASE 18, NDH18, PHOTOSYNTHETIC NDH SUBCOMPLEX B 5, PNSB5 | NDH18 AT5G43750 |
| NAD(P)H dehydrogenase (NDH) Complex | NADH DEHYDROGENASE-LIKE COMPLEX N, NDHN | NDHN AT5G58260 |
| Cytochrome b6f complex | Rieske iron-sulfur protein containing a [2Fe—2S] cluster, OetC | PetC At4g03280 |
| Cytochrome b6f complex | ferredoxin: NADP- reductase [FNR1 and FNR2] | FNR1 AT5G66190 FNR2 AT1G20020 |
| plastocyanin | PETE1, PLASTOCYANIN 1 | PETE1 AT1G76100 |
| plastocyanin | PETE2, PLASTOCYANIN 2 | PETE2 AT1G20340 |
| other | PPD1, PSBP-DOMAIN PROTEIN1 | PPD1 At4g15510 |
| other | PPD2, PSBP-DOMAIN PROTEIN2 | PPD2 At2g28605 |
| other | PPD4, PSBP-DOMAIN PROTEIN4 | PPD4 At1g77090 |
| other | PPD5, PSBP DOMAIN PROTEIN 5 | PPD5 At5g11450 |
| other | PPD6, PSBP-DOMAIN PROTEIN 6 | PPD6 At3g56650 |

TABLE 1-continued

Exemplary Plastid Perturbation Target Genes

| Category | Gene name(s) and/or Activity | Exemplary Genes Database Accession Numbers and/or SEQ ID NO |
|---|---|---|
| other | PPD7, PSBP-DOMAIN PROTEIN 7 | PPD7 At3g05410 |
| MSH1 interacting proteins identified by Yeast Two Hybrid | CAD9 (CINNAMYL ALCOHOL DEHYDROGENASE 9); binding/catalytic/oxidoreductase/zinc ion binding | CAD9 AT4G39330 |
| MSH1 interacting proteins identified by Yeast Two Hybrid | KAB1 (POTASSIUM CHANNEL BETA SUBUNIT); oxidoreductase/potassium channel | KAB1 AT1G04690 |
| MSH1 interacting proteins identified by Yeast Two Hybrid | GOS12 (GOLGI SNARE 12); SNARE binding | GOS12 AT2G45200 |
| MSH1 interacting proteins identified by Yeast Two Hybrid | ELI3-1 (ELICITOR-ACTIVATED GENE 3-1); binding/catalytic/oxidoreductase/zinc ion binding (CAD7), response to bacterium, plant-type hypersensitive response | ELI3-1 AT4G37980 |
| MSH1 interacting proteins identified by Yeast Two Hybrid | STT3B (staurosporin and temperature sensitive 3-like b); oligosaccharyl transferase | STT3B AT1G34130 |
| MSH1 interacting proteins identified by Yeast Two Hybrid | tRNA synthetase beta subunit family protein, FUNCTIONS IN: phenylalanine-tRNA ligase activity, RNA binding, magnesium ion binding, nucleotide binding, ATP binding (unknown to date) | AT1G72550 |
| MSH1 interacting proteins identified by Yeast Two Hybrid | high mobility group (HMG1/2) family protein, FUNCTIONS IN: sequence-specific DNA binding transcription factor activity; LOCATED IN: nucleus, chloroplast | AT4G23800 |
| MSH1 interacting proteins identified by Yeast Two Hybrid | Protein kinase superfamily protein, FUNCTIONS IN: protein kinase activity, ATP binding; INVOLVED IN: protein amino acid phosphorylation; LOCATED IN: chloroplast | AT3G24190 |
| MSH1 interacting proteins identified by Yeast Two Hybrid | Protein kinase superfamily protein, FUNCTIONS IN: inositol or phosphatidylinositol kinase activity, phosphotransferase activity (interacts with SNARE At2G45200) | AT1G64460 |
| MSH1 interacting proteins identified by Yeast Two Hybrid | RNA-binding (RRM/RBD/RNP motifs) family protein; FUNCTIONS IN: RNA binding, nucleotide binding, nucleic acid binding; (interactomes map) | AT1G20880 |
| MSH1 interacting proteins identified by Yeast Two Hybrid | unknown protein, LOCATED IN: chloroplast | AT5G55210 |
| MSH1 interacting proteins identified by Yeast Two Hybrid | ATPase, F0/V0 complex, subunit C protein; FUNCTIONS IN: ATPase activity; INVOLVED IN: ATP synthesis coupled proton transport (vacuole) | AT4G32530 |
| MSH1 interacting proteins identified by Yeast Two Hybrid | RNA binding: FUNCTIONS IN: RNA binding; mRNA processing, RNA processing | AT3G11964 |

Exemplary plastid perturbation target genes from *Arabidopsis* with the accession number for the corresponding sequences in the *Arabidopsis* genome database (on the world wide web at the address "Arabidopsis.org") are provided in Table 1. Orthologous genes from many crop species can be obtained through the BLAST comparison of the protein sequences of the *Arabidopsis* genes above to the genomic databases (NCBI and publically available genomic databases for specific crop species), as well as from the specific names of the subunits. Specifically the genome, cDNA, or EST sequences are available for apples, beans, barley, *Brassica napus*, rice, Cassava, Coffee, Eggplant, Orange, sorghum, tomato, cotton, grape, lettuce, tobacco, *papaya*, pine, rye, soybean, sunflower, peach, poplar, scarlet bean, spruce, cocoa, cowpea, maize, onion, pepper, potato, radish, sugarcane, wheat, and other species at the following internet or world wide web addresses: "compbio.dfci.harvard.edu/tgi/plant.html"; "genomevolution.org/wiki/index.php/Sequenced_plant_genomes"; "ncbi.nlm.nih.gov/genomes/ PLANTS/PlantList.html"; "plantgdb.org/"; "arabidopsis.org/portals/genAnnotation/other_genomesr"; "gramene.org/resources/"; "genomenewsnetwork.org/resources/sequenced_genomes/genome_guide_p1.shtml"; "jgi.doe.gov/programs/plants/index.jsr"; "chibba.agtec.uga.edu/duplication/"; "mips.helmholtz-muenchen.de/plant/genomes.jsp"; "science.co.il/biomedical/Plant-Genome-Databases.asp"; "jcvi.org/cms/index.php?id=16"; and "phyto5.phytozome.net/Phytozome_resources.php". The main protein complexes involved in photon capture and electron transport of photosystem II (PSII), NAD(P)H dehydrogenase (NDH), Cytochrome b6f complex, plastocyanin, photosystem I (PSI), and associated plastid proteins that represent certain plastid perturbation targets are also described in Grouneva, I., P. J. Gollan, et al. (2013) Planta 237(2): 399-412 Ifuku, K., S. Ishihara, et al. (2010). J Integr Plant Biol 52(8): 723-734.

In general, methods provided herewith for introducing epigenetic and/or genetic variation in plants simply require that plastid perturbation target gene expression be suppressed for a time sufficient to introduce the variation and/or in appropriate subsets of cells (i.e cells containing sensory plastids). As such, a wide variety of plastid perturbation target gene suppression methods can be employed to practice the methods provided herewith and the methods are not limited to a particular suppression technique.

Sequences of plastid perturbation target gene genes or fragments thereof from *Arabidopsis* and various crop plants are provided herewith. In certain embodiments, such genes may be used directly in either the homologous or a heterologous plant species to provide for suppression of the endogenous plastid perturbation target gene in either the homologous or heterologous plant species. A non-limiting, exemplary demonstration where an exemplary MSH1 plastid perturbation target gene from one species was shown to be effective in suppressing the endogenous MSH1 gene in both a homologous and a heterologous species is provided by Sandhu et al. 2007, where a transgene that provides for an MSH1 inhibitory RNA (RNAi) with tomato MSH1 sequences was shown to inhibit the endogenous MSH1 plastid perturbation target gene genes of both tomato and tobacco. A transgene that provides for a plastid perturbation target gene inhibitory RNA (RNAi) with maize plastid perturbation target gene sequences can be used in certain embodiments to inhibit the endogenous plastid perturbation target gene genes of millet, sorghum, and maize. Plastid perturbation target gene genes from other plants including, but not limited to, cotton, canola, wheat, barley, flax, oat, rye, turf grass, sugarcane, alfalfa, banana, broccoli, cabbage, carrot, cassava, cauliflower, celery, citrus, a cucurbit, eucalyptus, garlic, grape, onion, lettuce, pea, peanut, pepper, potato, poplar, pine, sunflower, safflower, soybean, blackberry, blueberry, sugar beet, sweet potato, tobacco, strawberry, sugar beet, sweet potato, Jatropha, Camelina, and Agave can be obtained by a variety of techniques and used to suppress expression of either the corresponding plastid perturbation target gene in those plants or the plastid perturbation target gene in a distinct plant. Methods for obtaining plastid perturbation target genes for various plants include, but are not limited to, techniques such as: i) searching amino acid and/or nucleotide sequence databases comprising sequences from the plant species to identify the plastid perturbation target gene by sequence identity comparisons; ii) cloning the plastid perturbation target gene by either PCR from genomic sequences or RT-PCR from expressed RNA; iii) cloning the plastid perturbation target gene from a genomic or cDNA library using PCR and/or hybridization based techniques; iv) cloning the plastid perturbation target gene from an expression library where an antibody directed to the plastid perturbation target gene protein is used to identify the plastid perturbation target gene containing clone; v) cloning the plastid perturbation target gene by complementation of an plastid perturbation target gene mutant or plastid perturbation target gene deficient plant; or vi) any combination of (i), (ii), (iii), (iv), and/or (v). The DNA sequences of the target genes can be obtained from the promoter regions or transcribed regions of the target genes by PCR isolation from genomic DNA, or PCR of the cDNA for the transcribed regions, or by commercial synthesis of the DNA sequence. RNA sequences can be chemically synthesized or, more preferably, by transcription of suitable DNA templates. Recovery of the plastid perturbation target gene from the plant can be readily determined or confirmed by constructing a plant transformation vector that provides for suppression of the gene, transforming the plants with the vector, and determining if plants transformed with the vector exhibit the characteristic responses that are typically observed in various plant species when MSH1 expression is suppressed that include leaf variegation, cytoplasmic male sterility (CMS), a reduced growth-rate phenotype, and/or delayed or non-flowering phenotype. The characteristic responses of MSH1 suppression have been described previously as developmental reprogramming or "MSH-dr1" (Xu et al. Plant Physiol. Vol. 159:711-720, 2012).

In certain embodiments, plastid perturbation target genes or fragments thereof used in the methods provided herein will have nucleotide sequences with at least 50%, 60%, 70%, 80%, 90%, 95%, 98%, 99%, or 100% nucleotide sequence identity to one or more of the plastid perturbation target genes or fragments thereof provided herein that include, but are not limited to, genes provided in Table 1 and orthologs thereof found in various crop plants. In certain embodiments, plastid perturbation target genes or fragments thereof used in the methods provided herein encode plastid perturbation target gene proteins or portions thereof will have amino acid sequences with at least 50%, 60%, 70%, 80%, 90%, 95%, 98%, 99%, or 100% amino acid sequence identity to one or more of the plastid perturbation target gene proteins provided herein that include, but are not limited to, the plastid perturbation target gene proteins encoded by genes provided in Table 1. In certain embodiments, plastid perturbation target genes or fragments thereof used in the methods provided herein will have nucleotide sequences with at least 50%, 60%, 70%, 80%, 90%, 95%, 98%, 99%, or 100% nucleotide sequence identity to one or more of the PPD3 plastid perturbation target genes fragments thereof, orthologs thereof, or homologs thereof, provided herein that include, but are not limited to, SEQ ID NO:16-40. In certain embodiments, plastid perturbation target gene genes or fragments thereof used in the methods provided herein encode plastid perturbation target gene proteins or portions thereof will have amino acid sequences with at least 50%, 60%, 70%, 80%, 90%, 95%, 98%, 99%, or 100% amino acid sequence identity to one or more of the PPD3 plastid perturbation target gene proteins or plastid perturbation target gene homologs provided herein that include, but are not limited to, the proteins encoded by SEQ ID NO:16-40. PPD3 plastid perturbation target gene genes from plants other than those provided herein can also be identified by the encoded regions with homology to the PsbP1 and PsbP2 gene domains that characterize many PPD3 genes.

It is anticipated that plastid perturbation target gene nucleic acid fragments of 18 to 20 nucleotides, but more preferably 21 nucleotides or more, can be used to effect suppression of the endogenous plastid perturbation target gene. In certain embodiments, plastid perturbation target gene nucleic acid fragments of at least 18, 19, 20, or 21 nucleotides to about 50, 100, 200, 500, or more nucleotides can be used to effect suppression of the endogenous plastid perturbation target gene. Regions of 20, 50, 100, 500, or more by are suitable for this purpose, with lengths of 100 to 300 bases of the target gene sequences preferable, and lengths of 300 to 500 bp or more being most preferable. For use in a hairpin or inverted repeat knockdown design, a spacer region with a sequence not related to the sequence of the genome of the target plant can be used. A hairpin construct containing 300 to 500 bp or more of a target gene sequence in the antisense orientation, followed by a spacer region whose sequence is not critical but can be a intron or non-intron. If the spacer is an intron, the caster bean catalase intron which is effectively spliced in both monocots and dicots (Tanaka, Mita et al. Nucleic Acids Res 18(23): 6767-6770, 1990), is known to those skilled in the art and is useful for the present embodiment. After the spacer the same target gene sequence in the sense orientation is present, such that the antisense and sense strands can form a double stranded RNA after transcription of the transcribed region. The target gene sequences are followed by a polyadenylation region. 3' polyadenylation regions known to those skilled in the art to function in monocots and dicot plants include but are not limited to the Nopaline Synthase (NOS) 3' region, the Octapine Synthase (OCS) 3' region, the Cauliflower Mosaic Virus 35S 3' region, the Mannopine Synthase (MAS) 3' region. Additional 3' polyadenylation regions from monocotyledonous genes such as those from rice, sorghum, wheat, and maize are available to those skilled in the art to provide similar polyadenylation region and function in DNA constructs in the present embodiments. In certain embodiments, a transgene designed to suppress a target gene in dicots is designed to have the following order: promoter/antisense to target gene/catalase intron/sense gene A/polyadenylation region. In embodiments where a gene is designed to suppress a target gene in monocots can have the following order: promoter/intron for monocots/antisense to target gene/catalase intron/sense gene A/polyadenylation region.

Sequences that provide for suppression of a plastid perturbation target gene can include sequences that exhibit complementarity to either strand of the promoter, 5' or 3' untranslated region, intron, coding regions, and/or any combination thereof. A target gene promoter region for gene suppression can include the transcription start site, the TATA box, and upstream regions. The promoter region for gene silencing can be about 20, 50, 80, or 100 nucleotides in length, and more preferably is about 100 to 500 nucleotides in length. The promoter region used for such suppression can be from different regions in the upstream promoter, preferably containing at least about 500 nucleotides upstream from the start of transcription, and most preferably containing at least about 500 nucleotides upstream from the start of translation of the native coding region of the native gene. This would include the UTR which may or may not be part of the promoter. A description of various recombinant DNA constructs that target promoter and/or adjoining regions of target genes are described in U.S. Pat. No. 8,293,975, which is incorporated herein by reference in its entirety.

For gene targets with closely related family members, sense, antisense or double hairpin suppression designs can include sequences from more than one family member, following the designs described above. In certain embodiments, a transgene to suppress two genes, target gene A and target gene B, is designed to have the following order: promoter/optional intron/antisense to target gene A/antisense to target gene B/spacer sequence/sense target gene B/sense gene A/polyadenylation region. In certain embodiments, this spacer sequence can be an intron. Exemplary embodiments include, but are not limited to, the following combinations of gene family members that can each be arranged in a single recombinant DNA construct any order that provides for hairpin formation and suppression of the gene targets:

(a) Construct 1: PsbQ-like PQL1, PsbQ-like, PsbQ-like PQL3, and any combination thereof;
(b) Construct 2: PsbO-1 and PsbO-2;
(c) Construct 3: PsbP1 and PsbP2;
(d) Construct 4: PsbQ-1 and PsbQ-2;
(e) Construct 5: FNR1 and FNR2;
(f) Construct 6: PETE1 and PETE2; and,
(g) Construct 7: PsbW and PsbW-like.

In certain embodiments, suppression of plastid perturbation target gene in a plant is effected with a transgene. Transgenes that can be used to suppress expression of plastid perturbation target gene include, but are not limited to, transgenes that produce dominant-negative mutants of a plastid perturbation target gene, a small inhibitory RNA (siRNA), a microRNA (miRNA), a co-suppressing sense RNA, and/or an anti-sense RNA that provide for inhibition of the endogenous plastid perturbation target gene. U.S. patents incorporated herein by reference in their entireties that describe suppression of endogenous plant genes by transgenes include U.S. Pat. Nos. 7,109,393, 5,231,020 and 5,283,184 (co-suppression methods); and U.S. Pat. Nos. 5,107,065 and 5,759,829 (antisense methods). In certain embodiments, transgenes specifically designed to produce double-stranded RNA (dsRNA) molecules with homology to the plastid perturbation target gene can be used to decrease expression of the endogenous plastid perturbation target gene. In such embodiments, the sense strand sequences of the dsRNA can be separated from the antisense sequences by a spacer sequence, preferably one that promotes the formation of a dsRNA (double-stranded RNA) molecule. Examples of such spacer sequences include, but are not limited to, those set forth in Wesley et al., Plant J., 27(6):581-90 (2001), and Hamilton et al., Plant J., 15:737-746 (1998). One exemplary and non-limiting vector that has been shown to provide for suppression of plastid perturbation target gene in tobacco and tomato has been described by Sandhu et al., 2007 where an intron sequence separates the sense and antisense strands of the plastid perturbation target gene sequence. The design of recombinant DNA constructs for suppression of gene expression are also described in Helliwell, C. and P. Waterhouse (2003). "Constructs and methods for high-throughput gene silencing in plants." Methods 30(4): 289-295.

In certain embodiments, transgenes that provide for plastid perturbation target gene suppression can comprise regulated promoters that provide for either induction or down-regulation of operably linked plastid perturbation target gene inhibitory sequences. In this context, plastid perturbation target gene inhibitory sequences can include, but are not limited to, dominant-negative mutants of plastid perturbation target gene, a small inhibitory RNA (siRNA), a micro-RNA (miRNA), a co-suppressing sense RNA, and/or an anti-sense RNA that provide for inhibition of the endogenous plastid perturbation target gene of a plant. Such promoters can provide for suppression of plastid perturbation target gene during controlled time periods by either providing or withholding the inducer or down regulator. Inducible promoters include, but are not limited to, a PR-1a promoter (U.S. Patent Application Publication Number 20020062502) or a GST II promoter (WO 1990/008826 A1). In other embodiments, both a transcription factor that can be induced or repressed as well as a promoter recognized by that transcription factor and operably linked to the plastid perturbation target gene inhibitory sequences are provided. Such transcription factor/promoter systems include, but are not limited to: i) RF2a acidic domain-ecdysone receptor transcription factors/cognate promoters that can be induced by methoxyfenozide, tebufenozide, and other compounds (U.S. Patent Application Publication Number 20070298499); ii) chimeric tetracycline repressor transcription factors/cognate chimeric promoters that can be repressed or de-repressed with tetracycline (Gatz, C., et al. (1992). Plant J. 2, 397-404), and the like.

In certain embodiments, a promoter that provides for selective expression of a heterologous sequence that suppresses expression of the target gene in cells containing sensory plastids is used. In certain embodiments, this promoter is an Msh1 or a PPD3 promoter. In certain embodiments, this promoter is an Msh1 or a PPD3 promoter and the operably linked heterologous sequence suppresses expression of a target gene provided in Table 1 (above). Msh1 promoters that can be used to express heterologous sequences in cells containing sensor plastids include, but are not limited to, the *Arabidopsis*, sorghum, tomato, and maize promoters provided herewith (SEQ ID NO:11, 12, 13, 14, and 41) as well as functional derivatives thereof that likewise provide for expression in cells that contain sensor plastids. In certain embodiments, deletion derivatives of the Msh1 promoters comprising about 1500 Bp, 1000 Bp, or about 750 Bp of SEQ ID NO:11, 12, 13, 14, and 41 can also be used to express heterologus sequences. PPD3 promoters that can be used to express heterologous sequences in cells containing sensor plastids include, but are not limited to, the *Arabidopsis*, rice, and tomato promoters provided herewith as SEQ ID NO:52, 53, and 54 as well as functional derivatives thereof that provide for expression in cells that contain sensor plastids. In certain embodiments, deletion derivatives of the Msh1 promoters comprising about 800 Bp, 600 Bp, or about 500 Bp of SEQ ID NO: 52, 53, and 54 can also be used to express heterologus sequences. In certain embodiments, PPD3 promoters comprising SEQ ID NO:52, 53, and 54 and an additional 200, 500, or 1000 basepairs of the endogenous 5'PPD3 promoter sequences can be used to express heterologus sequences. Additional 200, 500, or 1000 basepairs of the endogenous 5'PPD3 promoter sequences can be obtained by methods including, but not limited to, retrieval of sequences from databases provided herein and recovery of the adjoining promoter DNA by PCR amplification of genomic template sequences or by direct synthesis. In certain embodiments, recombinant DNA constructs for suppression of dicot target genes can comprise a MSH1 or PPD3 promoter from a dicotyledonous species such as *Arabidopsis*, soybeans or canola, is attached to a hairpin construct containing 300 to 500 bp or more of a target gene sequence in the antisense orientation, followed by a spacer region whose sequence is not critical but can be a intron or non-intron. The caster bean catalase intron (Tanaka, Mita et al. Nucleic Acids Res 18(23): 6767-6770, 1990), can be used as a spacer in certain embodiments. After the spacer the same target gene sequence in the sense orientation is present, such that the antisense and sense strands can form a double stranded RNA after transcription of the transcribed region. The target gene sequences are followed by a polyadenylation region. Various 3' polyadenylation regions known to function in monocots and dicot plants include but are not limited to the Nopaline Synthase (NOS) 3' region, the Octapine Synthase (OCS) 3' region, the Cauliflower Mosaic Virus 35S 3' region, the Mannopine Synthase (MAS) 3' region. In certain embodiments recombinant DNA constructs for suppression of monocot target genes can comprise MSH1 or PPD3 promoter from a monocot species such as rice, maize, sorghum or wheat can either be attached directly to the hairpin region or to a monocot intron before the hairpin region. Monocot introns that are beneficial to gene expression when located between the promoter and coding region are the first intron of the maize ubiquitin (described in U.S. Pat. No. 6,054,574, which is incorporated herein by reference in its entirety) and the first intron of rice actin 1 (McElroy, Zhang et al. Plant Cell 2(2): 163-171, 1990). Additional introns that are beneficial to gene expression when located between the promoter and coding region are the maize hsp70 intron (described in U.S. Pat. No. 5,859,347, which is incorporated herein by reference in its entirety), and the maize alcohol dehydrogenase 1 genes introns 2 and 6 (described in U.S. Pat. No. 6,342,660, which is incorporated herein by reference in its entirety).

In still other embodiments, transgenic plants are provided where the transgene that provides for plastid perturbation target gene suppression is flanked by sequences that provide for removal for the transgene. Such sequences include, but are not limited to, transposable element sequences that are acted on by a cognate transposase. Non-limiting examples of such systems that have been used in transgenic plants include the cre-lox and FLP-FRT systems.

Plastid perturbation target gene suppression can be readily identified or monitored by molecular techniques. In certain embodiments where the endogenous plastid perturbation target gene is intact but its expression is inhibited, production or accumulation of the RNA encoding plastid perturbation target gene can be monitored. Molecular methods for monitoring plastid perturbation target gene RNA expression levels include, but are not limited to, use of semi-quantitive or quantitative reverse transcriptase polymerase chain reaction (qRT-PCR) techniques. The use of semi-quantitive PCR techniques to monitor plastid perturbation target gene suppression resulting from RNAi mediated suppression of plastid perturbation target gene has been described (Sandhu et al. 2007). Various quantitative RT-PCR procedures including, but not limited to, TaqMan™ reactions (Applied Biosystems, Foster City, Calif. US), use of Scorpion™ or Molecular Beacon™ probes, or any of the methods disclosed in Bustin, S. A. (Journal of Molecular Endocrinology (2002) 29, 23-39) can be used. It is also possible to use other RNA quantitation techniques such as Quantitative Nucleic Acid Sequence Based Amplification (Q-NASBA™) or the Invader™ technology (Third Wave Technologies, Madison, Wis.).

In certain embodiments where plastid perturbation target gene suppression is achieved by use of a mutation in the endogenous plastid perturbation target gene of a plant, the presence or absence of that mutation in the genomic DNA can be readily determined by a variety of techniques. Certain techniques can also be used that provide for identification of the mutation in a hemizygous state (i.e. where one chromosome carries the mutated msh1 gene and the other chromosome carries the wild type plastid perturbation target gene gene). Mutations in plastid perturbation target DNA sequences that include insertions, deletions, nucleotide substitutions, and combinations thereof can be detected by a variety of effective methods including, but not limited to, those disclosed in U.S. Pat. Nos. 5,468,613; 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. For example, mutations can be detected by hybridization to allele-specific oligonucleotide (ASO) probes as disclosed in U.S. Pat. Nos. 5,468,613 and 5,217,863. U.S. Pat. No. 5,210,015 discloses detection of annealed oligonucleotides where a 5' labelled nucleotide that is not annealed is released by the 5'-3' exonuclease activity. U.S. Pat. No. 6,004,744 discloses detection of the presence or absence of mutations in DNA through a DNA primer extension reaction. U.S. Pat. No. 5,468,613 discloses allele specific oligonucleotide hybridizations where single or multiple nucleotide variations in nucleic acid sequence can be detected by a process in which the sequence containing the nucleotide variation is amplified, affixed to a support and exposed to a labeled sequence-specific oligonucleotide probe. Mutations can also be detected by probe ligation methods as disclosed in U.S. Pat. No. 5,800,944 where sequence of interest is amplified and hybridized to probes followed by ligation to detect a labeled part of the probe. U.S. Pat. Nos. 6,613,509 and 6,503,710, and references found therein provide methods for identifying mutations with mass spectroscopy. These various methods of identifying mutations are intended to be exemplary rather than limiting as the methods of the present invention can be used in conjunction with any polymorphism typing method to identify the presence of absence of mutations in an plastid perturbation target gene in genomic DNA samples. Furthermore, genomic DNA samples used can include, but are not limited to, genomic DNA isolated directly from a plant, cloned genomic DNA, or amplified genomic DNA. The use of mutations in endogenous PPD3 genes is specifically provided herein.

Mutations in endogenous plant plastid perturbation target gene genes can be obtained from a variety of sources and by a variety of techniques. A homologous replacement sequence containing one or more loss of function mutations in the plastid perturbation target gene and homologous sequences at both ends of the double stranded break can provide for homologous recombination and substitution of the resident wild-type plastid perturbation target gene sequence in the chromosome with a msh1 replacement sequence with the loss of function mutation(s). Such loss of function mutations include, but are not limited to, insertions, deletions, and substitutions of sequences within an plastid perturbation target gene that result in either a complete loss of plastid perturbation target gene function or a loss of plastid perturbation target gene function sufficient to elicit alterations (i.e. heritable and reversible epigenetic changes) in other chromosomal loci or mutations in other chromosomal loci. Loss-of-function mutations in plastid perturbation target gene include, but are not limited to, frameshift mutations, pre-mature translational stop codon insertions, deletions of one or more functional domains that include, but are not limited to, a DNA binding (Domain I), an ATPase (Domain V) domain, and/or a carboxy-terminal GIY-YIG type endonuclease domain, and the like. Also provided herein are mutations analogous the *Arabidopsis* msh1 mutation that are engineered into endogenous plastid perturbation target gene plant gene to obtain similar effects. Methods for substituting endogenous chromosomal sequences by homologous double stranded break repair have been reported in tobacco and maize (Wright et al., Plant J. 44, 693, 2005; D'Halluin, et al., Plant Biotech. J. 6:93, 2008). A homologous replacement msh1 sequence (i.e. which provides a loss of function mutation in an plastid perturbation target gene sequence) can also be introduced into a targeted nuclease cleavage site by non-homologous end joining or a combination of non-homologous end joining and homologous recombination (reviewed in Puchta, J. Exp. Bot. 56, 1, 2005; Wright et al., Plant J. 44, 693, 2005). In certain embodiments, at least one site specific double stranded break can be introduced into the endogenous plastid perturbation target gene by a meganuclease. Genetic modification of meganucleases can provide for meganucleases that cut within a recognition sequence that exactly matches or is closely related to specific endogenous plastid perturbation target gene sequence (WO/06097853A1, WO/06097784A1, WO/04067736A2, U.S. 20070117128A1). It is thus anticipated that one can select or design a nuclease that will cut within a target plastid perturbation target gene sequence. In other embodiments, at least one site specific double stranded break can be introduced in the endogenous plastid perturbation target gene target sequence with a zinc finger nuclease. The use of engineered zinc finger nuclease to provide homologous recombination in plants has also been disclosed (WO 03/080809, WO 05/014791, WO 07014275, WO 08/021207). In still other embodiments, mutations in endogenous plastid perturbation target gene genes can be identified through use of the TILLING technology (Targeting Induced Local Lesions in Genomes) as described by Henikoff et al. where traditional chemical mutagenesis would be followed by high-throughput screening to identify plants comprising point mutations or other mutations in the endogenous plastid perturbation target gene (Henikoff et al., Plant Physiol. 2004, 135:630-636). The recovery of mutations in endogenous PPD3 genes is specifically provided herein.

Any of the recombinant DNA constructs provided herein can be introduced into the chromosomes of a host plant via methods such as *Agrobacterium*-mediated transformation, *Rhizobium*-mediated transformation, *Sinorhizobium*-mediated transformation, particle-mediated transformation, DNA transfection, DNA electroporation, or "whiskers"-mediated transformation. Aforementioned methods of introducing transgenes are well known to those skilled in the art and are described in U.S. Patent Application No. 20050289673 (*Agrobacterium*-mediated transformation of corn), U.S. Pat. No. 7,002,058 (*Agrobacterium*-mediated transformation of soybean), U.S. Pat. No. 6,365,807 (particle mediated transformation of rice), and U.S. Pat. No. 5,004,863 (*Agrobacterium*-mediated transformation of cotton), each of which are incorporated herein by reference in their entirety. Methods of using bacteria such as *Rhizobium* or *Sinorhizobium* to transform plants are described in Broothaerts, et al., Nature. 2005, 10; 433(7026):629-33. It is further understood that the recombinant DNA constructs can comprise cis-acting site-specific recombination sites recognized by site-specific recombinases, including Cre, Flp, Gin, Pin, Sre, pinD, Int-B13, and R. Methods of integrating DNA molecules at specific locations in the genomes of transgenic plants through use of site-specific recombinases can then be used (U.S. Pat. No. 7,102,055). Those skilled in the art will further appreciate that any of these gene transfer techniques can be used to introduce the recombinant DNA constructs into the chromosome of a plant cell, a plant tissue or a plant.

Methods of introducing plant minichromosomes comprising plant centromeres that provide for the maintenance of the recombinant minichromosome in a transgenic plant can also be used in practicing this invention (U.S. Pat. No. 6,972,197 and U.S. Patent Application Publication 20120047609). In these embodiments of the invention, the transgenic plants harbor the minichromosomes as extrachromosomal elements that are not integrated into the chromosomes of the host plant. It is anticipated that such mini-chromosomes may be useful in providing for variable transmission of a resident recombinant DNA construct that suppresses expression of a plastid perturbation target gene.

In certain embodiments, it is anticipated that ppd3 suppression can be effected by exposing whole plants, or reproductive structures of plants, to stress conditions that result in suppression of an endogenous PPD3 gene. Such stress conditions include, but are not limited to, high light stress, and heat stress. Exemplary and non-limiting high light stress conditions include continuous exposure to about 300 to about 1200 µmol photons/m2.s for about 24 to about 120 hours. Exemplary and non-limiting heat stress conditions include continuous exposure to temperatures of about 32° C. to about 37° C. for about 2 hours to about 24 hours. Exemplary and non-limiting heat, light, and other environmental stress conditions that can provide for MSH1 suppression are also disclosed for heat (Shedge et al. 2010), high light stress (Xu et al. 2011) and other environmental stress conditions (Hruz et al. 2008) and can also be adapted to effect PPD3 suppression.

Methods where plastid perturbation target gene suppression is effected in cultured plant cells are also provided herein. In certain embodiments, plastid perturbation target gene suppression can be effected by culturing plant cells under stress conditions that result in suppression of endogenous plastid perturbation target gene. Such stress conditions include, but are not limited to, high light stress. Exemplary and non-limiting high light stress conditions include continuous exposure to about 300 to about 1200 µmol photons/m2.s for about 24 to about 120 hours. Exemplary and non-limiting heat stress conditions include continuous exposure to temperatures of about 32° C. to about 37° C. for about 2 hours to about 24 hours. Exemplary and non-limiting heat, light, and other environmental stress conditions also that can provide for plastid perturbation target gene suppression are also disclosed for heat (Shedge et al. 2010), high light stress (Xu et al. 2011) and other environmental stress conditions (Hruz et al. 2008). In certain embodiments, plastid perturbation target gene suppression is effected in cultured plant cells by introducing a nucleic acid that provides for such suppression into the plant cells. Nucleic acids that can be used to provide for suppression of plastid perturbation target gene in cultured plant cells include, but are not limited to, transgenes that produce a small inhibitory RNA (siRNA), a microRNA (miRNA), a co-suppressing sense RNA, and/or an anti-sense RNA directed to the plastid perturbation target gene. Nucleic acids that can be used to provide for suppression of plastid perturbation target gene in cultured plant cells include, but are not limited to, a small inhibitory RNA (siRNA) or a microRNA (miRNA) directed against the endogenous plastid perturbation target gene. RNA molecules that provide for inhibition of plastid perturbation target gene can be introduced by electroporation. Introduction of inhibitory RNAs to cultured plant cells to inhibit target genes can in certain embodiments be accomplished as disclosed in Vanitharani et al. (Proc Natl Acad Sci USA., 2003, 100(16):9632-6), Qi et al. (Nucleic Acids Res. 2004 Dec. 15; 32(22):e179), or J. Cheon et al. (Microbiol. Biotechnol. (2009), 19(8), 781-786). The suppression of endogenous PPD3 genes in cultured plant cells is specifically provided herein.

Methods where plastid perturbation target gene suppression is effected in vegetatively or clonally propagated plant materials are also provided herein. Such vegetatively or clonally propagated plant materials can include, but are not limited to, cuttings, cultured plant materials, and the like. In certain embodiments, recovery of such plant or clonally propagated plant materials that have been subjected to plastid perturbation can be accomplished by methods that allow for transient suppression of the plastid perturbation target gene. In certain non-limiting examples, plant or clonally propagated plant materials that have been subjected to plant plastid perturbation are recovered by placing recombinant DNA constructs that suppress a plastid perturbation target gene in vectors that provide for their excision or segregation. In certain embodiments, such excision can be facilitated by use of transposase-based systems or such segregation can be facilitated by use of mini-chromosomes. In certain embodiments, such excision or segregation can be facilitated by linking a transgene that provides for a "conditional-lethal" counter selection to the transgene that suppresses a plastid perturbation target in the recombinant DNA construct. Vegetatively or clonally propagated plant materials that have been subjected to plastid perturbation and lacking recombinant DNA constructs that suppress a plastid perturbation target gene can then be screened and/or selected for useful traits. Also provided are methods where vegetatively or clonally propagated plant materials are obtained from a plant resulting from a self or outcross or from a cultured plant cell, where either the plant or plant cell had been subjected to suppression of a plastid perturbation target gene. Such vegetatively or clonally propagated plant materials obtained from such plants resulting from a self or outcross or from a plant cell that have been subjected to plastid perturbation can also be screened and/or selected for useful traits. Also provided herein are methods where a sexually reproducing plant or plant population comprising useful traits is vegetatively or clonally propagated, and a plant or a plant population derived therefrom is then used to produce seed or a seed lot. In certain embodiments of any of the aforementioned methods, the plastid perturbation target gene can be a MSH1 or a PPD3 gene.

Plastid perturbation target gene suppression can also be readily identified or monitored by traditional methods where plant phenotypes are observed. For example, plastid perturbation target gene suppression can be identified or monitored by observing organellar effects that include leaf variegation, cytoplasmic male sterility (CMS), a reduced growth-rate phenotype, and/or delayed or non-flowering phenotype. Phenotypes indicative of MSH1 plastid perturbation target gene suppression in various plants are provided in WO 2012/151254, which is incorporated herein by reference in its entirety. These phenotypes that are associated with plastid perturbation target gene suppression are referred to herein as "discrete variation" ($V_D$). Plastid perturbation target gene suppression can also produce changes in plant phenotypes including, but not limited to, plant tillering, height, internode elongation and stomatal density (referred to herein as "MSH1-dr") that can be used to identify or monitor plastid perturbation target gene suppression in plants. Other biochemical and molecular traits can also be used to identify or monitor plastid perturbation target gene suppression in plants. Such molecular traits can include, but are not limited to, changes in expression of genes involved in cell cycle regulation, Giberrellic acid catabolism, auxin biosynthesis, auxin receptor expression, flower and vernalization regulators (i.e. increased FLC and decreased SOC/ expression), as well as increased miR156 and decreased miR172 levels. Such biochemical traits can include, but are not limited to, up-regulation of most compounds of the TCA, NAD and carbohydrate metabolic pathways, down-regulation of amino acid biosynthesis, depletion of sucrose in certain plants, increases in sugars or sugar alcohols in certain plants, as well as increases in ascorbate, alphatocopherols, and stress-responsive flavones apigenin, and apigenin-7-oglucoside, isovitexin, kaempferol 3-O-beta-glucoside, luteolin-7-O-glucoside, and vitexin. In certain embodiments, elevated plastochromanol-8 levels in plant stems can serve as a biochemical marker that can be used to identify or monitor plastid perturbation target gene suppression. In particular, plastochromanol-8 levels in stems of plants subjected to plastid perturbation target gene suppression can be compared to the levels in control plants that have not been subjected to such suppression to identify or monitor plastid perturbation target gene suppression. It is further contemplated that in certain embodiments, a combination of both molecular, biochemical, and traditional methods can be used to identify or monitor plastid perturbation target gene suppression in plants.

Plastid perturbation target gene suppression that results in useful epigenetic changes and useful traits can also be readily identified or monitored by assaying for characteristic DNA methylation and/or gene transcription patterns that occur in plants subject to such perturbations. In certain embodiments, characteristic DNA methylation and/or gene transcription patterns that occur in plants subject suppression of an MSH1 target gene can be monitored in a plant, a plant cell, plants, seeds, and/or processed products obtained therefrom to identify or monitor effects mediated by suppression of other target plant plastid perturbation genes. Such plant plastid perturbation genes that include, but are not limited to, genes provided herewith in the sequence listing and Table 1 are expected to give rise to the characteristic DNA methylation and/or gene transcription patterns that occur in plants subject suppression of an MSH1 target gene. Such characteristic DNA methylation and/or gene transcription patterns that occur in plants or seeds subjected suppression of an MSH1 target gene include, but are not limited to, those patterns disclosed in Example 2 of U.S. Provisional Patent Application No. 61/863,267, which is specifically incorporated herein by reference in its entirety. In certain embodiments, first generation progeny of a plant subjected to suppression of a plastid perturbation target gene will exhibit CG differentially methylated regions (DMR) of various discrete chromosomal regions that include, but are not limited to, regions that encompass the MSH1 locus. In certain embodiments, a CG hypermethylated region that encompasses the MSH1 locus will be about 5 to about 8 MBp (mega base pairs) in length. In certain embodiments, first generation progeny of a plant subjected to suppression of a plastid perturbation target gene will also exhibit changes in plant defense and stress response gene expression. In certain embodiments, a plant, a plant cell, a seed, plant populations, seed populations, and/or processed products obtained therefrom that has been subject to suppression of a plastid perturbation target gene will exhibit pericentromeric CHG hypermethylation and CG hypermethlation of various discrete or localized chromosomal regions. Such discrete or localized hypermethylation is distinct from generalized hypermethylation across chromosomes that have been previously observed (U.S. Pat. No. 6,444,469). Such CHG hypermethylation is understood to be methylation at the sequence "CHG" where H=A, T, or C. Such CG and CHG hypermethylation can be assessed by comparing the methylation status of a sample from plants or seed that had been subjected to suppression of a plastid perturbation target gene, or a sample from progeny plants or seed derived therefrom, to a sample from control plants or seed that had not been subjected to suppression of a plastid perturbation target gene. A variety of methods that provide for suppression of plastid perturbation target gene in a plant followed by recovery of progeny plants where plastid perturbation target gene function is recovered are provided herein. In certain embodiments, such progeny plants can be recovered by downregulating expression of a plastid perturbation target gene-inhibiting transgene or by removing the plastid perturbation target gene-inhibiting transgene with a transposase. In certain embodiments of the methods provided herein, plastid perturbation target gene is suppressed in a target plant or plant cell and progeny plants that express plastid perturbation target gene are recovered by genetic techniques. In one exemplary and non-limiting embodiment, progeny plants can be obtained by selfing a plant that is heterozygous for the transgene that provides for plastid perturbation target gene segregation. Selfing of such heterozygous plants (or selfing of heterozygous plants regenerated from plant cells) provides for the transgene to segregate out of a subset of the progeny plant population. Where a plastid perturbation target gene is suppressed by use of a recessive mutation in an endogenous plastid perturbation target gene can, in yet another exemplary and non-limiting embodiment, be crossed to wild-type plants that had not been subjected to plastid perturbation and then selfed to obtain progeny plants that are homozygous for a functional, wild-type plastid perturbation target gene allele. In other embodiments, a plastid perturbation target gene is suppressed in a target plant or plant cell and progeny plants that express the plastid perturbation target gene are recovered by molecular genetic techniques. Non limiting and exemplary embodiments of such molecular genetic techniques include: i) downregulation of an plastid perturbation target gene suppressing transgene under the control of a regulated promoter by withdrawal of an inducer required for activity of that promoter or introduction of a repressor of that promoter; or, ii) exposure of the an plastid perturbation target gene suppressing transgene flanked by transposase recognition sites to the cognate transposase that provides for removal of that transgene.

Plants or rootstocks subjected to plastid perturbation, and scions grafted to such rootstocks, as well as the progeny thereof, can exhibit a variety of nuclear chromosomal DNA methylation patterns that are absent from control plants, rootstocks, or scions that were not subjected to plastid perturbation. Such methylation patterns can include, but are not limited to, CG hypermethylation, pericentromeric CHG hypermethylation, and/or additional characteristic methylation patterns observed in plants or progeny thereof that had been subjected to suppression of MSH1 gene expression. Such methylation patterns can also include, but are not limited to, changes in 5-hydroxymethylation and in particular, the occurrence of 5-hydroxymethylcytosine (5-hmC). Changes in 5-hmC can be monitored by immunoassays (Quest 5-hmC™ DNA ELISA Kit, Zymo Research Corp., Irvine, Calif., USA; or EpiSeeker™ hydroxymethylated DNA Quantification Kit, Abeam, Inc., Cambridge, Mass.). It is anticipated that plants, plant parts, processed plant products, rootstocks, and scions provided herein or produced by the methods provided herein can be identified by comparing methylation patterns in the genomic DNA of such materials to the methylation patterns of control plants, plant parts, processed plant products, rootstocks, and scions.

In certain embodiments of the methods provided herein, progeny plants derived from plants where plastid perturbation target gene expression was suppressed that exhibit male sterility, dwarfing, variegation, and/or delayed flowering time and express functional plastid perturbation target gene are obtained and maintained as independent breeding lines or as populations of plants. It has been found that such phenotypes appear to sort, so that it is feasible to select a cytoplasmic male sterile plant displaying normal growth rate and no variegation, for example, or a stunted, male fertile plant that is highly variegated. We refer to this phenomenon herein as discrete variation ($V_D$). Exemplary and non-limiting illustrations of this phenomenon as it occurs in selfed plant populations that have lost an MSH1 plastid perturbation target gene-inhibiting transgene by segregation have been disclosed (WO 2012/151254, incorporated herein by reference in its entirety). It is further contemplated that such individual lines that exhibit discrete variation ($V_D$) can be obtained by any of the aforementioned genetic techniques, molecular genetic techniques, or combinations thereof.

Individual lines obtained from plants where plastid perturbation target gene expression was suppressed that exhibit discrete variation ($V_D$) can be crossed to other plants to obtain progeny plants that lack the phenotypes associated with discrete variation ($V_D$) (i.e. male sterility, dwarfing, variegation, and/or delayed flowering time). In certain embodiments, progeny of such outcrosses can be selfed to obtain individual progeny lines that exhibit significant phenotypic variation. Such phenotypic variation that is observed in these individual progeny lines derived from outcrosses of plants where plastid perturbation target gene expression was suppressed and that exhibit discrete variation to other plants is herein referred to as "quantitative variation" ($V_Q$). Certain individual progeny plant lines obtained from the outcrosses of plants where plastid perturbation target gene expression was suppressed to other plants can exhibit useful phenotypic variation where one or more traits are improved relative to either parental line and can be selected. Useful phenotypic variation that can be selected in such individual progeny lines includes, but is not limited to, increases in fresh and dry weight biomass relative to either parental line. An exemplary and non-limiting illustration of this phenomenon as it occurs in F2 progeny of outcrosses of plants that exhibit discrete variation to plants that do not exhibit discrete variation is provided in WO 2012/151254, which is incorporated herein by reference in its entirety Individual lines obtained from plants where plastid perturbation target gene expression was suppressed that exhibit discrete variation ($V_D$) can also be selfed to obtain progeny plants that lack the phenotypes associated with discrete variation ($V_D$) (i.e. male sterility, dwarfing, variegation, and/or delayed flowering time). Recovery of such progeny plants that lack the undesirable phenotypes can in certain embodiments be facilitated by removal of the transgene or endogenous locus that provides for plastid perturbation target gene suppression. In certain embodiments, progeny of such selfs can be used to obtain individual progeny lines or populations that exhibit significant phenotypic variation. Certain individual progeny plant lines or populations obtained from selfing plants where plastid perturbation target gene expression was suppressed can exhibit useful phenotypic variation where one or more traits are improved relative to the parental line that was not subjected to plastid perturbation target gene suppression and can be selected. Useful phenotypic variation that can be selected in such individual progeny lines includes, but is not limited to, increases in fresh and dry weight biomass relative to the parental line.

In certain embodiments, an outcross of an individual line exhibiting discrete variability can be to a plant that has not been subjected to plastid perturbation target gene suppression but is otherwise isogenic to the individual line exhibiting discrete variation. In certain exemplary embodiments, a line exhibiting discrete variation is obtained by suppressing plastid perturbation target gene in a given germplasm and can outcrossed to a plant having that same germplasm that was not subjected to plastid perturbation target gene suppression. In other embodiments, an outcross of an individual line exhibiting discrete variability can be to a plant that has not been subjected to plastid perturbation target gene suppression but is not isogenic to the individual line exhibiting discrete variation. Thus, in certain embodiments, an outcross of an individual line exhibiting discrete variability can also be to a plant that comprises one or more chromosomal polymorphisms that do not occur in the individual line exhibiting discrete variability, to a plant derived from partially or wholly different germplasm, or to a plant of a different heterotic group (in instances where such distinct heterotic groups exist). It is also recognized that such an outcross can be made in either direction. Thus, an individual line exhibiting discrete variability can be used as either a pollen donor or a pollen recipient to a plant that has not been subjected to plastid perturbation target gene suppression in such outcrosses. In certain embodiments, the progeny of the outcross are then selfed to establish individual lines that can be separately screened to identify lines with improved traits relative to parental lines. Such individual lines that exhibit the improved traits are then selected and can be propagated by further selfing. An exemplary and non-limiting illustration of this procedure where F2 progeny of outcrosses of plants that exhibit discrete variation to plants that do not exhibit discrete variation are obtained is provided in WO 2012/151254, which is incorporated herein by reference in its entirety. Such F2 progeny lines are screened for desired trait improvements relative to the parental plants and lines exhibiting such improvements are selected.

In certain embodiments, sub-populations of plants comprising the useful traits and epigenetic changes induced by suppression of the plastid perturbation target gene can be selected and bred as a population. Such populations can then be subjected to one or more additional rounds of selection for the useful traits and/or epigenetic changes to obtain subsequent sub-populations of plants exhibiting the useful trait. Any of these sub-populations can also be used to generate a seed lot. In an exemplary embodiment, plastid perturbed plants exhibiting an Msh1-dr phenotype can be selfed or outcrossed to obtain an F1 generation. A bulk selection at the F1, F2, and/or F3 generation can thus provide a population of plants exhibiting the useful trait and/or epigenetic changes or a seed lot. In certain embodiments, it is also anticipated that populations of progeny plants or progeny seed lots comprising a mixture of inbred an hybrid germplasms can be derived from populations comprising hybrid germplasm (i.e. plants arising from cross of one inbred line to a distinct inbred line). In certain embodiments, such sub-populations can comprise grafted plants comprising a scion grafted to rootstock that had been subjected to plastid perturbation. Sub-populations of grafted plants where the rootstock source plant is the progeny of a parental plant that had been subjected to plastid perturbation and that was selected for one or more useful traits can also be selected and bred as a population. Any of the aforementioned subpopulations can comprise 2 or more, 10 or more, 50 or more, 100 or more, 1000 or more, or 10,000 or more plants. Seed lots thus obtained from these exemplary method or other methods provided herein can comprise seed wherein at least 25%, 50%, 60%, 70%, 80%, 90%, or 95% of progeny plants grown from the seed exhibit a useful trait. The selection would provide the most robust and vigorous of the population for seed lot production. Seed lots produced in this manner could be used for either breeding or sale. In certain embodiments, a seed lot comprising seed wherein at least 25%, 50%, 60%, 70%, 80%, 90%, or 95% of progeny plants grown from the seed exhibit a useful trait associated with one or more epigenetic changes, wherein the epigenetic changes are associated with CG hyper-methylation and/or CHG hyper-methylation at one or more nuclear chromosomal loci in comparison to a control plant that does not exhibit the useful trait, and wherein the seed or progeny plants grown from said seed that is epigenetically heterogenous are obtained. A seed lot obtainable by these methods can include at least 100, 500, 1000, 5000, or 10,000 seeds.

In certain embodiments, methods for producing a seed lot comprising: (i) growing a population of plants, wherein said population comprises two or more of grafted plants comprising a scion and rootstock obtained from a plant that had been subjected to plastid perturbation, or from a parental plant that had been subjected to plastid perturbation; and (ii) obtaining a seed lot from the population are provided. Populations of grafted plants where the rootstock source plant is the progeny of a parental plant that had been subjected to plastid perturbation and that was selected for one or more useful traits can also be selected and bred as a population. Any of the aforementioned populations can comprise 2 or more, 10 or more, 50 or more, 100 or more, 1000 or more, or 10,000 or more plants. Seed lots thus obtained from these exemplary methods or other methods provided herein can comprise seed wherein at least 25%, 50%, 60%, 70%, 80%, 90%, or 95% of progeny plants grown from the seed exhibit a useful trait. The selection would provide the most robust and vigorous of the population for seed lot production. Seed lots produced in this manner could be used for either breeding or sale. In certain embodiments, a seed lot comprising seed wherein at least 25%, 50%, 60%, 70%, 80%, 90%, or 95% of progeny plants grown from the seed exhibit a useful trait associated with one or more epigenetic changes, wherein the epigenetic changes are associated with CG hyper-methylation and/or CHG hyper-methylation at one or more nuclear chromosomal loci in comparison to corresponding nuclear chromosomal loci of a control plant that does not exhibit the useful trait, and wherein the seed or progeny plants grown from said seed that is epigenetically heterogenous are obtained. A seed lot obtainable by these methods can include at least 100, 500, 1000, 5000, or 10,000 seeds.

Altered chromosomal loci that can confer useful traits can also be identified and selected by performing appropriate comparative analyses of reference plants that do not exhibit the useful traits and test plants obtained from a parental plant or plant cell that had been subjected to plastid perturbation target gene suppression and obtaining either the altered loci or plants comprising the altered loci. It is anticipated that a variety of reference plants and test plants can be used in such comparisons and selections. In certain embodiments, the reference plants that do not exhibit the useful trait include, but are not limited to, any of: a) a wild-type plant; b) a distinct subpopulation of plants within a given F2 population of plants of a given plant line (where the F2 population is any applicable plant type or variety); c) an F1 population exhibiting a wild type phenotype (where the F1 population is any applicable plant type or variety); and/or, d) a plant that is isogenic to the parent plants or parental cells of the test plants prior to suppression of plastid perturbation target gene in those parental plants or plant cells (i.e. the reference plant is isogenic to the plants or plant cells that were later subjected to plastid perturbation target gene suppression to obtain the test plants). In certain embodiments, the test plants that exhibit the useful trait include, but are not limited to, any of: a) any non-transgenic segregants that exhibit the useful trait and that were derived from parental plants or plant cells that had been subjected to transgene mediated plastid perturbation target gene suppression, b) a distinct subpopulation of plants within a given F2 population of plants of a given plant line that exhibit the useful trait (where the F2 population is any applicable plant type or variety); (c) any progeny plants obtained from the plants of (a) or (b) that exhibit the useful trait; or d) a plant or plant cell that had been subjected to plastid perturbation target gene suppression that exhibit the useful trait.

In general, an objective of these comparisons is to identify differences in the small RNA profiles and/or methylation of certain chromosomal DNA loci between test plants that exhibit the useful traits and reference plants that do not exhibit the useful traits. Altered loci thus identified can then be isolated or selected in plants to obtain plants exhibiting the useful traits.

In certain embodiments, altered chromosomal loci can be identified by identifying small RNAs that are up or down regulated in the test plants (in comparison to reference plants). This method is based in part on identification of altered chromosomal loci where small interfering RNAs direct the methylation of specific gene targets by RNA-directed DNA methylation (RdDM). The RNA-directed DNA methylation (RdDM) process has been described (Chinnusamy V et al. Sci China Ser C-Life Sci. (2009) 52(4): 331-343). Any applicable technology platform can be used to compare small RNAs in the test and reference plants, including, but not limited to, microarray-based methods (Franco-Zorilla et al. Plant J. 2009 59(5):840-50), deep sequencing based methods (Wang et al. The Plant Cell 21:1053-1069 (2009)), and the like.

In certain embodiments, altered chromosomal loci can be identified by identifying histone proteins associated with a locus and that are methylated or acylated in the test plants (in comparison to reference plants). The analysis of chromosomal loci associated with methylated or acylated histones can be accomplished by enriching and sequencing those loci using antibodies that recognize methylated or acylated histones. Identification of chromosomal regions associated with methylation or acetylation of specific lysine residues of histone H3 by using antibodies specific for H3K4me3, H3K9ac, H3K27me3, and H3K36me3 has been described (Li et al., Plant Cell 20:259-276, 2008; Wang et al. The Plant Cell 21:1053-1069 (2009).

In certain embodiments, altered chromosomal loci can be identified by identifying chromosomal regions (genomic DNA) that has an altered methylation status in the test plants (in comparison to reference plants). An altered methylation status can comprise either the presence or absence of methylation in one or more chromosomal loci of a test plant comparison to a reference plant. Any applicable technology platform can be used to compare the methylation status of chromosomal loci in the test and reference plants. Applicable technologies for identifying chromosomal loci with changes in their methylation status include, but not limited to, methods based on immunoprecipitation of DNA with antibodies that recognize 5-methylcytidine, methods based on use of methylation dependent restriction endonucleases and PCR such as McrBC-PCR methods (Rabinowicz, et al. Genome Res. 13: 2658-2664 2003; Li et al., Plant Cell 20:259-276, 2008), sequencing of bisulfite-converted DNA (Frommer et al. Proc. Natl. Acad. Sci. U.S.A. 89 (5): 1827-31; Tost et al. BioTechniques 35 (1): 152-156, 2003), methylation-specific PCR analysis of bisulfite treated DNA (Herman et al. Proc. Natl. Acad. Sci. U.S.A. 93 (18): 9821-6, 1996), deep sequencing based methods (Wang et al. The Plant Cell 21:1053-1069 (2009)), methylation sensitive single nucleotide primer extension (MsSnuPE; Gonzalgo and Jones Nucleic Acids Res. 25 (12): 2529-2531, 1997), fluorescence correlation spectroscopy (Umezu et al. Anal Biochem. 415(2):145-50, 2011), single molecule real time sequencing methods (Flusberg et al. Nature Methods 7, 461-465), high resolution melting analysis (Wojdacz and Dobrovic (2007) Nucleic Acids Res. 35 (6): e41), and the like.

Methods for introducing various chromosomal modifications that can confer a useful trait into a plant, as well as the plants, plant parts, and products of those plant parts are also provided herein. Chromosomal alterations and/or chromosomal mutations induced by suppression of plastid perturbation target gene can be identified as described herein. Once identified, chromosomal modifications including, but not limited to, chromosomal alterations, chromosomal mutations, or transgenes that provide for the same genetic effect as the chromosomal alterations and/or chromosomal mutations induced by suppression of plastid perturbation target gene can be introduced into host plants to obtain plants that exhibit the desired trait. In this context, the "same genetic effect" means that the introduced chromosomal modification provides for an increase and/or a reduction in expression of one or more endogenous plant genes that is similar to that observed in a plant that has been subjected to plastid perturbation target gene suppression and exhibits the useful trait. In certain embodiments where an endogenous gene is methylated in a plant subjected to plastid perturbation target gene suppression and exhibits both reduced expression of that gene and a useful trait, chromosomal modifications in other plants that also result in reduced expression of that gene and the useful trait are provided. In certain embodiments where an endogenous gene is demethylated in a plant subjected to plastid perturbation target gene suppression and exhibits both increased expression of that gene and a useful trait, chromosomal modifications in other plants that also result in increased expression of that gene and that useful trait are provided.

In certain embodiments, the chromosomal modification that is introduced is a chromosomal alteration. Chromosomal alterations including, but not limited to, a difference in a methylation state can be introduced by crossing a plant comprising the chromosomal alteration to a plant that lacks the chromosomal alteration and selecting for the presence of the alteration in F1, F2, or any subsequent generation progeny plants of the cross. In still other embodiments, the chromosomal alterations in specific target genes can be introduced by expression of a siRNA or hairpin RNA targeted to that gene by RNA directed DNA methylation (Chinnusamy V et al. Sci China Ser C-Life Sci. (2009) 52(4): 331-343; Cigan et al. Plant J 43 929-940, 2005; Heilersig et al. (2006) Mol Genet Genomics 275 437-449; Miki and Shimamoto, Plant Journal 56(4):539-49; Okano et al. Plant Journal 53(1):65-77, 2008).

In certain embodiments, the chromosomal modification is a chromosomal mutation. Chromosomal mutations that provide for reductions or increases in expression of an endogenous gene of a chromosomal locus can include, but are not limited to, insertions, deletions, and/or substitutions of nucleotide sequences in a gene. Chromosomal mutations can result in decreased expression of a gene by a variety of mechanisms that include, but are not limited to, introduction of missense codons, frame-shift mutations, premature translational stop codons, promoter deletions, mutations that disrupt mRNA processing, and the like. Chromosomal mutations that result in increased expression of a gene include, but are not limited to, promoter substitutions, removal of negative regulatory elements from the gene, and the like. Chromosomal mutations can be introduced into specific loci of a plant by any applicable method. Applicable methods for introducing chromosomal mutations in endogenous plant chromosomal loci include, but are not limited to, homologous double stranded break repair (Wright et al., Plant J. 44, 693, 2005; D'Halluin, et al., Plant Biotech. J. 6:93, 2008), non-homologous end joining or a combination of non-homologous end joining and homologous recombination (reviewed in Puchta, J. Exp. Bot. 56, 1, 2005; Wright et al., Plant J. 44, 693, 2005), meganuclease-induced, site specific double stranded break repair (WO/06097853A1, WO/06097784A1, WO/04067736A2, U.S. 20070117128A1), and zinc finger nuclease mediated homologous recombination (WO 03/080809, WO 05/014791, WO 07014275, WO 08/021207). In still other embodiments, desired mutations in endogenous plant chromosomal loci can be identified through use of the TILLING technology (Targeting Induced Local Lesions in Genomes) as described (Henikoff et al., Plant Physiol. 2004, 135:630-636).

In other embodiments, chromosomal modifications that provide for the desired genetic effect can comprise a transgene. Transgenes that can result in decreased expression of an gene by a variety of mechanisms that include, but are not limited to, dominant-negative mutants, a small inhibitory RNA (siRNA), a microRNA (miRNA), a co-suppressing sense RNA, and/or an anti-sense RNA and the like. U.S. patents incorporated herein by reference in their entireties that describe suppression of endogenous plant genes by transgenes include U.S. Pat. Nos. 7,109,393, 5,231,020 and 5,283,184 (co-suppression methods); and U.S. Pat. Nos. 5,107,065 and 5,759,829 (antisense methods). In certain embodiments, transgenes specifically designed to produce double-stranded RNA (dsRNA) molecules with homology to the endogenous gene of a chromosomal locus can be used to decrease expression of that endogenous gene. In such embodiments, the sense strand sequences of the dsRNA can be separated from the antisense sequences by a spacer sequence, preferably one that promotes the formation of a dsRNA (double-stranded RNA) molecule. Examples of such spacer sequences include, but are not limited to, those set forth in Wesley et al., Plant J., 27(6):581-90 (2001), and Hamilton et al., Plant J., 15:737-746 (1998). Vectors for inhibiting endogenous plant genes with transgene-mediated expression of hairpin RNAs are disclosed in U.S. Patent Application Nos. 20050164394, 20050160490, and 20040231016, each of which is incorporated herein by reference in their entirety.

Transgenes that result in increased expression of a gene of a chromosomal locus include, but are not limited to, a recombinant gene fused to heterologous promoters that are stronger than the native promoter, a recombinant gene comprising elements such as heterologous introns, 5' untranslated regions, 3' untranslated regions that provide for increased expression, and combinations thereof. Such promoter, intron, 5' untranslated, 3' untranslated regions, and any necessary polyadenylation regions can be operably linked to the DNA of interest in recombinant DNA molecules that comprise parts of transgenes useful for making chromosomal modifications as provided herein.

Exemplary promoters useful for expression of transgenes include, but are not limited to, enhanced or duplicate versions of the viral CaMV35S and FMV35S promoters (U.S. Pat. No. 5,378,619, incorporated herein by reference in its entirety), the cauliflower mosaic virus (CaMV) 19S promoters, the rice Act1 promoter and the Figwort Mosaic Virus (FMV) 35S promoter (U.S. Pat. No. 5,463,175; incorporated herein by reference in its entirety). Exemplary introns useful for transgene expression include, but are not limited to, the maize hsp70 intron (U.S. Pat. No. 5,424,412; incorporated by reference herein in its entirety), the rice Act1 intron (McElroy et al., 1990, The Plant Cell, Vol. 2, 163-171), the CAT-1 intron (Cazzonnelli and Velten, Plant Molecular Biology Reporter 21: 271-280, September 2003), the pKANNIBAL intron (Wesley et al., Plant J. 2001 27(6):581-90; Collier et al., 2005, Plant J 43: 449-457), the PIV2 intron (Mankin et al. (1997) Plant Mol. Biol. Rep. 15(2): 186-196) and the "Super Ubiquitin" intron (U.S. Pat. No. 6,596,925, incorporated herein by reference in its entirety; Collier et al., 2005, Plant J 43: 449-457). Exemplary polyadenylation sequences include, but are not limited to, and *Agrobacterium* tumor-inducing (Ti) plasmid nopaline synthase (NOS) gene and the pea ssRUBISCO E9 gene polyadenylation sequences.

Plant lines and plant populations obtained by the methods provided herein can be screened and selected for a variety of useful traits by using a wide variety of techniques. In particular embodiments provided herein, individual progeny plant lines or populations of plants obtained from the selfs or outcrosses of plants where plastid perturbation target gene expression was suppressed to other plants are screened and selected for the desired useful traits.

In certain embodiments, the screened and selected trait is improved plant yield. In certain embodiments, such yield improvements are improvements in the yield of a plant line relative to one or more parental line(s) under non-stress conditions. Non-stress conditions comprise conditions where water, temperature, nutrients, minerals, and light fall within typical ranges for cultivation of the plant species. Such typical ranges for cultivation comprise amounts or values of water, temperature, nutrients, minerals, and/or light that are neither insufficient nor excessive. In certain embodiments, such yield improvements are improvements in the yield of a plant line relative to parental line(s) under abiotic stress conditions. Such abiotic stress conditions include, but are not limited to, conditions where water, temperature, nutrients, minerals, and/or light that are either insufficient or excessive. Abiotic stress conditions would thus include, but are not limited to, drought stress, osmotic stress, nitrogen stress, phosphorous stress, mineral stress, heat stress, cold stress, and/or light stress. In this context, mineral stress includes, but is not limited to, stress due to insufficient or excessive potassium, calcium, magnesium, iron, manganese, copper, zinc, boron, aluminum, or silicon. In this context, mineral stress includes, but is not limited to, stress due to excessive amounts of heavy metals including, but not limited to, cadmium, copper, nickel, zinc, lead, and chromium.

Improvements in yield in plant lines obtained by the methods provided herein can be identified by direct measurements of wet or dry biomass including, but not limited to, grain, lint, leaves, stems, or seed. Improvements in yield can also be assessed by measuring yield related traits that include, but are not limited to, 100 seed weight, a harvest index, and seed weight. In certain embodiments, such yield improvements are improvements in the yield of a plant line relative to one or more parental line(s) and can be readily determined by growing plant lines obtained by the methods provided herein in parallel with the parental plants. In certain embodiments, field trials to determine differences in yield whereby plots of test and control plants are replicated, randomized, and controlled for variation can be employed (Giesbrecht F G and Gumpertz M L. 2004. Planning, Construction, and Statistical Analysis of Comparative Experiments. Wiley. New York; Mead, R. 1997. Design of plant breeding trials. In Statistical Methods for Plant Variety Evaluation. eds. Kempton and Fox. Chapman and Hall. London). Methods for spacing of the test plants (i.e. plants obtained with the methods of this invention) with check plants (parental or other controls) to obtain yield data suitable for comparisons are provided in references that include, but are not limited to, any of Cullis, B. et al. J. Agric. Biol. Env. Stat. 11:381-393; and Besag, J. and Kempton, R A. 1986. Biometrics 42: 231-251).

In certain embodiments, the screened and selected trait is improved resistance to biotic plant stress relative to the parental lines. Biotic plant stress includes, but is not limited to, stress imposed by plant fungal pathogens, plant bacterial pathogens, plant viral pathogens, insects, nematodes, and herbivores. In certain embodiments, screening and selection of plant lines that exhibit resistance to fungal pathogens including, but not limited to, an *Alternaria* sp., an *Ascochyta* sp., a *Botrytis* sp.; a *Cercospora* sp., a *Colletotrichum* sp., a *Diaporthe* sp., a *Diplodia* sp., an *Erysiphe* sp., a *Fusarium* sp., *Gaeumanomyces* sp., *Helminthosporium* sp., *Macrophomina* sp., a *Nectria* sp., a *Peronospora* sp., a *Phakopsora* sp., *Phialophora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp, a *Pythium* sp., a *Rhizoctonia* sp., a *Scerotium* sp., a *Sclerotinia* sp., a *Septoria* sp., a *Thielaviopsis* sp., an *Uncinula* sp, a *Venturia* sp., and a *Verticillium* sp. is provided. In certain embodiments, screening and selection of plant lines that exhibit resistance to bacterial pathogens including, but not limited to, an *Erwinia* sp., a *Pseudomonas* sp., and a *Xanthamonas* sp. is provided. In certain embodiments, screening and selection of plant lines that exhibit resistance to insects including, but not limited to, aphids and other piercing/sucking insects such as *Lygus* sp., lepidoteran insects such as *Armigera* sp., *Helicoverpa* sp., *Heliothis* sp., and *Pseudoplusia* sp., and coleopteran insects such as *Diabroticus* sp. is provided. In certain embodiments, screening and selection of plant lines that exhibit resistance to nematodes including, but not limited to, *Meloidogyne* sp., *Heterodera* sp., *Belonolaimus* sp., *Ditylenchus* sp., *Globodera* sp., *Naccobbus* sp., and *Xiphinema* sp. is provided.

Other useful traits that can be obtained by the methods provided herein include various seed quality traits including, but not limited to, improvements in either the compositions or amounts of oil, protein, or starch in the seed. Still other useful traits that can be obtained by methods provided herein include, but are not limited to, increased biomass, non-flowering, male sterility, digestability, seed filling period, maturity (either earlier or later as desired), reduced lodging, and plant height (either increased or decreased as desired). Still other useful traits that can be obtained by methods provided herein include, but are not limited to, delayed leaf senescence, increased flower number, improved architecture for high density planting, improved photosynthesis, increased root mass, increased cell number, improved seedling vigor, improved seedling size, increased rate of cell division, improved metabolic efficiency, and increased meristem size.

In addition to any of the aforementioned traits, particularly useful traits for sorghum that can be obtained by the methods provided herein also include, but are not limited to: i) agronomic traits (flowering time, days to flower, days to flower-post rainy, days to flower-rainy; ii) fungal disease resistance (sorghum downy mildew resistance—glasshouse, sorghum downy mildew resistance-field, sorghum grain mold, sorghum leaf blight resistance, sorghum rust resistance; iii) grain related trait: (Grain dry weight, grain number, grain number per square meter, Grain weight over panicle. seed color, seed luster, seed size); iv) growth and development stage related traits (basal tillers number, days to harvest, days to maturity, nodal tillering, plant height, plant height-postrainy); v) inflorescence anatomy and morphology trait (threshability); vi) Insect damage resistance (sorghum shoot fly resistance-post-rainy, sorghum shoot fly resistance-rainy, sorghum stem borer resistance); vii) leaf related traits (leaf color, leaf midrib color, leaf vein color, flag leaf weight, leaf weight, rest of leaves weight); viii) mineral and ion content related traits (shoot potassium content, shoot sodium content); ix) panicle related traits (number of panicles, panicle compactness and shape, panicle exertion, panicle harvest index, panicle length, panicle weight, panicle weight without grain, panicle width); x) phytochemical compound content (plant pigmentation); xii) spikelet anatomy and morphology traits (glume color, glume covering); xiii) stem related trait (stem over leaf weight, stem weight); and xiv) miscellaneous traits (stover related traits, metabolised energy, nitrogen digestibility, organic matter digestibility, stover dry weight).

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Grafting of Arabidopsis Msh1 Rootstock to Wild-Type Scions

Arabidopsis thaliana Col-0 wildtype and msh1 advanced generation mutant (chm1-1; Abdelnoor et al. Proc. Natl. Acad. Sci. USA 100(10): 5968-5973, 2003; Redei, G. P. (1973) Mutat. Res. 18, 149-162) were used for reciprocal grafting experiments. Three different rootstock-scion combinations were made as shown in Table 2 below. Arabidopsis inflorescence stem wedge grafting was done according to Nissar et al. Plant Methods 2012, 8:50, 2012. All successful grafts were grown under controlled environment conditions with 16 hr photoperiods. Individual graft lines were harvested and progeny plants were analyzed at 12 hr photoperiod. Col-0 and msh1 non-grafted plants were included as control plants.

TABLE 2

Plant grafts

| Grafted plant | Rootstocks | Scions (from different plants) |
|---|---|---|
| 1 (Col-0 on Col-0) | Col-0 | Col-0 |
| 2 (Col-0 on msh1) | Col-0 | msh1 |
| 3 (msh1 on Col-0) | msh1 | Col-0 |

Figure 3:
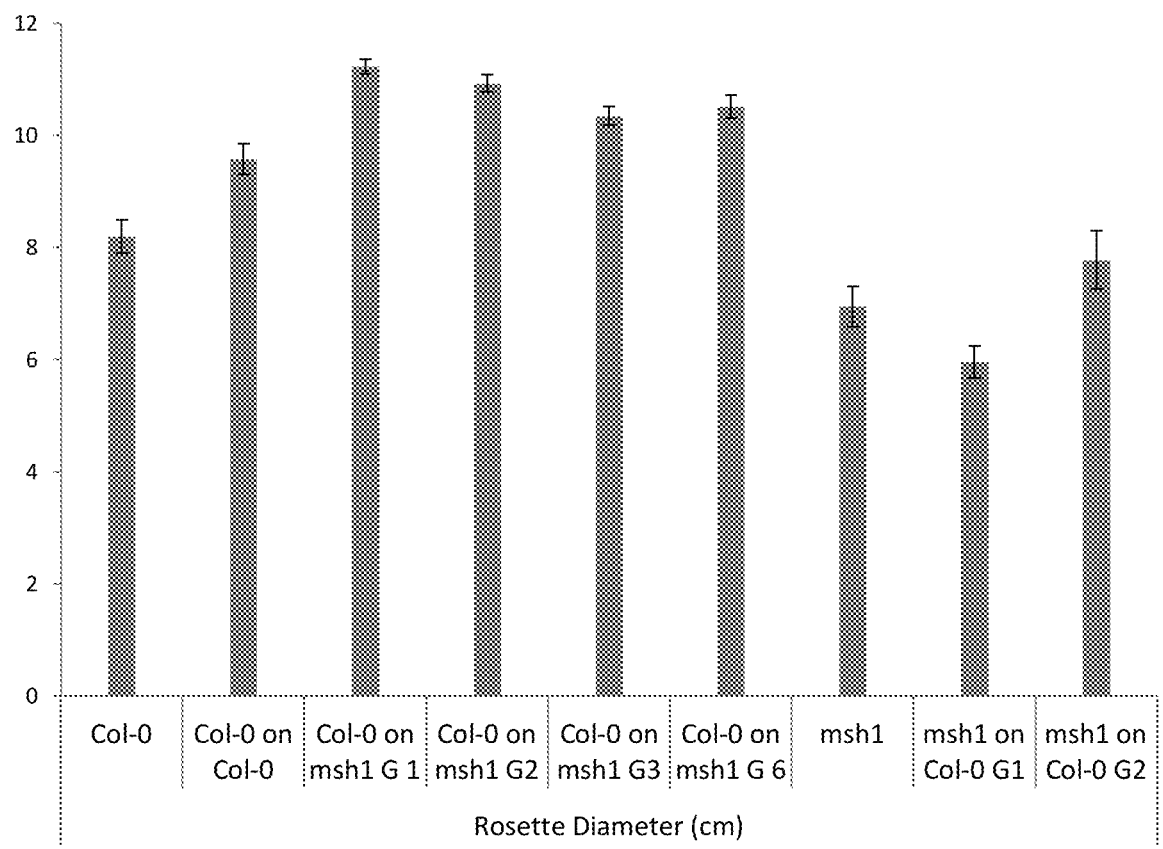
FIG. 3 illustrates, from left to right, the differences in rosette diameter (in cm) for the indicated plants: (a) progeny of an ungrafted wild-type Columbia-0 ecotype plant (Col-0); (b) progeny of a wild-type Columbia-0 ecotype scion grafted to wild-type Columbia-0 ecotype rootstock (Col-0 on Col-0); (c, d, e, f) first, second, third, and sixth independent grafts of a wild-type Columbia-0 ecotype scion to msh1 rootstock (Col-0 on msh1 G1, Col-0 on msh1 G2, and Col-0 on msh1 G3, and Col-0 on msh1 G6, respectively); and (g) first and second grafts of a msh1 scion grafted to wild-type Columbia-0 ecotype rootstock (msh1 on Col-0 G1 and msh1 on Col-0 G2, respectively).
Figure 4:
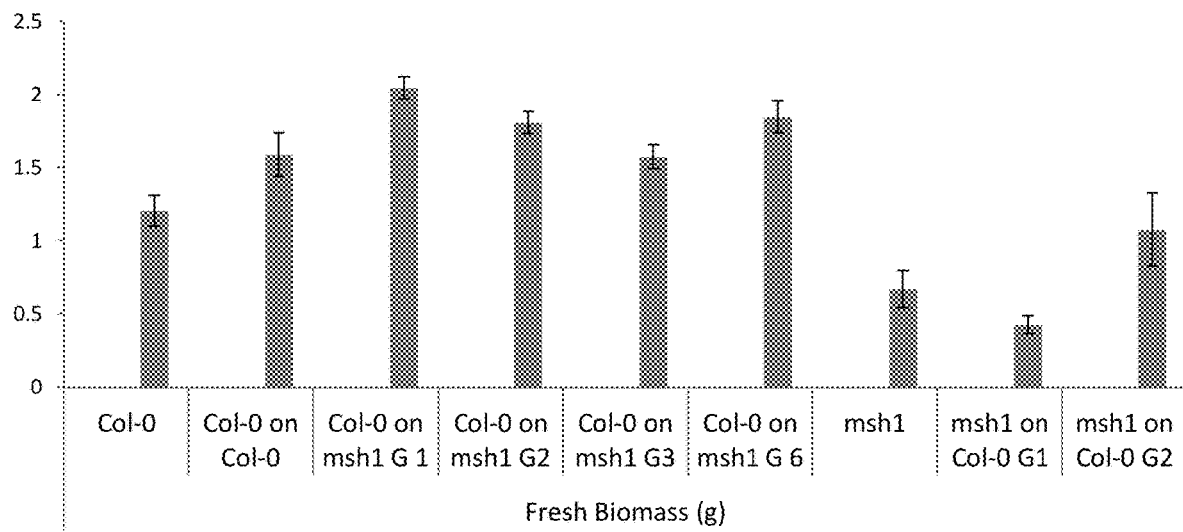
FIG. 4 illustrates, from left to right, the differences in fresh biomass (in grams) for the indicated plants: (a) progeny of an ungrafted wild-type Columbia-0 ecotype plant (Col-0); (b) progeny of a wild-type Columbia-0 ecotype scion grafted to wild-type Columbia-0 ecotype rootstock (Col-0 on Col-0); (c, d, e, f) first, second, third, and sixth independent grafts of a wild-type Columbia-0 ecotype scion to msh1 rootstock (Col-0 on msh1 G1, Col-0 on msh1 G2, and Col-0 on msh1 G3, and Col-0 on msh1 G6, respectively); and (g) first and second grafts of a msh1 scion grafted to wild-type Columbia-0 ecotype rootstock (msh1 on Col-0 G1 and msh1 on Col-0 G2, respectively).

Results of these experiments are shown in FIGS. 1, 2, 3, and 4. In FIGS. 3 and 4, the results obtained with progeny from independent grafts (i.e. Col-0 on msh1 G1, Col-0 on msh1 G2, Col-0 on msh1 G3, and Col-0 on msh1 G6; and msh1 on Col-0 G1 and msh1 on Col-0 G2) show the range of variation that occurs across grafts (replicates) of the experiment. Progeny of the Col-0 on msh1 grafted plant exhibited improved seedling vigor in comparison to progeny from control grafts (Col-0 on Col-0 and msh1 on Col-0) and control plants (Col-0 and msh1). Progeny of the Col-0 on msh1 grafted plants exhibited increased rosette diameter (FIG. 3) and increased biomass (FIG. 4) in comparison to progeny from control grafts (Col-0 on Col-0 and msh1 on Col-0) and control plants (Col-0 and msh1).

Figure 5:
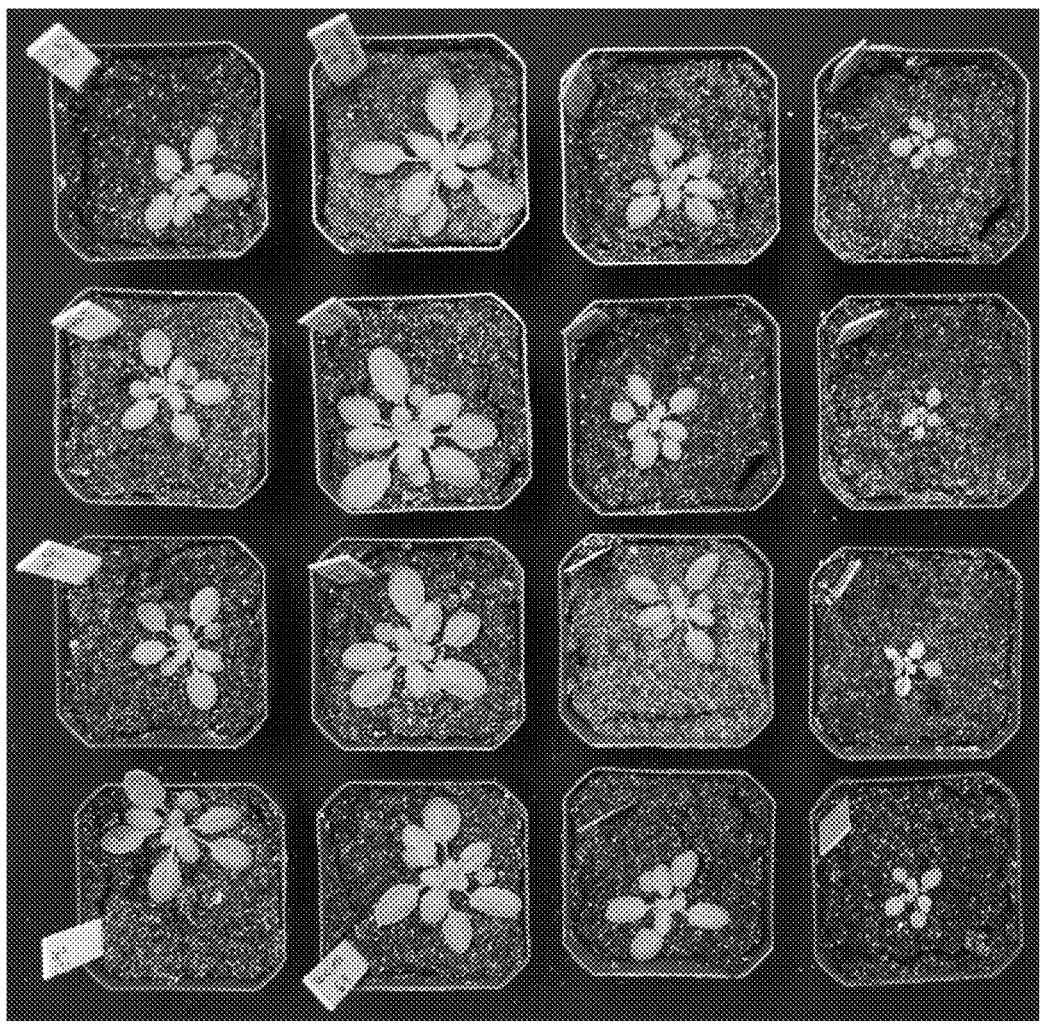
FIG. 5 illustrates second generation progeny plants obtained through self-pollination from the indicated plants (Col-0) or grafted plants (Col-0/msh1: Col-0 scion on msh1 roots; Col-0/Col-0: Col-0 scion on Col-0 roots); msh1/Col-0; msh1 scion on Col-0 roots).

Second generation progeny plants obtained by selfing first progeny plants obtained from the grafted plants are shown in FIG. 5. These materials are derived from selfing the first generation lines that are shown in FIGS. 1-4. All second generation progeny plants are grown at a 12 hr photoperiod as described previously, The Col-0/msh1 progeny plants exhibited a strikingly larger rosette size in comparison to Col-0 control plants or control progeny from the Col-0/Col-0 and msh1/Col-0 grafts. These results demonstrate that the improved growth effects exhibited by progeny plants obtained from the Col-0/msh1 graft are heritable.

TABLE 3

Nucleotide Sequences provided in the Sequence Listing

| Internet Accession Information | SEQ ID NO | Comments |
|---|---|---|
| The Arabidopsis Information Resource (TAIR) 1009043787 on the internet (world wide web) at arabidopsis.org | 1 | Arabidopsis MSH1 Full length cDNA (DNA sequence) |

TABLE 3-continued

Nucleotide Sequences provided in the Sequence Listing

| Internet Accession Information | SEQ ID NO | Comments |
|---|---|---|
| The *Arabidopsis* Information Resource (TAIR) 1009118392 on the internet (world wide web) at arabidopsis.org | 2 | *Arabidopsis* MSH1 Protein (amino acid sequence) |
| NCBI AY856369 on the world wide web at ncbi.nlm.nih.gov/nuccore | 3 | Soybean MSH1 >gi|61696668|gb|AY856369.1| *Glycine max* DNA mismatch repair protein (MSH1) complete cds; (DNA sequence) |
| NCBI Accession AY856370 on the world wide web at ncbi.nlm.nih.gov/nuccore | 4 | *Zea mays* MSH1 gi|61696670|gb|AY856370.1| *Zea mays* DNA mismatch repair protein (MSH1), complete cds; (DNA sequence) |
| NCBI Accession AY866434.1 on the world wide web at ncbi.nlm.nih.gov/nuccore | 5 | Tomato MSH1 >gi|61696672|gb|AY866434.1| *Lycopersicon esculentum* DNA mismatch repair protein (MSH1), partial cds; (DNA sequence) |
| NCBI XM002448093.1 on the world wide web at ncbi.nlm.nih.gov/nuccore | 6 | *Sorghum* MSH1 >gi|242076403:1-3180 *Sorghum bicolor* hypothetical protein; (DNA sequence) |
| Os04g42784.1 Rice Genome Annotation Project - MSU Rice Genome Annotation (Osa1) Release 6.1 Internet address rice.plantbiology.msu.edu/index.shtml | 7 | Rice (*Oryza sativa*) MSH1 coding sequence (DNA sequence) |
| *Brachypodium* Bradi5g15120.1 On the world wide web at gramene.org/Brachypodium_distachyon/ Gene/Summary?db=core;g=BRADI5G1 5120;r=5:18500245-18518223;t=BRADI5G15120.1 | 8 | *Brachypodium* MSH1 coding region (DNA sequence) |
| GSVIVT01027931001 On the world wide web at genoscope.cns.fr/spip/Vitis-vinifera-e.html | 9 | *Vitis Vinifera* MSH1 cDNA (DNA sequence) |
| Cucsa.255860.1 On the internet (world wide web) at phytozome.net/ | 10 | Cucumber (*Cucumis sativa*) MSH1 coding sequence; (DNA sequence) |
| GenBank Accession ES831813.1 on the world wide web at ncbi.nlm.nih.gov/nucest | 11 | Cotton (*Gossypium hirsutum*) MSH1 partial cDNA sequence (EST); (DNA sequence) |
| Oryza_sativa_msh1_2000up >Rice-LOC_Os04g42784 | 12 | Oryza_sativa_msh1_Promoter and 5' UTR |
| Solanum_lycopersicum_2000up >Tomato-Solyc09g090870.2 | 13 | Solanum_lycopersicum msh1 promoter and 5' UTR |
| Sorghum_bicolor_MSH1_2000up_Phyt ozome>Sb06g021950 | 14 | *Sorghum bicolor* msh1 promoter and 5' UTR |
| Arabidopsis-Col0-MSH1 | 15 | Arabidopsis-Col0-MSH1 promoter and 5' UTR |
| >gi|145337631|ref|NM_106295.3| *Arabidopsis thaliana* photosystem II reaction center PsbP family protein cDNA, complete cds | 16 | *Arabidopsis* PPD3 coding region |
| >gi|297839518|ref|XM_002887595.1| *Arabidopsis lyrata* subsp. *lyrata* hypothetical protein, cDNA | 17 | *Arabidopsis* PPD3 coding region |
| >gi|449522158|ref|XM_004168047.1| PREDICTED: *Cucumis sativus* psbP domain-containing protein 3, chloroplastic-like (LOC101211525), cDNA | 18 | *Cucumis sativus* PPD3 coding region |
| >gi|255539323|ref|XM_002510681.1| *Ricinus communis* conserved hypothetical protein cDNA | 19 | *Ricinus communis* PPD3 coding region |
| >gi|359491869|ref|XM_002273296.2| PREDICTED: *Vitis vinifera* psbP domain-containing protein 3, chloroplastic-like (LOC100263326), cDNA | 20 | *Vitis vinifera* PPD3 coding region |

TABLE 3-continued

Nucleotide Sequences provided in the Sequence Listing

| Internet Accession Information | SEQ ID NO | Comments |
|---|---|---|
| >gi\|357467178\|ref\|XM_003603826.1\|*Medicago truncatula* PsbP domain-containing protein (MTR_3g116110) cDNA, complete cds | 21 | *Medicago truncatula* PPD3 coding region |
| >gi\|224083365\|ref\|XM_002306962.1\|*Populus trichocarpa* predicted protein, cDNA | 22 | *Populus trichocarpa* PPD3 coding region |
| >gi\|388521576\|gb\|BT149056.1\| *Lotus japonicus* clone JCVI-FLLj-8L12 unknown cDNA | 23 | *Lotus japonicus* PPD3 coding region |
| gi\|470131466\|ref\|XM_004301567.1\| PREDICTED: *Fragaria vesca* subsp. *vesca* psbP domain-containing protein 3, chloroplastic-like (LOC101302662), mRNA | 24 | *Fragaria vesca* PPD3 coding region |
| >gi\|356517169\|ref\|XM_003527214.1\| PREDICTED: *Glycine max* psbP domain-containing protein 3, chloroplastic-like (LOC100805637), mRNA | 25 | *Glycine max* PPD3 coding region |
| *Solanum lycopersicum* psbP domain-containing protein 3, chloroplastic-like (LOC101247415), mRNA | 26 | *Solanum lycopersicum* PPD3 coding region |
| >gi\|502130964\|ref\|XM_004500773.1\| PREDICTED: *Cicer arietinum* psbP domain-containing protein 3, chloroplastic-like (LOC101499898), transcript variant X2, mRNA | 27 | *Cicer arietinum* PPD3 coding region |
| >gi\|241989846\|dbj\|AK330387.1\| *Triticum aestivum* cDNA, clone: SET4_F09, cultivar: Chinese Spring | 28 | *Triticum aestivum* PPD3 coding region |
| >gi\|115477245\|ref\|NM_001068754.1\| *Oryza sativa* Japonica Group Os08g0512500 (Os08g0512500) mRNA, complete cds | 29 | *Oryza sativa* PPD3 coding region |
| >gi\|357141873\|ref\|XM_003572329.1\| PREDICTED: *Brachypodium distachyon* psbP domain-containing protein 3, chloroplastic-like (LOC100840022), mRNA | 30 | *Brachypodium distachyon* PPD3 coding region |
| >gi\|242383886\|emb\|FP097685.1\| *Phyllostachys edulis* cDNA clone: bphylf043n24, full insert sequence | 31 | *Phyllostachys edulis* PPD3 coding region |
| >gi\|326512571\|dbj\|AK368438.1\| *Hordeum vulgare* subsp. *vulgare* mRNA for predicted protein, partial cds, clone: NIASHv2073K06 | 32 | *Hordeum vulgare* PPD3 coding region |
| >gi\|195613363\|gb\|EU956394.1\| *Zea mays* clone 1562032 thylakoid lumen protein mRNA, complete cds | 33 | *Zea mays* PPD3 coding region |
| >gi\|242082240\|ref\|XM_002445844.1\| *Sorghum bicolor* hypothetical protein, mRNA | 34 | *Sorghum bicolor* PPD3 coding region |
| >gi\|514797822\|ref\|XM_004973837.1\| PREDICTED: *Setaria italica* psbP domain-containing protein 3, chloroplastic-like (LOC101754517), mRNA | 35 | *Setaria italica* PPD3 coding region |
| >gi\|270145042\|gb\|BT111994.1\| *Picea glauca* clone GQ03308_J01 mRNA sequence | 36 | *Picea glauca* PPD3 coding region |
| >gi\|215274040\|gb\|EU935214.1\| *Arachis diogoi* clone AF1U3 unknown mRNA | 37 | *Arachis diogoi* PPD3 coding region |
| >gi\|168003548\|ref\|XM_001754423.1\| *Physcomitrella patens* subsp. *patens* predicted protein (PHYPADRAFT_175716) mRNA, complete cds | 38 | *Physcomitrella patens* PPD3 coding region |
| >gi\|302809907\|ref\|XM_002986600.1\| *Selaginella moellendorffii* hypothetical protein, mRNA | 39 | *Selaginella moellendorffii* PPD3 coding region |
| >gi\|330318510\|gb\|HM003344.1\| *Camellia sinensis* clone U10BcDNA 3162 | 40 | *Camellia sinensis* PPD3 coding region |
| Zea_mays_2000up_phytozome >GRMZM2G360873 | 41 | *Zea mays* Msh1 promoter and 5' UTR |
| AT5G67120RING-F | 42 | primer |
| AT5G67120RING-R | 43 | primer |
| AT1G20690SWI-F | 44 | primer |

TABLE 3-continued

Nucleotide Sequences provided in the Sequence Listing

| Internet Accession Information | SEQ ID NO | Comments |
|---|---|---|
| AT1G20690SWI-R | 45 | primer |
| AT3g271501stMir2-F | 46 | primer |
| AT3g271501stMir2-R | 47 | primer |
| AT3g271502ndMir2-F | 48 | primer |
| AT3g271502ndMir2-R | 49 | primer |
| RNAi-F | 50 | primer |
| RNAi-R | 51 | primer |
| upstream_1 kb\| photosystem II reaction center PsbP family protein mRNA | 52 | *Arabidopsis thaliana* PPD3 promoter |
| upstream_1 kb\|*Oryza sativa* Japonica Group Os08g0512500 (Os08g0512500) mRNA | 53 | *Oryza sativa* PPD3 promoter |
| upstream_1 kb\|PREDICTED: *Solanum lycopersicum* psbP domain-containing protein 3, chloroplastic-like | 54 | *Solanum lycopersicum* PPD3 promoter |

Sequence Listing is provided herewith as a computer readable form (CRF) named "46589_125058_SEQ_LST.txt" and is incorporated herein by reference in its entirety. This sequence listing contains SEQ ID NO:1-54 that are referred to herein.

Example 3

Graft Transmission of the Enhanced Growth Phenotype in Tomato

MSH1 suppression lines in Rutgers background were developed previously (Sandhu et al. Proc Natl Acad Sci USA 104:1766-70, 2007), and progenies from two independent transformation events (T17 and T20) were used in this study. Both lines were confirmed to contain a single transgene copy (Sandhu et al., 2007). Two MSH1-RNAi transgene-null plants each from T17 and T20, showing mild dwarfing phenotype, were crossed with wild type inbred Rutgers reciprocally to generate F1 seeds, and F1 plants were selfed to produce epiF2 families. Progenies from T17 crosses were followed to the epiF4 in both greenhouse and field, while progenies from T20 were followed to the epiF2 in the greenhouse. Plants in the greenhouse were germinated on MetroMix™ 200 medium (SunGro, USA) and maintained at 26-28° C. with 15-h day length and at 20-22.8° C. with 9-h dark periods. Primers Tom-CD1F:5'-CGCAGG-TATCACGA-GGCAAGTGCTAA-3' (SEQ ID NO: 55) and Intro-PIR (new):5'-GTGTACTCATGTGCATCTGACTT-GAC-3' (SEQ ID NO: 56) were used to genotype for the transgene.

Tube Grafting was carried out with tomato seedlings at the two- to four-leaf stage following the procedure described by Rivard and Louws (Grafting for Disease Resistance in Heirloom Tomatoes College of Agriculture and Life Sciences, ed. North Carolina Cooperative Extension Service, 2006). MSH1-RNAi plants with and without transgene were used in the grafting experiments (scion/rootstock): wild type/wild type, wild type/mild-DR (transgene null) and reciprocal, and wild type/dwarf-DR (transgenic) and reciprocal. Fruits from each grafted plant were harvested separately and derived seed planted as the first progeny. Each grafted combination involved at least two replicates, with the experiment repeated three times.

Figure 6A:
FIG. 6A, B, C illustrates graft transmission of the enhanced growth phenotype in tomato, (A) First-generation progeny of grafted Rutgers wild type scion on MSH1-suppressed transgenic dwarf-DR rootstock (right) and wild type scion on wild type rootstock control (left). Photo shows 7-week-old plants. Rutgers wild type scion on transgenic dwarf-DR rootstock progeny plants display greater plant height, evident at 7 weeks (student-t Test, $\alpha<0.05$) (B), and higher fruit yields (student-t Test, $\alpha<0.05$) (C) in the greenhouse. Fruit were harvested at 14 weeks. Error bar is mean±SE. For fruit yield, n=4, for plant height, n=12.
Figure 6B:
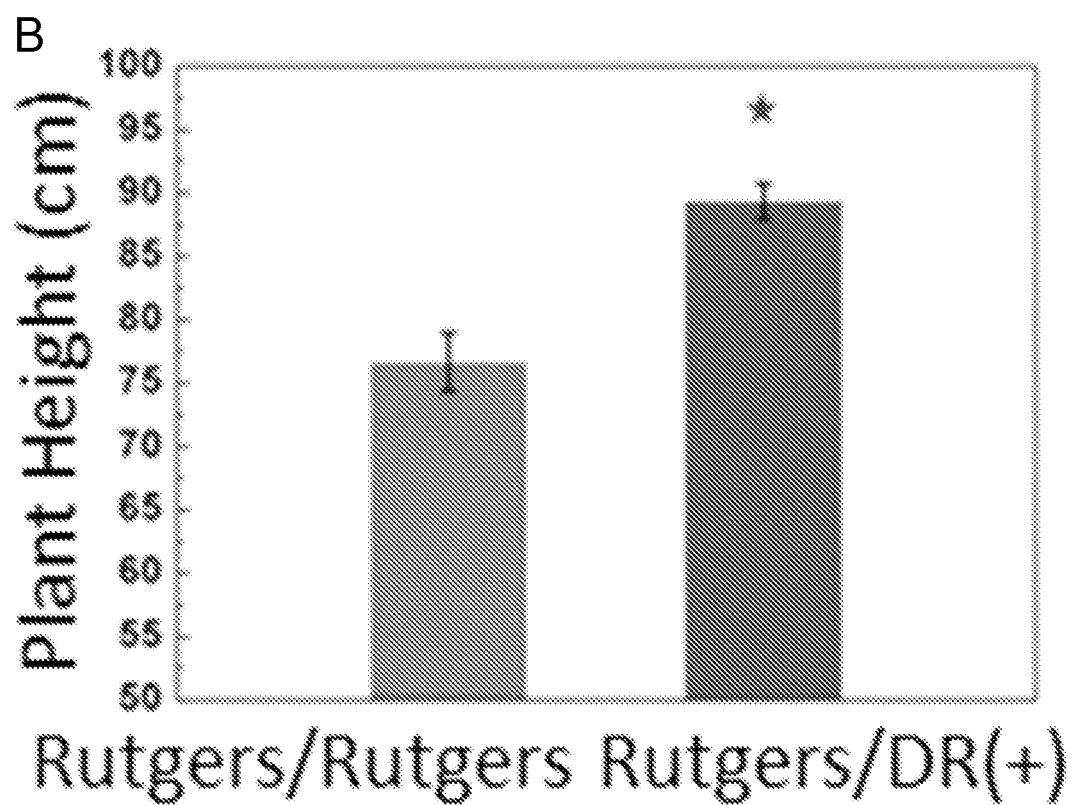
Figure 6C:
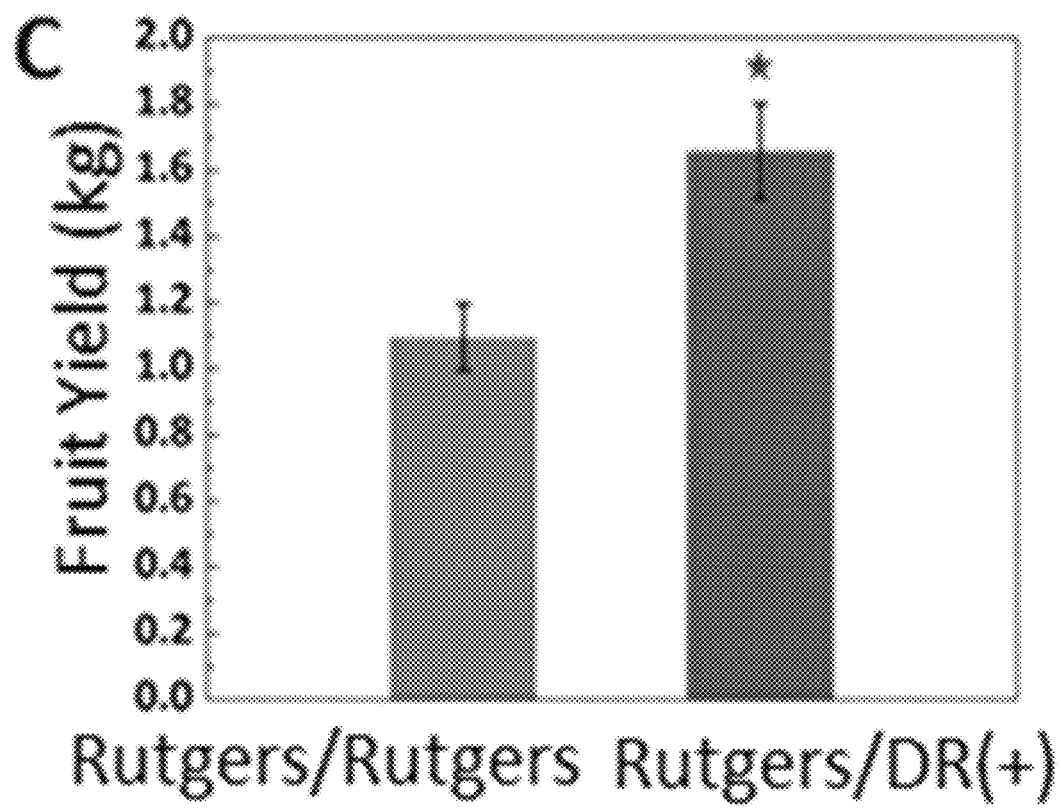

While we detected no significant growth change in progeny coming from wild type grafted to wild type, progeny from wild type scion grafted to the MSH1-RNAi transgenic line as rootstock showed markedly enhanced early growth rate (FIG. 6A). The tomato progeny obtained from wild type scion grafted to the MSH1-RNAi transgenic line as rootstock showed greater plant height (FIG. 6B) and greater fruit yield (FIG. 6C). As in the case of *Arabidopsis*, these results further support the hypothesis that enhanced growth vigor is non-genetic and likely includes a mobile signal within the plant.

Example 4

MSH1 is Localized to a Special Plastid Type and is Associated with PPD3

Earlier studies of MSH1 showed that the protein functions in both mitochondria and plastids. To further investigate the role of MSH1 in plastids, the MSH1 promoter and full-length gene were fused to GFP and stably transformed to *Arabidopsis* ecotype Col-0. While MSH1-GFP signal was detected in nearly all plant tissues throughout development, the spatial pattern of expression appeared to be largely restricted to epidermal cells, vascular parenchyma, meristems and reproductive tissues (FIGS. 7 and 8). This expression pattern was confirmed with gene constructions that included only the MSH1 promoter fused to uidA to assess GUS expression. These experiments demonstrated that the unusual spatial pattern for MSH1 accumulation is directed by the gene's promoter.

Figure 7A:
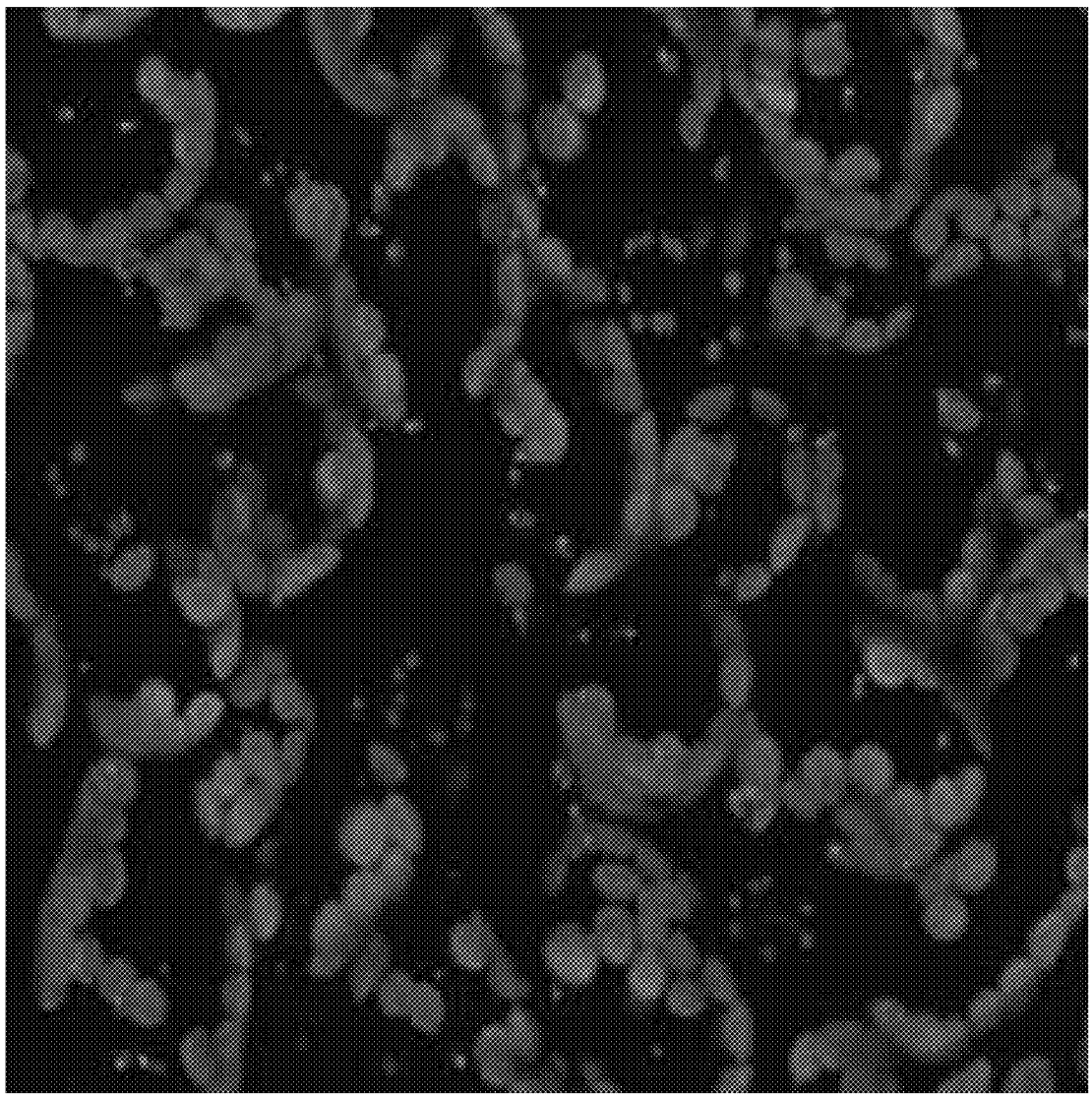
FIG. 7A-J illustrates that MSH1 is located in distinct epidermal and vascular parenchyma plastids. (A) Laser confocal micrograph of the leaf lamina of an *Arabidopsis* MSH1-GFP stable transformant. Mesophyll chloroplasts autofluoresce red. (B) Laser confocal Z-scheme perpendicular rotation to allow simultaneous visualization of optical sections. Note the lack of GFP fluorescence below the top (epidermal) layer. (C) Enlargement from panel A to allow discrimination of the smaller sized plastids containing MSH1-GFP. (D) Laser confocal micrograph of the midrib region of an *Arabidopsis* MSH1-GFP stable transformant. Note the dense population of smaller sized plastids with GFP signal. (E) Confocal Z-scheme perpendicular rotation of the midrib section. Note the dense GFP signal through all layers. (F) MSH1-GUS localization to plastids in the vascular parenchyma of the leaf midrib. (G) Floral stem cross-section of an *Arabidopsis* MSH1-GUS stable transformant. Note the intensity of GUS staining within the vascular parenchyma cells. (H) MSH1-GUS expression in a cleared root of an *Arabidopsis* stable transformant. (I) MSH1-GUS localization pattern in a cleared *Arabidopsis* leaf. Note the intense staining of the vascular tissue and epidermal trichomes. (J) Leaf cross-section showing MSH1-GFP localization by laser confocal microscopy. Yellow arrow indicates vascular bundle.
Figure 7B:
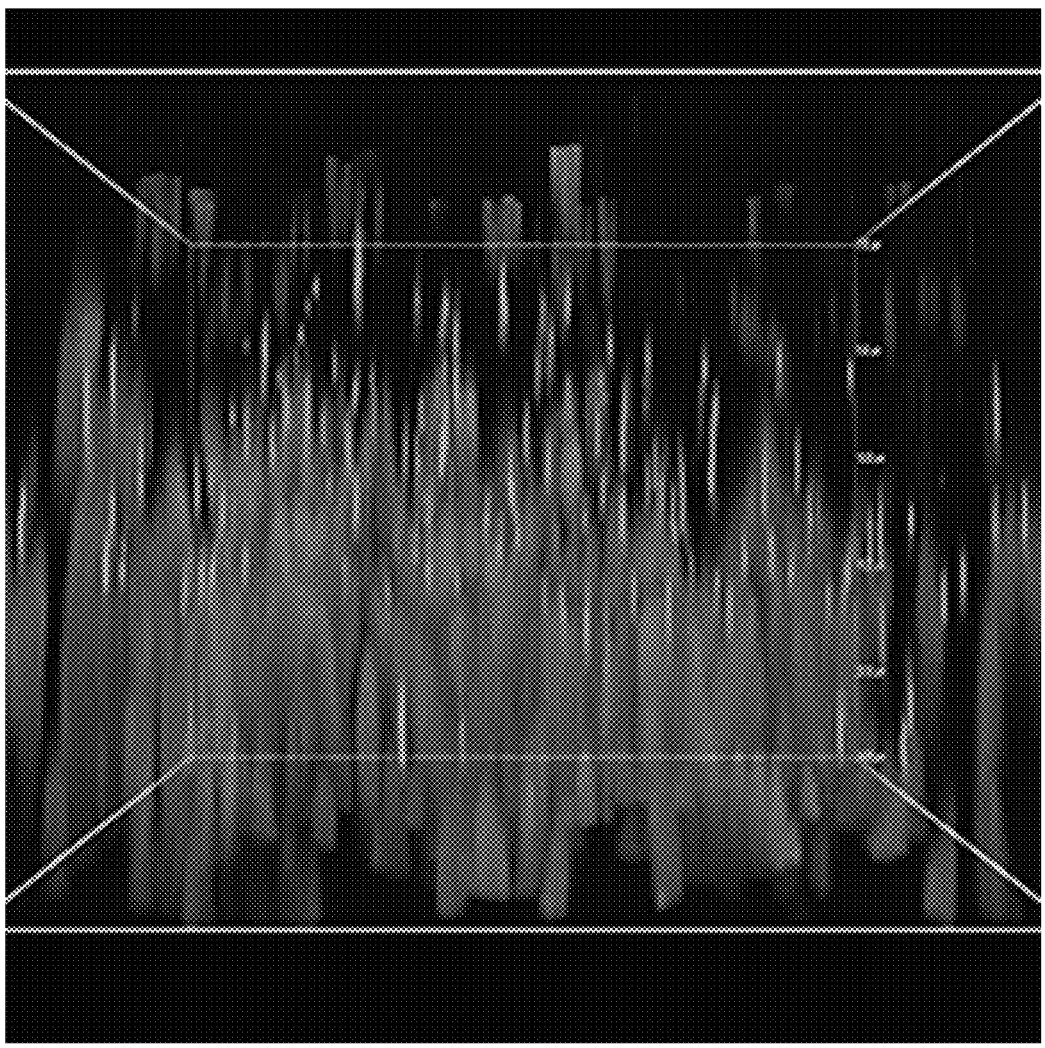
Figure 7C:
Figure 7D:
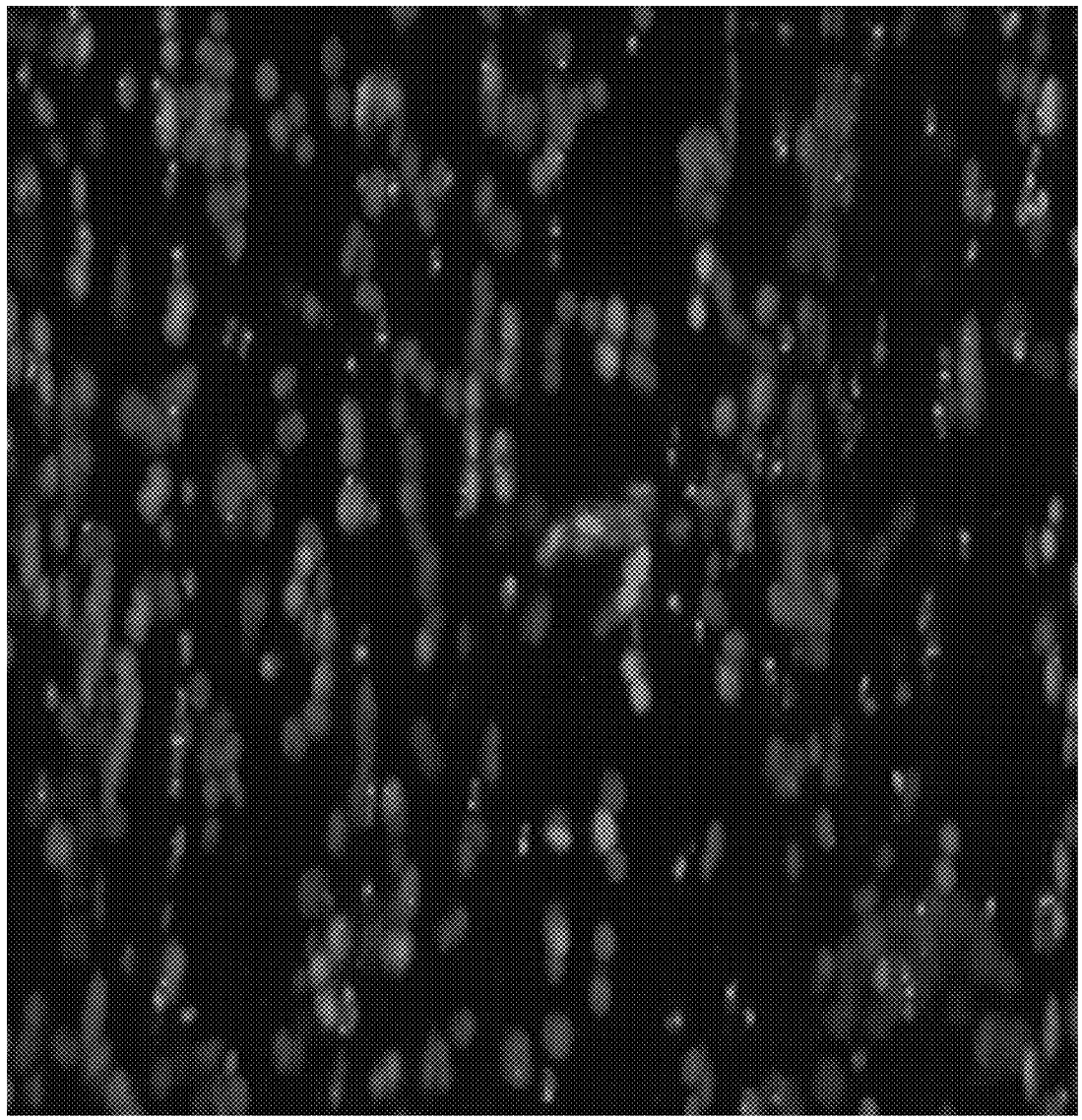
Figure 7E:
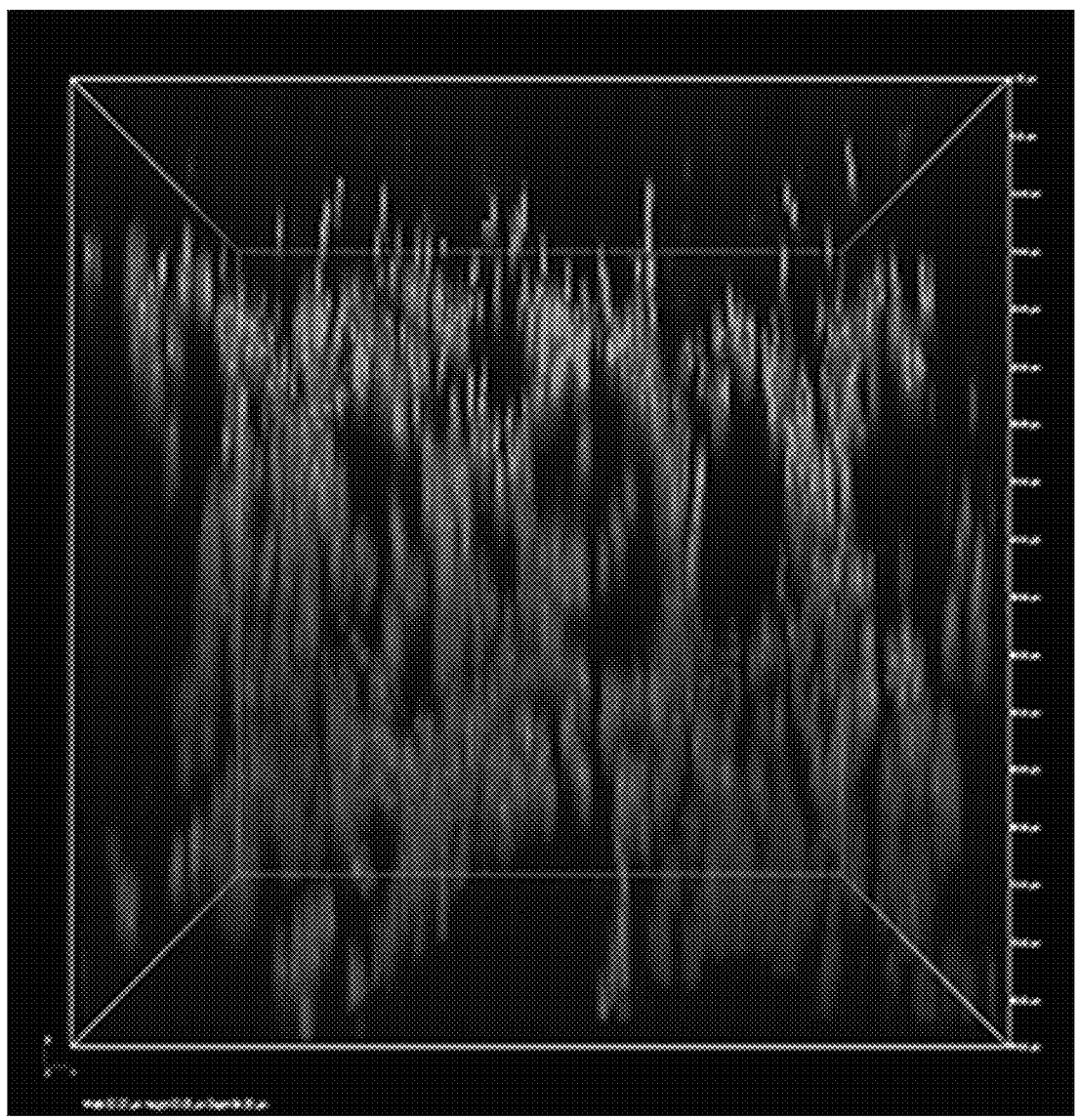
Figure 7F:
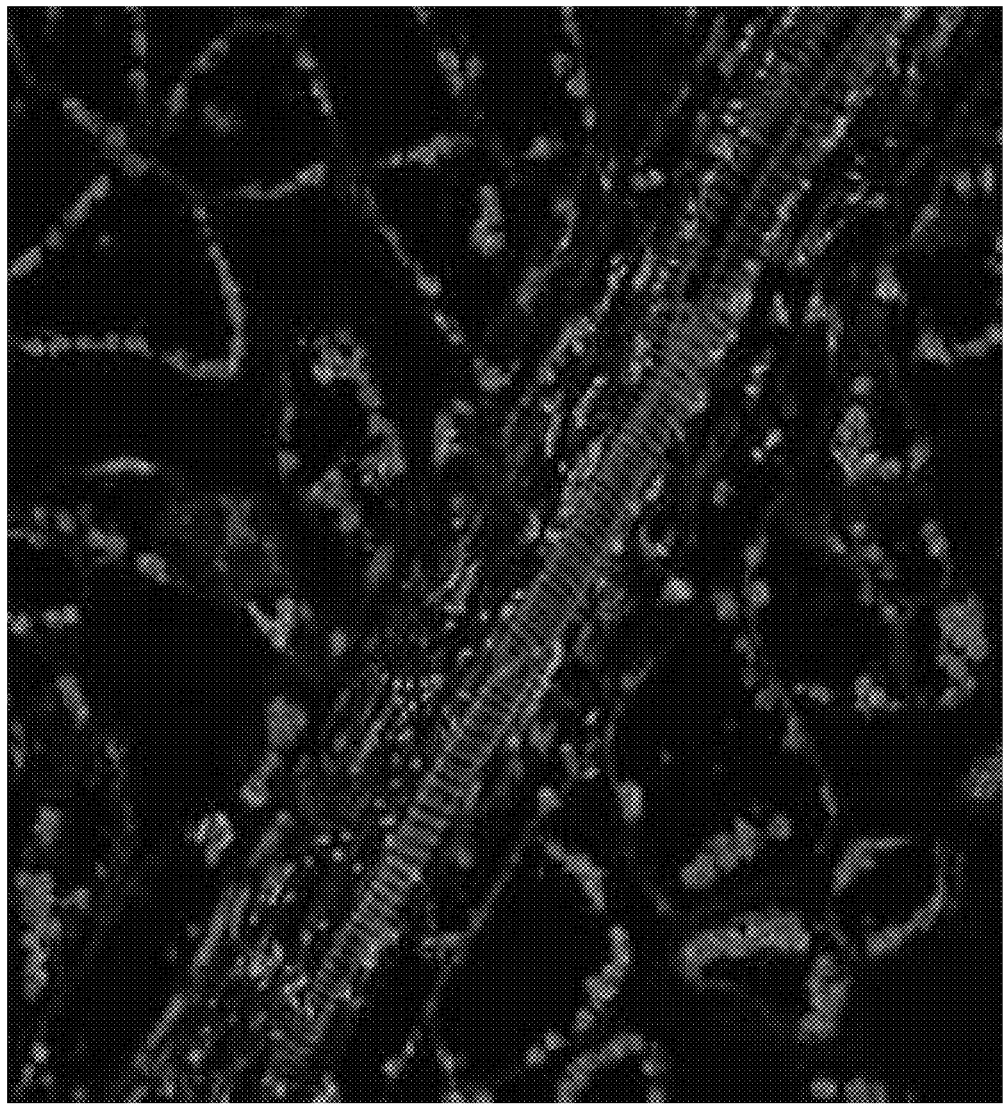
Figure 7G:
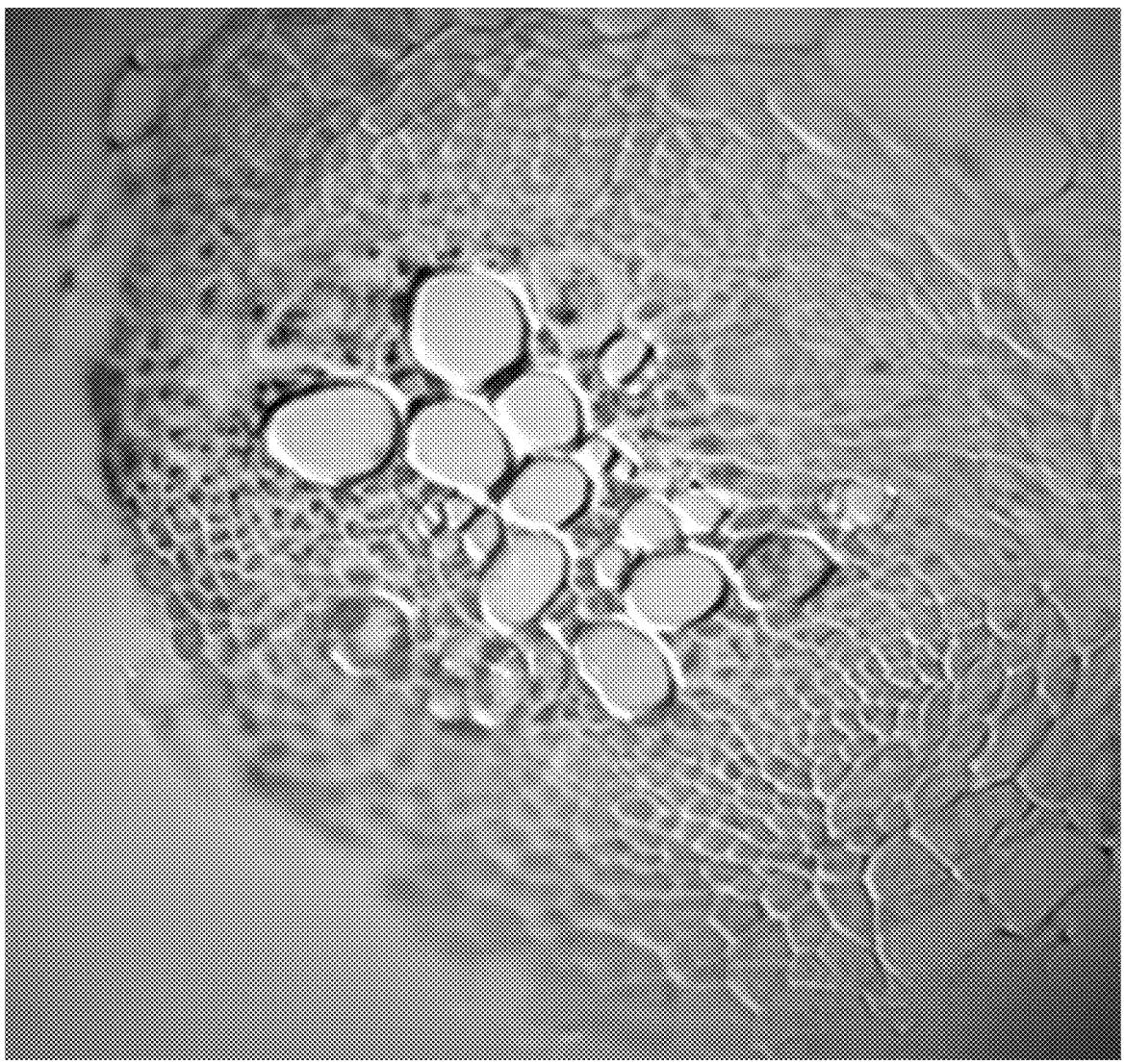
Figure 7H:
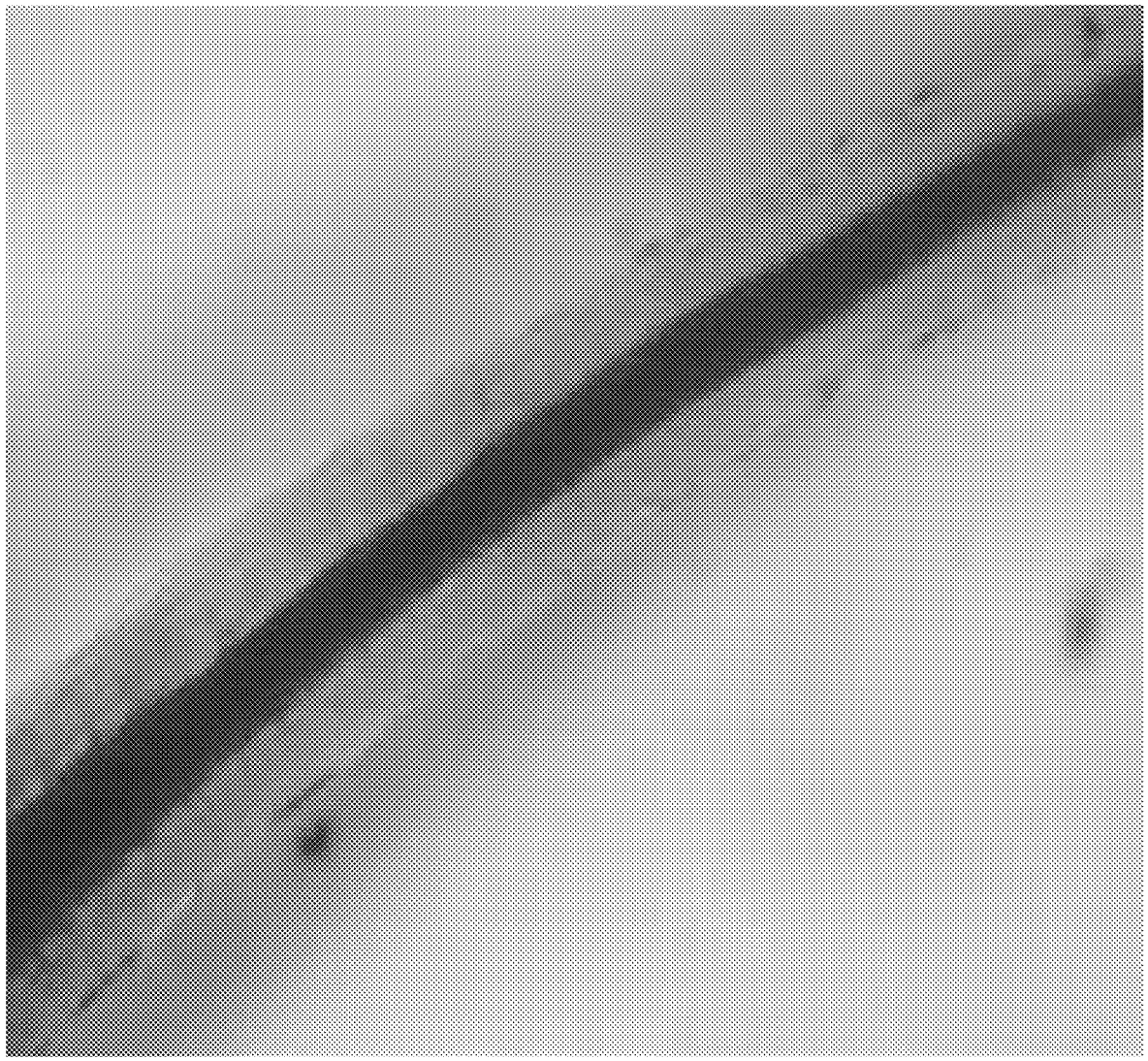
Figure 7I:
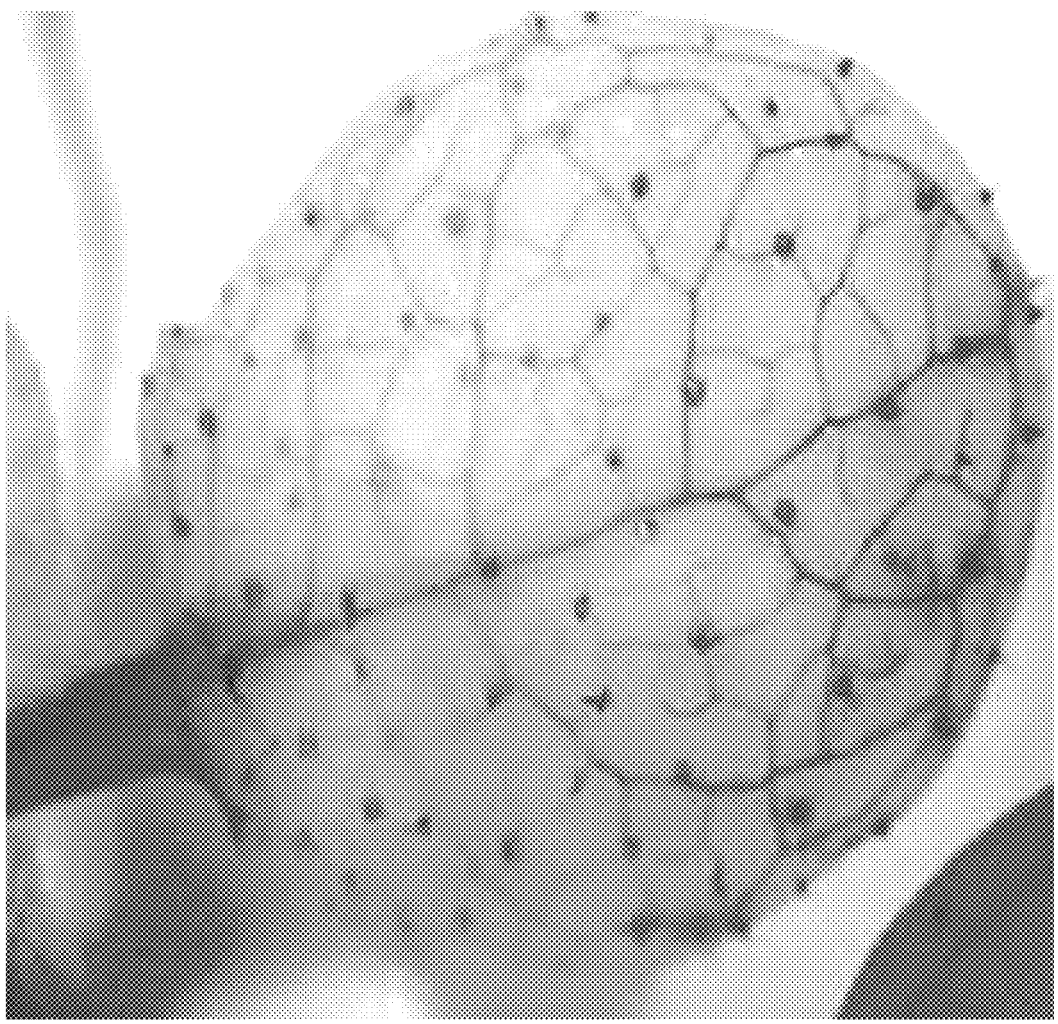
Figure 7J:
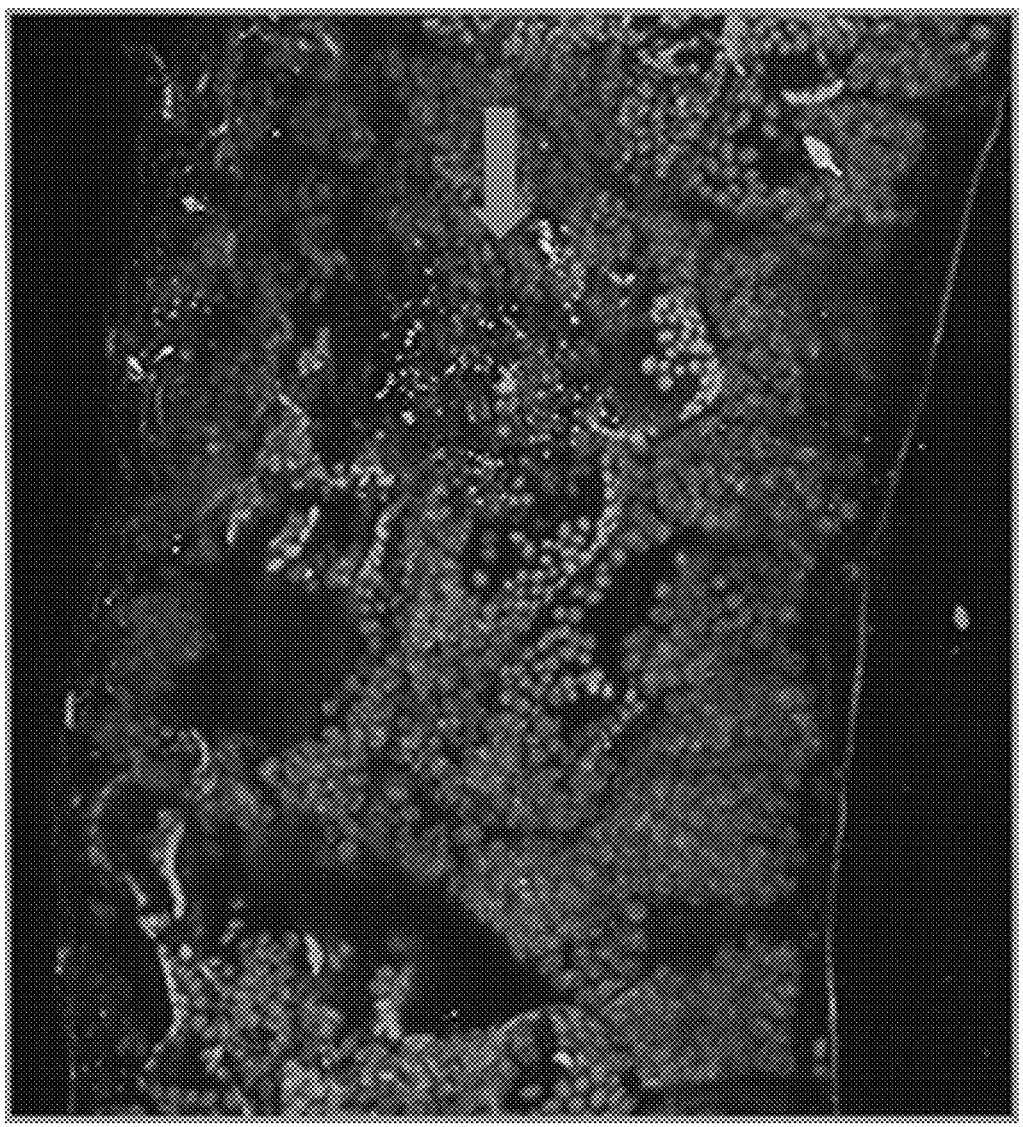

Analysis by laser scanning confocal microscopy suggested that in the leaf lamina region, GFP signal resided only on the upper surface of cells. However, nearing the midrib, the signal was detected in nearly all cell layers (FIG. 7B, E). At higher resolution, one is able to observe GFP as punctate signals from within plastid structures that are visibly smaller than mesophyll chloroplasts (FIG. 7C). The size difference was more readily estimated by electron microscopy, where these smaller plastids approximate 30-40% the size of the mesophyll chloroplasts in neighboring cells (FIG. 9).

Figure 10A:
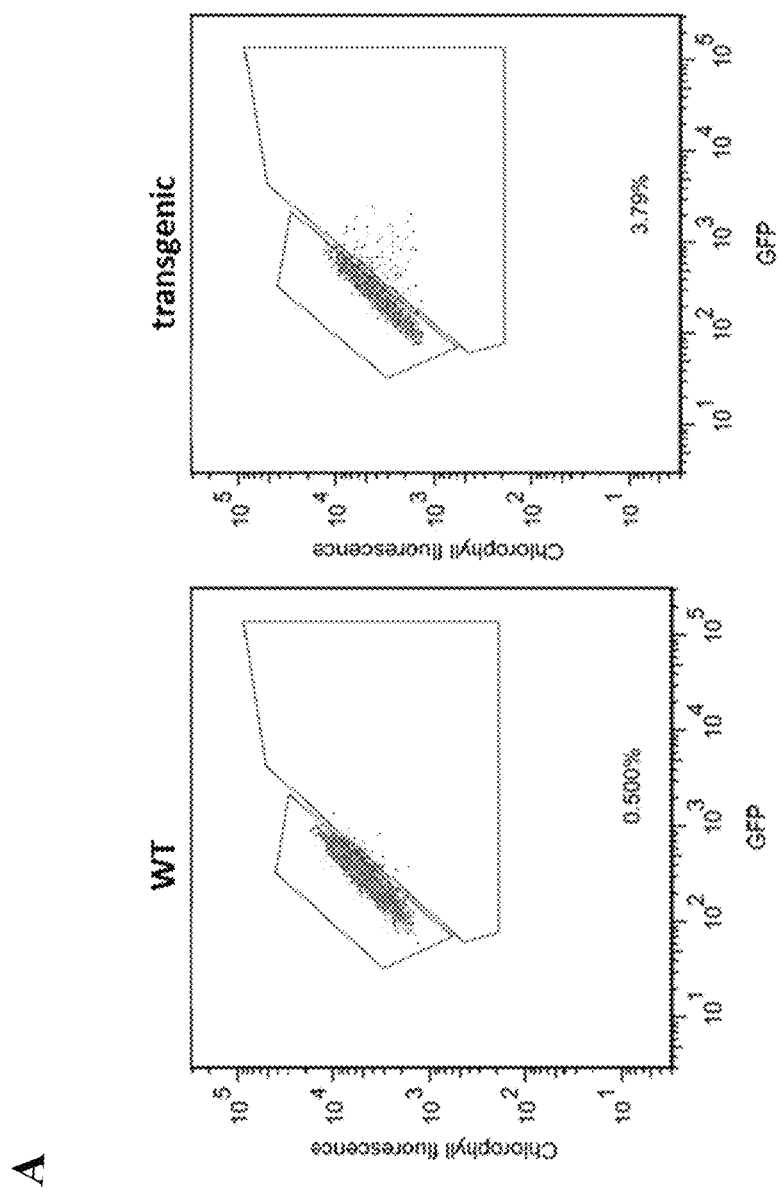
FIG. 10A, B shows that sensory plastids comprise ca 2-3% of the plastids derived from crude plastid extractions. Fluorescence-activated cell sorting (FACS) analysis was carried out with total leaf crude plastid extractions derived from (A) *Arabidopsis* and (B) tobacco plants stably transformed with the *Arabidopsis* full-length MSH1-GFP fusion construct, comparing to wildtype as negative control for plastid autofluorescence. Plots show GFP fluorescence (X axis) over background auto-fluorescence of chlorophyll. The percentage in each plot of GFP sorted chloroplasts in wildtype and transgenic lines is indicated at the bottom of each plot.
Figure 10B:
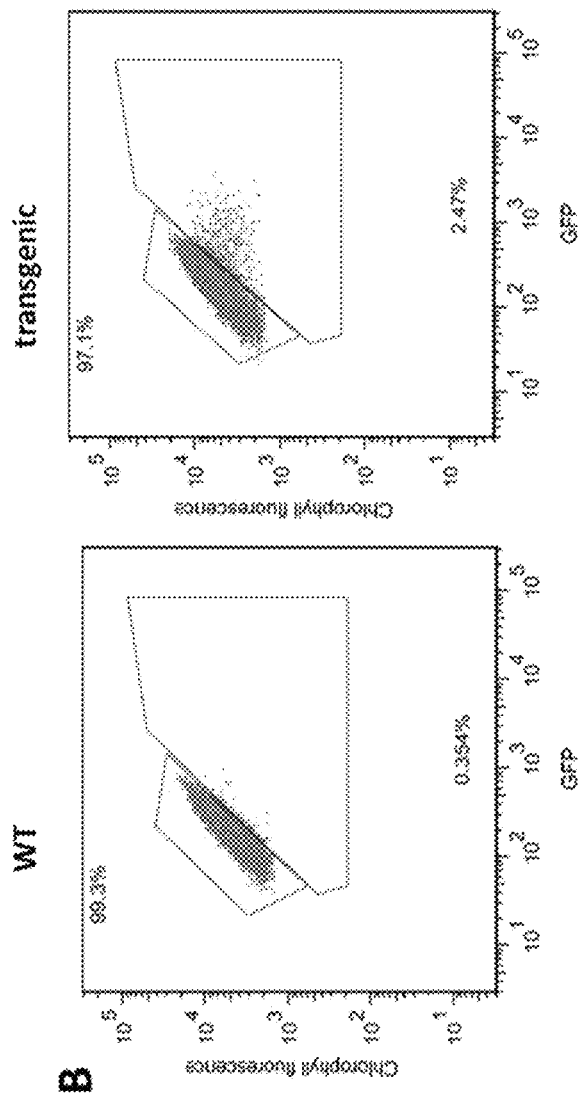

The smaller, MSH1-associated plastids display less extensive thylakoid membrane and granal stacking, and contained far fewer visible plastoglobuli than did mesophyll chloroplasts (FIG. 9B). While their autofluorescence signal was lower than mesophyll chloroplasts, they contained abundant starch. MSH1 expression has been shown previously to be modulated by abiotic stress (Shedge et al. 2010, Xu et al. 2011), and so we have termed these unusual MSH1-associated organelles 'sensory' plastids. To learn whether these organelles, and their unusual association with MSH1, can be generalized to other plant species, we stably transformed the *Arabidopsis* MSH1-GFP gene construct to tobacco (*Nicotiana tabacum* L). Confocal microscopy in tobacco revealed a similar pattern of smaller organelles in the epidermal cells, as well as a seemingly specialized association by MSH1 to these organelles (FIG. 9C-E). In both *Arabidopsis* and tobacco, crude plastid preparations were analyzed by fluorescence-activated cell sorting (FACS) to estimate the fraction of plastids that contain MSH1. Results from these experiments suggest that MSH1-containing sensory plastids comprise approximately 2-3% of the total intact plastids isolated from leaves (FIG. 10).

Figure 11A:
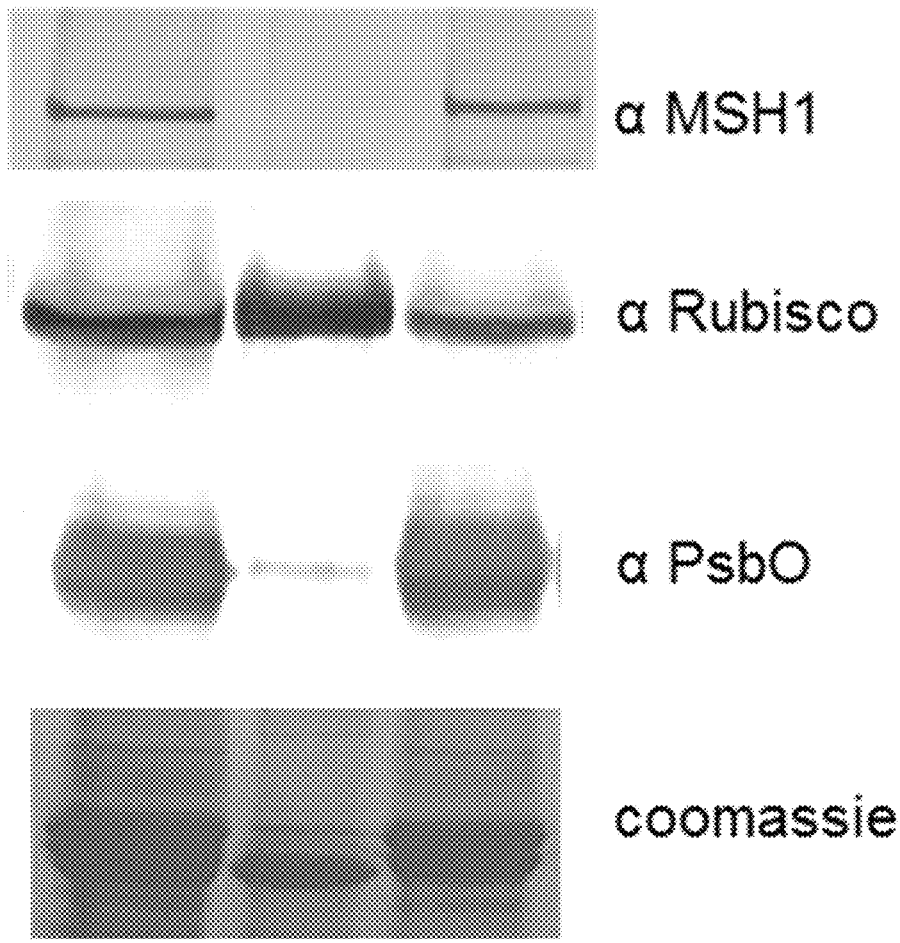
Figure 11C:
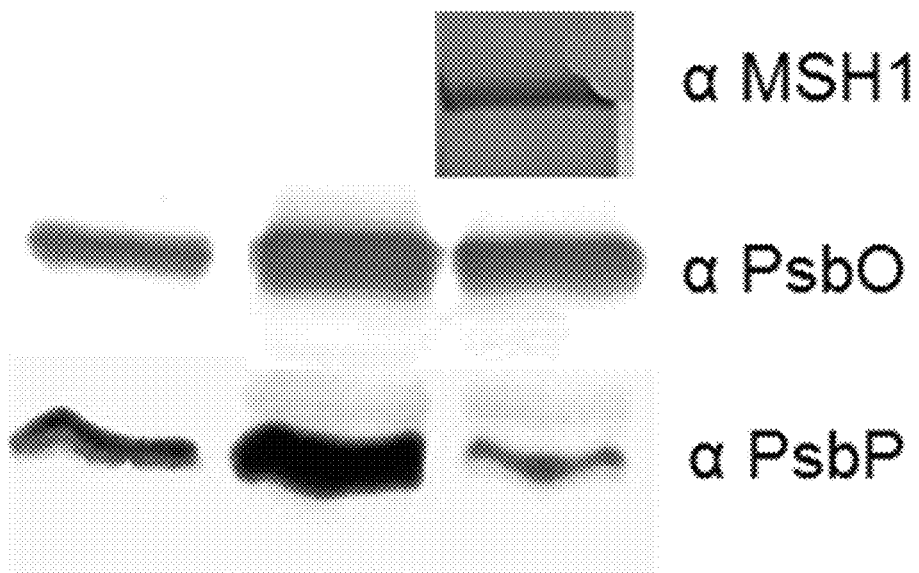
Figure 13A:
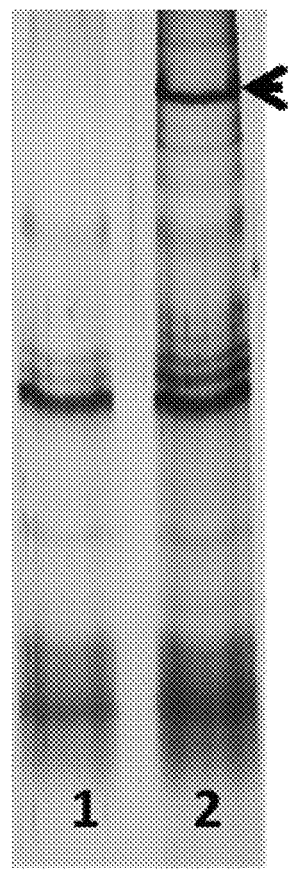
FIG. 13A-C shows that MSH1 interacts with components of the photosynthetic electron transport chain. (A) MSH1 coIP assay products, with msh1 negative control in lane 1 and wildtype in lane 2. Arrow indicates MSH1 protein. This assay produced PsbA and PetC as putative interaction partners to MSH1. (B) Yeast 2-hybrid assay with full-length MSH1 as bait in one-on-one assay with PsbA and PetC, allowed to incubate for one week, suggesting weak interaction. (C) Yeast 2-hybrid experiments with MSH1 full-length or individual domains as bait in combination with various components of the PSII oxygen evolving complex (PsbO1/O2, PPD3), D1 (PsbA) and PetC from the neighboring B6F complex. Note the weak signal observed for PsbA and PetC.
Figure 13B:
Figure 13C:
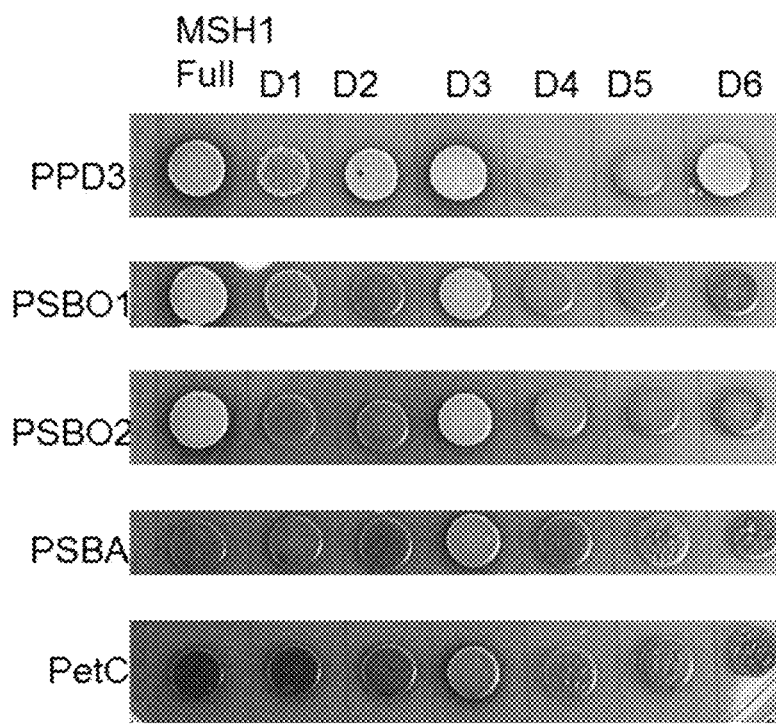

MSH1 resides on the thylakoid membrane and interacts with photosynthetic components The punctate GFP signal observed within the sensory plastids suggests that MSH1 is likely compartmented within the organelle. Because the MSH1 protein is in low abundance, we opted to carry out cell fractionation experiments in an *Arabidopsis* stable MSH1-GFP transformant that is expressed under the control of the native promoter. Plastid fractionations resulted in co-purification of MSH1 with the thylakoid membrane (FIG. 11). This association persisted with mild detergent or salt washes, implying that the protein may be membrane-associated. To investigate possible MSH1 protein partners within the plastid, we carried out yeast 2-hybrid and co-immunoprecipitation experiments. Yeast 2-hybrid studies, with full-length MSH1 as bait in multiple matings, identified sixteen genes as putative interactors. Of these, three were selected for further investigation based on their plastid localization and consistent reproducibility in subsequent one-on-one matings. Two of the three plastid proteins, PsbO1 and PsbO2, are members of the photosystem II oxygen evolving complex, and the third, PPD3, is a 27.5 kDa PsbP domain-containing protein also thought to reside in the lumen (Ifuku et al. 2010). CoIP experiments with MSH1 did not produce PsbO1 or PsbO2, but did produce PPD3 (FIG. 12), as well as two additional components of the photosynthetic apparatus, PsbA (D1) and PetC. Since PsbA and PetC were not identified by yeast 2-hybrid screening, we introduced these into one-on-one matings with MSH1, producing weak signals for positive interaction (FIG. 13B MSH1 can be subdivided to six intervals based on cross-species protein alignments (Abdelnoor et al. 2006), with domain 1 containing a DNA binding domain, Domain V containing an ATPase domain and Domain VI encoding a GIY-YIG endonuclease domain. We subcloned MSH1 in accordance with these intervals, and conducted yeast 2-hybrid matings with each MSH1 domain as bait. From these experiments, we observed positive interaction with PPD3 at Domains 2, 3, and 6. All other putative partners produced positive interaction with Domain 3 (FIG. 13C). While Domain 3-4 appears to be bordered on both sides by short hydrophobic intervals, it is not clear whether MSH1 may span or anchor to the thylakoid membrane.

MSH1 and PPD3 are coexpressed and appear to be functional interactors.

Figure 15:
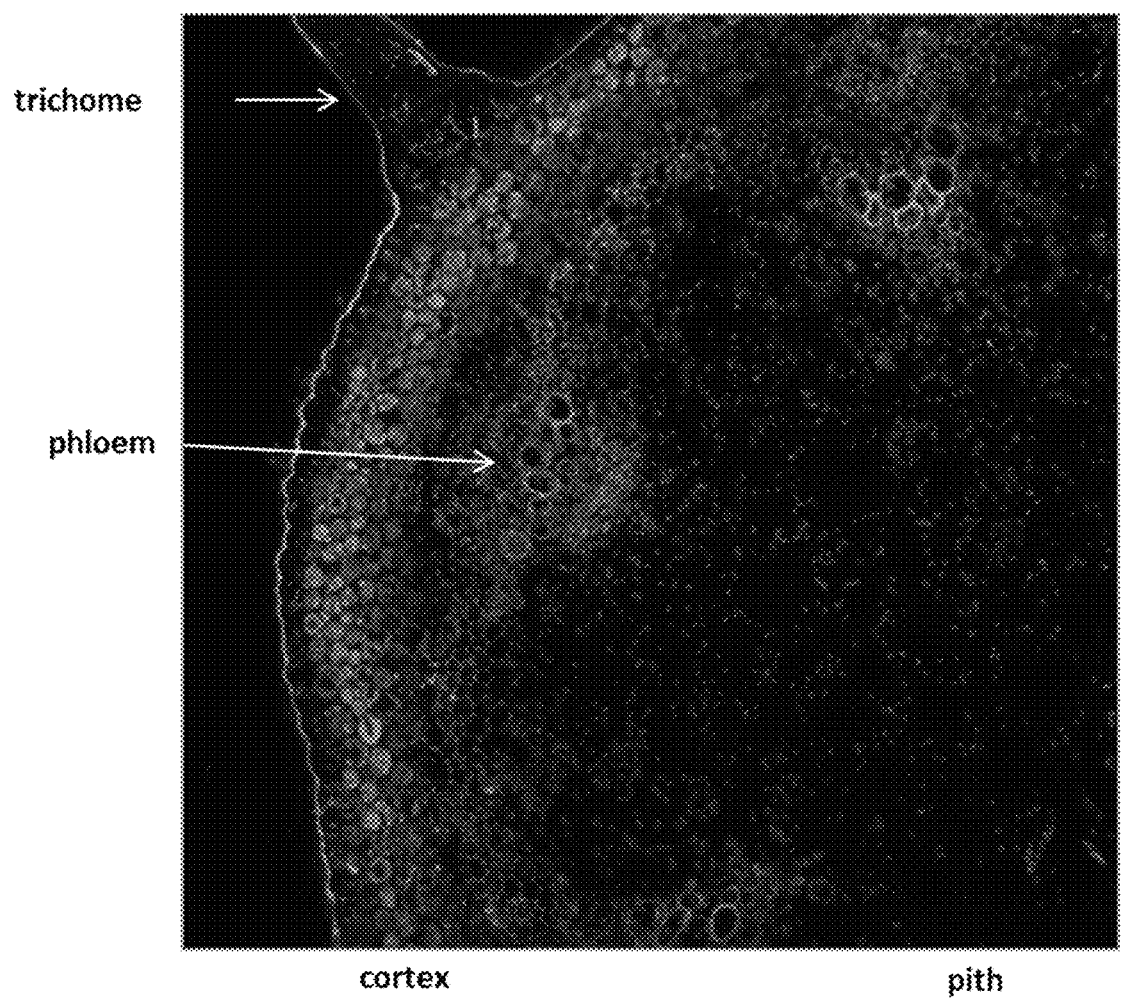
FIG. 15 shows that PsbO2-GFP expression in a cross-section of the floral stem. Xylem is visualized as blue, chloroplast autofluorescence is in red (in plastids that are not disturbed by sectioning. The PsbO2 protein is a lumenal protein. We presume that the chloroplasts that appear green are those that have been disrupted by sectioning, while those below that appear red likely are intact. Under photosynthetically active wavelengths, the lumen is likely to maintain a very low pH, which would prevent visualization of GFP.

The most convincing MSH1 protein interactions data from coIP and yeast 2-hybrid experiments was derived for PPD3, a protein of unknown function. Consequently, we pursued this candidate in more detail. Full-length PPD3-GFP fusion constructs were developed to test the expression and localization pattern of PPD3. We observed, by laser scanning confocal microscopy, that PPD3 also localized to small sized plastids within the epidermal layer and the vascular parenchyma (FIG. 14). This was in contrast, for example, to PsbO2, which localized predominantly to mesophyll plastids, but also to the vascular bundle plastids (FIG. 15).

Three TDNA insertion mutants were obtained for PPD3 in *Arabidopsis*, located at three sites in the gene, one in an exon, one intronic, and one in the promoter (FIG. 15A). While the promoter mutant, ppd3-Sail2, reduced expression of the gene, the exon mutant ppd3-gabi produced the strongest effect on expression and also on phenotype. Growth of the ppd3-gabi mutant at 10-hour day length produced aerial rosettes and extended, woody growth that is reminiscent of what we observe in MSH1-dr lines (FIG. 15D).

MSH1 and PPD3 mutants both give rise to similar plastid redox changes.

Figure 8A:
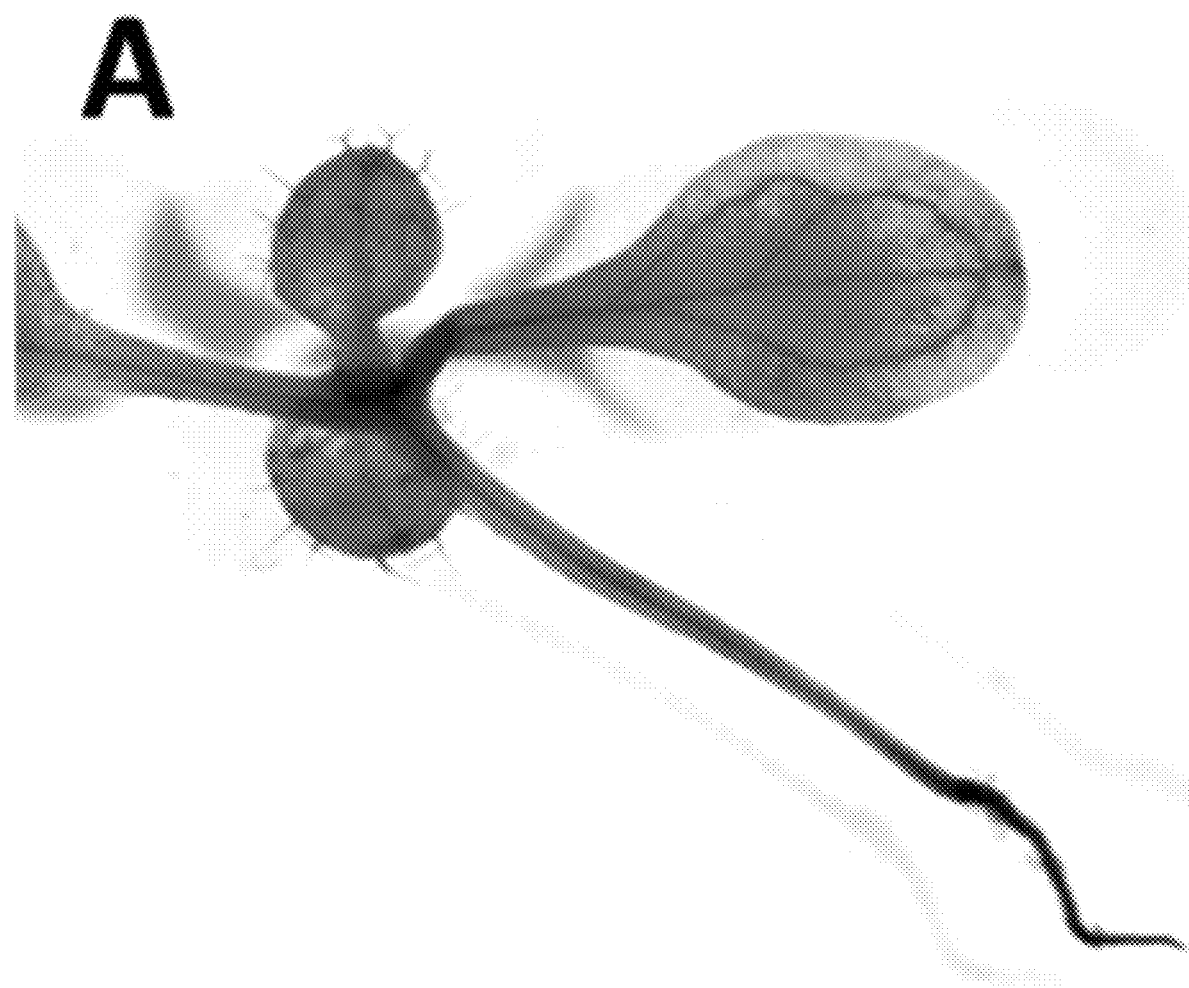
FIG. 8A-G shows that MSH1 is expressed predominantly in reproductive tissues and in vascular tissues throughout the plant. (A) MSH1-GUS expression in an *Arabidopsis* stable transformant seedling. MSH1 expression at the meristem (B) and root tip (C). (D) MSH1-GUS expression in the ovule; note enhanced expression evident in the funiculus. (E) MSH1-GUS localization in developing pollen within a cleared anther. (F) MSH1-GFP expression within a petal, showing enhanced localization within vascular tissues. (G) MSH1-GUS localization within the *Arabidopsis* flower.
Figure 8B:
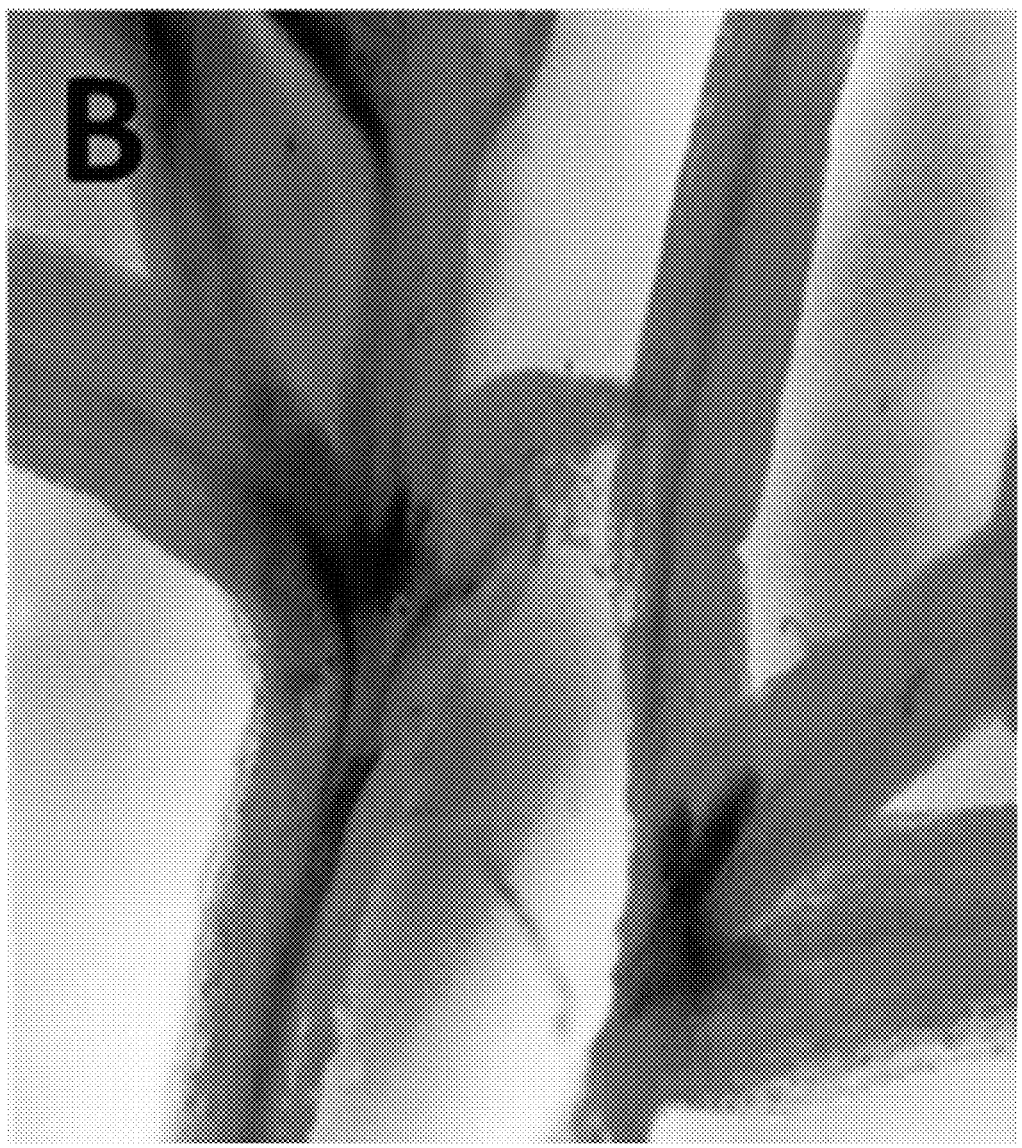
Figure 8C:
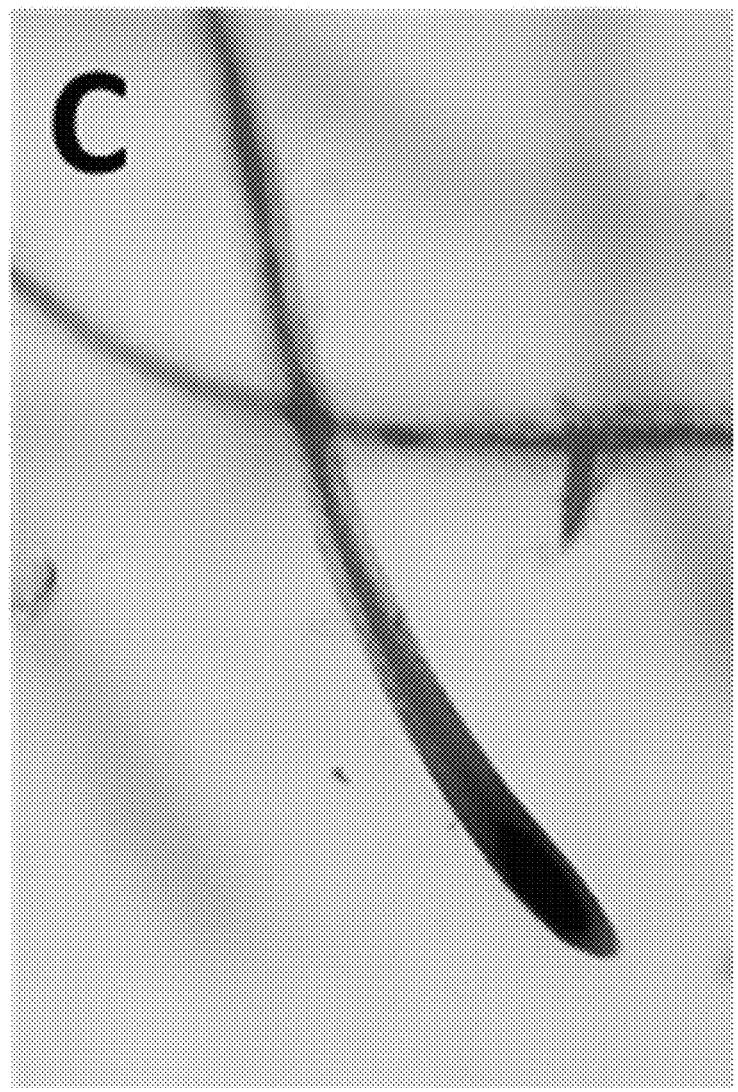
Figure 8D:
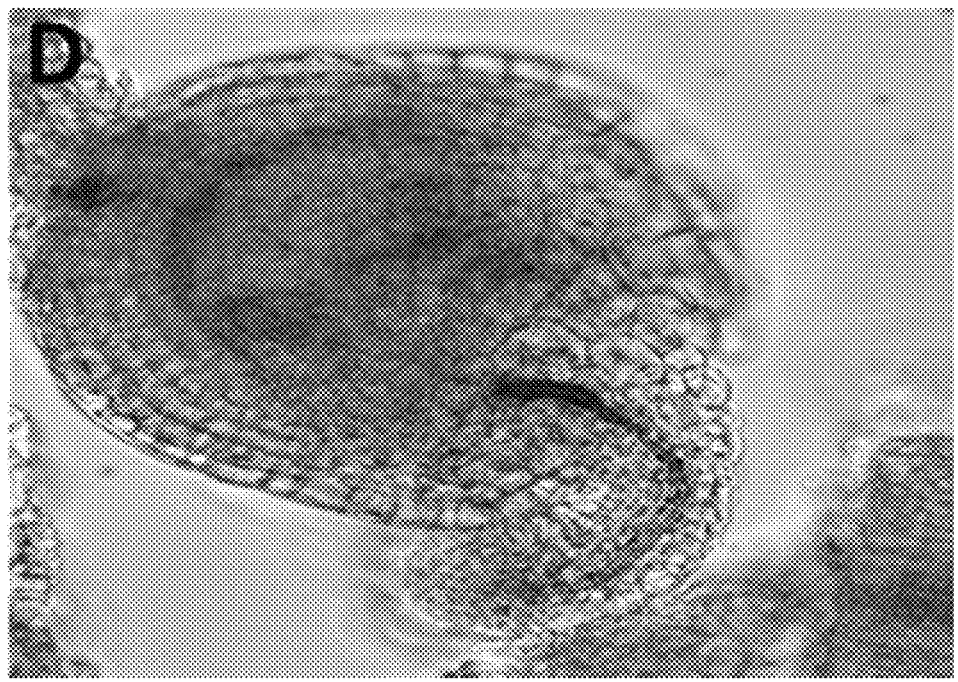
Figure 8E:
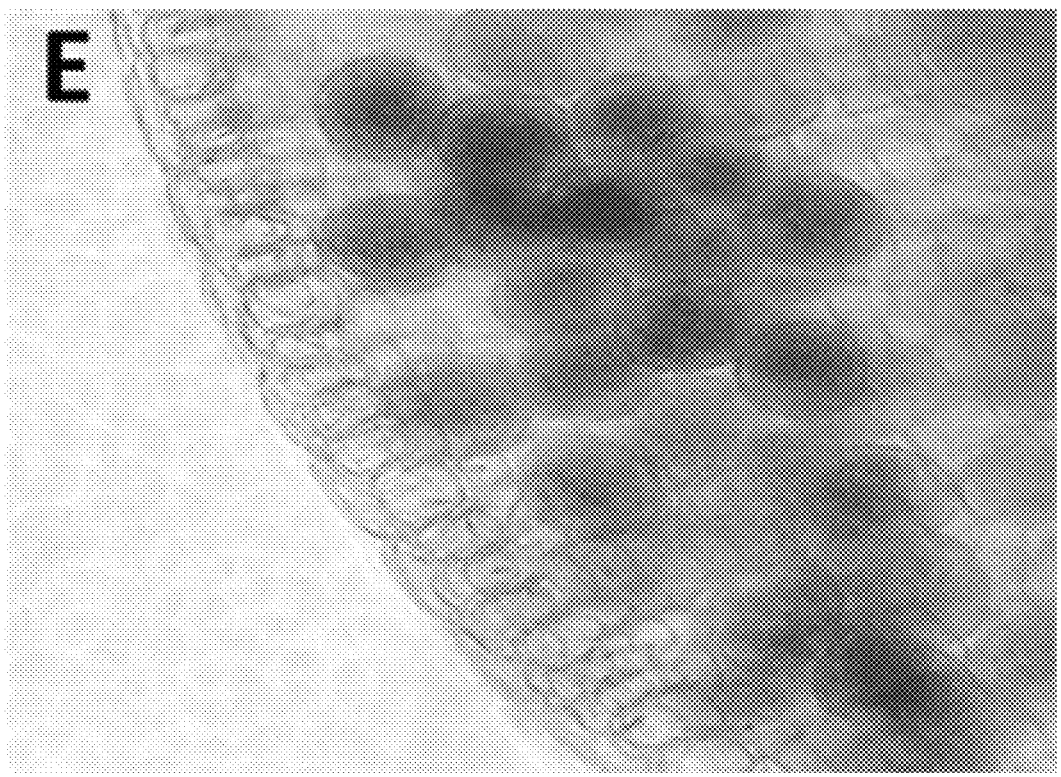
Figure 8F:
Figure 8G:
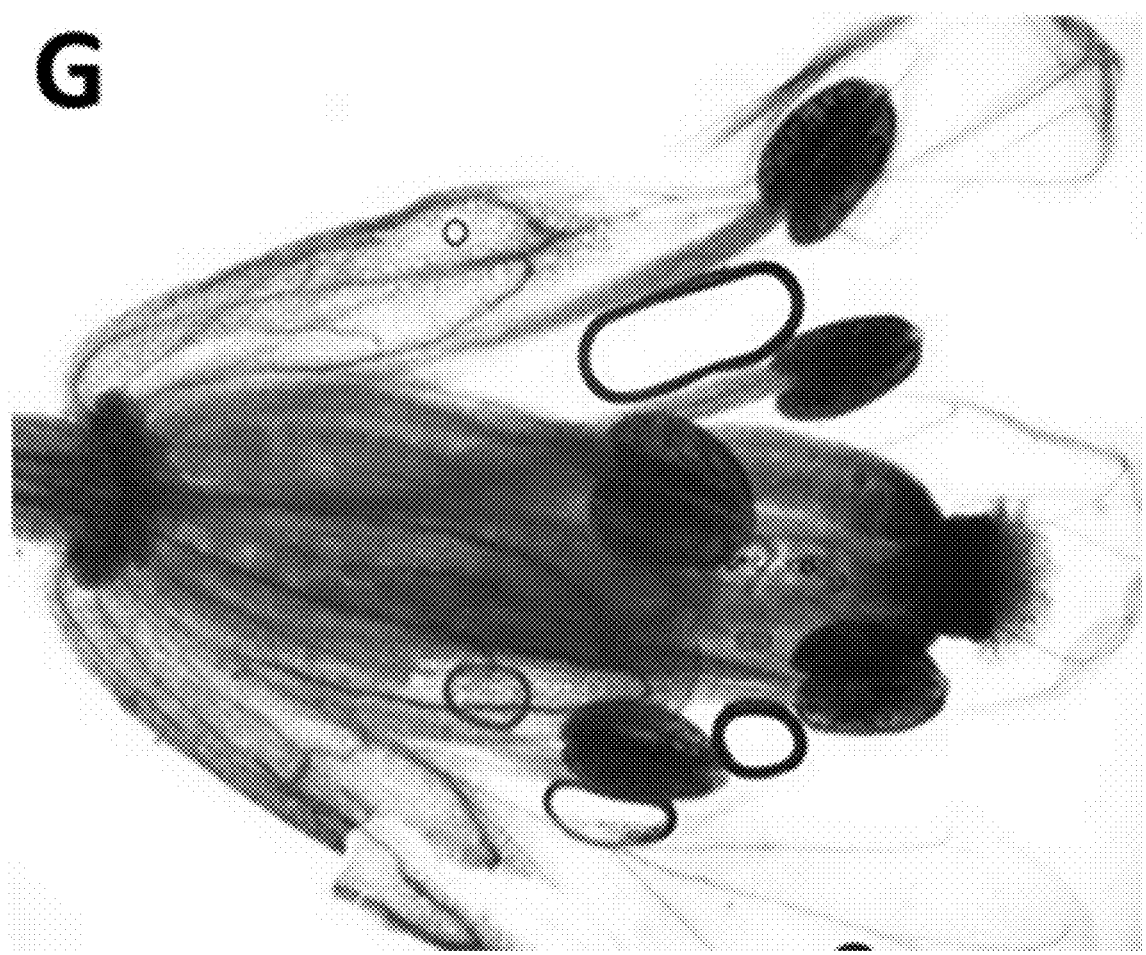
Figure 16A:
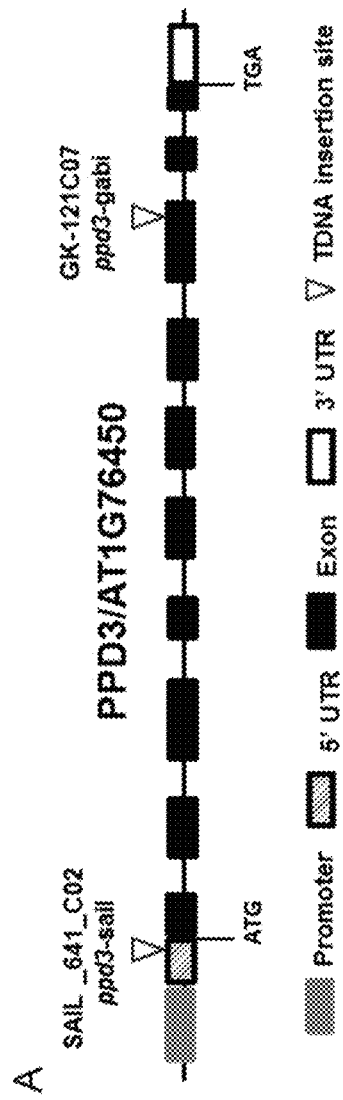
FIG. 16A-D of Example 1 shows that the ppd3 mutant resembles the msh1 dr phenotype. (A) Diagram of the PPD3 gene in *Arabidopsis* and the T-DNA insertion mutation site. (B) PCR-based genotyping of three PPD3 T-DNA insertion mutants. (C) RT-PCR assay of PPD3 expression in three T-DNA insertion mutants. (D) ppd3-gabi mutant phenotype under conditions of 10-hour day length, displaying aerial rosettes similar to msh1-dr.
Figure 16B:
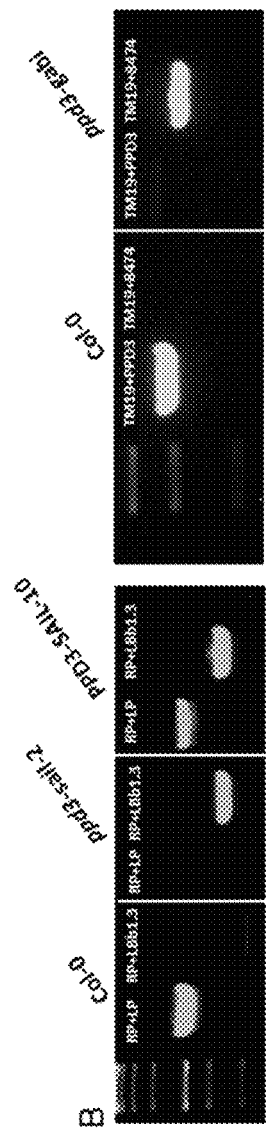
Figure 16C:
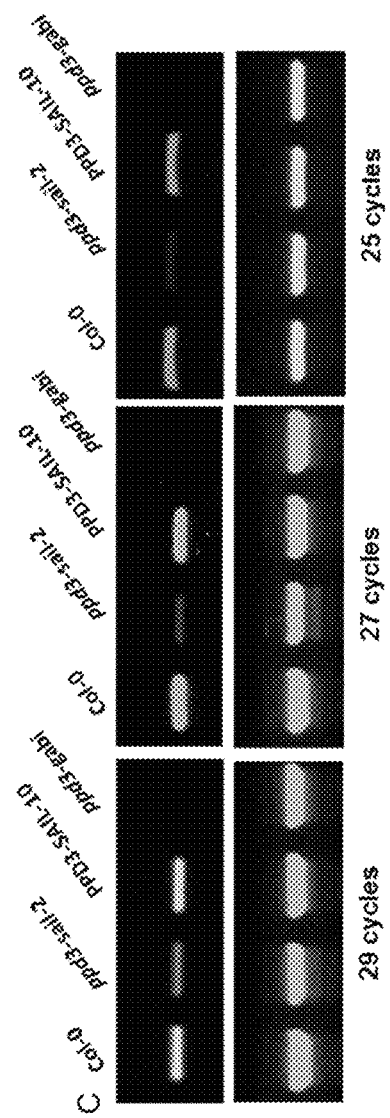
Figure 16D:

No significant differences between wildtype and msh1 mutant were apparent in amounts, oxidation rates and reduction rates of the cytochrome b6/f complex or P700, and no major defects were observed in O-J-I-P fluorescence induction curves for assessing the efficiency of PSII closure (data not shown). However, the msh1 mutant displayed higher plastoquinone levels, in more highly reduced state, than in wildtype (FIG. 8A). This effect was more pronounced in the stem, where MSH1 expression and sensory plastids are also expected to be highest, but was less evident in the leaf. Plastochromanol-8 levels were also higher in the stem of the msh1 mutant, relative to wildtype (FIG. 16B). These observations imply that redox status of the mutant is altered. What is intriguing about these results, is that they are more pronounced in the stem than in the leaf, consistent with the hypothesis that sensory plastids, where MSH1 functions, show the most significant effects of MSH1 disruption, perhaps comprising a transmissible signal within the plant.

Figure 17A:
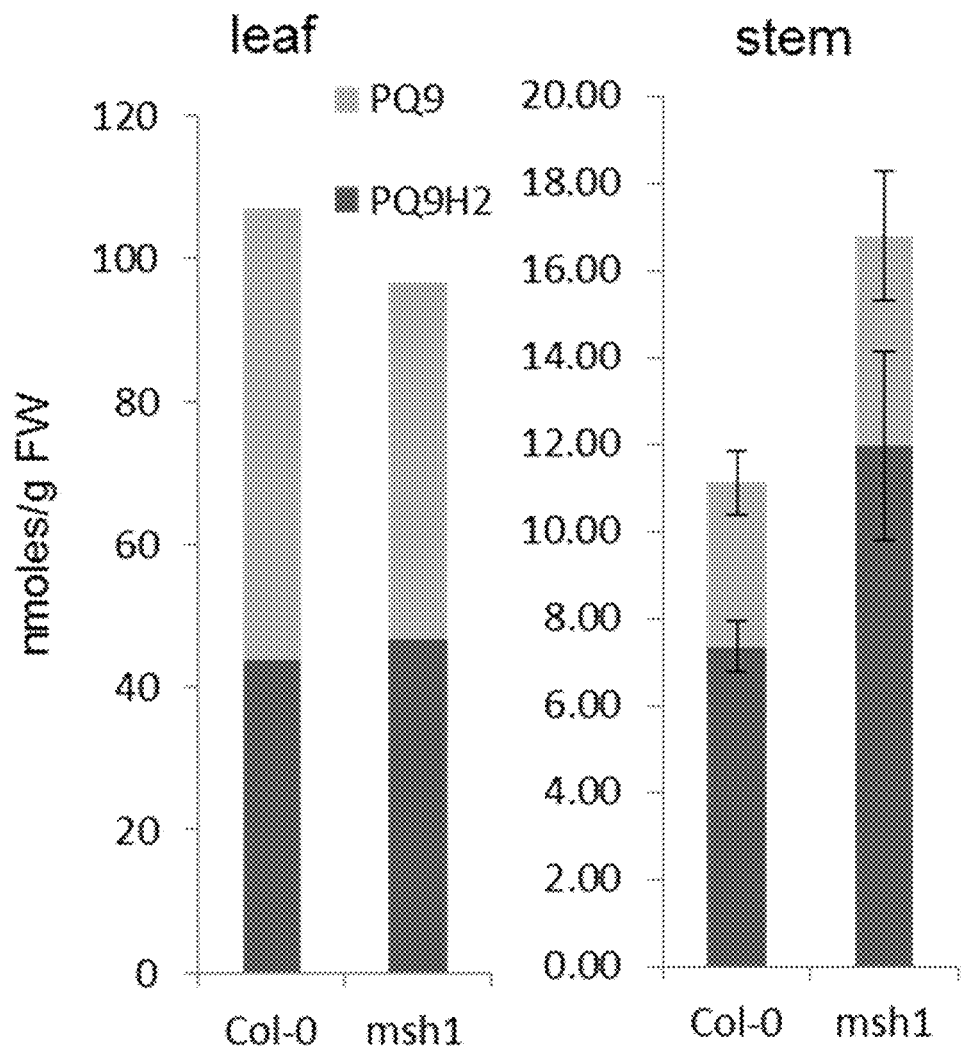
FIG. 17A-B shows that the msh1 mutant displays altered plastid redox features. (A) Plastoquinone (PQ9) levels, reduced and oxidized) in *Arabidopsis* were assayed in wild type (Col-0) and the msh1 mutant, testing both leaf (where mesophyll chloroplasts predominate and MSH1 levels are very low) and in stem (where sensory plastids are in greater abundance and MSH1 levels are higher). (B) Plastochromanol-8 (PC8) levels were measured in both leaf and stem. The observation of changes in plastoquinone level, redox state (becoming more highly reduced), and increases in PC-8 levels in the stem of the msh1 mutant suggests that the changes we observe may be more pronounced in the sensory plastids of the msh1 mutant. Note the difference in Y-axis scales to allow more detailed evaluation of stem effects.
Figure 17B:
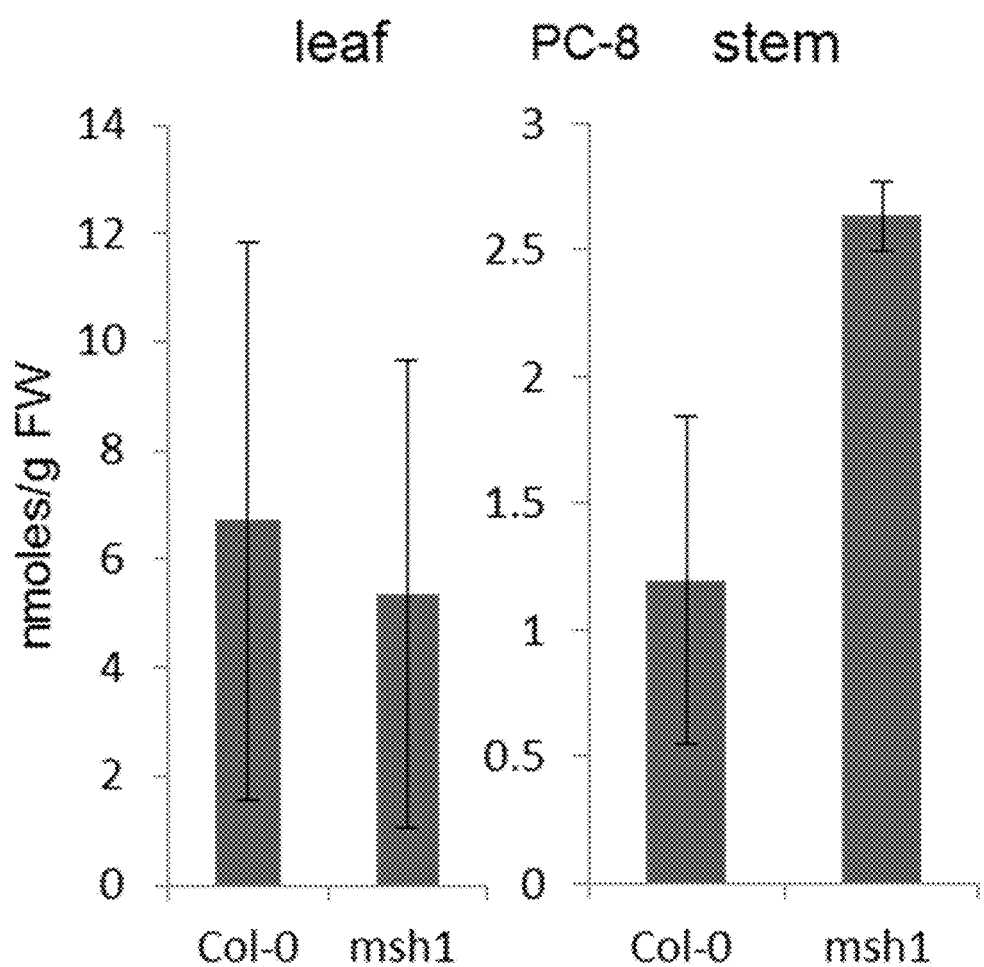
Figure 18A:
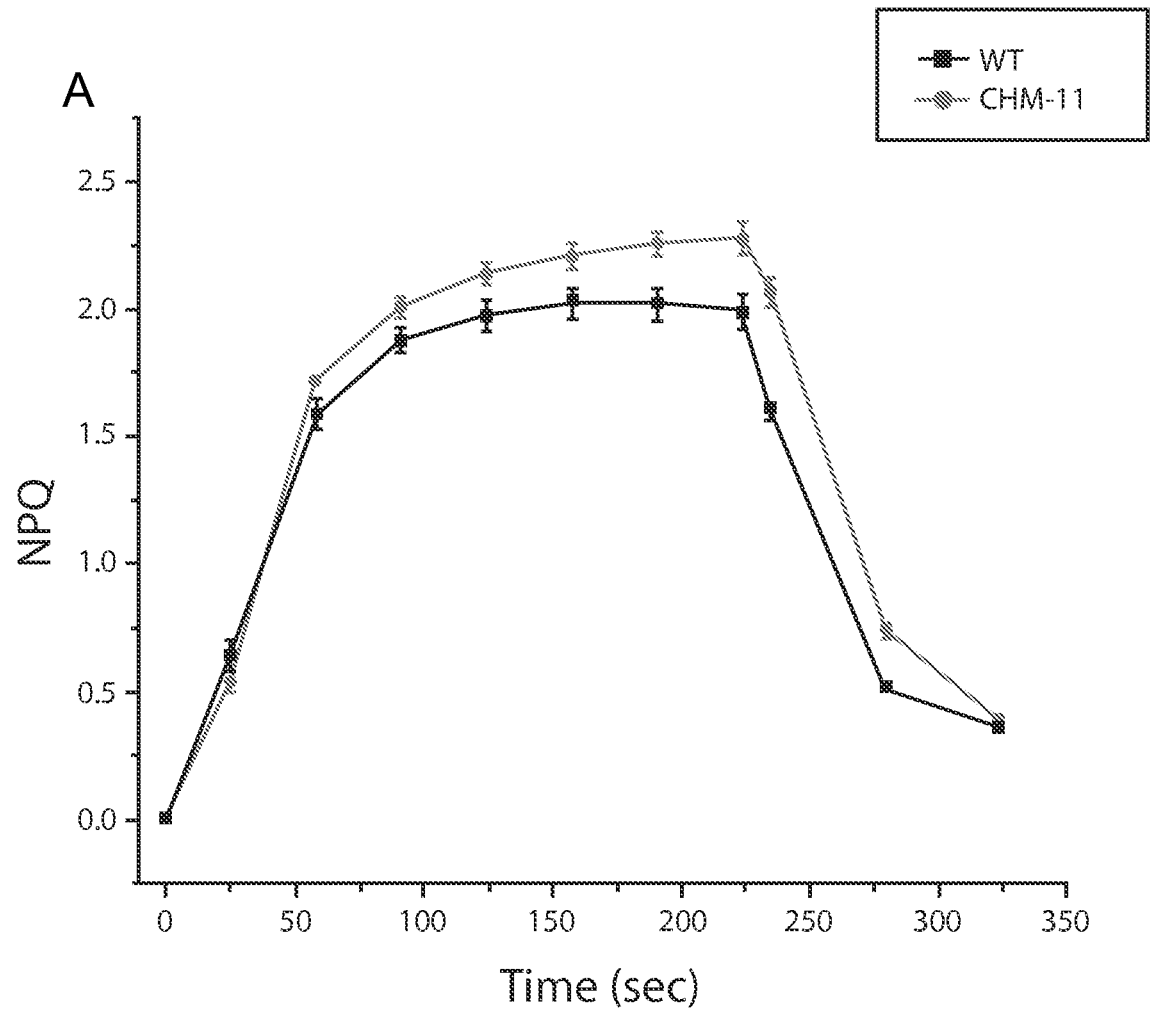
FIG. 18A-B shows that the msh1 and ppd3 mutants are similar in non-photochemical quenching (NPQ) properties of their plastids. Fluorometric measurements of chlorophyll fluorescence for calculation of NPQ was carried out in *Arabidopsis* wildtype (Col-0), two msh1 mutants, chm1-1 and 17-34, and two ppd3 mutants, ppd3-Gabi and ppd3-Sail. Both the msh1 and ppd3 mutants develop NPQ faster than WT in the light. The NPQ in these mutants then decays slower in the dark, with differences significant at the $P<0.05$ level.
Figure 18B:
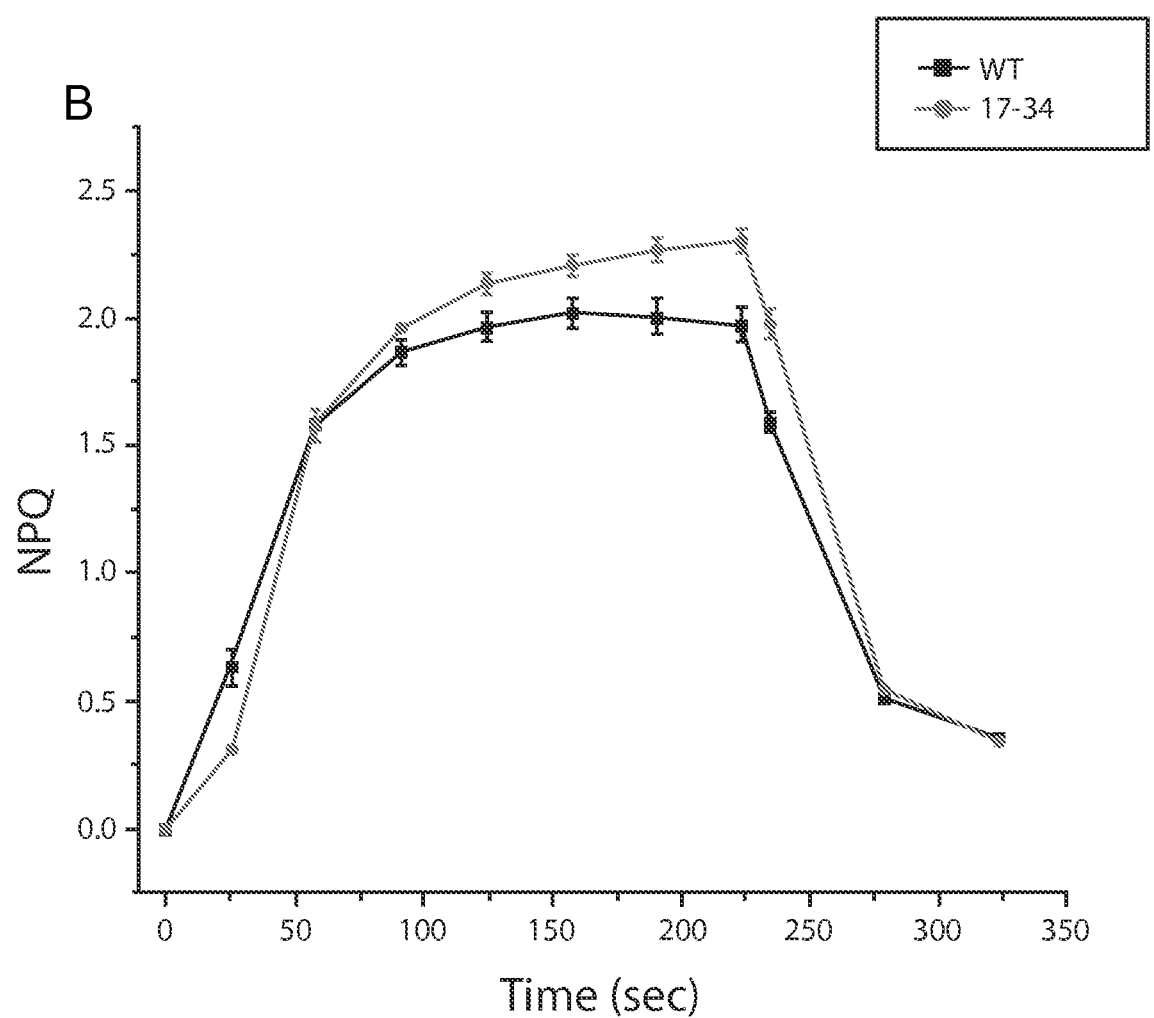

The msh1 mutant effect on plastid redox properties was also evident in enhanced non-photochemical quenching rates in the light, followed by slower decay rates in the dark (FIG. 17). A nearly identical effect was measured in the ppd3 mutants, consistent with a likely functional interaction between MSH1 and PPD3.

Example 5

Methylation in MSH1 Suppressed Plants

A plant's phenotype is comprised of both genetic and non-genetic influences. Control of epigenetic effects, thought to be influenced by environment, is not well defined. Transgenerational epigenetic phenomena are thought to be important to a plant's ability to pre-condition progeny for abiotic stress tolerance. MSH1 is a mitochondrial and plastid protein, and MSH1 gene disruption leads to enhanced abiotic stress and altered development. Genome methylation changes occur immediately following disruption of MSH1, changes that are most pronounced in plants displaying the altered developmental phenotype. These developmental changes are inherited independent of MSH1 in subsequent generations, and lead to enhanced growth vigor via reciprocal crossing to wildtype, implying that loss of MSH1 function leads to programmed epigenetic changes.

Plant phenotypes respond to environmental change, an adaptive capacity that is, at least in part, trans-generational. Genotype x environment interaction in plant populations involves both genetic and epigenetic factors to define a plant's phenotypic range of response. The epigenetic aspect of this interplay is generally difficult to measure. Previously we showed that depletion of a single nuclear-encoded protein, MSH1, from the plastid causes dramatic and heritable changes in development. The changes are fully penetrant in the progeny of these plants. Here we show that crossing these altered plants with isogenic wild type restores normal growth and produces a range of phenotypic variation with markedly enhanced vigor that is heritable. In *Arabidopsis*, these growth changes are accompanied by redistribution of DNA methylation and extensive gene expression changes. MSH1 mutation results in very early changes in both CG and CHG methylation that drive toward hypermethylation, with pronounced changes in pericentromeric regions, and with apparent association to developmental reprogramming. Crosses to wildtype result in a significant redistribution of DNA methylation within the genome. Variation in growth observed in this study is non-genetic, suggesting that plastid perturbation by MSH1 depletion constitutes a novel means of inducing epigenetic changes in plants.

Evidence exists in support of a link between environmental sensing and epigenetic changes in plants and animals (1-3). Trans-generational heritability of these changes remains a subject of investigation (4-5), but studies in *Arabidopsis* indicate that it is feasible to establish new and stable epigenetic states (6-7). Much of what has been learned in plants derives from studies exploiting *Arabidopsis* DNA methylation mutants to disrupt the genomic methylation architecture of the plant and provide evidence of epigenomic variation in plant adaptation (8). In maize and *Arabidopsis*, heritable DNA methylation differences are observed among inbred lines (9) and resulting hybrids that may be related to heterosis (10). In natural *Arabidopsis* populations, epiallelic variation is highly dynamic and found largely as CG methylation within gene-rich regions of the genome (11-12).

Here we demonstrate that loss of MSH1 results in a pattern of early methylome changes in the genome that are most pronounced in plants that demonstrate developmental reprogramming. These effects involve heritable pericentromeric CHG and localized CG hypermethylation. These genome methylation changes may underlie the trans-generational nature of non-genetic phenotypes observed with MSH1 depletion.

A genetic strategy for organelle perturbation involves mutation or RNAi suppression of MUTS HOMOLOG 1 (MSH1). MSH1 is a mitochondrial- and chloroplast-targeted protein unique to plants and involved in organelle genome stability (13, 14). MSH1 disruption also effects developmental reprogramming (MSH1-dr) (15). A range in MSH1-dr phenotype intensity occurs, and the changes in transcript and metabolite patterns seen in MSH1-dr selections are characteristic of plant abiotic stress responses (14-15).

FIG. 19 shows the crossing process used in this study. *Arabidopsis* experiments were carried out in the inbred ecotype Columbia-0. Crossing wildtype Col-0 with the msh1 mutant results in a heritable, enhanced growth phenotype that, by the F3 generation (epi-F3), produces markedly larger rosettes and stem diameter, early flowering, and enhanced plant vigor (FIG. 19E-G).

Figure 23:
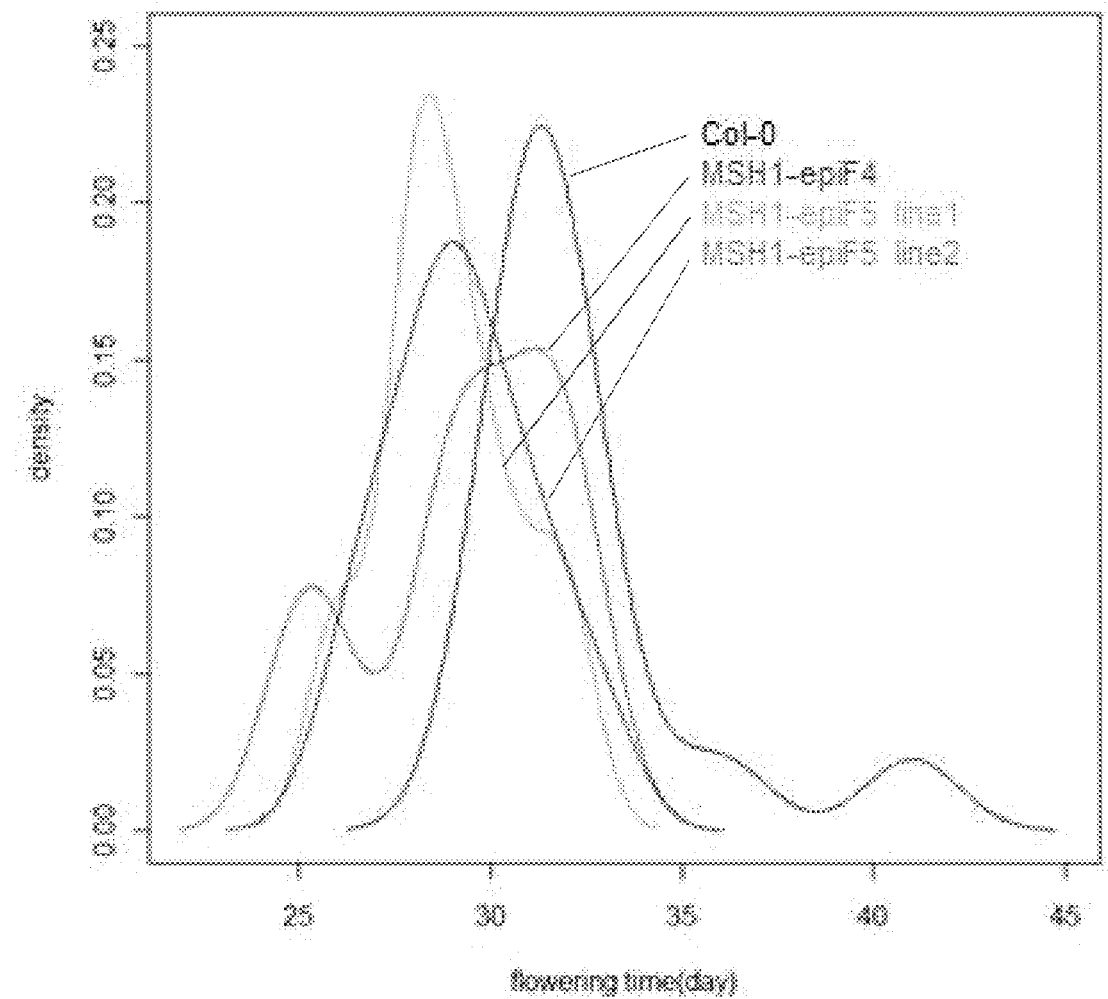
FIG. 23 shows the distribution of flowering time in *Arabidopsis* Col-0, epiF4 and epiF5 lines. Each distribution is plotted based on 15-20 plants.
Figure 24A:
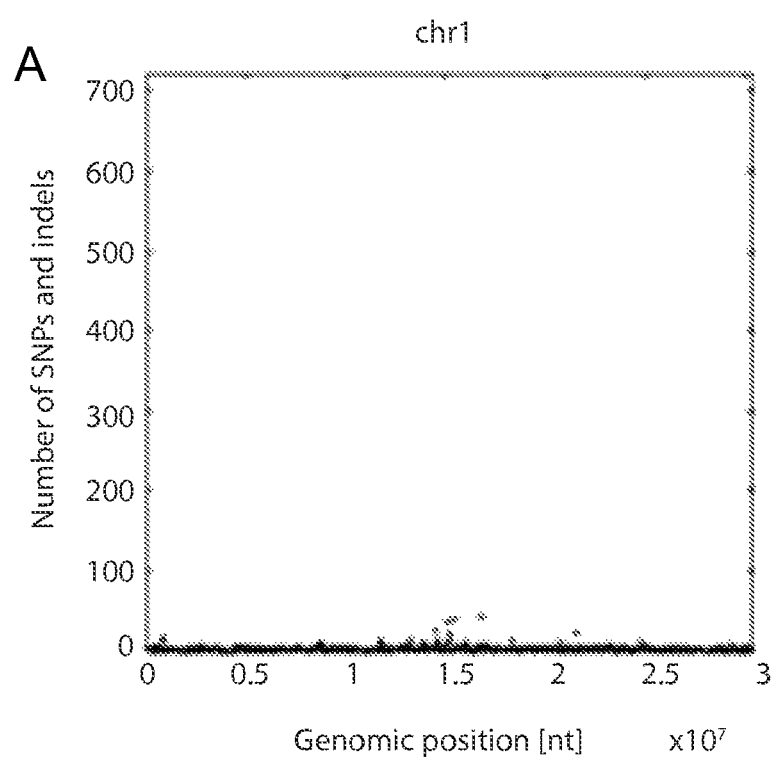
FIG. 24A-F shows the distribution of msh1 SNPs and indels versus Col-0 across the genome. Each dot represents the number of SNPs and indels found in a window of 50 kbp. Note that the Y-axis has been synchronized with the maximum number found on chr4 to enable comparisons between chromosomes. The region 7,800,000-9,850,000 bp on chr4, a likely introgressed segment from Ler, contains 8582 of the total 12,771 SNPs and indels. The overlap between these data and the known SNPs and small indels of Ler vs. Col-0 (17) is 72% and 67% for SNPs and indels, respectively.
Figure 24B:
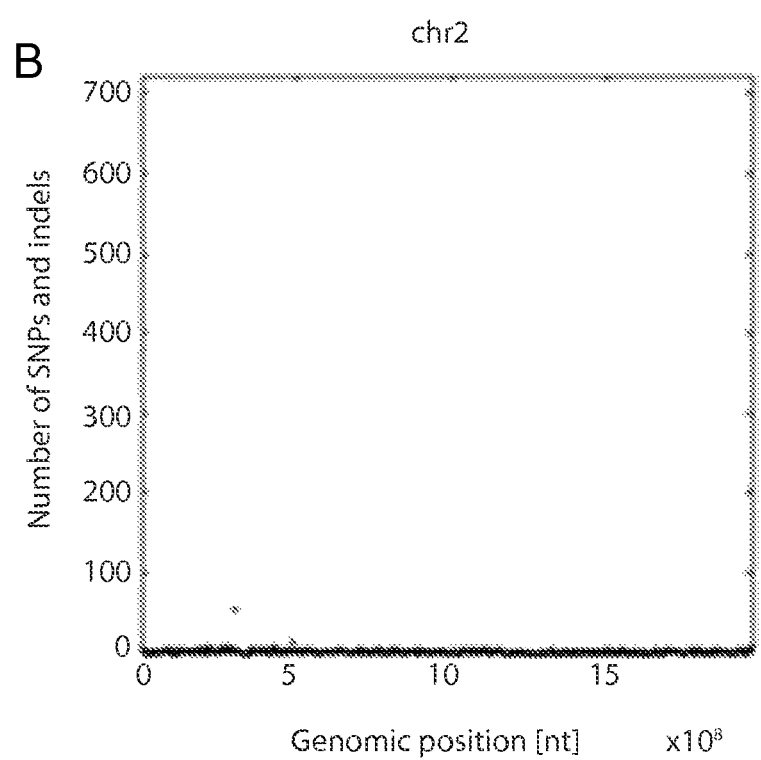
Figure 24C:
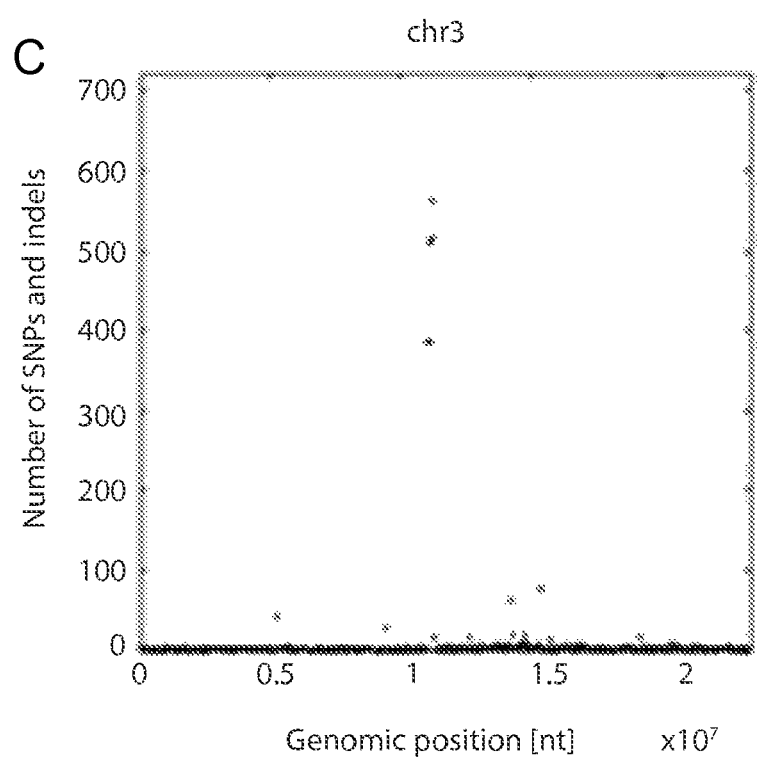
Figure 24D:
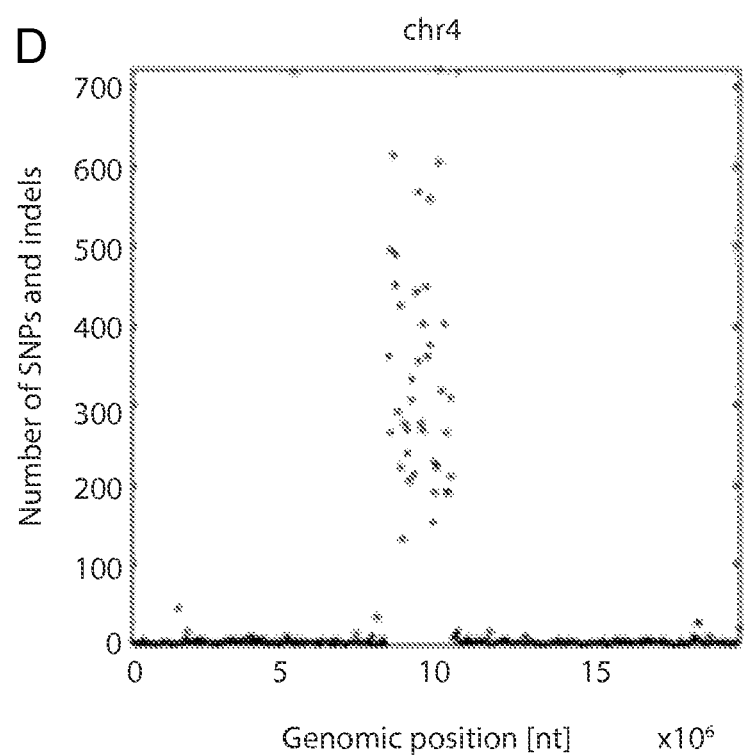
Figure 24E:
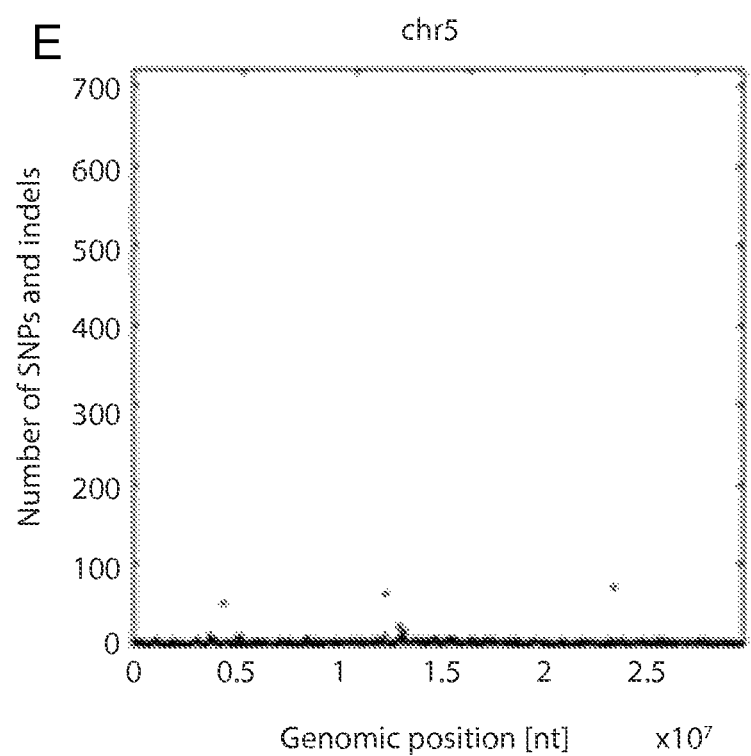
Figure 24F:
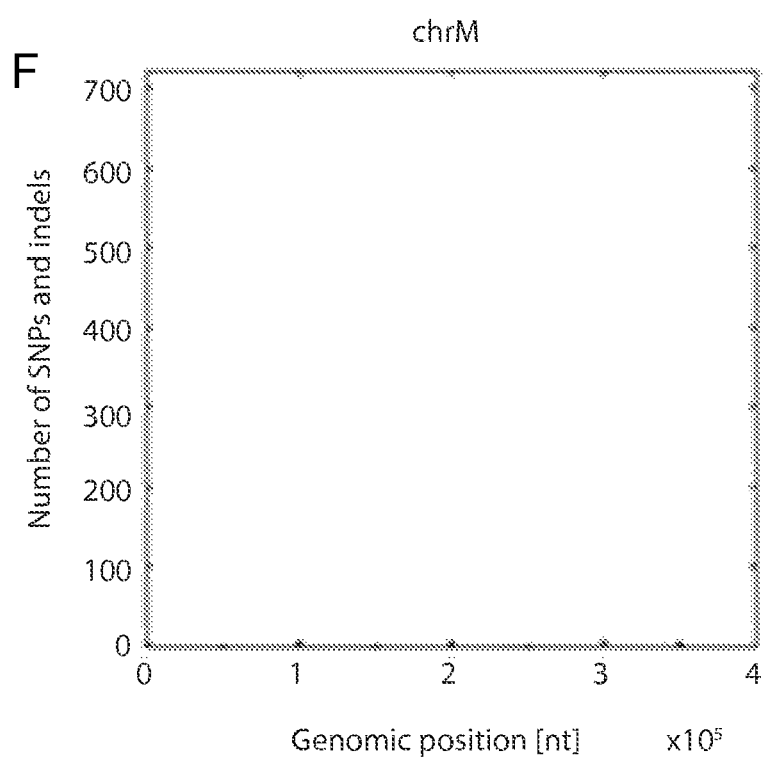

To test whether the *Arabidopsis* genome, with msh1 mutation, has undergone genomic rearrangement to account for the rapid developmental reprogramming, paired-end genome-wide sequencing, alignment and de novo partial assembly of the mutant genome was conducted. The long-standing chm1-1 mutant, first identified over 30 years ago, was used for these experiments, providing the best opportunity to test for any evidence of genome instability caused by MSH1 mutation. The analysis produced 14,416 contigs (n50=40,761 bp) containing 118.5 Mbp; mapping these contigs against Col-0 covers 72 Mbp. Alignment of paired-end reads to the Col-0 public reference sequence produced 95% alignment and identified 12,771 SNPs and indels, with one 2-Mbp interval, on chromosome 4, accounting for 8,582 (FIG. 23). The chm1-1 mutant used in this study is a Col-0 mutant once crossed to Ler (13). Comparing SNPs and indels in the chromosome 4 region with those in a recent study of Ler×Col-0 (16) accounts for 5060 of 6985 SNPs (72%) and 1073 of 1597 indels (67%), consistent with an Ler introgressed segment. Of the remaining 4188 SNP/indels, 72% (2996) reside in non-genic regions. This SNP mutation rate is likely consistent with natural SNP frequencies (11), suggesting that no significant, unexplained genome alterations were detected in the msh1 mutant.

Figure 25A:
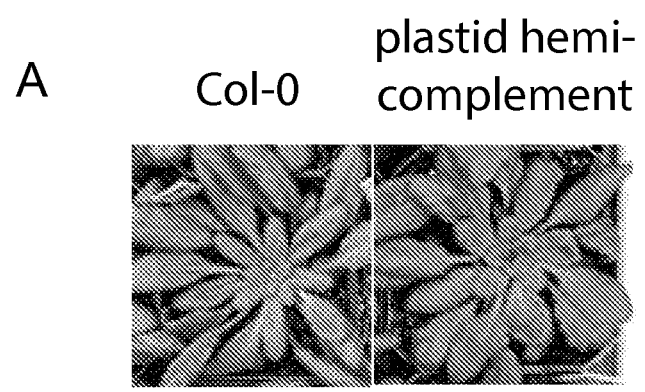
FIG. 25A-C shows *Arabidopsis* F1 plants resulting from crosses of the msh1 chloroplast hemi-complementation line×Col-0 wildtype. Transgene-mediated chloroplast hemi-complementation of msh1 restores the wildtype phenotype. However, crossing of these hemi-complemented lines to Col-0 results in range from 10% to 77% of the plants displaying leaf curl in independent F1 progenies (F1). The cause of this phenotype is not yet known, but it is heritable in derived F2 populations (F2).
Figure 25B:
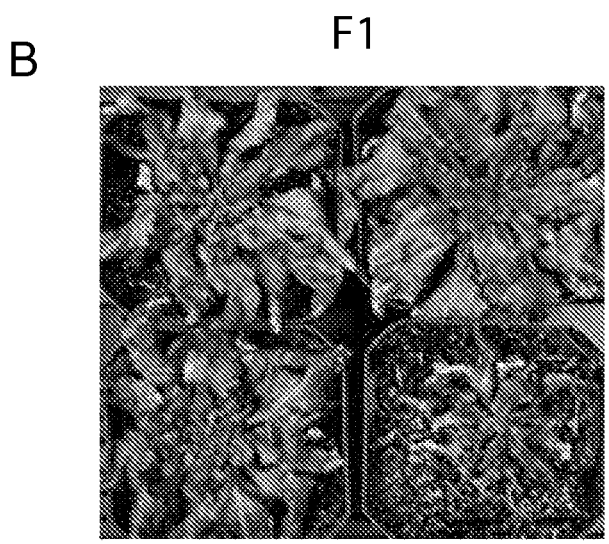
Figure 25C:
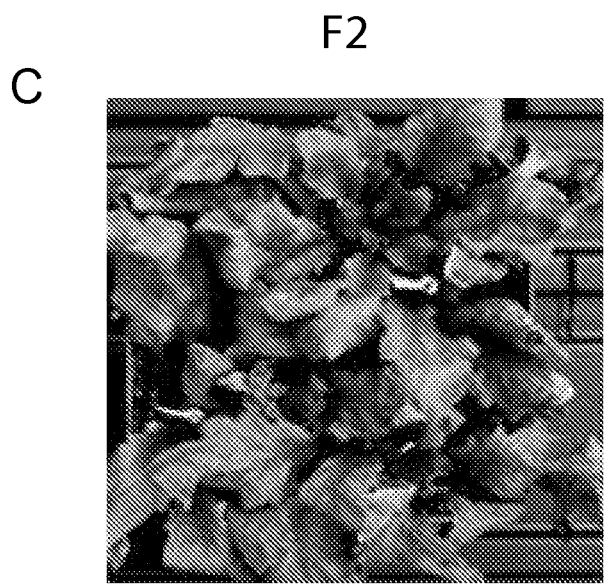
Figure 26A:
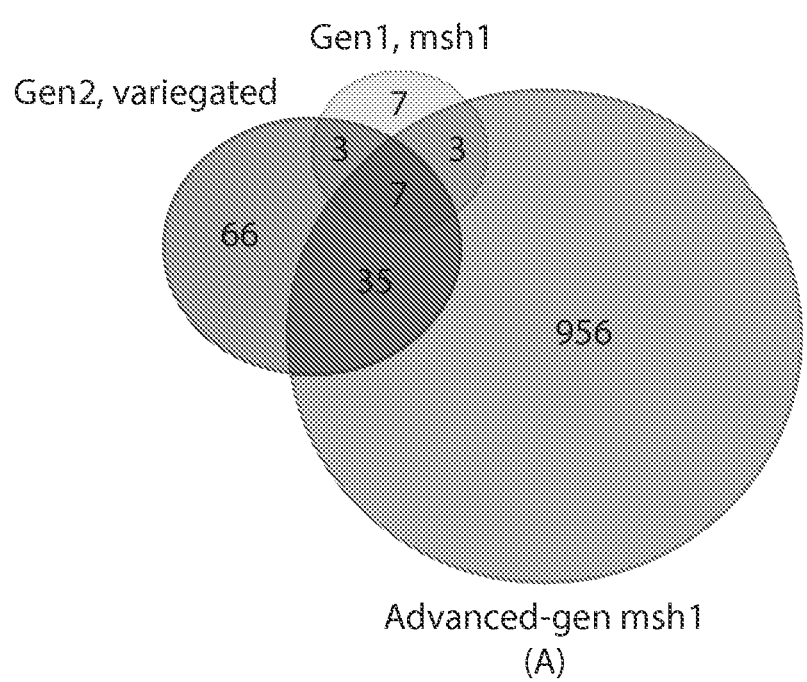
FIG. 26A-D shows the Venn Diagrams of the overlapping DMRs for CG (A)(B)(C), and CHG (D).
Figure 26B:
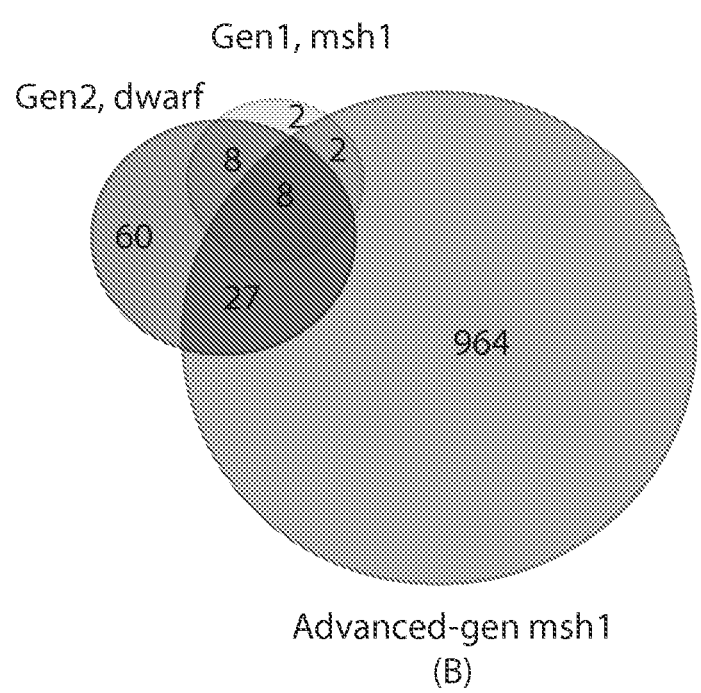
Figure 26C:
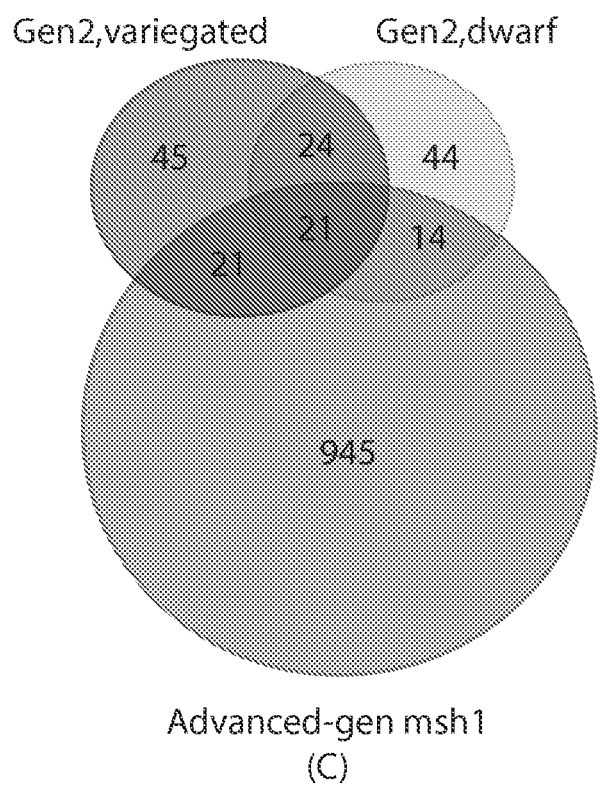
Figure 26D:
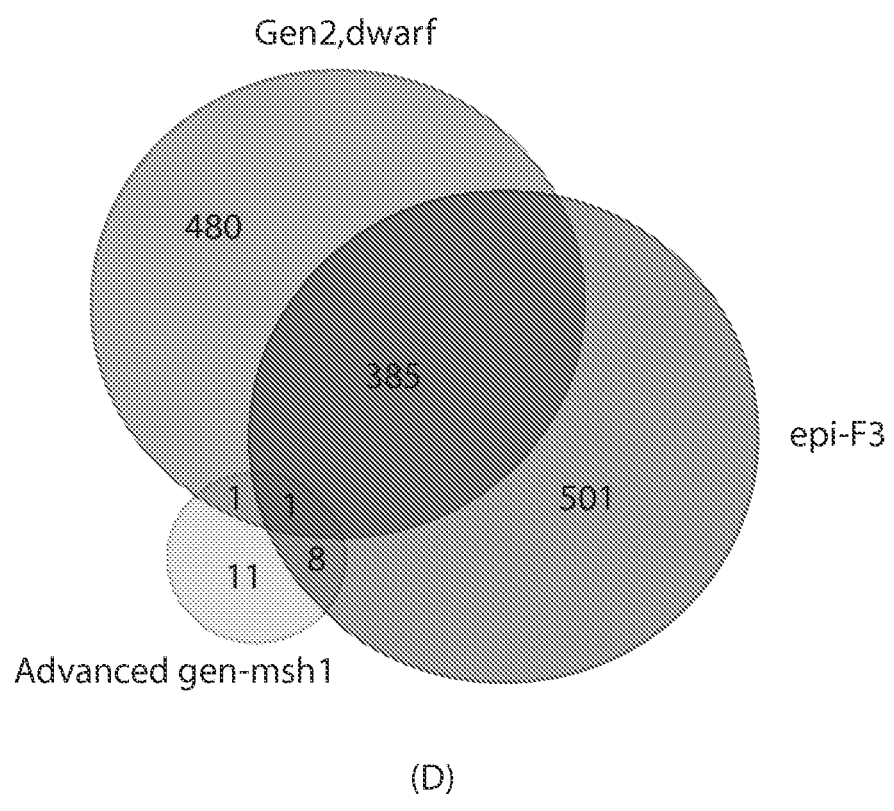

Altered plant development in *Arabidopsis* msh1 is conditioned by chloroplast changes (15). We found that the enhanced growth in MSH1-epiF2 lines also appeared to emanate from these organelle effects. *Arabidopsis* MSH1 hemi-complementation lines, derived by introducing a mitochondrial-versus chloroplast-targeted MSH1 transgene to msh1 (14), distinguish mitochondrial and chloroplast contributions to the phenomenon. Chloroplast hemi-complementation lines (SSU-MSH1) crossed as female to wild type (Col-0) produced F1 phenotypes resembling wild type (FIG. 20, Table 5), although 10% to 77% of independent F1 progenies showed slow germination, slow growth, leaf curling and delayed flowering (FIG. 25). The curling phenotype may be a mitochondrial effect; it resembles altered salicylic acid pathway regulation, which has shown epigenetic influence (17). In F1 progeny from crosses to the mitochondrial-complemented line (AOX-MSH1), over 30% showed enhanced growth, larger rosette diameter, thicker floral stems and earlier flowering time, resembling MSH1-epiF3 phenotypes (FIG. 20; Table 5). These results were further confirmed in derived F2 populations (FIG. 20), and imply that growth enhancement arises from the MSH1-dr phenomenon.

Figure 19A:
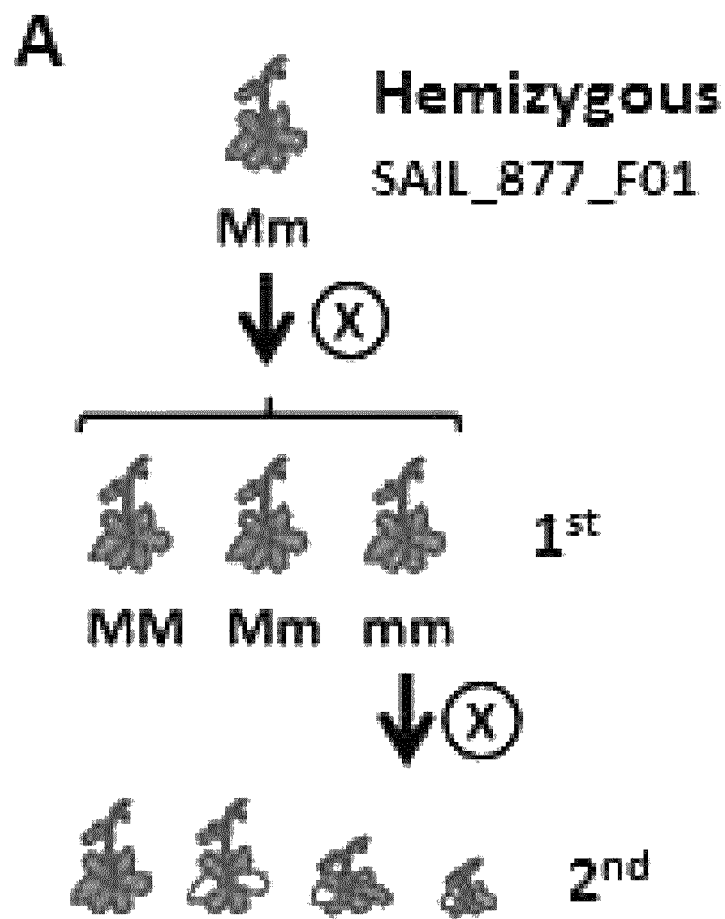
FIG. 19A-G shows the enhanced growth phenotype of MSH1-epi lines in *Arabidopsis*. (A) Crossing and selection procedure to derive early generation msh1 materials for methylome analysis. (B) First-generation msh1 phenotypes for segregating progeny from a single hemizygous plant. Null msh1 plants are marked with triangles. Plants shown are 33 days old. (C) Segregating second generation siblings from a single null msh1 first generation parent. Note the size variation and extensive variegation in the second generation. Plants are 33 days old. (D) Crossing strategy for epiF3 and epiF4 families. (E) Enhanced growth phenotype of the epiF4. (F) *Arabidopsis* epiF4 plants show enhanced plant biomass, rosette diameter and flower stem diameter relative to Col-0. Data are shown as mean±SE from >6 plants. (G) The *Arabidopsis* epiF4 phenotype at flowering.
Figure 19B:
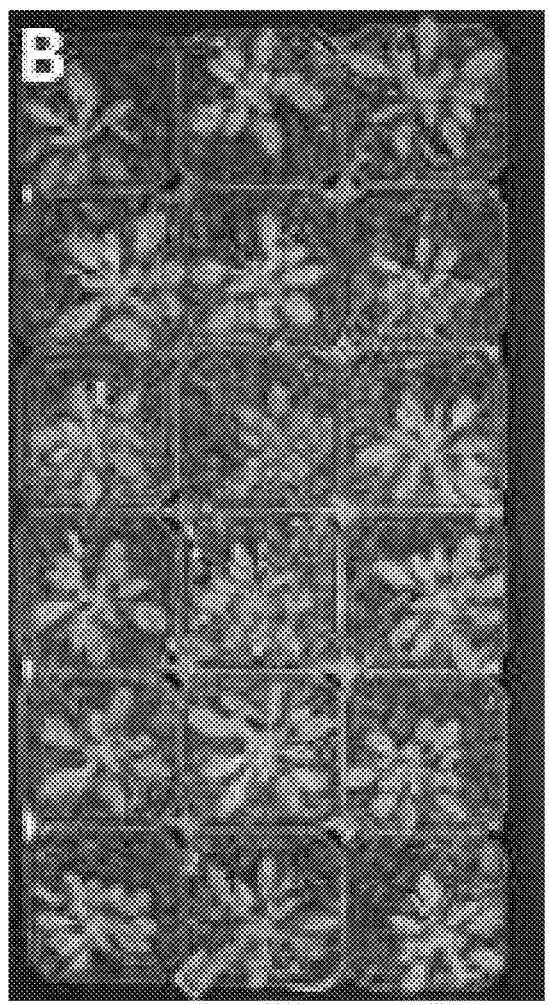
Figure 19C:
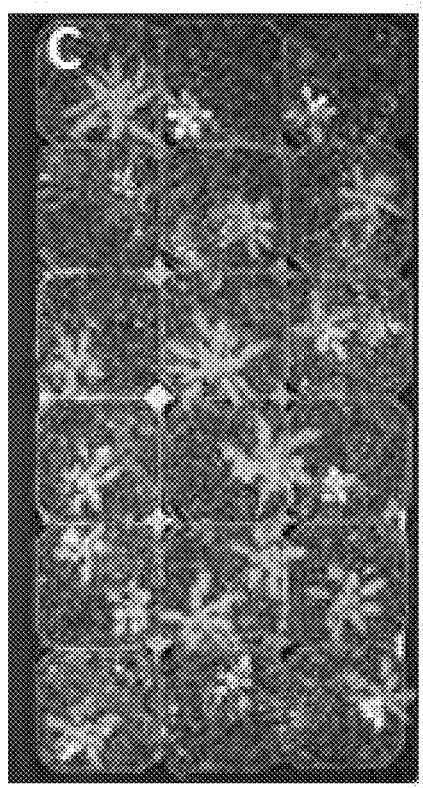
Figure 19D:
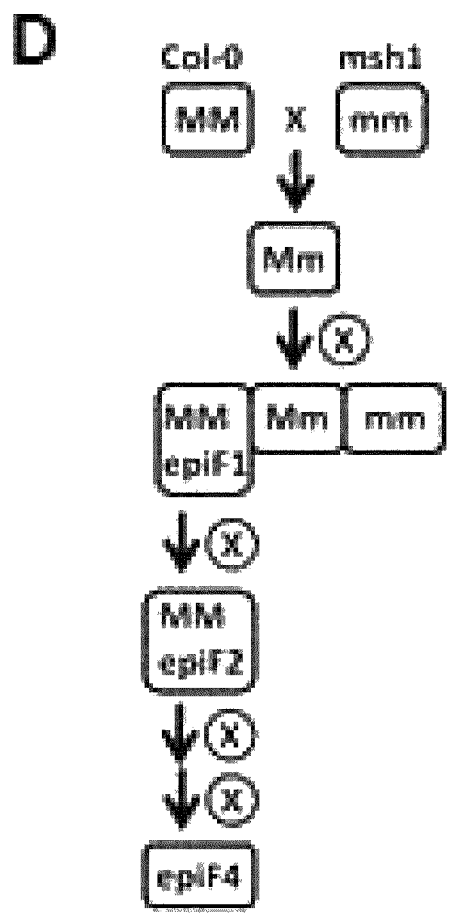
Figure 19E:
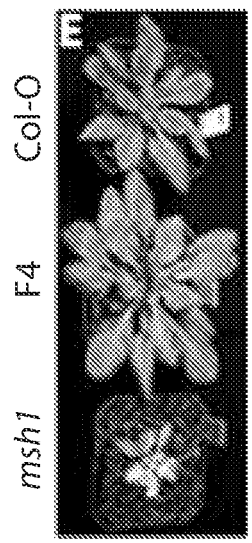
Figure 19F:
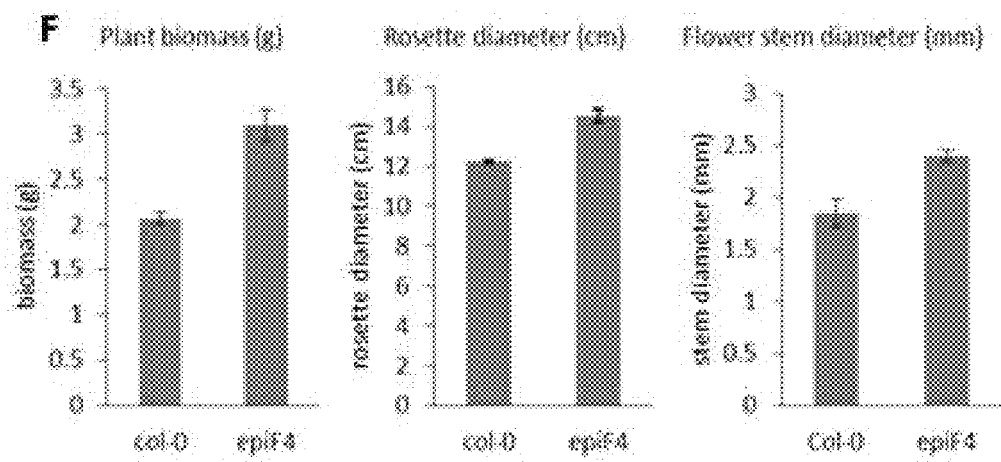
Figure 19G:
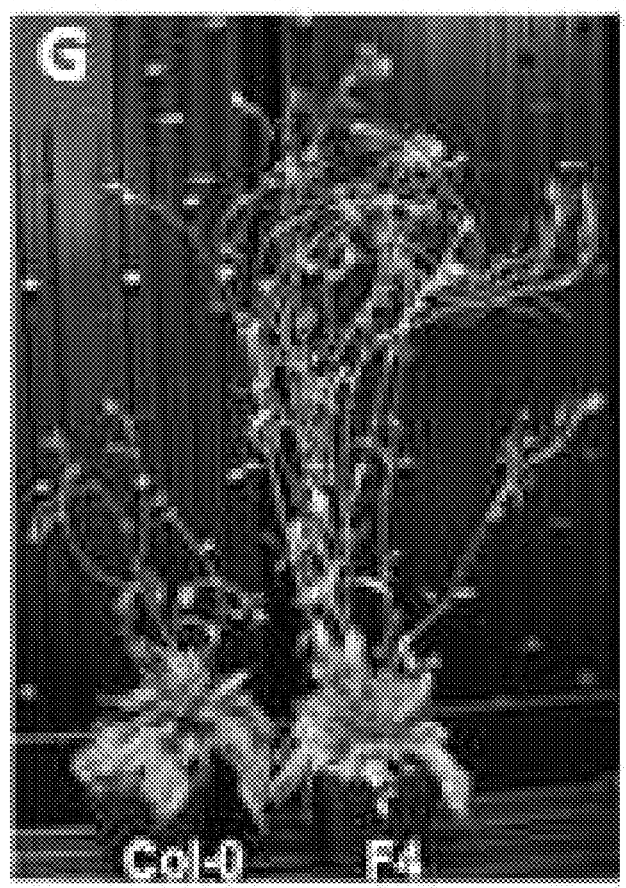
Figure 20A:
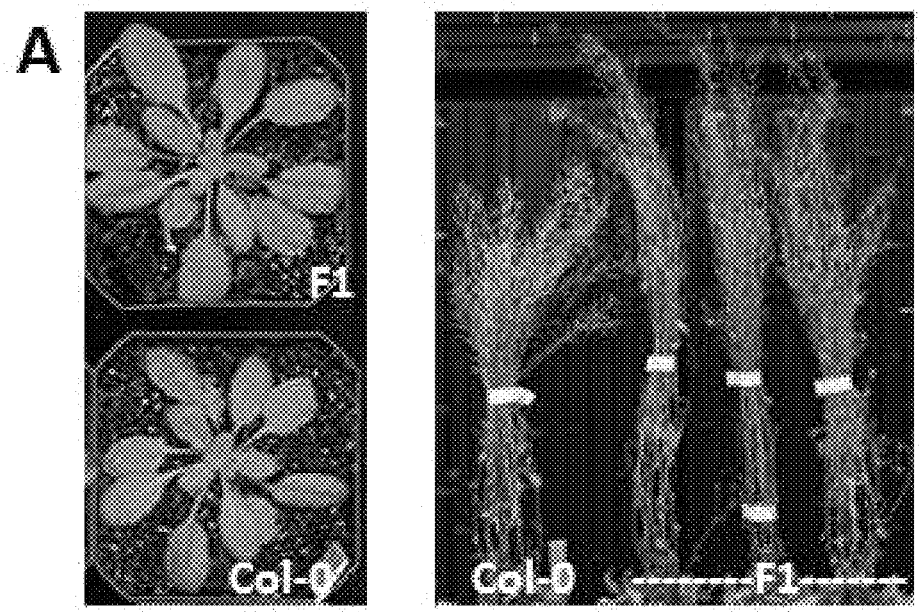
FIG. 20A-F shows MSH1-epi enhanced growth in *Arabidopsis* is associated with chloroplast effects. (A) Mitochondrial hemi-complementation line AOX-MSH1×Col-0 F1. (B) Plastid-complemented SSU-MSH1×Col-0 F2 appears identical to Col-0 wildtype. (C) Rosette diameter and fresh biomass of SSU-MSH1-derived F2 lines relative to Col-0. (D) Mitochondrial-complemented AOX-MSH1×Col-0 F2 showing enhanced growth. (E) Rosette diameter and fresh biomass of AOX-MSH1-derived F2 lines is significantly greater ($P<0.05$) than Col-0. (F) Enhanced growth phenotype in the F2 generation of A0X-MSH1×Col-0.
Figure 20B:
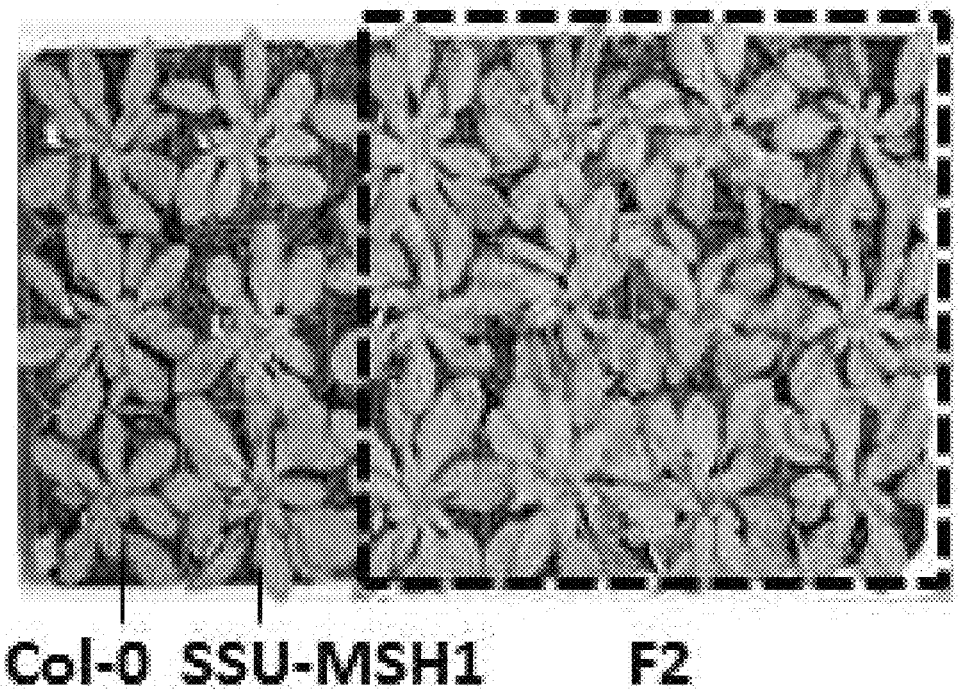
Figure 20C:
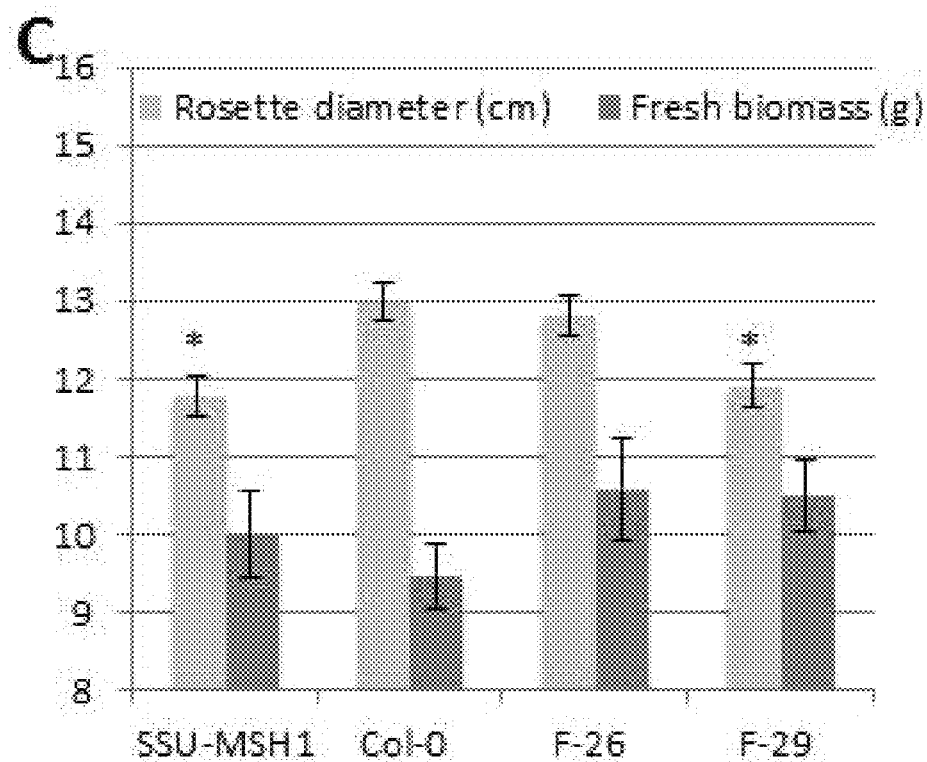
Figure 20D:
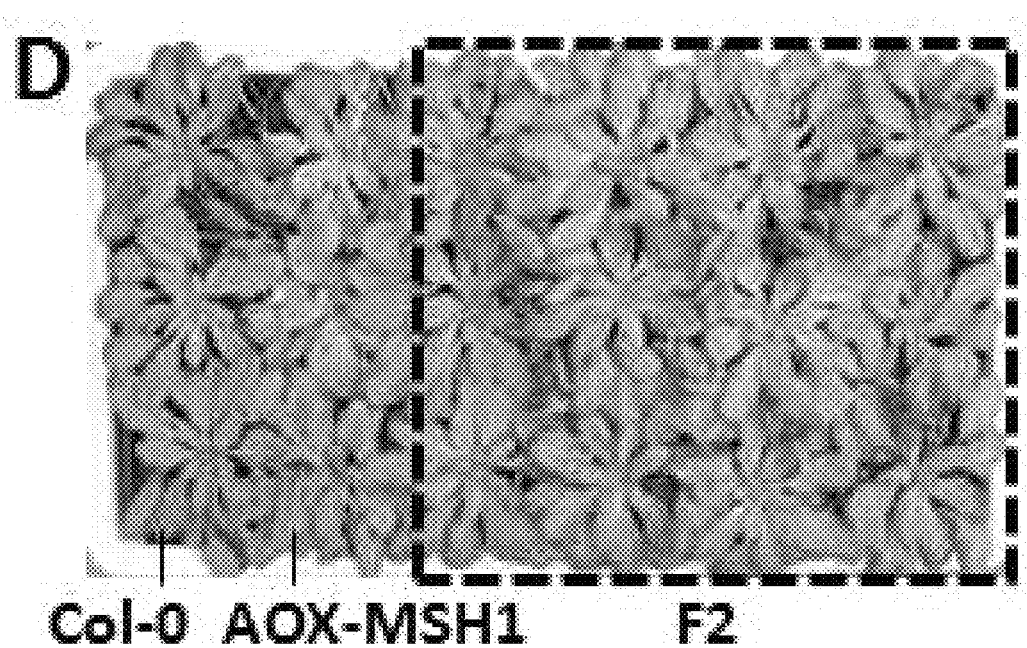
Figure 20E:
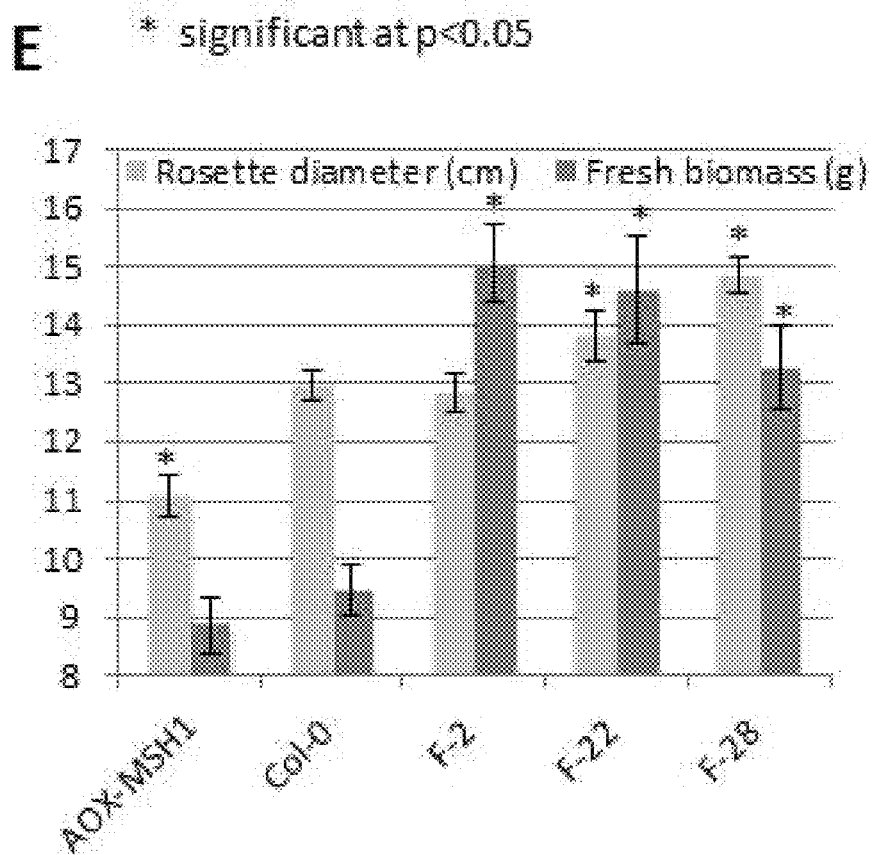
Figure 20F:
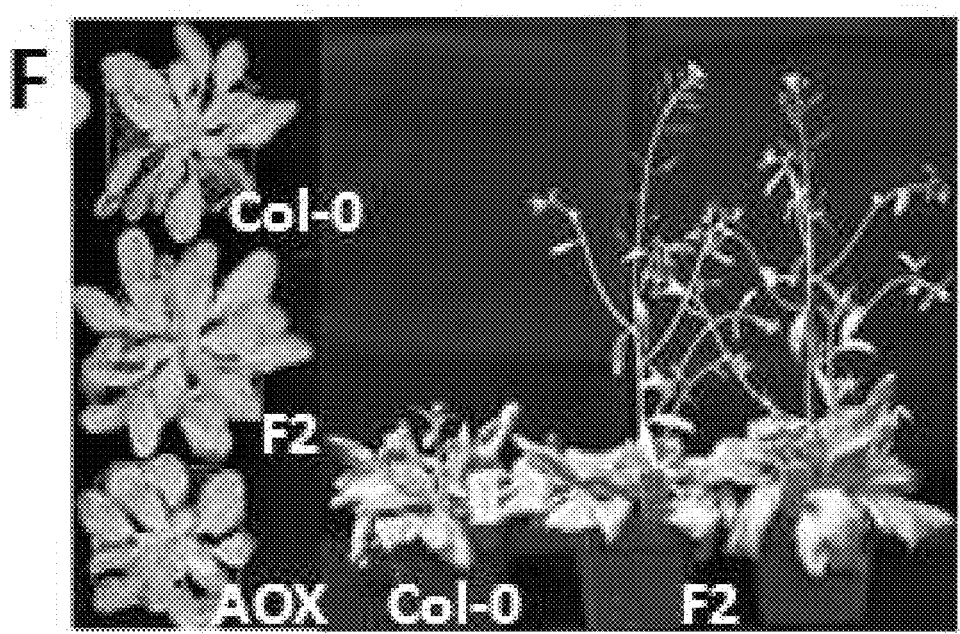

*Arabidopsis* wild type, first-, second- and advanced-generation msh1 mutants, and msh1-epiF3 plants, all Col-0, were investigated for methylome variation. Bisulfite treatment and genomic DNA sequence analysis (18) was carried out on progeny from an MSH1/msh1 heterozygous T-DNA insertion line, producing first generation msh1/msh1, MSH1/msh1, and MSH1/MSH1 full-sib progeny segregants for comparison (FIG. 19A). All first-generation plants appeared normal, with only very mild variegation visible on the leaves of the msh1/msh1 segregants (FIG. 19B). These lines were compared to two second-generation msh1/msh1 lines from a parallel lineage (FIG. 19C), one a normal-growth, variegated line and one a dwarfed dr line. The advanced-generation mutant is chm1-1, with which we have carried out all of our previous studies. Methylation changes between the first-generation msh1 mutant and its wild type MSH1/MSH1 sib involved 20 CG differentially methylated regions (DMRs) (Table 4 below). The CG DMRs were clustered on Chromosome 3, forming a peak adjacent to the MSH1 gene (FIG. 21). Whether proximity of this peak to MSH1 has functional significance or is mere coincidence is not yet known.

TABLE 4

| Lines | CpG | | CHG | | CHH | |
|---|---|---|---|---|---|---|
| | DMP | DMR | DMP | DMR | DMP | DMR |
| Gen 1, het | 6664 | 8 | 349 | 0 | 359 | 8 |
| Gen1, msh1 | 11073 | 20 | 1176 | 0 | 887 | 16 |
| Gen2, variegated | 28860 | 111 | 2885 | 4 | 1631 | 28 |
| Gen2, dwarf | 29680 | 103 | 39307 | 867 | 4625 | 45 |
| Advanced-gen msh1 | 61046 | 1001 | 5519 | 21 | 571 | 2 |

By generation 2, the variegated, normal growth line displayed 111 CG DMRs and the dwarfed, dr line displayed 103, both retaining the DMR peak on Chromosome 3 (Table 4, FIG. 21). Of the 20 CG DMRs observed in generation 1, 10 were retained in the variegated line and 16 were present in the dwarfed dr line (FIG. 26). CHG differential methylation varied markedly in the generation 2 lines, with 4 CHG DMRs in the variegated line versus 867 CHG DMRs in the dwarfed dr line (Table 4). The advanced-generation msh1 mutant, compared to Col-0, showed 1001 CG DMRs, of which 56 were shared with early generation lines. Whereas the advanced-generation msh1 mutant showed 21 CHG DMRs with significant overlap to those CHG DMRs seen in early generation, the epi-F3 line showed 385 CHG DMRs (43%) with significant overlap to those seen in the dwarf line of generation 2 (FIG. 26). As negative control for background, we compared the MSH1/msh1 (het) first-generation segregant to the same MSH1/MSH1 first-generation segregant used in the above comparisons, revealing only 6664 CG DMPs and 8 DMRs (Table 4).

Figure 22A:
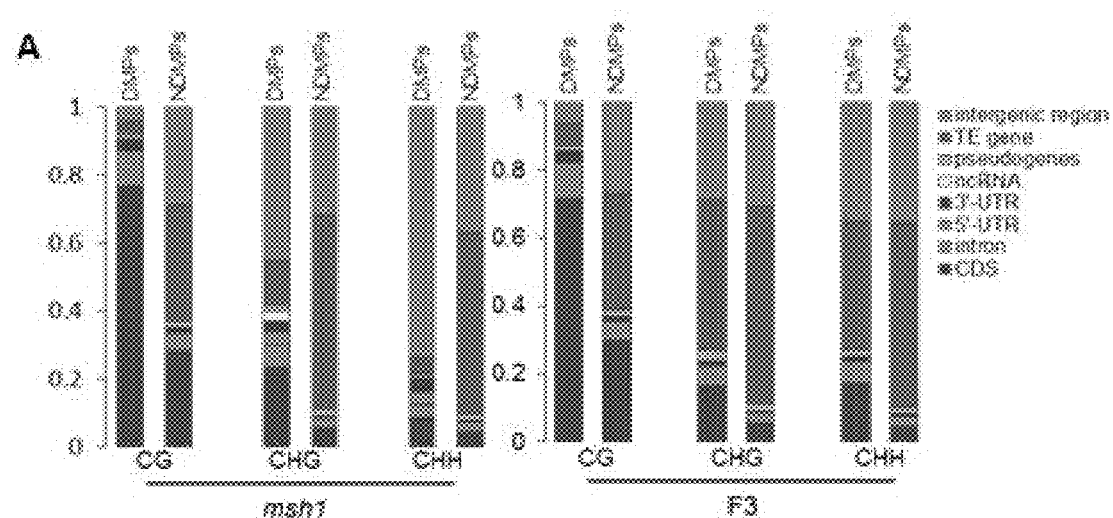
FIG. 22A-D shows hypermethylation trends in first, second and advanced generation msh1 and epiF3 lines (A) Relative contributions of CG, CHG and CHH methylation to differential methylated positions (DMPs) and non-differential methylated positions (NDMPs) of the genome in the msh1 and epiF3 lines relative to Col-0. (B) Relative distribution of DMPs within genes in the msh1 and epiF3 lines. (C) Relative proportion of hyper- and hypomethylation CG and CHG changes in early generation msh1 versus a MSH1/MSH1 sib, and advanced generation msh1 and epiF3 relative to wildtype Col-0. (D) Heat map of CHG analysis. The heatmap values represent the DMP number within the sliding windows along each chromosome (window size=100 kb, moving distance=5 kb). The arrow to the right of each shows approximate location of centromere.
Figure 22B:
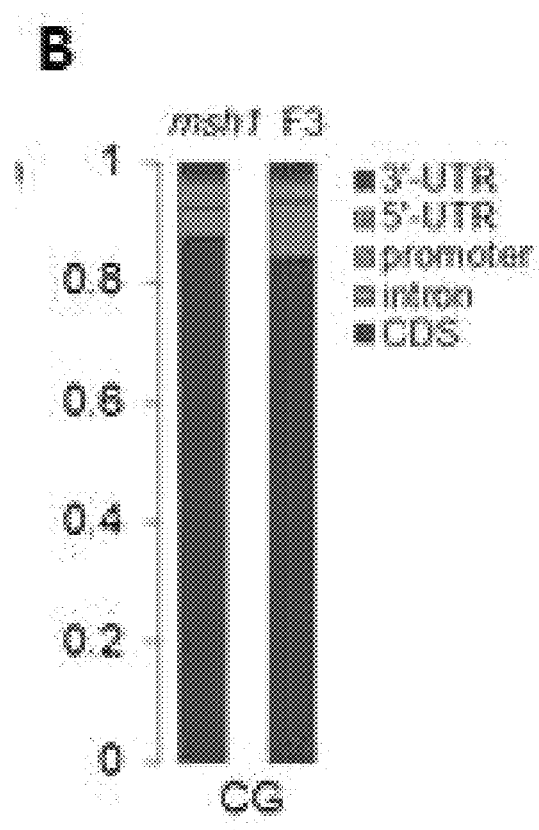
Figure 22C:
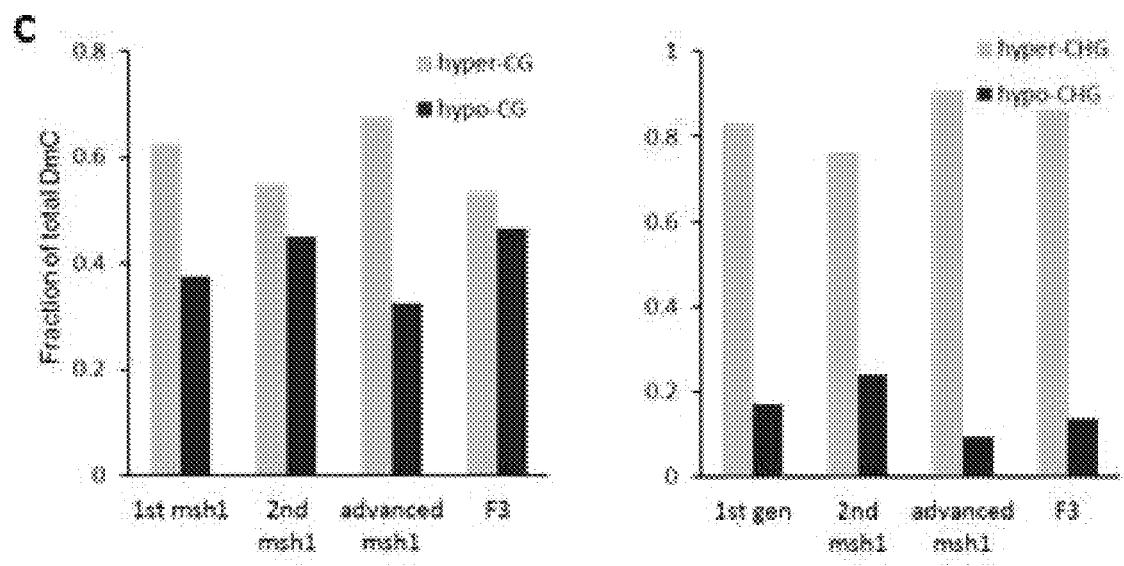
Figure 22D:
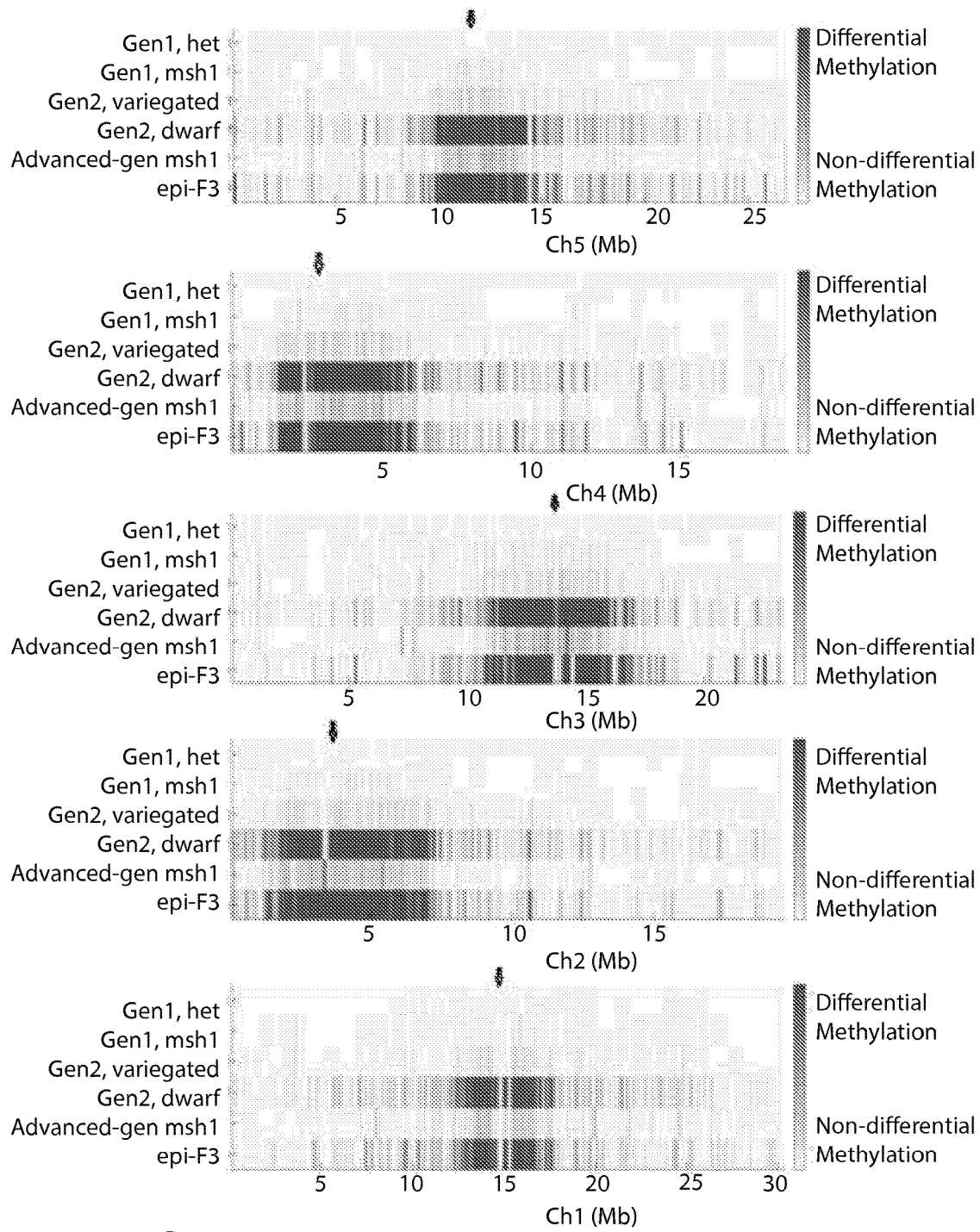
Figure 27:
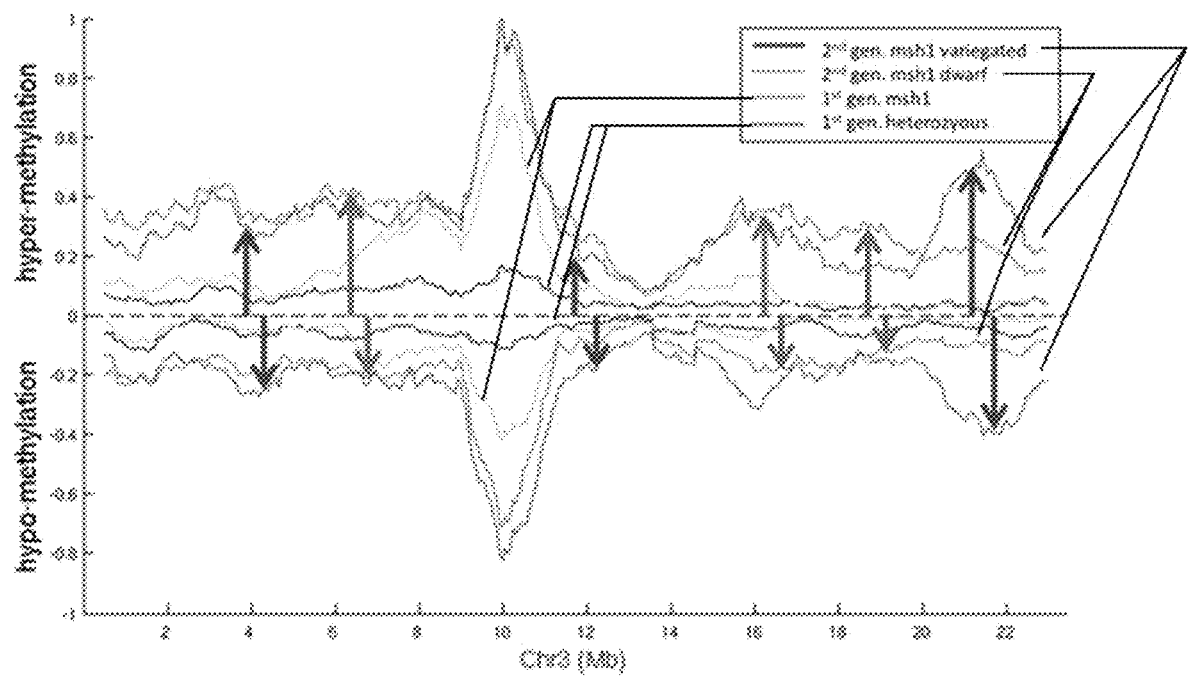
FIG. 27 shows an example of CG DMP distribution plotted by hypermethylation versus hypomethylation along Chromosome 3. Lighter arrows show regions where the asymmetry is particularly pronounced in the msh1 second generation dwarfed (dr) lines.

CG changes in methylation were largely in gene body regions (FIG. 22A-B). While CG DMRs generally include both loss and gain of methylation by a coordinated activity of both DNA methyl transferases and DNA glycosylases to maintain DNA methylation balance in the genome (11, 12), a disturbance in this balance is particularly evident in the second- and advanced-generation msh1 mutant lines (FIGS. 22C, 27). This tendency toward hypermethylation is also particularly pronounced for CHG DMRs from generation 1 to advanced (FIG. 22C). Comparison of Col-0 and the epiF3 line, derived from crossing an early generation (gen 3) line to Col-0, showed over 2000 CG DMRs with interspersed genomic intervals of hypermethylation (FIG. 21). In the epiF3 line, methylation changes are dramatically redistributed in the genome, presumably the consequence of recombination following the cross to wildtype (FIG. 21).

Figure 28:
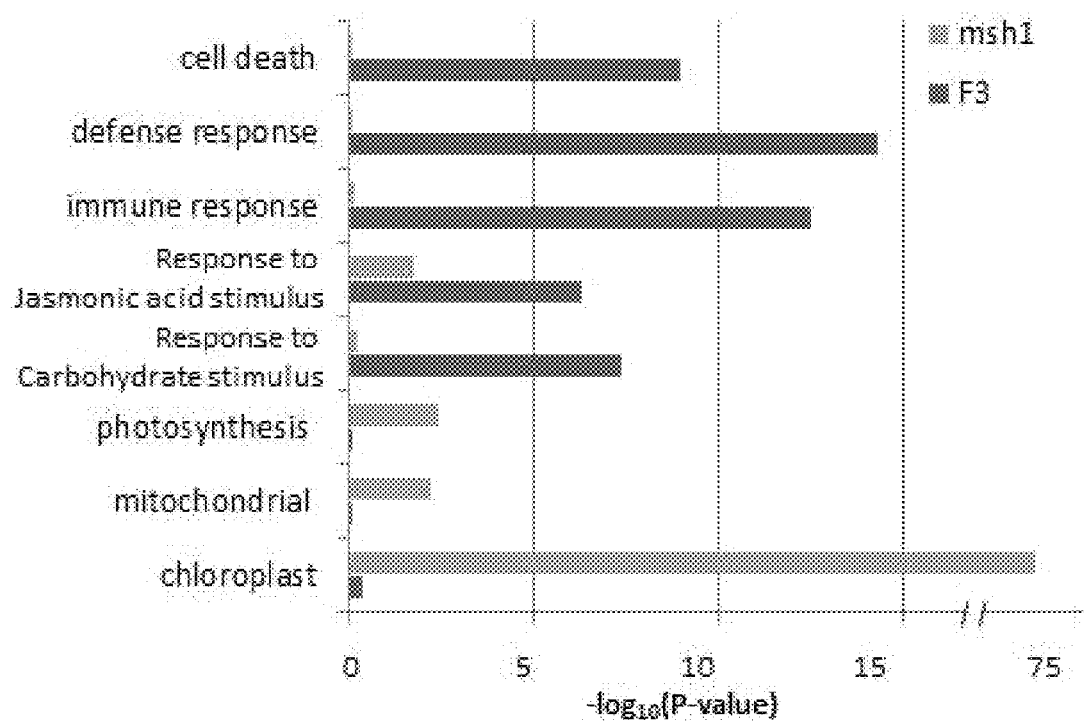
FIG. 28 shows the Gene ontology distribution of genes with significantly altered expression levels in msh1 versus those in epiF3 based on transcript profile analysis.

Gene expression changes in msh1 occurred for plant defense and stress response networks, while the epi-F3 lines showed predominant changes in expression of regulatory, protein turnover and several classes of kinase genes (FIG. 28). These data reflect formation of two strikingly distinct and rapid plant transitions, from wildtype to msh1-dr, and from msh1-dr to epi-F3 enhanced growth, as evidenced by plant growth phenotype, methylome and transcriptome data.

CG DMPs occurred mostly in gene coding regions, resembling natural epigenetic variation (11, 12), and gene-associated CG DMPs were located within gene bodies (FIG. 22). Non-differential methylation distributions in wildtype Col-0 versus MSH1-epiF3 and msh1, seen as blue lines in FIG. 21, showed good correspondence to that reported by an earlier *Arabidopsis* study of natural methylation variation in Col-0 (11). The striking differences were seen in distribution of differential methylation. The Becker et al. (11) analysis of natural variation showed fairly uniform distribution of CG differential methylation spanning each chromosome, which was also the case for advanced-generation msh1, similarly maintained by serial self-pollination (FIG. 21).

What distinguished advanced-generation msh1 methylation from that previously reported in Col-0 was the striking tendency toward hypermethylation, comprising 88% of the DMRs and 70% of total DMPs, which is not observed in natural variation patterns (11). First- and second-generation msh1 showed discrete regions of differential methylation, reflective of msh1 changes with greatly reduced background "noise" (FIG. 21). Particularly intriguing was the observation of CHG hypermethylation changes in the second-generation dwarfed dr segregants but not observed in the full-sib variegated, normal growth segregants. These changes are concentrated in pericentromeric regions of the chromosome. The second generation following msh1 depletion is the point at which the developmental reprogramming phenotype, involving dwarfing, delayed maturity transition and flowering, and woody perennial growth at short day length, is fully evident in over 20% of the plants (15). We are investigating the possible association of these pericentromeric changes with development of the dr phenotype and the derived MSH1-epiF3 enhanced growth phenotype. The hemi-complementation data suggest that development of the MSH1-dr phenotype is prerequisite to the enhanced growth effects that follow crossing to wildtype.

MSH1-epiF3 lines are developed by crossing early-generation msh1 to wild type and self-pollinating the F1 two generations. These enhanced growth lines showed hypomethylation at 33% of DMRs and 45% of total DMPs. Intervals of differential methylation were redistributed in the genome following crosses to wildtype (FIG. 21), a phenomenon that may prove useful for future mapping of growth enhancing determinants.

Gene expression patterns in wildtype, msh1-dr, and enhanced growth epiF3 lines show profound changes in only one or two generations with the altered expression of MSH1. Natural reprogramming of the epigenome in plants can occur during reproductive development (19-20), when MSH1 expression is most pronounced (21). MSH1 steady state transcript levels decline markedly in response to environmental stress (14, 22). These observations suggest that MSH1 participates in environmental sensing to allow the plant to dramatically alter its growth. MSH1 suppression is a previously unrecognized process for altering plant phenotype, and may act through epigenetic remodeling to relax genetic constraint on phenotype in response to environmental change (23).

The near-identical MSH1-dr phenotypes in six different plant species (15) indicate that changes observed with MSH1 suppression are non-stochastic, programmed effects. The phenotypic transition to msh1-dr is accompanied by a significant alteration in methylome pattern that, likewise, appears non-stochastic. At least two pronounced methylome changes occur immediately upon mutation of msh1, a concentration of CG differential methylation on Chromosome 3 adjacent to and encompassing MSH1, and heritable pericentromeric CHG hyper-methylation changes in second-generation plants displaying the msh1-dr phenotype and epiF3 lines showing enhanced growth.

Crossing msh1-dr and Col-0, each with differing methylome patterns, results in redistribution of DMRs within the epi-F3 genome. Enhanced growth capacity of the resulting progeny may be the consequence of a phenomenon akin to heterosis or transgressive segregation (24, 25). Pericentromeric intervals of a chromosome tend to retain heterozygosity and have been suggested to contribute disproportionately to heterosis (26).

Methods

Plant materials and growth conditions. *Arabidopsis* Col-0 and msh1 mutant lines were obtained from the *Arabidopsis* stock center and grown at 12 hr day length at 22° C. MSH1-epi F3 lines were derived by crossing MSH1-dr lines with wild type plants and self-pollinating two generations. *Arabidopsis* plant biomass and rosette diameters were measured for 4-week-old plants. *Arabidopsis* flowering time was measured as date of first visible flower bud appearance. For hemi-complementation crosses, mitochondrial (AOX-MSH1) and plastid (SSU-MSH1) complemented homozygous lines were crossed to Col-0 wildtype plants. Each F1 plant was genotyped for transgene and wildtype MSH1 allele and harvested separately. Three F2 families from AOX-MSH1×Col-0 and two F2 families from SSU-MSH1× Col-0 were evaluated for growth parameters. All families were grown under the same conditions, and biomass, rosette diameter and flowering time were measured. Two-tailed Student t-test was used to calculate p-values.

Bisulfite treatment of DNA for PCR analysis. *Arabidopsis* genomic DNA was bisulfite treated using the MethylEasy™ Xceed kit according to manufacturer's instructions. PCR was performed using primers listed in Table 6, and the PCR products were cloned (Topo TA cloning kit, Invitrogen) and DNA-sequenced. Sequence alignment was performed using the T-Coffee multiple sequence alignment server (27).

Bisulfite treated genomic library construction and sequencing. *Arabidopsis* genomic DNA (15 ug) prepared from Col-0, msh1 and epi-F3 plants was sonicated to peak range 200 bp to 600 bp. Sonicated DNA (12 ug) was treated with Mung Bean Nuclease (New England Biolabs), phenol/chloroform extracted and ethanol precipitated. Mung Bean Nuclease-treated genomic DNA (3 ug) was end-repaired and 3' end-adenylated with Illumina (San Diego Calif.) Genomic DNA Samples Prep Kit. The adenylated DNA fragment was ligated to methylation adapters (Illumina). Samples were column purified and fractionated in agarose. A fraction of 280 bp to 400 bp was gel purified with the QIAquick™ Gel Purification kit (Qiagen, Valencia, Calif.). Another 3 ug of Mung Bean Nuclease treated genomic DNA was used to repeat the process, and the two fractions pooled and subjected to sodium bisulfite treatment with the MethylEasy™ Xceed kit (Human Genetic Signatures Pty Ltd, North Ryde, Australia). Three independent library PCR enrichments were carried out with 10 ul from total 30 ul bisulfate treated DNA as input template. The PCR reaction mixture was 10 ul DNA, 5 ul of 10× pfuTurbo Cx buffer, 0.7 ul of PE1.0 primer, 0.7 ul PE2.0 primer, 0.5 ul of dNTP (25 mM), 1 ul of PfuTurbo Cx Hotstart™ DNA Polymerase (Stratagene, Santa Clara, Calif.), and water to total volume 50 ul. PCR parameters were 95° C. for 2 min, followed by 12 cycles of 95° C. 30 sec, 65° C. 30 sec and 72° C. 1 min, then 72° C. for 5 min. PCR product was column-purified and equal volumes from each reaction were pooled to final concentration of 10 nM.

Libraries were DNA sequenced on the Illumina Genome Analyzer II with three 36-cycle TruSeq sequencing kits v5 to read 116 nucleotides of sequence from a single end of each insert (V8 protocol).

DNA Sequence analysis and identification of differentially methylated cytosines (DMCs).

FASTQ files were aligned to the TAIR10 reference genome using Bismark (28), which was also used to determine the methylation state of cytosines. One mismatch was allowed in the first 50 nucleotides of the read. Bismark only retains reads that can be uniquely mapped to a location in the genome. Genomic regions with highly homologous sequences at other locations of the genome were filtered out.

Only cytosine positions identified as methylated in at least two reads for at least one of the genotypes and sequenced at least four times in each of the genotypes were used for the identification of DMCs. For these cytosine positions, the number of reads indicating methylation or non-methylation for each genotype was tabulated using R (http://www.r-project.org). Fisher's exact test was carried out for testing differential methylation at each position. Adjustment for multiple testing over the entire genome was done as suggested in Storey and Tibshirani (29) and a false discovery rate (FDR) of 0.05 was used for identifying differentially methylated CG cytosines. A less stringent threshold was used for identifying differentially methylated cytosines of CHG and CHH, i.e. adjustment for multiple testing was done for cytosines where a p-value smaller than 0.05 and a false discovery rate (FDR) of 0.035 was used. Methylome sequence data were uploaded to the Gene Expression Omnibus with accession number GSE36783.

Mapping DMCs to genomic context and identifying differentially methylated regions (DMRs)

TAIR10 annotation The "ftp" site "ftp.arabidopsis.org/home/tair/Genes/TAIR10_genome_release/TAIR10_gff3" was used to determine the counts for DMCs or non-differentially methylated cytosines in gene coding regions, 5'-UTRs, 3'-UTRs, introns, pseudogenes, non-coding RNAs, transposable element genes, and intergenic regions. Intergenic regions were defined as regions not corresponding to any annotated feature.

For each methylation context (CG, CHG, CHH), the genome was scanned for regions enriched in DMCs using a 1-kb window in 100-bp increments. Windows with at least four DMCs were retained and overlapping windows were merged into regions. Regions with at least 10 DMCs were retained with the boundary trimmed to the furthest DMCs in the region.

Microarray analysis. Microarray experiments were carried out as described previously (14). Total RNA was extracted from 8-week-old Col-0 and MSH1-epiF3 *Arabidopsis* plants using TRIzol (Invitrogen) extraction procedures followed by purification on RNeasy columns (Qiagen). Three hybridizations were performed per genotype with RNA extractions from single plants for each microarray chip. Samples were assayed on the Affymetrix GeneChip oligonucleotide 22K ATH1 array (Affymetrix) according to the manufacturer's instructions. Expression data from Affymetrix GeneChips were normalized using the Robust Multichip Average method (30). Tests for differential expression between genotypes were performed with the limma package (31). The false discovery rate is controlled at 0.1 for identifying differentially expressed genes. Gene ontology analysis is carried out using DAVID v6.7 (32). The microarray data have been deposited at the Gene Expression Omnibus with accession number GSE43993.

Genome sequencing, de-novo genome assembly and SNP analysis of msh1. Genome sequencing was carried out at the Center for Genomics and Bioinformatics at Indiana University. The 20 nM dilutions were made for DNA samples prepared from mutant msh1 and one epiF5 line. Preparation of single stranded DNA used 5 ul 20 nM dilution and 5 ul 0.2N NaOH incubated for 5 min and diluted with 990 ul Illumina HT1 Hyb buffer for 100 pM ssDNA stocks. 100 ul of 100 pM stock, 397 ul Ht1 buffer and 3 ul PhiX 10 nM ssDNA control were loaded to the flowcell of the Illumina MiSeq™ and processing was according to manufacturer's instructions.

Raw paired-end reads (mate 1: 300 bp; mate 2: 230 bp) were quality trimmed with a Phred quality threshold of 20 and reads with a subsequent length of less than 50 bases were removed. Illumina TruSeq adapter (index 22) was trimmed (prefixed with 'A' user for adapter ligation), removing from the adapter match to the 3' end of the read. A second pass of adapter trimming without the 'A' prefix was done to remove adapter dimers. Ambiguous bases were trimmed from the 5' and 3' end of reads, and those reads with more than 1% number of ambiguous bases were completely removed. A second pass of quality filtering was performed, again with bases lower than a Phred quality score of 20 being trimmed, and reads of less than 50 bases being removed. A PhiX (RefSeq: NC_001422) spike-in was removed by mapping the reads via bowtie233 (version 2.0.6) against the PhiX genome and filtering out any hits from the FASTQ files via a custom Perl script (available upon request). The resulting FASTQ files were synchronized, such that only full mate-pairs remained, while orphans (only one mate exists) were stored in a separate file. Cutadapt (33) (version 1.2.1) was used for the adapter removal, and the NGS-QC toolkit (34) (version 2.3) and fastq_quality_trimmer (35) (part of FASTX Toolkit 0.0.13.2) were used for the removal of ambiguous bases and quality filtering, respectively.

The msh1 genome was assembled using Velvet (36) with a kmer value of 83, an insert length of 400 bases, a minimum contig length of 200 bases, and the short paired (the PE reads) and a short read (the orphans) FASTQ files. The expected coverage (-exp_cov) and coverage cutoff (-cov_cutoff) were determined manually to be 25 and 8, respectively, by inspecting the initial weighted coverage of the first assembly. Resulting contigs were mapped back to Col-0 via blastn (37)(version 2.2.26+) using an e-value of 10-20 and coverage was determined with a custom Perl script (available upon request).

For the SNP and indel detection between msh1 and Col-0, the PE reads were aligned against the TAIR10 reference version of the Col-0 genome sequence via the short read aligner Bowtie2 (38) using the-very-sensitive option and allowing one mismatch per seed (-N 1). Only the best alignment was reported and stored in a SAM file. The SAM file was processed via samtools mpileup (39)(version 0.1.18) and subsequently filtered by a minimum read depth of 20, a minimum mapping quality of 30, and a minimum SNP or indel Phred quality score of 30 (p<=0.001).

The SNPs and small indels were compared to supplementary data files from Lu et al. (16) with custom made Perl scripts (available upon request). The msh1 genome sequence data has been uploaded to the Short Read Archive under sample number SAMN0919714.

Table 5. Analysis of phenotype data from individual $Arabidopsis$ $F_2$ families derived by crossing hemi-complementation lines×Col-0 wildtype. SSU-MSH1 refers to lines transformed with the plastid-targeted form of MSH1; AOX-MSH1 refers to lines containing the mitochondrial-targeted form of the MSH1 transgene. In all genetic experiments using hemi-complementation, presence/absence of the transgene was confirmed with a PCR-based assay.

TABLE 5

|  | Rosette diameter | | | | | Fresh biomass | | | | |
| --- | --- | --- | --- | --- | --- | --- | --- | --- | --- | --- |
|  | Mean (cm) | N | Std. Error | Std. Dev | p-value | Mean (g) | N | Std. Error | Std. Dev | p-value |
| AOX-MSH1 | 11.07 | 36 | 0.37 | 2.23 | <0.001 | 8.86 | 10 | 0.47 | 1.33 | NS |
| SSU-MSH1 | 11.76 | 18 | 0.26 | 1.10 | <0.001 | 10 | 10 | 0.55 | 1.55 | NS |
| Col-0 | 12.98 | 42 | 0.24 | 1.59 | — | 9.45 | 10 | 0.43 | 1.36 | — |
| F-2 (AOX-MSH1 × Col-0) | 12.83 | 21 | 0.34 | 1.57 | NS | 15.07 | 10 | 0.66 | 2.07 | <0.001 |
| F-22 (AOX-MSH1 × Col-0) | 13.82 | 21 | 0.42 | 192 | <0.10 | 14.62 | 10 | 0.92 | 2.24 | <0.001 |
| F-28 (AOX-MSH1 × Col-0) | 14.85 | 21 | 0.31 | 142 | <0.001 | 13.27 | 10 | 0.70 | 1.99 | <0.001 |
| F-26 (SSU-MSH1 × Col-0) | 12.82 | 20 | 0.25 | 112 | NS | 10.57 | 10 | 0.66 | 1.74 | NS |
| F-29 (SSU-MSH1 × Col-0) | 11.9 | 21 | 0.27 | 125 | <0.001 | 10.5 | 10 | 0.45 | 1.19 | NS |

†P values are based on two-tailed Student t-test comparing to Col-0
NS = Not Significant

TABLE 6

Primers used in the study

| Primer name | Sequence |
| --- | --- |
| For bisulfate sequencing: | |
| AT5G67120RING-F | 5'-TTTTTAGGAATTATTGAGTATTATTGA-3' (SEQ ID NO: 42) |
| AT5G67120RING-R | 5'-AAATAAAAATCATACCCACATCCC-3' (SEQ ID NO: 43) |
| AT1G20690SWI-F | 5'-TGTTGAATTATTAAGATATTTAAGAT-3' (SEQ ID NO: 44) |
| AT1G20690SWI-R | 5'-TCAACCAATAAAAATTACCATCTAC-3' (SEQ ID NO: 45) |

TABLE 6-continued

Primers used in the study

| Primer name | Sequence |
|---|---|
| AT3g271501stMir2-F | 5'-TAAGTTTTTTTTAAGAGTTTGTATTTGTAT-3' (SEQ ID NO: 46) |
| AT3g271501stMir2-R | 5'-TAAAAATAATCAAAACCTAACTTAC-3' (SEQ ID NO: 47) |
| AT3g271502ndMir2-F | 5'-ATTGTTTATTAAATGTTTTTTAGTT-3' (SEQ ID NO: 48) |
| AT3g271502ndMir2-R | 5'-CTAACAATTCCCAAAACCCTTATC-3' (SEQ ID NO: 49) |
| For PCR assay of MSH1-RNA1 transgene: | |
| RNAi-F | 5'-GTGTACTCATCTGGATCTGTATTG-3' (SEQ ID NO: 50) |
| RNAi-R | 5'-GGTTGAGGAGCCTGAATCTCTGAAC-3' (SEQ ID NO: 51) |

References for Example 5
1. Bonasio, R., Tu, S. & Reinberg, D. (2010) Molecular signals of epigenetic states. Science 33: 612-616
2. Mirouze, M. & Paszkowski, J. (2011) Epigenetic contribution to stress adaptation in plants. Curr Opin Plant Biol. 14:267-274
3. Dowen, R. H. et al. (2012) Widespread dynamic DNA methylation in response to biotic stress. Proc. Natl. Acad. Sci. USA 109: E2183-2191
4. Youngson, N. A. & Whitelaw, E. (2008) Transgenerational epigenetic effects. Annu. Rev. Genom. Human Genet 9: 233-257
5. Paszkowski, J. & Grossniklaus, U. (2011) Selected aspects of transgenerational epigenetic inheritance and resetting in plants. Curr. Opin. Plant Biol. 14: 195-203
6. Reinders, J. et al. (2009) Compromised stability of DNA methylation and transposon immobilization in mosaic Arabidopsis epigenomes. Genes Dev. 23: 939-950
7. Johannes, F. et al. (2009) Assessing the impact of transgenerational epigenetic variation on complex traits. PLoS Genet. 5: e1000530
8. Roux, F. et al. (2011) Genome-wide epigenetic perturbation jump-starts patterns of heritable variation found in nature. Genetics 188: 1015-1017.
9. Eichten, S. R. et al. (2011) Heritable epigenetic variation among maize inbreds. PLoS Genet. 7: e1002372.
10. Shen, H. et al. (2012) Genome-wide analysis of DNA methylation and gene expression changes in two Arabidopsis ecotypes and their reciprocal hybrids. Plant Cell 24: 875-892
11. Becker, C. et al. (2011) Spontaneous epigenetic variation in the Arabidopsis thaliana methylome. Nature 480: 245-249
12. Schmitz, R. J. et al. (2011) Transgenerational epigenetic instability is a source of novel methylation variants. Science 334: 369-373
13. Abdelnoor, R. V. et al. (2003) Substoichiometric shifting in the plant mitochondrial genome is influenced by a gene homologous to MutS. Proc. Natl. Acad. Sci. USA 100: 5968-5973
14. Xu, Y.-Z. et al. (2011) MutS HOMOLOG1 is a nucleoid protein that alters mitochondrial and plastid properties and plant response to high light. Plant Cell 23: 3428-3441
15. Xu, Y.-Z. et al. (2012) The chloroplast triggers developmental reprogramming when MUTS HOMOLOG1 is suppressed in plants. Plant Physiol. 159: 710-720
16. Lu, P. et al. (2012) Analysis of Arabidopsis genome-wide variations before and after meiosis and meiotic recombination by resequencing Landsberg erecta and all four products of a single meiosis. Genome Res. 22: 508-518
17. Stokes, T. L., Kunkel, B. N. & Richards, E. J. (2002) Epigenetic variation in Arabidopsis disease resistance. Genes Dev 16: 171-182
18. Lister, R. et al. (2008) Highly integrated single-base resolution maps of the epigenome in Arabidopsis. Cell 133: 523-36
19. Hsieh, T.-F., et al. (2009) Genome-wide demethylation of Arabidopsis endosperm. Science 324: 1451-1454
20. Gehring, M., Bubb, K. L. & Henikoff, S. (2009) Extensive demethylation of repetitive elements during seed development underlies gene imprinting. Science 324: 1447-1451
21. Shedge, V., Arrieta-Montiel, M. P., Christensen, A. C. & Mackenzie, S. A. (2007) Plant mitochondrial recombination surveillance requires unusual RecA and MutS homologs. Plant Cell 19: 1251-1264
22. Shedge, V., Davila, J., Arrieta-Montiel, M. P., Mohammed, S. & Mackenzie S. A. (2010) Extensive rearrangement of the Arabidopsis mitochondrial genome elicits cellular conditions for thermotolerance. Plant Physiol. 152: 1960-1970
23. Kalisz, S. & Kramer, E. M. (2008) Variation and constraint in plant evolution and development. Hered. 100: 171-177
24. Greaves, I., Groszmann, M., Dennis, E. S. & Peacock, W. J. (2012) Trans-chromosomal methylation. Epigenetics 7:800-805
25. Shivaprasad, P. V., Dunn, R. M., Santos, B. A., Bassett, A. & Baulcombe, D. C. (2012) Extraordinary transgressive phenotypes of hybrid tomato are influenced by epigenetics and small silencing RNAs. EMBO J 31: 257-266
26. McMullen M. D., et al. (2009) Genetic properties of the maize nexted association mapping population. Science 7: 737-740

27. Notredame, C., Higgins, D. G. & Heringa, J. (2000) T-Coffee: A novel method for fast and accurate multiple sequence alignment. *J Mol. Biol.* 302: 205-217
28. Krueger, F. & Andrews, S. R. (2011) Bismark: a flexible aligner and methylation caller for Bisulfite-Seq applications. *Bioinformatics* 27:1571-1572
29. Storey, J. D. & Tibshirani, R. (2003) Statistical significance for genome-wide studies. *Proc. Natl. Acad. Sci. USA* 100: 9440-9445
30. Bolstad, B., Irizarry, R. A., Astrand, M. & Speed T. (2003) A comparison of normalization methods for high density oligonucleotide array data based on bias and variance. *Bioinformatics* 19: 195-193
31. Smyth, G. K. (2004) Linear models and empirical Bayes methods for assessing differential expression in microarray experiments. *Stat. Appl. Genet. Mol. Biol.* 3: Article 3
32. Huang, D. W., Sherman, B. T. & Lempicki, R. A. (2009) Systematic and integrative analysis of large gene lists using DAVID Bioinformatics Resources. *Nat. Protoc.* 4:44-57
33. Martin M. (2011) Cutadapt removes adapter sequences from high-throughput sequencing reads. EMBnet Journal, Vol 17, No 1.
34. Langmead, B. & Salzberg, S. NGS QC Toolkit: A toolkit for quality control of next generation sequencing data. *PLoS ONE* 7(2): e30619
35. Hannon Lab. FASTX-Toolkit. On the interne at "hannonlab.cshl.edu/fastx_toolkit/"
36. Zerbino D R, McEwen G K, Margulies E H, Birney E. (2009) Pebble and Rock Band: Heuristic Resolution of Repeats and Scaffolding in the Velvet Short-Read de Novo Assembler. *PLoS ONE* 4(12): e8407
37. Camacho, C. et al. (2012) BLAST+: architecture and applications. *BMC Bioinformatics* 10, 421 (2009). Fast gapped-read alignment with Bowtie 2. *Nat. Methods* 9: 357-359
38. Li, H. et al. (2009) The Sequence alignment/map (SAM) format and SAMtools. *Bioinformatics* 25: 2078-2079.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A grafted plant comprising a scion to which a rootstock had been grafted, wherein:
   (i) the scion is from a wild type plant;
   (ii) MSH1 gene expression is suppressed in the rootstock;
   (iii) the rootstock confers an improvement in yield or growth rate in progeny of the grafted plant in comparison to a control plant, wherein the control plant comprises either: (a) progeny of a scion grafted to rootstock that had not been subjected to suppression of MSH1 gene expression; (b) a whole plant that lacks any root graft and that had not been subjected to suppression of MSH1 gene expression; (c) a wild-type plant; or (d) progeny of a plant that is isogenic to the plant source of the scion of the grafted plant; and,
   (iv) the MSH1 gene expression is suppressed in the rootstock by a mutation in an endogenous MSH1 gene of the rootstock or by a small inhibitory RNA (siRNA), a microRNA (miRNA), a co-suppressing sense RNA, and/or an anti-sense RNA having complementarity to the endogenous MSH1 gene promoter, 5' or 3' untranslated region, intron, coding region, and/or any combination thereof.

2. The grafted plant of claim 1, wherein MSH1 gene expression is suppressed in the rootstock and the rootstock confers to the grafted plant an improvement in yield or growth rate in comparison to a control plant.

3. The grafted plant of claim 1, wherein the scion contains one or more epigenetic changes in one or more nuclear chromosomes, wherein the epigenetic changes are absent from the nuclear chromosomes of a control plant or are absent from the nuclear chromosomes of a plant from which the scion was obtained.

4. The grafted plant of claim 3, wherein the epigenetic change(s) are also present in the rootstock.

5. The grafted plant of claim 3, wherein the epigenetic changes are associated with the improvement in the useful trait.

6. The grafted plant of claim 3, wherein the rootstock contain(s) one or more epigenetic changes in one or more nuclear chromosomes that are absent from nuclear chromosomes of rootstock obtained from a plant or nuclear chromosomes of a parent plant thereof that had not been subjected to suppression of MSH1 gene expression.

7. The grafted plant of claim 3, wherein the scion and/or the rootstock exhibit CG hypermethylation of a region encompassing a MSHI locus in comparison to a control plant that had not been subjected to suppression of MSH1 gene expression.

8. The grafted plant of claim 3, wherein the scion and/or the rootstock exhibit pericentromeric CHG hyper-methylation in comparison to a control plant that had not been subjected to suppression of MSH1 gene expression.

9. The grafted plant of claim 3, wherein the scion and/or the rootstock exhibit CG hypermethylation and/or CHG hypermethylation at one or more nuclear chromosomal loci in comparison to corresponding nuclear chromosomal loci of a control plant that had not been subjected to suppression of MSH1 gene expression.

10. The grafted plant of claim 1, where said plant is selected from the group consisting of a crop plant, a tree, a bush, turf grass, pasture grass, and a vine.

11. The grafted plant of claim 10, wherein the crop plant is selected from the group consisting of corn, soybean, cotton, canola, wheat, rice, tomato, tobacco, millet, potato, sugarbeet, cassava, alfalfa, barley, oats, sugarcane, sunflower, strawberry, and sorghum.

12. A progeny plant produced by a method comprising the steps of:
   (a) obtaining a population of progeny plants from the grafted plant of claim 1, wherein the population of progeny plants is a first, second, or third generation of progeny plants obtained by selfing the grafted plant or by selfing the first or second generation progeny plants;
   (b) screening the population of progeny plants for plants having improved yield or growth rate in comparison to control plants; and (c) selecting a progeny plant from the population for an improvement in yield or growth rate in comparison to a control plant, wherein said progeny plant exhibits said improvement in yield or growth rate and exhibits a nuclear chromosomal DNA methylation pattern that is distinct from the control plant nuclear chromosomal DNA methylation pattern, and wherein the control plant is grown under the same environmental conditions as the selected progeny plants and comprises either: (i) progeny of a scion grafted to rootstock that had not been subjected to suppression of MSH1 gene expression; (ii) a whole plant that lacks any root graft and that had not been subjected to suppression of MSH1 gene expression; (iii) a wild-type plant; or (iv) progeny of a plant that is isogenic to the plant source of the scion of the grafted plant.

13. A selected population of progeny plants produced by a method comprising the steps of:

(a) obtaining a population of progeny plants from the grafted plant of claim 1, wherein the population of progeny plants is a first, second, or third generation of progeny plants obtained by selfing the grafted plant or by selfing the first or second generation progeny plants;

(b) screening the population of progeny plants for improved yield or growth rate in comparison to a control plant population; and (c) selecting a population of progeny plants for an improvement in yield or growth rate in comparison to control plants, wherein said selected population of progeny plants exhibits said improvement in yield or growth rate and exhibits a nuclear chromosomal DNA methylation pattern that is distinct from a control plant nuclear chromosomal DNA methylation pattern, and wherein the control plant is grown under the same environmental conditions as the selected population of progeny plants and comprises either: (i) progeny of a scion grafted to rootstock that had not been subjected to suppression of MSH1 gene expression; (ii) a whole plant that lacks any root graft and that had not been subjected to suppression of MSH1 gene expression; (iii) a wild-type plant; or (iv) progeny of a plant that is isogenic to the plant source of the scion of the grafted plant.

14. The grafted plant of claim 1, wherein the MSH1 gene expression is suppressed in the rootstock of the grafted plant by a mutation in an endogenous MSH1 gene of the rootstock.

* * * * *